US009637516B2

(12) United States Patent
Parthasaradhi Reddy et al.

(10) Patent No.: US 9,637,516 B2
(45) Date of Patent: May 2, 2017

(54) BETULINIC ACID PROLINE DERIVATIVES AS HIV INHIBITORS

(71) Applicant: HETERO RESEARCH FOUNDATION, Hyderabad, Andhra Pradesh (IN)

(72) Inventors: Bandi Parthasaradhi Reddy, Hyderabad (IN); Kura Rathnakar Reddy, Hyderabad (IN); Lanka Vl Subrahmanyam, Hyderabad (IN); Gazula Levi David Krupadanam, Hyderabad (IN); Mukkera Venkati, Hyderabad (IN); Neela Sudhakar, Hyderabad (IN); Kallem Srinivas Reddy, Hyderabad (IN)

(73) Assignee: HETERO RESEARCH FOUNDATION, Andhra Pradesh (IN)

( * ) Notice: Subject to any disclaimer, the term of this patent is extended or adjusted under 35 U.S.C. 154(b) by 9 days.

(21) Appl. No.: 14/758,309

(22) PCT Filed: Dec. 26, 2013

(86) PCT No.: PCT/US2013/077751
§ 371 (c)(1),
(2) Date: Jun. 29, 2015

(87) PCT Pub. No.: WO2014/105926
PCT Pub. Date: Jul. 3, 2014

(65) Prior Publication Data
US 2015/0337004 A1    Nov. 26, 2015

(30) Foreign Application Priority Data
Dec. 31, 2012   (IN) ............................ 5533/CHE/2012

(51) Int. Cl.
*A61K 31/58*       (2006.01)
*C07J 43/00*       (2006.01)
*C07J 53/00*       (2006.01)
*C07J 63/00*       (2006.01)

(52) U.S. Cl.
CPC ............ *C07J 53/002* (2013.01); *C07J 63/008* (2013.01)

(58) Field of Classification Search
CPC .................................................... C07J 63/008
USPC ............................................ 540/95; 514/176
See application file for complete search history.

(56) References Cited

U.S. PATENT DOCUMENTS

| | | | |
|---|---|---|---|
| 4,598,095 | A | 7/1986 | Nishimura et al. |
| 5,679,828 | A | 10/1997 | Lee et al. |
| 6,670,345 | B1 | 12/2003 | Ramadoss et al. |
| 7,923,573 | B2 | 4/2011 | Tamaki et al. |
| 2002/0068757 | A1 | 6/2002 | Lin et al. |
| 2004/0204389 | A1 | 10/2004 | Chen et al. |
| 2006/0194774 | A1 | 8/2006 | Selzer et al. |
| 2006/0205697 | A1 | 9/2006 | Robinson et al. |
| 2008/0207573 | A1 | 8/2008 | Yager et al. |
| 2008/0214516 | A1 | 9/2008 | Selzer et al. |
| 2011/0015196 | A1 | 1/2011 | Parthasaradhi Reddy et al. |
| 2011/0152229 | A1 | 6/2011 | Chen et al. |
| 2011/0218204 | A1 | 9/2011 | Parthasaradhi Reddy et al. |
| 2014/0221328 | A1 | 8/2014 | Parthasaradhi Reddy et al. |
| 2015/0119373 | A1 | 4/2015 | Reddy et al. |

FOREIGN PATENT DOCUMENTS

| | | |
|---|---|---|
| CA | 2223513 A1 | 12/1996 |
| CA | 2767642 C | 1/2011 |
| CN | 1861627 A | 11/2006 |
| CN | 10128774 A | 10/2008 |
| EP | 1218402 B1 | 5/2004 |
| WO | 9502071 | 1/1995 |
| WO | 9858675 | 12/1998 |
| WO | 0046235 | 8/2000 |
| WO | 0107646 A2 | 2/2001 |
| WO | 02091858 A1 | 11/2002 |
| WO | WO03037908 A1 | 5/2003 |
| WO | 2005090380 A1 | 9/2005 |
| WO | 2006053255 A2 | 5/2006 |
| WO | 2006105356 A2 | 10/2006 |
| WO | 2007141383 A1 | 12/2007 |
| WO | 2007141389 A1 | 12/2007 |
| WO | 2007141390 A1 | 12/2007 |
| WO | 2007141391 A1 | 12/2007 |
| WO | 2007141392 A2 | 12/2007 |
| WO | 2008057420 A2 | 5/2008 |
| WO | 2008127364 A2 | 10/2008 |
| WO | 2009082818 A1 | 7/2009 |
| WO | 2009082819 A1 | 7/2009 |
| WO | 2009100532 A1 | 8/2009 |
| WO | 2010132334 A1 | 11/2010 |
| WO | 2011007230 A2 | 1/2011 |
| WO | 2011100308 A1 | 8/2011 |

(Continued)

OTHER PUBLICATIONS

Fujioka et al. "Anti-AIDS Agents, 11. Betulinic Acid and Platanic Acid as anti-HIV Principles from Syzigium Claviflorum, and the Anti-HIV Activity of Structurally Related Triterpenoids", Journal of Natural Products, 1994, vol. 57, No. 2, pp. 243-247. A
Aguado et al., "Enantidivergent synthesis of cyclobutyl-(Z)-a,βdehydro-a-amino acid derivatives fom (-)cis-pinononic acid", Tetrahedron: Asymmetry 14, 2003, pp. 217-223.
Aguilera et al., "Stereodivergent synthesis of the first bis(cyclobutane) y-dipeptides and mixed y-oligomers", Tetrahedron: Asymmetry 19, 2008, pp. 302-308.
Antimonova et al., "Synthesis of Betulonic Acid Amindes", Chemistry of Natural Compounds, 2008, vol. 44, No. 3, pp. 327-333.
Averett, D. "Anti-HIV compound assessment by two novel high capacity assays", Journal of Virological Methods, 1989, vol. 23, pp. 263-276.

(Continued)

*Primary Examiner* — Barbara P Badio
(74) *Attorney, Agent, or Firm* — Cantor Colburn LLP

(57) ABSTRACT

The invention relates to novel betulinic acid derivatives and related compounds, and pharmaceutical compositions useful for the therapeutic treatment of viral diseases and particularly HIV mediated diseases.

14 Claims, No Drawings

(56) References Cited

FOREIGN PATENT DOCUMENTS

| | | | |
|---|---|---|---|
| WO | 2011153315 | A1 | 12/2011 |
| WO | 2011153319 | A1 | 12/2011 |
| WO | WO2012095705 | A1 | 7/2012 |
| WO | 2013020245 | A1 | 2/2013 |
| WO | 2013090664 | A1 | 6/2013 |
| WO | 2013090683 | A1 | 6/2013 |
| WO | 2013117137 | A1 | 8/2013 |
| WO | 2013160810 | A2 | 10/2013 |
| WO | 2014093941 | A1 | 6/2014 |

OTHER PUBLICATIONS

Balzarini et al., "9-(2phosphonylmethoxyethyl)adenine (PMEA) effectively inhibits retrovirus replication in vitro and simian immunodeficiency virus infection in rhesus monkeys", AIDS, 1991; 5:21-28.
Barre-Sinoussi et al., "Isolation of a T-Lymphotropic Retrovirus from a Patient at Risk for Acquired Immune Deficiency Syndrome (AIDS)", Science, 1983, vol. 220, pp. 868-871.
Broder et al., "A Pathogenic Retrovirus (HTLV-III) Linked to AIDS", The New England Journal Medicine, 1984, vol. 311, No. 20, pp. 1292-1297.
Cecilia et al., "Neutralization Profiles of Primary Human Immunodeficiency Virus Type 1 Isolates in the Context of Coreceptor Usage", Journal of Virology, Sep. 1998, vol. 72, No. 9, pp. 6988-6996.
Clark et al., "Synthesis and antiviral activity of 2'-deoxy-2'-fluoro-2'-C-methyl purine nucleosides as inhibitors of hepatitis C virus RNA replication", Bioorganic & Medicinal Chemistry Letters 16 (2006), pp. 1712-1715.
Cole, S.P.C., "Rapid chemosensitivity testing of human lung tumor cells using the MTT assay", Cancer Chemotherapy and Pharmacology, 1986, 17, pp. 259-263.
Connor et al., "Characterization of the Functional Properties of env Genes from Long-Term Survivors of Human Immunodeficiency Virus Type 1 Infection", Journal of Virology, 1996, vol. 70, No. 8, pp. 5306-5311.
Daluge et al., "5-Chloro-2',3'-Dideoxy-3'-Fluorouridine (935U83), a Selective Anti-Human Immonudeficiency Virus Agent with an Improved Metabolic and Toxicological Profile", Antimicrobial Agents and Chemotherapy, 1994, vol. 38, No. 7, pp. 1590-1603.
Erice et al., "Anti-Human Immunodeficiency Virus Type 1 Activity of an Anti-CD4 lmmunoconjugate Containing Pokeweed Antiviral Protein", Antimicrobial Agents and Chemotherapy, Apr. 1993, vol. 37, No. 4, pp. 835-838.
Flekhter et al, "Sythesis and Antiinflammatory Activity of New Acylated Betulin Derivatives", Pharmaceutical Chemistry Journal, 2002, vol. 36, No. 9, pp. 488-491.
Greene, T. W. and P. G. M. Wuts, "Protective Groups in Organic Synthesis", 3rd edition, John Wiley & Sons, Inc., New York, 1999.
Harrington et al., "Direct detection of infectious HIV_1 in blood using a centrifugation-indicator cell assay", Journal of Virological Methods, 2000, vol. 88, pp. 111-115.
Hashimoto, F., et al., "Anti-AIDS Agents—XXVIL. Synthesis and Anti-HIV Activity of Betulinic Acid and Dihydrobetulinic Acid Derivatives", Bioorganic & Medicinal Chemistry, 1997, vol. 5, No. 12, pp. 2133-2143.
International Search Report; International Application No. PCT/US2013/077751; International Filing Date Dec. 26, 2013; Date of Mailing Mar. 18, 2014; 6 pages.
Jeong H-J et al: "Preparation of amino acid conjugates of betulinic acid with activity against human melanoma", Bioorganic & Medicinal Chemistry Letters, Pergamon, Amsterdam, NL, vol. 9, No. 8, Apr. 19, 1999, pp. 1201-1204.
Kanamoto et al., "Anti-Human Immunodeficiency Virus Activity of YK-FH312 (a Betulinic Acid Derivative), a Novel Compound Blocking Viral Maturation", Antimicrobial Agents and Chemotherapy, 2001, pp. 1225-1230.
Kashiwada et al., "Betulinic Acid and Dihydrobetulinic Acid Derivatives as Potent Anti-HIV Agents", J. Med. Chem. 1996, 39, pp. 1016-1017.
Koyanagi et al., "Selective Cytotoxicity of AIDS Virus Infection Towards HTLV-I-Transformed Cell Lines", Int. J. Cancer, 1985, vol. 36, pp. 345-451.
Li et al., PA-457: A potent HIV inhibitor that disrupts core condensation by targeting a late step in Gag processing Proc. Natl. Acad. Sci. 2003, pp. 13555-13560.
Meek et al., "Inhibition of HIV-1 protease in infected T-lymphocytes by synthetic peptide analogues", Nature, 1990, vol. 343, pp. 90-92.
Mimoto et al., "Structure-Activity Relationship of Small-Sized HIV Protease Inhibitors Containing Allophenylnorstatine", J. Med. Chem., 1999, vol. 42, No. 10, pp. 1789-1802.
Mitsuya et al., "Inhibition of the in vitro infectivity and cytopathic effect of human T-Iymphotrophic virus type III/ lymphadenopathy-associated virus (HTLV-III/LAV) by 2',3'-dideoxynucleosides", Proc. Natl. Acad. Sci. USA, 1986, vol. 83, pp. 1911-1915.
Moglioni et al., "Divergent Routes to Chiral Cyclobutane Synthons from (-)-a-Pinene and Their Use in the Steroselective Synthesis of Dehydro Amino Acids", J. Org. Chem. 2000, 65, pp. 3934-3940.
Mosmann, T., Rapid Calorimetric Assay for Cellular Growth and Survival: Application to Proliferation and Cytotoxicity Assays. Journal of Immunological Methods, 65 (1983) 55-63.
Nair et al., "A Facile and Efficient Synthesis of 3,3-Dimethyl Isopropylidene Proline (+)-3-Carene", J. Org. Chem., 2010, vol. 75, No. 4, pp. 1285-1288.
Popik et al., "Human Immunodeficiency Virus Type 1 Uses Lipid Raft-Colocalized CD4 and Chernokine Receptors for Productive Entry into CD4+ T Cells", J. of Virology, 2002, pp. 4709-4722.
Qian Keduo et al: "Anti-AIDS agents 81, Design, synthesis, and structure-activity relationship study of betulinic acid and moronic acid derivatives as potent HIV maturation inhibitors.", Journal of Medicinal Chemistry Apr. 22, 2010, vol. 53, No. 8, pages.
Ravi et al, "HIV-1 long terminal repeat promoter regulated dual reporter: Potential use in screening of transcription modulators", Analytical Biochemistry, 2007, vol. 360, pp. 315-317.
Roda Rani et al., "A conserved molecular action of native and recombinant Epap-1 in inhibition of HIV-1 gp120 mediated viral entry", Archives of Biochemistry and Biophysics, 2006, vol. 456, pp. 79-92.
Roos et al., "LuSIV Cells: A Reporter Cell Line for the Detection and Quantation of a Single Cycle of HIV and SIV Replication", Virology, 2000, vol. 273, pp. 307-315.
Sakalian et al., "3-O-(3',3'-Dimethysuccinyl) Betulinic Acid Inhibits Maturation of the Human Immunodeficiency Virus Type 1 Gag Precursor Assemble In Vitro", J. of Virology, 2006, pp, 5716-5722.
Schwartz et al., "A Rapid Colorimetric Test for the Study of Anti-HIV Agents", AIDS Research and Human Retroviruses, 1998m vol. 4, No. 6, pp. 441-448.
Sun, I., et al., "Anti-AIDS Agents, 34. Synthesis and Structure-Activity Relationships of Betulin Derivatives as Anti-HIV Agents", J. Med. Chem. 1998, vol. 41, pp. 4648-4657.
Uckun et al., "TXU (Anti-CD7)-Pokeweed Antiviral Protein as a Potent Inhibitor of Human Immunodeficiency Virus", Antimicrobial Agents and Chemotherapy, Feb. 1998, vol. 42, No. 2, pp. 383-388.
Written Opinion of the International Searching Authority; International Application No. PCT/US2013/077751; International Filing Date Dec. 26, 2013; Date of Mailing Mar. 18, 2014; 12 pages.
Zhou et al., "Inhibition of HIV-1 Maturation via Drug Association with the Viral Gag Protein in Immature HIV-1 Particles", J. of Bio. Chem. vol. 280, No. 51, pp. 42149-42155, 2005.
Zhou et al., "Small-Molecule Inhibition of Human Immunodeficiency Virus Type 1 Replication by Specific Targeting of the Final Step of Virion Maturation", J. of Virology, 2004, pp. 922-929.
Zhu, YM., et al., "Synthesis and Anti-HIV Activity Oleanolic Acid Derivatives", Bioorganic & Medicinal Chemistry Letters, 2001, vol. 11, pp. 3115-3118.
Fedyuk N.V. et al., Problems of Virology 1992, (3) 135, Abstract Only, 1 page.
Pau et al., Antiretroviral Therapy, Infect. Dis. Clin. N. Am., 2014, 28, 371-402.

(56) References Cited

OTHER PUBLICATIONS

Taiwo et al., "Unmet therapeutic needs in the new era of combination antiretroviral therapy for HIV-1", J. antimicrob Chemother 2010; 65: 1100-1107.

Weislow et al., New Soluble-Formazan Assay for HIV-1 Cytopathic Effects: Application to High-Flux Screening of Synthetic and Natural Products for AIDS-Antiviral Activity, J. Natl. Cancer Inst. 81, 577-586, 1989.

BETULINIC ACID PROLINE DERIVATIVES AS HIV INHIBITORS

This application is a U.S. National Stage application of International Application No. PCT/US2013/077751 which claims the benefit of Indian Provisional Patent Application No. 5533/CHE/2012 filed on 31 Dec. 2012; which is incorporated herein by reference in its entirety.

FIELD OF THE INVENTION

The present invention relates to novel betulinic acid proline derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220, 868-871; N. Eng. J. Med. 1984, 311, 1292-1297). AIDS is characterized by the destruction of the immune system, particularly of CD4+ T-cells. HIV is a retrovirus, and the HIV life cycle encompasses several crucial steps, starting from the attachment of the virus to the host cell membrane and finishing with the release of progeny virons from the cell.

The natural compound betulinic acid, isolated from *Syzygium clavifolium* and several other plant species was found to possess anti-HIV activity. Chemical modifications were undertaken by several research groups in an attempt to identify potent anti-HIV agents by making semi-synthetic analogs of betulinic acid, leading to the discovery of bevirimat as a compound with a novel mechanism of action (J. Nat. Prod. 199457(2):243-7; J. Med. Chem. 1996, 39(5), 1016). Further studies shown that bevirimat acts by disrupting Gag processing (Proc. Natl. Acad. Sci. USA 2003, 100(23):13555-60; Antimicrob. Agents. Chemother. 2001, 45(4), 1225-30; J. Virol. 2004, 78(2): 922-9; J. Biol. Chem. 2005, 280(51):42149-55; J. Virol. 2006, 80(12): 5716-22) and to be a first-in-class maturation inhibitor with a potent activity against HIV-1. Bevirimaet went up to phase 2 clinical trials, in clinic despite optimal plasma concentrations, not all patients given bevirimat have a robust viral load reduction. It was reported that non-respondant patients had more frequent base line Gag polymorphisms near the capsid SP-1 cleavage site than responders. (HIV gag polymorphism determines treatment response to bevirimat. XVII inter national HIV drug resistance work shop Jun. 10-14, 2008, Sitges, Spain).

Encouraged by these developments, medicinal chemists started exploring betulinic acid derivatives and related compounds intensively for their therapeutic activities. For example, WO 2011/153319, WO 2011/153315, WO 2011/007230, WO 2009/082819, and WO 2009/100532 disclosed novel 17β lupine derivatives as anti-HIV agents in an attempt to overcome gag polymorphism issues mentioned above. The patent publication WO 2008/057420 describes extended triterpene derivatives as antiretroviral agents; WO 2007/141391 describes betulin derived compounds useful as antiprotozoal agents; WO 2007/141390 describes preparation of betulin derived compounds as antiviral agents; WO 2008/127364 describes preparation of betulinic acid derivatives for use in antiviral and anticancer pharmaceutical compositions; US 2008/0207573 describes preparation of triterpene derivatives for therapeutic use in the treatment of viral infections; WO 2007/141389 describes preparation of betulin derived compounds as antibacterial agents; US 2004/0204389 describes anti-HIV agents with dual sites of action; WO 2007/002411 describes antiviral compounds; CN 1861627 describes antitumor agents; WO 2006/053255 describes novel betulin derivatives, preparation and use thereof; WO 2009/082818 describes novel C-21 keto lupine derivatives preparation and use thereof; and WO 2006/105356 describes methods of manufacturing bioactive 3-esters of betulinic aldehyde and betulinic acid.

Some additional references disclose betulinic acid related compounds. For example, WO 2007/141383 describes betulin derivatives as antifeedants for plant pests; U.S. Pat. No. 6,670,345 describes use of betulinic acid and its derivatives for inhibiting cancer growth and process for the manufacture of betulinic acid; WO 2002/091858 describes anxiolytic marcgraviaceae compositions containing betulinic acid, betulinic acid derivatives, and methods of preparation and use; WO 2000/046235 describes preparation of novel betulinic acid derivatives for use as cancer growth inhibitors; WO 2007/141392 describes cosmetic and pharmaceutical compositions comprising betulonic acid and betulin derivatives; and Pharmaceutical Chemistry Journal, 2002, 36(9), 29-32 describes synthesis and anti-inflammatory activity of new acylated betulin derivatives.

Given the fact of the world wide epidemic level of AIDS, there is a strong continued need for new effective drugs for treatment of HIV infected patients, disease conditions and/or disorders mediated by HIV by discovering new compounds with novel structures and/or mechanism of action(s).

SUMMARY OF THE INVENTION

The present invention relates to the compounds of the formula (1):

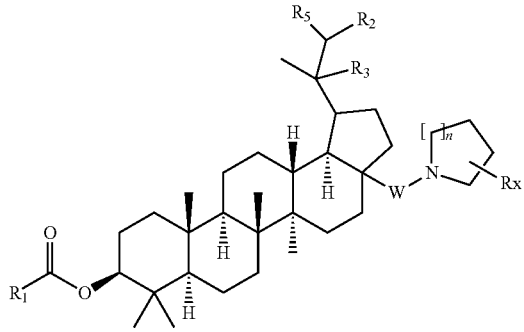

Formula (1)

wherein, $R_1$ can be substituted or unsubstituted alkyl,

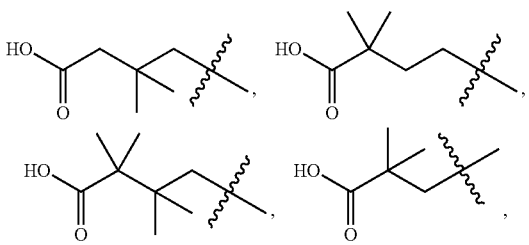

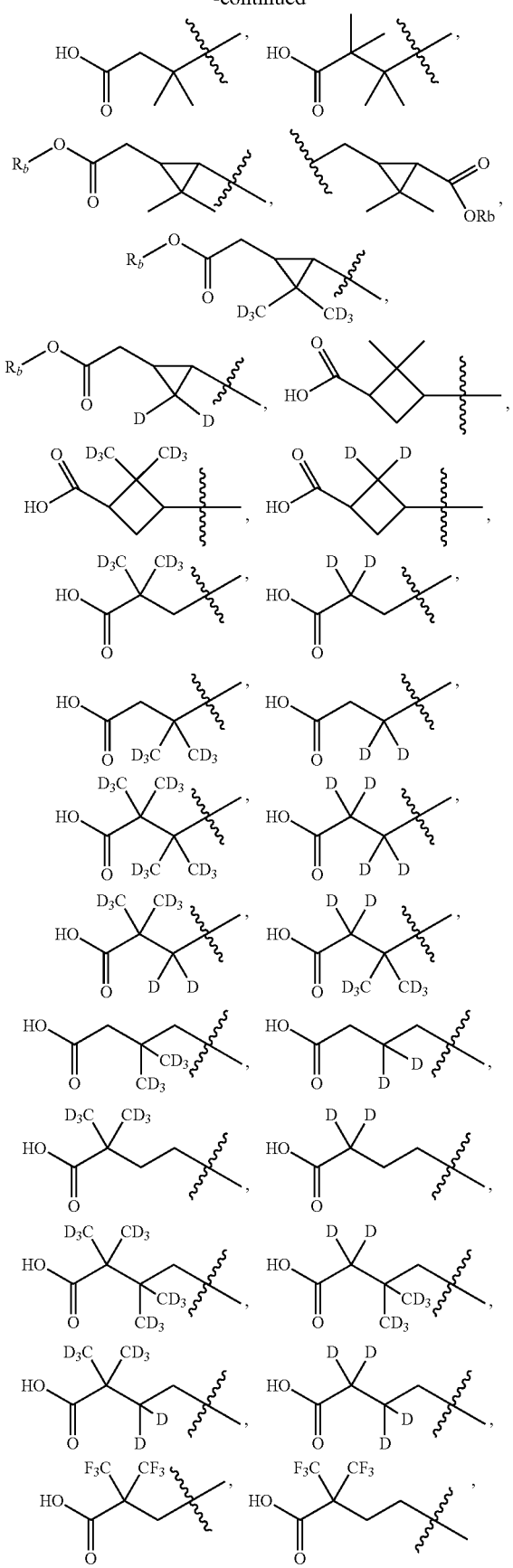

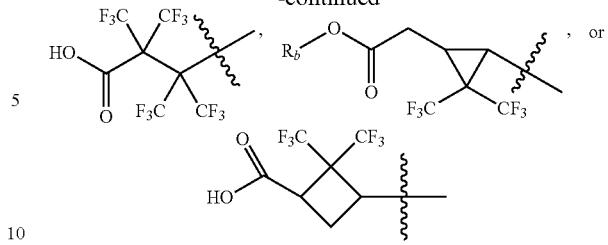

(wherein Rb can be H, substituted or unsubstituted alkyl, or substituted or unsubstituted cycloalkyl);

$R_3$ and $R_4$ can be independently selected from H, OH, substituted or unsubstituted alkyl, substituted or unsubstituted alkoxy, substituted or unsubstituted alkoxylalkoxy, or substituted or unsubstituted aminoacids and specifically amino acids are substituted by substituted or unsubstituted alkyl, phosphoric acid, or phosphorus prodrugs or $R_3$ and $R_4$ can be together with their adjacent carbons to form a bond or $R_3$ and $R_4$ can be together with their adjacent carbons form cyclopropyl;

W can be a bond, C(O), C(S), or $CR_6R_7$;

Rx can be H, substituted or unsubstituted alkyl, substituted or unsubstituted cycloalkyl, substituted or unsubstituted aryl, substituted or unsubstituted heterocyclyl, or substituted or unsubstituted heteroaryl and specifically heterocycles are imidazoles, oxazoles, oxadiazoles, thiazoles, thiadizoles, isothiazoles, isothiadiazoles, pyridines, pyrazines, pyrimidines, or pyridazines;

$R_5$, $R_6$ and $R_7$ can be independently selected from H, D, $CD_3$, $CH_2CD_3$, $CH(CD_3)_2$, $CO_2R_d$ (wherein $R_d$ can be H, substituted or unsubstituted alkyl, or substituted or unsubstituted cycloalkyl), or substituted or unsubstituted alkyl;

n can be an integer from 1 to 3.

Pharmaceutically acceptable salts of the compounds of the formula (1) are also contemplated. Likewise, pharmaceutically acceptable solvates, including hydrates, of the compounds of the formula (1) are contemplated.

It should be understood that the formula (1) structurally encompasses all stereoisomers, including enatiomers, diastereomers, racemates, and combinations thereof which may be contemplated from the chemical structure of the genus described herein.

It should be understood that the formula (1) structurally encompasses all tautomers.

Also contemplated are prodrugs of the compounds of the formula (1), including ester prodrugs.

According to one embodiment, there is provided a compound of formula (1), wherein Rx is substituted or unsubstituted 1,2,4-oxadiazol and substituted or unsubstituted imidazol. Most specifically the substitutents are t-butyl, substituted or unsubstituted phenyl, pyridine, and thiophene.

According to one embodiment, there is provided a compound of formula (1), wherein $R_1$ is

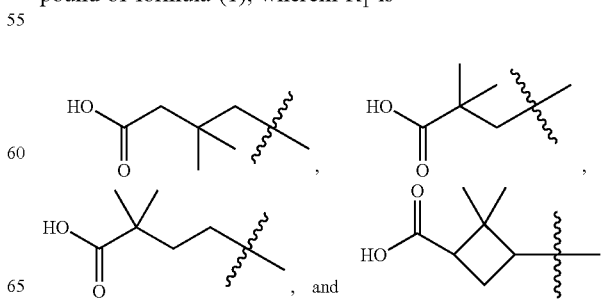

According to one embodiment, there is provided a compound of formula (1), wherein R₃ and R₄ are together with their adjacent carbons form cyclopropyl.

According to one embodiment, there is provided a compound of formula (1), wherein R₃ and R₄ are together with their adjacent carbons form a bond.

According to one embodiment, there is provided a compound of formula (1), wherein R₃ and R₄ is hydrogen.

According to one embodiment, there is provided a compound of formula (1), wherein $R_5$ is H.

According to one embodiment, there is provided a compound of formula (1), wherein W is C(O).

According to one embodiment, there is provided a compound of formula (1), wherein n is 1.

Accordingly, one other aspect of the present invention provides compounds of formula (1A):

Formula (1A)

wherein, $R_1$ can be substituted or unsubstituted alkyl, (wherein Rb can be H, substituted or unsubstituted alkyl, or substituted or unsubstituted cycloalkyl);

$R_3$ and $R_4$ can be independently selected from H, OH, substituted or unsubstituted alkyl, substituted or unsubstituted alkoxy, substituted or unsubstituted alkoxylalkoxy, or substituted or unsubstituted aminoacids and specifically amino acids are substituted by substituted or unsubstituted alkyl, phosphoric acid phosphoric ester, or phosphorus prodrugs or $R_3$ and $R_4$ can be together with their adjacent carbons to form a bond or $R_3$ and $R_4$ can be together with their adjacent carbons to form cyclopropyl or epoxide;

$R_2$ can be H, substituted or unsubstituted alkyl, substituted or unsubstituted cycloalkyl, substituted or unsubstituted aryl, substituted or unsubstituted heterocyclyl, or substituted or unsubstituted hetero aryl and $R_2$ is specifically substituted or unsubstituted isopropyl, t-butyl, phenyl, pyridine, pyrazine, thiophene or chromene;

W can be a bond, C(O), C(S), or $CR_6R_7$;

$R_5$, $R_6$ and $R_7$ can be independently selected from H, D, $CD_3$, $CH_2CD_3$, $CH(CD_3)_2$, $CO_2R_d$ (wherein $R_d$ can be H, substituted or unsubstituted alkyl, or substituted or unsubstituted cycloalkyl), or substituted or unsubstituted alkyl;

n can be an integer from 1 to 3.

Pharmaceutically acceptable salts of the compounds of the formula (1A) are also contemplated. Likewise, pharmaceutically acceptable solvates, including hydrates, of the compounds of the formula (1A) are contemplated.

It should be understood that the formula (1A) structurally encompasses all stereoisomers, including enatiomers, diastereomers, racemates, and combinations thereof which may be contemplated from the chemical structure of the genus described herein.

It should be understood that the formula (1A) structurally encompasses all tautomers.

Also contemplated are prodrugs of the compounds of the formula (1A), including ester prodrugs.

According to one embodiment, there is provided a compound of formula (1A), wherein $R_1$ is

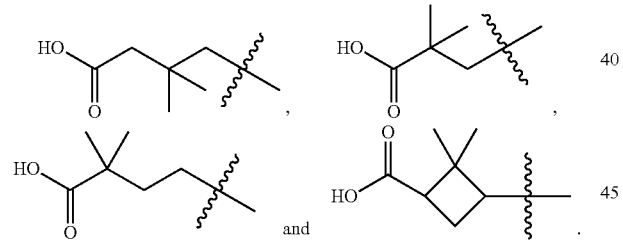

and

According to one embodiment, there is provided a compound of formula (1A), wherein $R_2$ is substituted or unsubstituted phenyl and pyridine.

According to one embodiment, there is provided a compound of formula (1A), wherein $R_3$ and $R_4$ are together with their adjacent carbons form cyclopropyl.

According to one embodiment, there is provided a compound of formula (1A), wherein $R_3$ and $R_4$ are together with their adjacent carbons form a bond.

According to one embodiment, there is provided a compound of formula (1A), wherein $R_5$ is H.

According to one embodiment, there is provided a compound of formula (1A), wherein W is C(O).

According to one embodiment, there is provided a compound of formula (1A), wherein n is 1.

Accordingly, one other aspect of the present invention provides compounds of formula (1B):

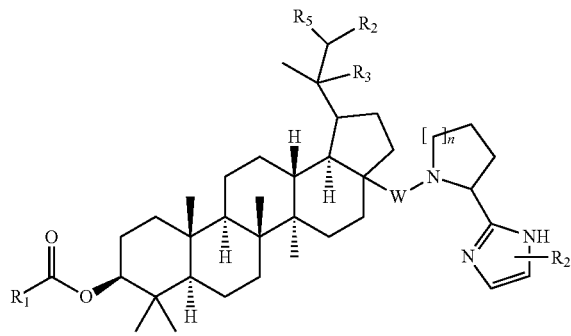

Formula (1B)

wherein, $R_1$ can be H, substituted or unsubstituted alkyl,

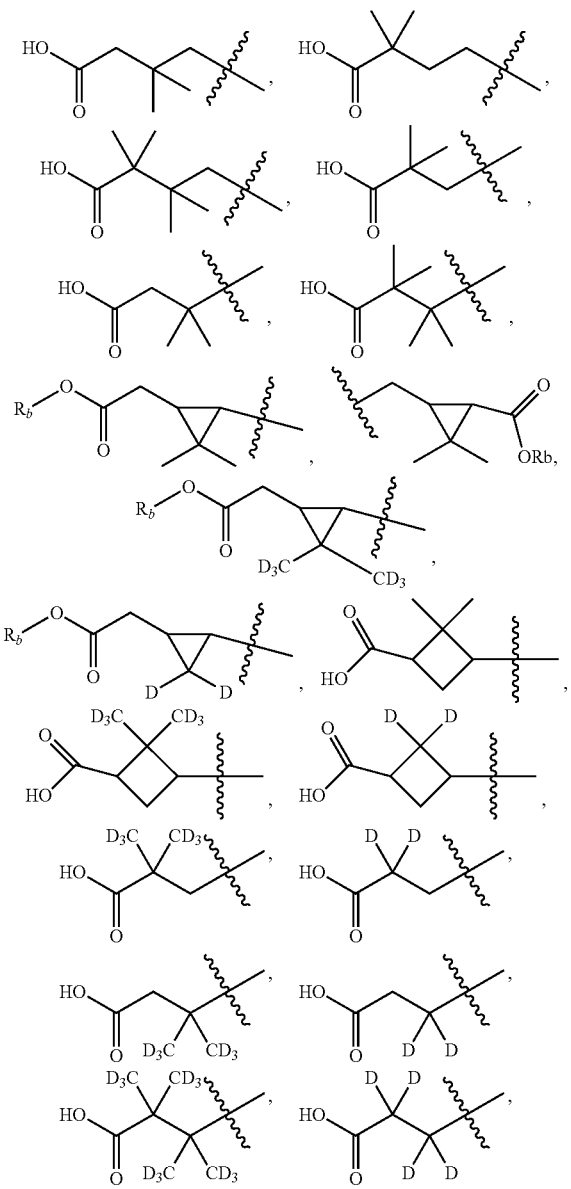

-continued

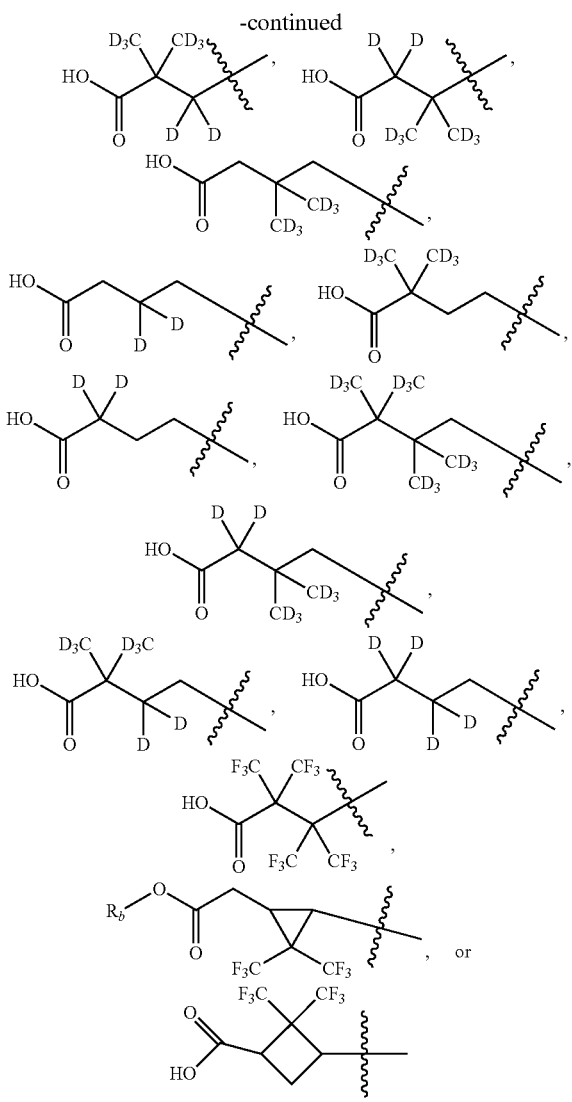

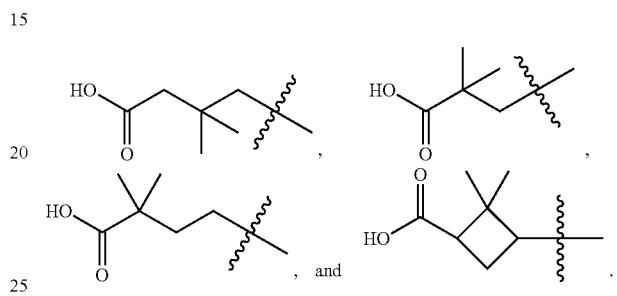

(wherein Rb can be H, substituted or unsubstituted alkyl, or substituted or unsubstituted cycloalkyl);

$R_3$ and $R_4$ can be independently selected from H, OH, substituted or unsubstituted alkyl, substituted or unsubstituted alkoxy, substituted or unsubstituted alkoxylalkoxy, or substituted or unsubstituted aminoacids and specifically amino acids are substituted by substituted or unsubstituted alkyl, phosphoric acid, or phosphorus prodrugs or $R_3$ and $R_4$ can be together with their adjacent carbons to form a bond or $R_3$ and $R_4$ can be together with their adjacent carbons to form cyclopropyl;

$R_2$ can be H, substituted or unsubstituted alkyl, substituted or unsubstituted cycloalkyl, substituted or unsubstituted aryl, substituted or unsubstituted heterocyclyl, or substituted or unsubstituted heteroaryl and $R_2$ is specifically substituted or unsubstituted isopropyl, t-butyl, phenyl, pyridine, pyrazine, thiophene or chromene;

W can be a bond, C(O), C(S), or $CR_6R_7$;

$R_5$, $R_6$ and $R_7$ can be independently selected from H, D, $CD_3$, $CH_2CD_3$, $CH(CD_3)_2$, $CO_2R_d$ (wherein $R_d$ can be H, substituted or unsubstituted alkyl, or substituted or unsubstituted cycloalkyl), or substituted or unsubstituted alkyl;

n can be an integer from 1 to 3.

Pharmaceutically acceptable salts of the compounds of the formula (1B) are also contemplated. Likewise, pharmaceutically acceptable solvates, including hydrates, of the compounds of the formula (1B) are contemplated.

It should be understood that the formula (1B) structurally encompasses all stereoisomers, including enatiomers, diastereomers, racemates, and combinations thereof which may be contemplated from the chemical structure of the genus described herein.

It should be understood that the formula (1B) structurally encompasses all tautomers.

Also contemplated are prodrugs of the compounds of the formula (1B), including ester prodrugs.

According to one embodiment, there is provided a compound of formula (1B), wherein $R_1$ is According to one embodiment, there is provided a compound of formula (1B), wherein $R_2$ is substituted or unsubstituted phenyl and pyridine.

According to one embodiment, there is provided a compound of formula (1B), wherein $R_2$ is t-butyl, substituted or unsubstituted phenyl, pyridine, and thiophene. Most specifically the substitutents are methoxy, nitro, methyl, cyano, fluoro, chloro, hydroxyl, and 2-methoxyethoxyl.

According to one embodiment, there is provided a compound of formula (1B), wherein $R_3$ and $R_4$ are together with their adjacent carbons form cyclopropyl.

According to one embodiment, there is provided a compound of formula (1B), wherein $R_3$ and $R_4$ are together with their adjacent carbons form a bond.

According to one embodiment, there is provided a compound of formula (1B), wherein $R_3$ and $R_4$ is hydrogen.

According to one embodiment, there is provided a compound of formula (1B), wherein $R_5$ is H.

According to one embodiment, there is provided a compound of formula (1B), wherein W is C(O).

According to one embodiment, there is provided a compound of formula (1B), wherein n is 1.

Below are the representative compounds, which are illustrative in nature only and are not intended to limit to the scope of the invention (Nomenclature has been generated from Chem. Draw Ultra 11.0 version):

2,2-dimethyl-4-oxo-4-((1R,3aS,5aR,5bR,7aR,9S,11aR, 11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy)butanoic acid (Compound 1), 3,3-dimethyl-5-oxo-5-((1R,3aS,5aR,5bR,7aR,9S,11aR, 11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy)pentanoic acid (Compound 2), 2,2-dimethyl-4-oxo-4-((1R,3aS,5aR,5bR,7aR,9S,11aR, 11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yloxy)butanoic acid (Compound 3), 3,3-dimethyl-5-oxo-5-((1R,3aS,5aR,5bR,7aR,9S,11aR, 11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yloxy)pentanoic acid (Compound 4), 2,2-dimethyl-4-oxo-4-((1R,3aS,5aR,5bR,7aR,9S,11aR, 11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yloxy)butanoic acid (Compound 5), 3,3-dimethyl-5-oxo-5-((1R,3aS,5aR,5bR,7aR,9S,11aR, 11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yloxy)pentanoic acid (Compound 6), 2,2-dimethyl-3-(((1R,3aS,5aR,5bR,7aR,9S,11aR,11bR, 13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy)carbonyl)cyclobutanecarboxylic acid (Compound 7), 2,2-dimethyl-4-oxo-4-((1R,3aS,5aR,5bR,7aR,9S,11aR, 11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)butanoic acid (Compound 8), 3,3-dimethyl-5-oxo-5-((1R,3aS,5aR,5bR,7aR,9S,11aR, 11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)pentanoic acid (Compound 9), 2,2-dimethyl-4-oxo-4-((1R,3aS,5aR,5bR,7aR,9S,11aR, 11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yloxy)butanoic acid (Compound 10), 3,3-dimethyl-5-oxo-5-((1R,3aS,5aR,5bR,7aR,9S,11aR, 11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yloxy)pentanoic acid (Compound 11), 2,2-dimethyl-4-oxo-4-((1R,3aS,5aR,5bR,7aR,9S,11aR, 11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yloxy)butanoic acid (Compound 12), 3,3-dimethyl-5-oxo-5-((1R,3aS,5aR,5bR,7aR,9S,11aR, 11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yloxy)pentanoic acid (Compound 13), (1R,3S)-2,2-dimethyl-3-((((1R,3aS,5aR,5bR,7aR,9S,11aR, 11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)carbonyl)cyclobutanecarboxylic acid (Compound 14), (1R,3S)-3-(1R,3aS,5aR,5bR,7aR,9S,11aR,11bR,13aR, 13bR)-3a-(2-(5-(4-methoxyphenyl)-1H-imidazol-2-yl)pyrrolidine-1-carbonyl)-5a,5b,8,8,11a-pentamethyl-1-(prop-1-en-2-yl) icosahydro-1H-cyclopenta[a]chrysen-9-yl)oxy)carbonyl)-2,2-dimethyl cyclobutane-1-carboxylic acid (Compound 15), (1R,3S)-2,2-dimethyl-3-((((1R,3aS,5aR,5bR,7aR,9S,11aR, 11bR,13aR,13bR)-5a,5b,8,8,11a-pentamethyl-1-(prop-1-en-2-yl)-3a-((S)-2-(5-(pyridin-4-yl)-1H-imidazol-2-yl) pyrrolidine-1-carbonyl)icosahydro-1H-cyclopenta[a]chrysen-9-yl)oxy)carbonyl)cyclo butane-1-carboxylic acid (Compound 16), (1R,3S)-2,2-dimethyl-3-(1R,3aS,5aR,5bR,7aR,9S,11aR, 11bR,13aR,13bR)-5a,5b,8,8,11a-pentamethyl-3a-(2-(5-(4-nitrophenyl)-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid (Compound 17), (1R,3S)-2,2-dimethyl-3-(1R,3aS,5aR,5bR,7aR,9S,11aR, 11bR,13aR,13bR)-5a,5b,8,8,11a-pentamethyl-1-(prop-1-en-2-yl)-3a-(2-(5-(p-tolyl)-1H-imidazol-2-yl)pyrrolidine-1-carbonyl)icosahydro-1H-cyclopenta[a]chrysen-9-yl)oxy)carbonyl)cyclobutane-1-carboxylic acid (Compound 18), (1R,3S)-3-(1R,3aS,5aR,5bR,7aR,9S,11aR,11bR,13aR, 13bR)-3a-(2-(5-(4-cyano phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy) carbonyl)-2,2-dimethylcyclobutane-1-carboxylic acid (Compound 19), 2,2-dimethyl-5-oxo-5-((1R,3aS,5aR,5bR,7aR,9S,11aR, 11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)pentanoic acid (Compound 20), (1R,3S)-3-((((1 S,3aS,5aR,5bR,7aR,9S,11aR,11bR,13aR, 13bR)-1-isopropyl-5a,5b,8,8,11a-pentamethyl-3a-((S)-2-(5-phenyl-1H-imidazol-2-yl)pyrrolidine-1-carbonyl)icosahydro-1H-cyclopenta[a]chrysen-9-yl)oxy)carbonyl)-2,2-dimethylcyclobutane-1-carboxylic acid (Compound 21), (1R,3S)-3-((((1 S,3aS,5aR,5bR,7aR,9S,11aR,11bR,13aR, 13bR)-3a-((S)-2-(5-(4-fluorophenyl)-1H-imidazol-2-yl) pyrrolidine-1-carbonyl)-1-isopropyl-5a,5b,8,8,11a-pentamethylicosahydro-1H-cyclopenta[a]chrysen-9-yl)oxy) carbonyl)-2,2-dimethylcyclobutane-1-carboxylic acid (Compound 22), 4-(((1S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl)oxy)-2,2-dimethyl-4-oxobutanoic acid (Compound 23), (1R,3S)-3-((((1 S,3aS,5aR,5bR,7aR,9S,11aR,11bR,13aR, 13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl) oxy)carbonyl)-2,2-dimethylcyclobutane-1-carboxylic acid (Compound 24), 4-(((1S,3aS,5aR,5bR,7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl)oxy)-2,2-dimethyl-4-oxobutanoic acid (Compound 25), 5-(((1S,3aS,5aR,5bR,7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl)oxy)-3,3-dimethyl-5-oxopentanoic acid (Compound 26), (1S,3R)-2,2-dimethyl-3-((((1R,3aS,5aR,5bR,7aR,9S,11aR, 11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid (Compound 27), 4-(1R,3aS,5aR,5bR,7aR,9S,11aR,11bR,13aR,13bR)-3a-((R)-2-(5-(4-chlorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid (Compound 28), 2,2-dimethyl-3-((((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yl)oxy)carbonyl)cyclobutane-1-carboxylic acid (Compound 29), 2,2-dimethyl-4-oxo-4-(((1R,3aS,5aR,5bR,7aR,9S,11aR,11bR,13aR,13bR)-5a,5b,8,8,11a-pentamethyl-1-(1-methylcycloprop yl)-3a-((S)-2-(5-(pyridin-3-yl)-1H-imidazol-2-yl)pyrrolidine-1-carbonyl)icosahydro-1H-cyclopenta[a]chrysen-9-yl)oxy)butanoic acid (Compound 30), 3,3-dimethyl-5-oxo-5-((1R,3aS,5aR,5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)pentanoic acid (Compound 31), 2,2-dimethyl-3-((((1R,3aS,5aR,5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)carbonyl)cyclobutane-1-carboxylic acid (Compound 32), 4-(((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl)oxy)-2,2-dimethyl-4-oxobutanoic acid (Compound 33), 4-(((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid (Compound 34), 3-((((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Compound 35), 3-((((1R,3aS,5aR,5bR,7aR,9S,11aR,11bR,13aR,13bR)-3a-((S)-2-(5-(4-hydroxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Compound 36), 3-((((1R,3aS,5aR,5bR,7aR,9S,11aR,11bR,13aR,13bR)-3a-((S)-2-(5-(4-(2-methoxyethoxy)phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid (Compound 37), 2,2-dimethyl-4-oxo-4-((1R,3aS,5aR,5bR,7aR,9S,11aR,11bR,13aR,13bR)-5a,5b,8,8,11a-pentamethyl-1-(1-methylcycloprop yl)-3a-((S)-2-(5-(thiophen-2-yl)-1H-imidazol-2-yl)pyrrolidine-1-carbonyl)icosahydro-1H-cyclopenta[a]chrysen-9-yl)oxy)butanoic acid (Compound 38), 2,2-dimethyl-4-oxo-4-((1R,3aS,5aR,5bR,7aR,9S,11aR,11bR,-13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)butanoic acid (Compound 39), 3,3-dimethyl-5-oxo-5-(((1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl)oxy)pentanoic acid (Compound 40), 2,2-dimethyl-3-((((1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid (Compound 41), 3-((((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl) oxy) carbonyl)-2,2-dimethylcyclobutane-1-carboxylic acid (Compound 42), 2,2-dimethyl-3-((((1R,3aS,5aR,5bR,7aR,9S,11aR,11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yl)oxy)carbonyl)cyclobutane-1-carboxylic acid (Compound 43), or pharmaceutically acceptable salts, solvates, including hydrates and prodrugs of compounds are also contemplated.

The present invention also provides a pharmaceutical composition that includes at least one compound as described herein and at least one pharmaceutically acceptable excipient (such as a pharmaceutically acceptable carrier or diluent). Specifically, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in a therapeutically effective amount to cause that infection, specifically in the form of a pharmaceutical composition.

Also provided herein are processes for preparing compounds described herein.

The invention provides a method for preventing; ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as pesistant generalized limphadenopathy, fever and weight loss, or an etroviral infection genetically related to AIDS.

Anti HIV inhibitory potential of the compounds of present invention may be demonstrated by any one or more methodologies known in the art, such as by using the assays described in Mosmann T, December 1983, Journal of immunological methods, 65 (1-2), 55-63 and SPC Cole, cancer chemotherapy and Pharmacology, 1986, 17, 259-263.

DETAILED DESCRIPTION OF THE INVENTION

The present invention provides betulinic acid proline derivatives and related compounds, which may be used as antiviral particularly as anti-HIV compounds and processes for the synthesis of these compounds. Pharmaceutically acceptable salts, pharmaceutically acceptable solvates, enantiomers, diastereomers of the derivatives, together with pharmaceutically acceptable carriers, excipients or diluents, which can be used for the treatment of diseases, condition and/or disorders mediated by viral infections, are also provided.

The following definitions apply to the terms as used herein:

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkoxy" refers to a straight or branched hydrocarbon chain with oxygen radical consisting carbon and hydrogen atoms, containing saturation or unsaturation, having from one to eight carbon atoms, and which is attached through oxygen atom to the rest of the molecule by a single bond, e.g., methyloxy, ethyloxy, n-propyloxy, 1-methylethyloxy (isopropyloxy), n-butyloxy, n-pentyloxy, and 1,1-dimethylethyloxy (t-butyloxy).

The term "alkoxylalkoxy" refers to a straight or branched hydrocarbon chain with oxygen radical consisting carbon atom, hydrogen atom and alkoxy groups, containing saturation or unsaturation, having from one to eight carbon atoms, and which is attached through oxygen atom to the rest of the molecule by a single bond, e.g., 2-(methyloxy)ethyloxy, 2-(ethyloxy)ethyloxy, 2-(n-propyloxy)ethyloxy, and 3-(isopropyloxy)butyloxy.

The term "amino acid" refers to a straight or branched hydrocarbon chain containing an amine group, a carboxylic acid group, and a side-chain that is specific to each amino acid and which is attached through the nitrogen atom of the amine group to the rest of the molecule by a single bond, e.g., alanine, valine, isoleucine, leucine, phenylalanine, or tyrosine.

The term "acyl group" is used to denote a linear or branched aliphatic acyl group (specifically a $C_{2-6}$ alkanoyl group) or an aromatic acyl group, which contains 2 to 10 carbon atoms. Examples include an acetyl group, a propionyl group, a pivaloyl group, a butyryl group, an isobutyryl group, a valeryl group and a benzoyl group, more specifically an acetyl group.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups and spirobicyclic groups, e.g., spiro (4,4) non-2-yl.

The term "cycloalkenyl" refers to a cyclic ring-containing radical having from 3 to about 8 carbon atoms with at least one carbon-carbon double bond, such as cyclopropenyl, cyclobutenyl, and cyclopentenyl.

The term "aryl" refers to an aromatic radical having from 6 to 14 carbon atoms such as phenyl, naphthyl, tetrahydronapthyl, indanyl, and biphenyl.

The term "arylalkyl" refers to an aryl group as defined above directly bonded to an alkyl group as defined above, e.g., $-CH_2C_6H_5$ and $-C_2H_5C_6H_5$.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or Spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, tetrazoyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl. The heterocyclic ring radical may be attached to the main structure at any heteroatom or carbon atom that results in the creation of a stable structure.

The term "heterocyclylalkyl" refers to a heterocyclic ring radical directly bonded to an alkyl group. The heterocylylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

"Substituted" refers to 1-3 substituents on the same position or on different positions with the same groups or different groups. Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, $-COOR^m$, $-C(O)R^x$, $-C(S)\ R^m$, $-C(O)NR^mR^y$, $-C(O)ONR^mR^y$, $-NR^mCONR^yR^z$, $-N(R^m)SOR^y$, $-N(R^m)SO_2R^y$, $-(=N-N(R^m)R^y)$, $-NR^mC(O)OR^y$, $-NR^mR^y$, $-NR^mC(O)R^y$, $-NR^mC(S)R^y$, $-NR^mC(S)NR^yR^z$, $-SONR^mR^y$, $-SO_2NR^mR^y$, $-OR^m$, $-OR^mC(O)NR^yR^z$, $-OR^mC(O)OR^y$, $-OC(O)R^m$, $-OC(O)NR^mR^y$, $-R^mNR^yC(O)R^z$, $-R^mOR^y$, $-R^mC(O)OR^y$, $-R^mC(O)NR^yR^z$, $-R^mC(O)R^y$, $-R^mOC(O)R^y$, $-SR^m$, $-SOR^m$, $-SO_2R^m$, and $-ONO_2$, wherein $R^m$, $R^y$ and $R^z$ are independently selected from hydrogen, substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "prodrug" means a compound that is transformed in vivo to yield a compound of Formula (1), (1A), (1B) or a pharmaceutically acceptable salt, hydrate or solvate, or metabolite of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compounds of the present invention may form salts. Non-limiting examples of pharmaceutically acceptable salts forming part of this invention include salts derived from inorganic bases salts of organic bases salts of chiral bases, salts of natural amino acids and salts of non-natural amino acids. Certain compounds of the present invention are capable of existing in stereoisomeric forms (e.g., diastereomers, enantiomers, racemates, and combinations thereof). With respect to the overall compounds described by the Formula (1), (1A) or (1B), the present invention extends to these stereoisomeric forms and to mixtures thereof. To the extent prior art teaches synthesis or separation of particular stereoisomers, the different stereoisomeric forms of the present invention may be separated from one another by the methods known in the art, or a given isomer may be obtained by stereospecific or asymmetric synthesis. Tautomeric forms and mixtures of compounds described herein are also contemplated.

Pharmaceutically acceptable solvates includes hydrates and other solvents of crystallization (such as alcohols). The compounds of the present invention may form solvates with low molecular weight solvents by methods known in the art.

Pharmaceutical Compositions

The pharmaceutical compositions provided in the present invention include at least one compound described herein and at least one pharmaceutically acceptable excipient (such as a pharmaceutically acceptable carrier or diluent). Specifically, the contemplated pharmaceutical compositions include a compound(s) described herein in an amount sufficient to treat viral infection in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick-, sustained-, or delayed-release of the active ingredient after administration to the subject by employing procedures known in the art.

The pharmaceutical compositions described herein may be prepared, e.g., as described in Remington: The Science and Practice of Pharmacy, $20^{th}$ Ed., 2003 (Lippincott Williams & Wilkins). For example, the active compound can be mixed with a carrier, or diluted by a carrier, or enclosed within a carrier, which may be in the form of an ampule, capsule, or sachet. When the carrier serves as a diluent, it may be a solid, semi-solid, or liquid material that acts as a vehicle, excipient, or medium for the active compound.

The pharmaceutical compositions may be, for example, capsules, tablets, aerosols, solutions, suspensions, liquids, gels, or products for topical application.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is specifically suitable.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Exemplary carriers for tablets, dragees, or capsules include lactose, cornstarch, and/or potato starch. A syrup or elixir can be used in cases where a sweetened vehicle can be employed.

A typical tablet that may be prepared by conventional tabletting techniques.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, specifically aqueous solutions with the active compound dissolved in polyhydroxylated castor oil.

Methods of Screening

Antiviral HIV activity and cytotoxicity of compounds present invention can be measured in parallel by following the methods published in the literature.

The cytotoxic effect of compounds can be analyzed by measuring the proliferation of cells using the 3-(4,5-Dimethylthiazol-2-yl)-2,5-diphenyl tetrazlium bromide (MTT) staining Cells ($5 \times 10^3$ cells well) will be incubated in in 96 well plates in the presence or absence of compounds. At the end of treatment, 20 µl of MTT (5 mg/ml in PBS) will be added to each well and incubated for an additional 4 hours at 37° C. The purple-blue MTT formazan precipitate will be dissolved in a triplex reagent containing 10% SDS, 5% isobutanol and 10 mmol/lit HCl. The activity of mitochondria, reflecting cellular growth and viability, will be evaluated by measuring the optical density at 570 nm on micro titer plate.

Action of compounds on replication of HIV in Sup-T1 cells can be determined by the method published by Roda Rani et al., 2006 (Archives of Biochemistry and Biophysics, Volume 456, Issue 1, 1 Dec. 2006, Pages 79-92).

Briefly, $1 \times 10^6$ Sup-T1 cells with 100% cell viability will be seeded in RPMI 1640, 0.1% FBS four 12 well plates. Increasing concentrations of Epap-1 peptides will be added to the cells and will be infected with $HIV1_{93\ IN\ 101}$ each at final concentration of virus equivalent to 2 ng of p24 per ml. The infected cells will be incubated at 37 C and 5% CO2 incubator for 2 hours. After 2 hrs the cells will be pelleted at 350 g for 10 min, supernatant will be discarded and cell will be held with RPMI 1640 containing 10% FBS. The cells will be resuspended in the same medium with increasing concentrations of Epap-1 peptides and will be incubated for 96 hours. The cells will be supplemented with peptides at every 24 hours. The supernatants will be collected after 96 hours and analyzed using P24 antigen capture assay kit (SAIC Fredrick). The infection in the absence of Epap-1 will be considered to be 0% inhibition Azidothymidine (AZT) will be taken as positive control.

Action of compound on virus entry and quantification of virus entered can be done in terms of GFP expression by the following the methods published J. Virol. 72, 6988 (1998) by in Cecilia et al., and Analytical Biochemistry Volume 360, Issue 2, 15 Jan. 2007, Pages 315-317 (Dyavar S. Ravi and Debashis Mitra).

Briefly, cells will be seeded in to wells of 24 well plates 1 day prior to the experiment. The cells will be transfected with Tat-reporter. The virus inoculum will be adjusted to 1,000-4,000 TCID 50 ml in assay medium (DMEM, 10% FCS, glutamine and antibiotics), 50 µl aliquots will be incubated with serial dilutions of compounds (50 µl) for 1 hr at 37° C. The reporter expression will be quantified at appropriate time calculated inhibitory doses referrers to the concentration of these agents in this preincubation mixture.

Other relevant references useful for screening antiviral HIV activity are: Averett, D. R. 1989. Anti-HIV compound assessment by two novel high capacity assays. J. Virol. Methods 23: 263-276; Schwartz, O., et al. 1998; A rapid and simple colorimeric test from the study of anti HIV agents. AIDS Res. and Human Retroviruses, 4(6):441-447; Daluge, S. M., et al. 1994. 5-Chloro-2',3'-deoxy-3'fluorouridine (935U83), a selective anti human immunodeficiency virus agent with an improved metabolic and toxicological profile; Antimicro. Agents and Chemotherapy, 38(7):1590-1603; H. Mitsuya and S. Border, Inhibition of the in vitro infectivity and cytopathic effect of human T-lymphotropic virus type lymphadenopathy-associated virus (HLTV-IIILAV) by 2,3'-dideoxynucleosides, Proc. Natl. Acad. Sci. USA, 83, 1911-15(1986); Pennington et al., Peptides 1990; Meek T. D et al., Inhibition of HIV-1 protease in infected T-limphocytes by synthetic peptide analogues, Nature, 343, p90 (1990); Weislow et al., J. Natl. Cancer Inst. 81, 577-586, 1989; T. Mimoto et al., J. Med. Chem., 42, 1789-1802, 1999; Uckun et al 1998, Antimicobial Agents and Chemotherapy 42:383; for P24 antigen assay Erice et al., 1993, Antimicrob. Ag. Chemotherapy 37: 385-383; Koyanagi et al., Int. J. Cancer, 36, 445-451, 1985; Balzarini et al. AIDS (1991), 5, 21-28; Connor et al., Journal of virology, 1996, 70, 5306-5311; Popik et al., Journal of virology, 2002, 76, 4709-4722; Harrigton et al., Journal of Virology Methods, 2000, 88, 111-115; Roos et al., Virology 2000, 273, 307-315; Fedyuk N. V. et al; Problems of Virology 1992, (3)P135; Mosmann T, December 1983, Journal of immunological methods, 65 (1-2), 55-63; SPC Cole, cancer chemotherapy and Pharmacology, 1986, 17, 259-263.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 0107646, WO 0165957, or WO 03037908; US publication Nos. U.S. Pat. No. 4,598,095 or US 20020068757; EP publication Nos. EP 0989862 or EP 0724650; Bioorganic & Medicinal Chemistry Letters, 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV, HCV, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the available drugs, e.g. anti-viral drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in Scheme-1 to 3. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereoisomers of the compounds in these schemes, unless otherwise specified, are also encompassed within the scope of this invention.

Compounds of the present invention can be synthesized from naturally occurring Betulinic acid or betulinal. Key intermediates required for synthesizing analogues are either commercially available, or can be prepared by the methods published in the literature. For example, the key intermediates in the present invention were prepared by modifying the procedures published in Journal of organic chemistry 2010, 75, 1285-1288; Journal of organic chemistry 2000, 65, 3934-3940; Tetrahedron: asymmetry 2008, 19, 302-308; or Tetrahedron: asymmetry 2003, 14, 217-223.

Compounds of formula 6 (n and $R_2$ are same as defined above & $R_2$ is more specifically, substituted or unsubstituted phenyl and pyridine) can be prepared as described in Scheme 1. The cyano compounds of formula 1 can be converted to oxime compounds of formula 2 in the presence of hydroxyl amine HCl, potassium carbonate, sodium carbonate or the like in the solvents such as methanol, ethanol or the like. The oxime compounds of formula 2 can be coupled with BOC protected proline compounds of formula 3 to get the compound of prolinated compounds of formula 4 in the presence of suitable coupling agents such as 1-ethyl-3-(3-dimethylaminopropyl) carbodiimide) hydrochloride (EDCI), 2-(1H-7-Azabenzotriazol-1-yl)-1,1,3,3-tetramethyl uronium hexafluorophosphate (HATU), 1-Hydroxybenzotriazole (HOBt) monohydrate or the like with suitable bases such as triethylamine, N,N-diisopropylethylamine, pyridine or the like with nicotinylchloride or benzoylchloride in the solvents such as N,N-Dimethylformamide, dichloromethane, ethyl acetate, THF or the like. The prolinated compounds of formula 4 can be cyclised to proline-cyclic compounds of formula 5 in the presence of pyridine, para-toluenesulphonylchloride, or the like in the solvents such as acetonitrile, N,N-diisopropylethylamine, pyridine or the like. The proline-cyclic compounds (BOC protected) of formula 5 can be deprotected to give NH proline compounds of formula 6 in the presence of TFA, HCl or the like in the solvents such as DCM, ethyl acetate or the like.

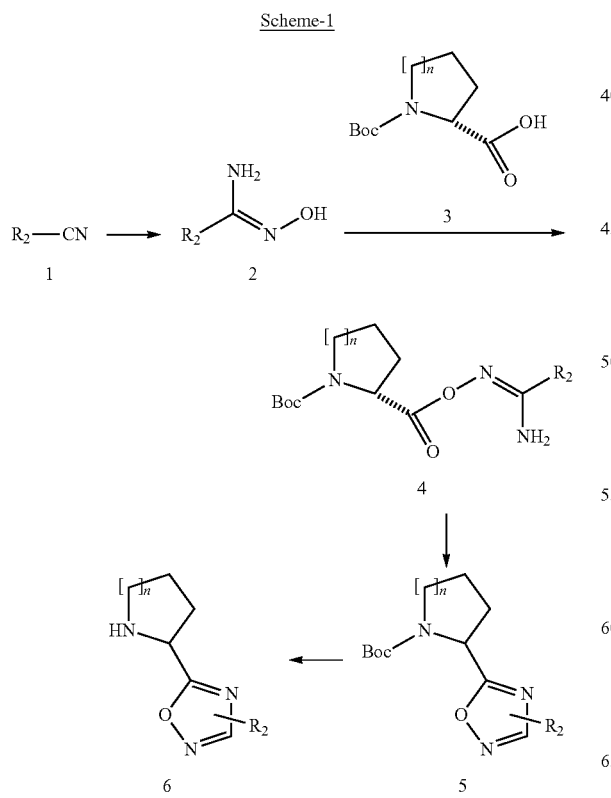

Scheme-1

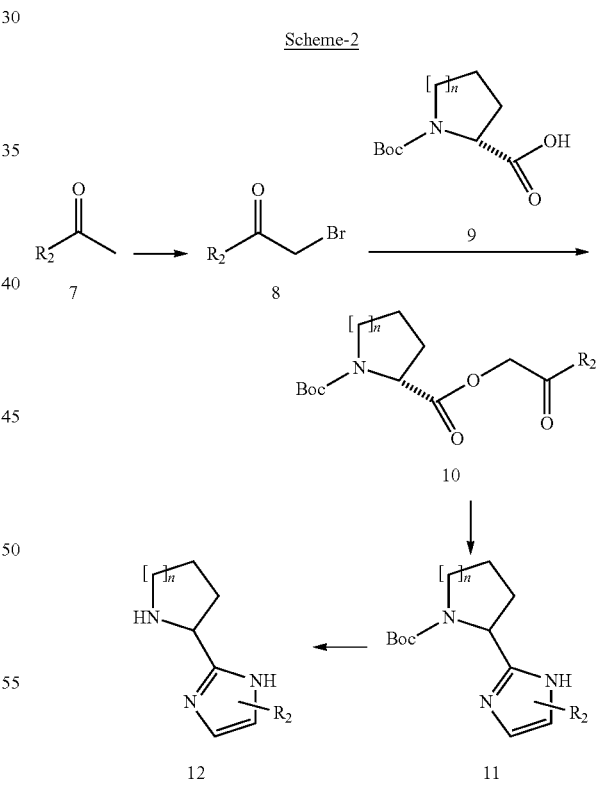

Scheme-2

Compounds of formula 12 (n and $R_2$ are same as defined above & $R_2$ is more specifically t-butyl, substituted or unsubstituted phenyl, pyridine, and thiophene) can be prepared as described in Scheme 2. The acetyl compounds of formula 7 can be converted to bromo compounds of formula 8 in the presence of bromine, N-bromosuccinimide, or the like in the solvents such as THF, diethylether, or the like.

The bromo compounds of formula 8 can be coupled with BOC protected proline compounds of formula 9 to get the compound of prolinated compounds of formula 10 in the presence of suitable coupling agents such as DIPEA, TEA, potassium carbonate or the like in the solvents such as N,N-Dimethylformamide, dichloromethane, dichloroethane, or the like. The prolinated compounds of formula 10 can be cyclised to proline-cyclic compounds of formula 11 in the presence of ammonium acetate, or the like in the solvents such as toluene, xylene, or the like. The proline-cyclic compounds (BOC protected) of formula 11 can be deprotected to give NH proline compounds of formula 12 in the presence of TFA, HCl or the like in the solvents such as DCM, ethyl acetate or the like.

Compounds of formula 18 [Formula (1), when W=CO] ($R_1$, $R_3$, $R_4$, $R_5$, $R_x$, and n are same as defined above & $R_x$ is more specifically substituted or unsubstituted 1,2,4-oxadiazol or imidazol and the substituents are more specifically t-butyl, substituted or unsubstituted phenyl, pyridine, and thiophene) can be prepared as described in Scheme 3. Reacting a C-3 alcohol with a suitable ester forming reagents like anhydrides, acid halides or mixed anhydrides in the presence of a base like triethyl amine, diisopropyl ethyl mine, or pyridine in an inert solvent like DCM, toluene, THF or a basic solvent like pyridine with or without addition of a catalyst like DMAP. For example a C-3 alcohol of compounds of the formula 13 can be protected by an acetyl group in the presence of acetic anhydride (as Scheme-3

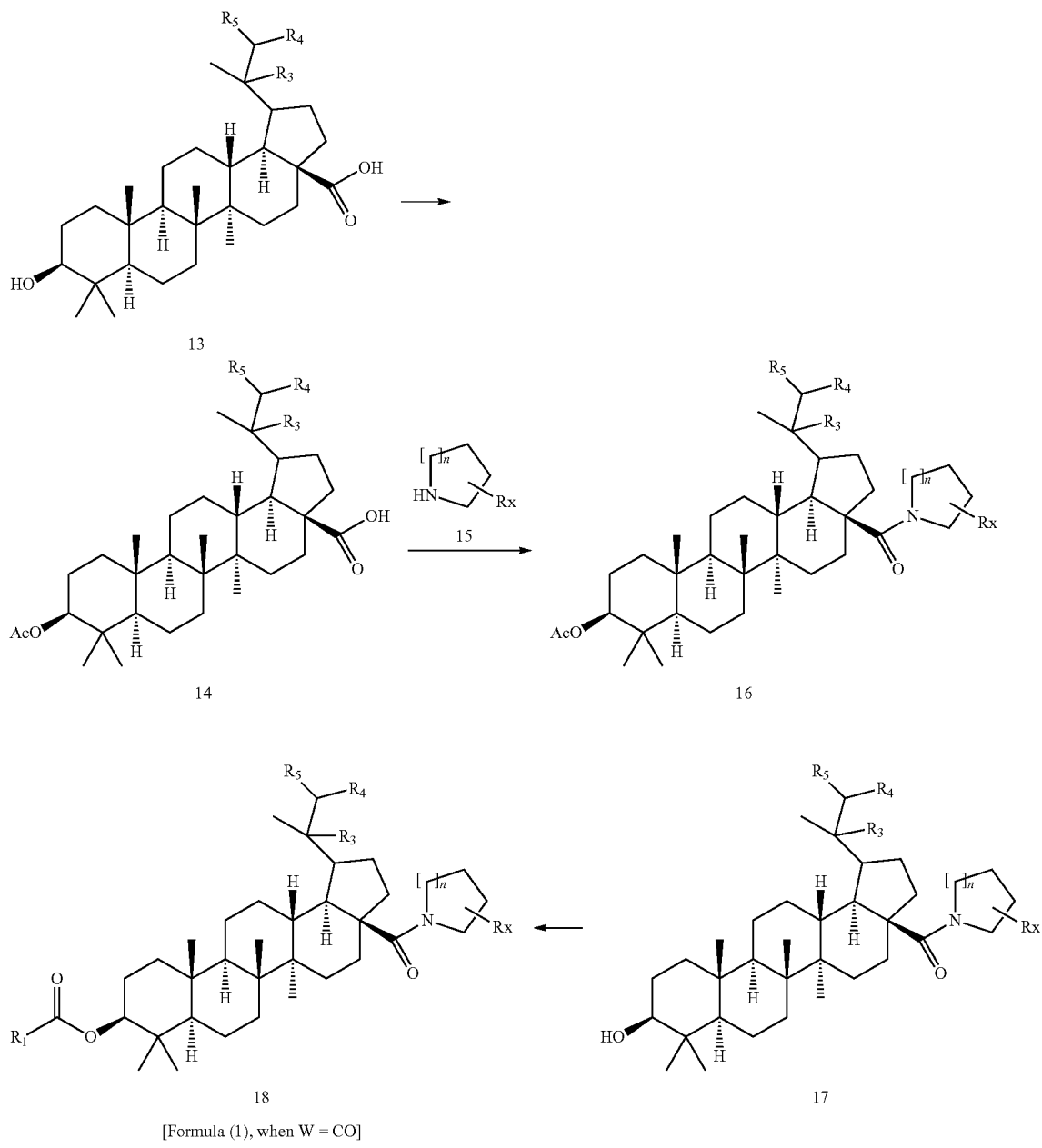

[Formula (1), when W = CO]

described in T. W. Greene and P. G. M. Wuts, protective groups in organic synthesis, 3rd edition, John Wiley & sons, New York, 1999) in the solvents such as pyridine or the like to give the C-3 acetyl compounds of formula 14. The C-3 acetyl (C-28 acid) compounds of formula 14 can be couple with substituted proline compounds of formula 15 (synthesized as described in Scheme 1 and 2) to give the C-28 cyclic amide compounds of formula 16 in the presence of oxylylchloride, TEA or the like in the presence of solvents such as DCM, or the like. The C-28 cyclic amide (C-3 ester) compounds of formula 16 can be hydrolysed to give C-3 hydroxy compounds of formula 17 in the presence of bases such as potassium carbonate, sodium hydroxide, ammonia or the like in the solvents such as methanol:THF, methanol:water, 1,4-dioxane, methanol or the like. The C-3 hydroxy compounds of formula 17 can be reacted with corresponding acid anhydrides, half protected diacids or their mixed anhydrides or acid chlorides to give the corresponding compounds of present invention represented by formula 18 [Formula (1), when W=CO] in the presence a base like triethyl amine, 4-Dimethylaminopyridine, diisopropyl ethyl mine or pyridine or the like in the solvents such as for example, DCM, toluene, EtOAc, THF or the like.

EXPERIMENTAL

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and examples may be further implemented as disclosed by variously altering the following examples, substituents, reagents, or conditions.

EXAMPLES

Example 1

Preparation of 2,2-dimethyl-4-oxo-4-((1R,3aS,5aR,5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy)butanoic acid Step 1: Synthesis of (Z)—N'-hydroxybenzimidamide

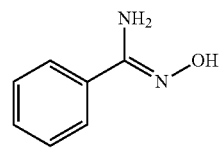

To the stirred solution of benzonitrile (12.0 g, 116.5 mmol) in 100 mL of methanol at room temperature was added $K_2CO_3$ (24.1 g, 174.6 mmol) and stirred for 10 minutes, then added hydroxylamine hydrochloride (16 g, 231.8 mmol) (dissolved in 120 mL of methanol) and stirred for 10 minutes at room temperature and refluxed for about 6 hours. After completion of the reaction (monitored by TLC), the reaction mixture was filtered, concentrated and the crude product was dissolved 1N EtOAc, washed with water, brine and dried over $Na_2SO_4$. The solvent was evaporated and used without further purification. Wt: 10.0 g.

Step 2: Synthesis of (S,Z)-tert-butyl 2-((amino(phenyl)methyleneaminooxy)carbonyl)pyrrolidine-1-carboxylate

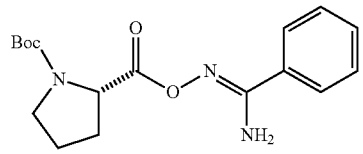

To a stirred solution of Boc-proline (15.8 g, 73.05 mmol) in DCM (200 mL), EDCI (21.05 g, 109.5 mmol) and HOBt (13.4 g, 88.1 mmol) were added at room temperature and after 10 minutes, (Z)—N'-hydroxybenzimidamide (step 1, 10.0 g, 73.05 mmol) was added and the reaction mass was allowed to stir at room temperature for about 12 hours. After completion of the reaction (monitored by TLC), the reaction mixture was diluted with DCM and washed with water, saturated with brine and the organic layer was concentrated under reduced pressure, the resulting crude was proceeded to next step without further purification. Wt: 18.0 g.

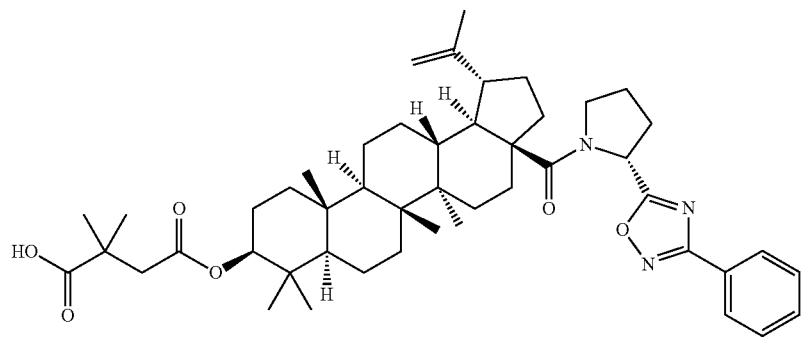

Step 3: Synthesis of (S)-tert-butyl 2-(3-phenyl-1,2,4-oxadiazol-5-yl)pyrrolidine-1-carboxylate

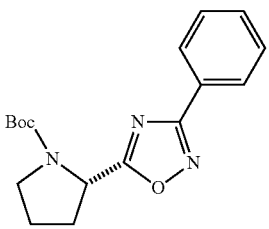

To a stirred solution of (S,Z)-tert-butyl 2-((amino(phenyl)methyleneaminooxy)carbonyl)pyrrolidine-1-carboxylate (step 2, 18.0 g, 54.05 mmol) in pyridine (80 mL) at room temperature and refluxed for about 24 hours. After completion of the reaction (monitored by TLC), the reaction mixture was diluted with EtOAc, washed with water, 1N HCl, water, brine and dried over $Na_2SO_4$. The solvent was evaporated and purified by silicagel column (100-200 mesh, elution 20% EtOAc in hexane) to afford the title compound (Wt: 13.0 g) as an off white solid. $^1H$ NMR (300 MHz, $CDCl_3$): δ 8.06-8.08 (m, 2H), 7.47-7.50 (m, 2H), 5.05-5.22 (m, 1H), 3.48-3.62 (m, 2H), 2.07-2.43 (m, 3H), 1.95 (s, 9H); Mass: 315 [M+Na]$^+$ 338 (100%).

Step 4: Synthesis of (S)-3-phenyl-5-(pyrrolidin-2-yl)-1,2,4-oxadiazole

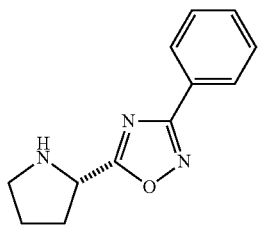

A solution with (S)-tert-butyl 2-(3-phenyl-1,2,4-oxadiazol-5-yl)pyrrolidine-1-carboxylate (step 3, 12.0 g, 38.21 mmol) in TFA:DCM (1:2, 3 mL) stirred at 0° C.-room temperature for about 1 hour. After completion of the reaction (monitored by TLC), the solvent was evaporated and the crude was dissolved in DCM and proceeded for next step without further purification.

Step 5: Synthesis of 1R,3aS,5aR,5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yl acetate

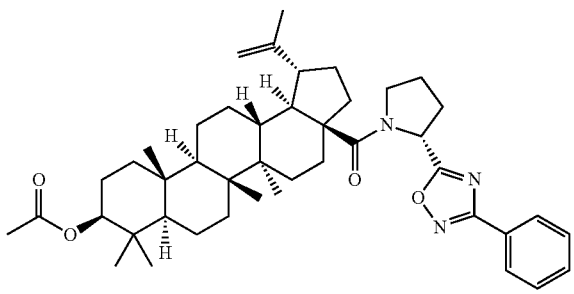 [SMILES: C=C(C)[C@@H]1CC[C@]2(C(=O)N3CCC[C@@H]3c3nc(-c4ccccc4)no3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in WO 2013/160810 A2, 14.0 g, 27.89 mmol) in DCM (100 mL), Oxolyl chloride (15.0 mL, 119.0 mmol) in DCM (20 mL) was added at 0° C. and stirred at room temperature for about 3 hours. After completion of the reaction (monitored by TLC), the solvent was evaporated under nitrogen atmosphere and dissolved in DCM (4 mL), which was added to the above stirred solution of (S)-3-phenyl-5-(pyrrolidin-2-yl)-1,2,4-oxadiazole (step 4, 6.0 g, 27.80 mmol) at 0° C. and allowed to stir at room temperature for about 16 hours. After completion of the reaction (monitored by TLC), the reaction mixture was diluted with DCM and washed with water, 1N HCl, water, brine and dried over $Na_2SO_4$. The solvent was evaporated and purified by silica gel column (100-200 mesh, elution 15% EtOAc in hexane) to afford the title compound (Wt: 10.0 g) as an off white solid. $^1H$ NMR (300 MHz, $CDCl_3$): δ 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H); Mass: 695 [M+1]$^+$ 696 (100%).

Step 6: Synthesis of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(3-phenyl-1,2,4-oxadiazol-5-yl)pyrrolidin-1-yl)methanone

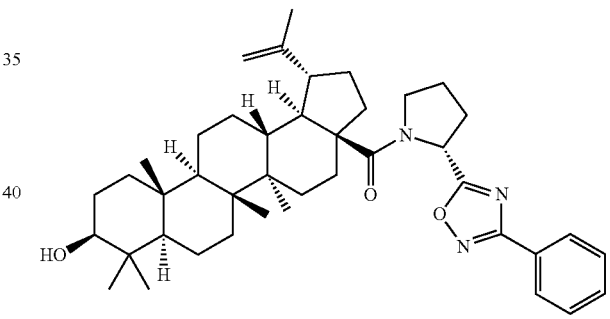

To a stirred solution of (1R,3aS,5aR,5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yl acetate (step 5, 10.0 g, 210.3 mmol) in MeOH (80 mL) was added potassium carbonate (13.8 g, 100.7 mmol) at 0° C. and allowed to stir at room temperature for about 16 hours. After completion of the reaction (monitored by TLC), the volatiles were evaporated and the aqueous layer was extracted with ethyl acetate and the organic layer was washed with water, brine and dried over $Na_2SO_4$. Then the solvent was evaporated and the resulting crude was purified by silicagel column (100-200 mesh, elution 15% EtOAc in hexane) to afford the title compound (Wt: 5.3 g) as an off white solid. $^1H$ NMR (300 MHz, $CDCl_3$): δ 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H); Mass: 653 [M+1]$^+$ 654 (100%).

Step 7: Synthesis of 2,2-dimethyl-4-oxo-4-((1R, 3aS,5aR,5bR,7aR,9S,11aR,11bR,13aR,13bR)-5a,5b, 8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy) butanoic acid 2,2-Dimethylsuccinic anhydride (3.6 mL, 28.67 mmol) was added to a stirred solution of ((1R,3aS,5aR,5bR,7aR, 9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(3-phenyl-1,2,4-oxadiazol-5-yl)pyrrolidin-1-yl)methanone (step 6, 5.3 g, 8.11 mmol) and DMAP (1.48 g, 12.13 mmol) in Toluene (150 mL) at room temperature and refluxed for about 24 hours. After completion of the reaction (monitored by TLC), the reaction mixture was diluted with EtOAc, washed with water, 1N HCl, water, brine and dried over $Na_2SO_4$, the solvent was evaporated and purified by silicagel column (100-200 mesh, elution 5% MeOH/DCM) to afford the title compound (Wt: 5.0 g) as an off white solid. $^1$H NMR (300 MHz, $CDCl_3$): δ 0.79-0.93 (m, 8H), 0.93 (s, 6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 781 [M+1]$^+$ 782 (100%); HPLC Purity: 89.0%.

Example 2

Preparation of 3,3-dimethyl-5-oxo-5-((1R,3aS,5aR, 5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl) icosahydro-1H-cyclopenta[a]chrysen-9-yloxy) pentanoic acid

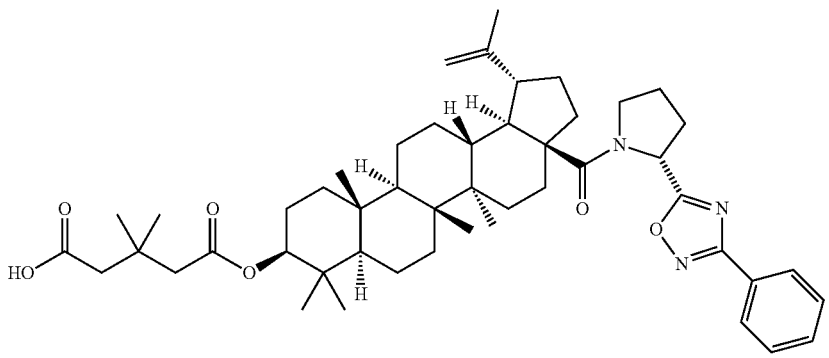 [SMILES: C=C(C)[C@@H]1CC[C@]2(C(=O)N3CCC[C@@H]3c3nc(-c4ccccc4)no3)CC[C@]3(C)[C@H](CC[C@@H]4[C@@]5(C)CC[C@H](OC(=O)CC(C)(C)CC(=O)O)C(C)(C)[C@@H]5CC[C@]43C)[C@@H]12]

3,3-Dimethyl glutaric anhydride (0.50 g, 3.52 mmol) was added to a stirred solution of ((1R,3aS,5aR,5bR,7aR,9S, 11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(3-phenyl-1,2,4-oxadiazol-5-yl)pyrrolidin-1-yl)methanone (Example 1-step 6, 0.50 g, 0.71 mmol) and DMAP (0.35 g, 2.86 mmol) in pyridine (10 mL) at room temperature and refluxed for about 24 hours. After completion of the reaction (monitored by TLC), the reaction mixture was diluted with EtOAc, washed with water, 1N HCl, water, brine and dried over $Na_2SO_4$, the solvent was evaporated and purified by silicagel column (100-200 mesh, elution 5% MeOH/DCM) to afford the title compound (Wt: 0.20 g) as an off white solid. $^1$H NMR (300 MHz, $CDCl_3$): δ 0.79-0.93 (m, 8H), 0.93 (s, 6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 795 [M+1]$^+$ 796 (100%); HPLC Purity: 92.0%.

Example 3

Preparation of 2,2-dimethyl-4-oxo-4-(((1R,3aS,5aR,5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yloxy)butanoic acid

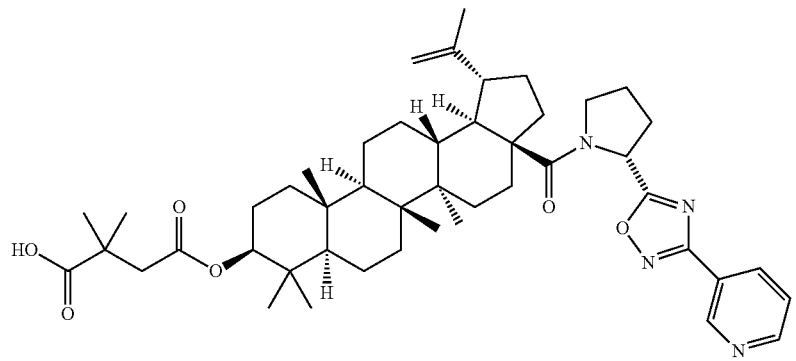 [SMILES: C=C(C)[C@@H]1CC[C@]2(C(=O)N3CCC[C@@H]3c3nc(-c4cccnc4)no3)CC[C@]3(C)[C@H](CC[C@@H]4[C@@]5(C)CC[C@H](OC(=O)CC(C)(C)C(=O)O)C(C)(C)[C@@H]5CC[C@]43C)[C@@H]12]

Step 1: Synthesis of (Z)—N'-hydroxynicotinimidamide

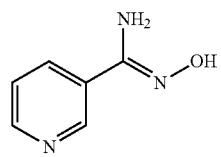

To the stirred solution of nicotinonitrile (12.0 g, 116.5 mmol) in 100 mL of methanol at room temperature was added K$_2$CO$_3$ (24.1 g, 174.6 mmol) and stirred for about 10 minutes, then added hydroxylamine hydrochloride (16 g, 231.8 mmol) (dissolved in 120 mL of methanol) and stirred for about 10 minutes at room temperature and refluxed for about 6 hours. After completion of the reaction (monitored by TLC), the reaction mixture was filtered, concentrated and the crude product was dissolved in EtOAc, washed with water, brine and dried over Na$_2$SO$_4$, the solvent was evaporated and used without further purification. Wt: 10.0 g.

Step 2: Synthesis of (S,Z)-tert-butyl 2-((amino(pyridin-3-yl)methyleneaminooxy)carbonyl)pyrrolidine-1-carboxylate

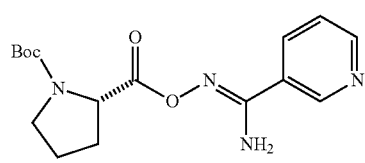 [SMILES: CC(C)(C)OC(=O)N1CCC[C@H]1C(=O)O/N=C(\N)c1cccnc1]

To a stirred solution of Boc-proline (15.8 g, 73.05 mmol) in DCM (200 mL), EDCI (21.05 g, 109.5 mmol) and HOBt (13.4 g, 88.1 mmol) were added at room temperature and after 10 minutes, (Z)—N'-hydroxynicotinimidamide (step 1, 10.0 g, 73.05 mmol) was added and the reaction mass was allowed to stir at room temperature for about 12 hours. After completion of the reaction (monitored by TLC), the reaction mixture was diluted with DCM and washed with water, saturated brine and the organic layer was concentrated under reduced pressure, the resulting crude was proceeded to next step without further purification. Wt: 18.0 g.

Step 3: Synthesis of (5)-tert-butyl 2-(3-(pyridin-3-yl)-1,2,4-oxadiazol-5-yl)pyrrolidine-1-carboxylate

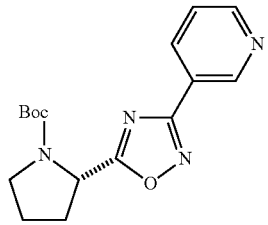 [SMILES: CC(C)(C)OC(=O)N1CCC[C@H]1c1nc(-c2cccnc2)no1]

To a stirred solution of (S,Z)-tert-butyl 2-((amino(pyridin-3-yl)methyleneaminooxy)carbonyl)pyrrolidine-1-carboxylate (step 2, 18.0 g, 54.05 mmol) in pyridine (80 mL) at room temperature and refluxed for about 24 hours. After completion of the reaction (monitored by TLC), the reaction mixture was diluted with EtOAc, washed with water, 1N HCl, water, brine and dried over Na$_2$SO$_4$, the solvent was evaporated and purified by silicagel column (100-200 mesh, elution 20% EtOAc in hexane) to afford the title compound (Wt: 12.0 g) as an off white solid. $^1$H NMR (300 MHz, CDCl$_3$): δ 8.06-8.08 (m, 2H), 7.47-7.50 (m, 2H), 5.05-5.22 (m, 1H), 3.48-3.62 (m, 2H), 2.07-2.43 (m, 3H), 1.95 (s, 9H); Mass: 316 [M+1]$^+$ 317 (100%).

Step 4: synthesis of (S)-3-(pyridin-3-yl)-5-(pyrrolidin-2-yl)-1,2,4-oxadiazole

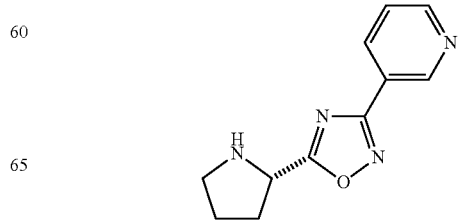

A solution with (S)-tert-butyl 2-(3-(pyridin-3-yl)-1,2,4-oxadiazol-5-yl)pyrrolidine-1-carboxylate (step 3, 12.0 g, 38.21 mmol) in TFA: DCM (1:2) (40 mL) stirred at 0° C.-room temperature for about 1 hour. After completion of the reaction (monitored by TLC), the solvent was evaporated and the crude was dissolved in DCM and proceeded to next step without further purification.

Step 5: Synthesis (1R,3aS,5aR,5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yl acetate

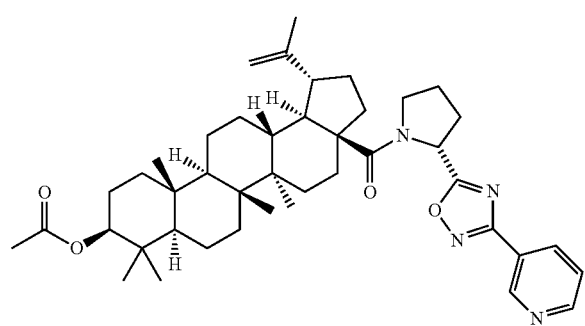 [SMILES: C=C(C)[C@@H]1CC[C@]2(C(=O)N3CCC[C@@H]3c3nc(-c4cccnc4)no3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in WO 2013/160810 A2, 4.0 g, 8.03 mmol) in DCM (80 mL), Oxolyl chloride (2.9 mL, 22.83 mmol) in DCM (5 mL) was added at 0° C. and stirred at room temperature for about 3 hours. After completion of the reaction (monitored by TLC), the solvent was evaporated under nitrogen atmosphere and dissolved in DCM (4 mL), which was added to the above stirred solution of (S)-3-(pyridin-3-yl)-5-(pyrrolidin-2-yl)-1,2,4-oxadiazole (step 4, 2.05 g, 9.49 mmol) at 0° C. and allowed to stir at room temperature for about 16 hours. After completion of the reaction (monitored by TLC), the reaction mixture was diluted with DCM and washed with water, 1N HCl, brine and dried over Na$_2$SO$_4$. The solvent was evaporated and purified by silicagel column (100-200 mesh, elution 15% EtOAc in hexane) to afford the title compound (Wt: 2.0 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.30-7.33 (m, 2H), 8.45 (s, 1H), 10.50 (s, 1H); Mass: 696 [M+1]$^+$ 697 (100%).

Step 6: Synthesis of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(3-(pyridin-3-yl)-1,2,4-oxadiazol-5-yl)pyrrolidin-1-yl)methanone

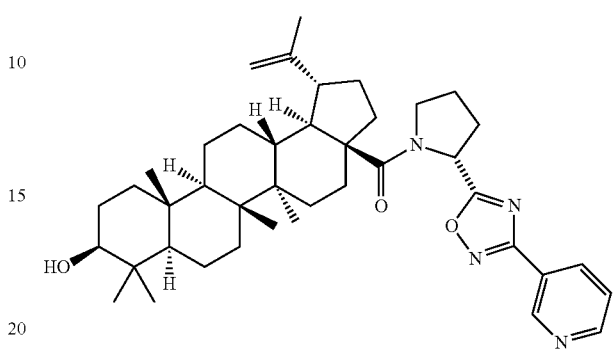

To a stirred solution of (1R,3aS,5aR,5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yl acetate (step 5, 6 g, 2.29 mmol) in MeOH (20 mL) was added potassium carbonate (2.2 g, 15.94 mmol) at 0° C. and allowed to stir at room temperature for about 16 hours. After completion of the reaction (monitored by TLC), the volatile was evaporated and the aqueous layer was extracted with ethyl acetate and the organic layer was washed with water, brine and dried over Na$_2$SO$_4$, then the solvent was evaporated and the resulting crude was purified by silicagel column (100-200 mesh, elution 15% EtOAc in hexane) to afford the title compound (Wt: 0.80 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.30-7.33 (m, 2H), 8.45 (s, 1H), 10.50 (s, 1H); Mass: 654 [M+1]$^+$ 655 (100%).

Step 7: Synthesis of 2,2-dimethyl-4-oxo-4-((1R,3aS,5aR,5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yloxy)butanoic acid 2,2-Dimethylsuccinic anhydride (0.2 mL, 1.56 mmol) was added to a stirred solution of (1R,3aS,5aR,5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yl acetate (step 6, 0.40 g, 0.61 mmol) and DMAP (0.11 g, 0.90 mmol) in Toluene (20 mL) at room temperature and refluxed for about 24 hours. After completion of the reaction (monitored by TLC), the reaction mixture was diluted with EtOAc, washed with water, 1N HCl, water, brine and dried over Na$_2$SO$_4$, the solvent was evaporated and purified by silicagel column (100-200 mesh, elution 5% MeOH/DCM) to afford the title compound (Wt: 0.40 g) as an off white solid. $^1$H NMR (300 MHz, CDCl$_3$): δ 0.79-0.93 (m, 8H), 0.93 (s, 6H), 1.07-1.26 (m, 10H), 1.29-1.56 (m, 12H), 1.69-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 2H), 8.45 (s, 1H), 10.50 (s, 1H); Mass: 782 [M+1]$^+$ 783 (100%); HPLC Purity: 86%.

Example 4

Preparation of 3,3-dimethyl-5-oxo-5-((1R,3aS,5aR, 5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yloxy)pentanoic acid

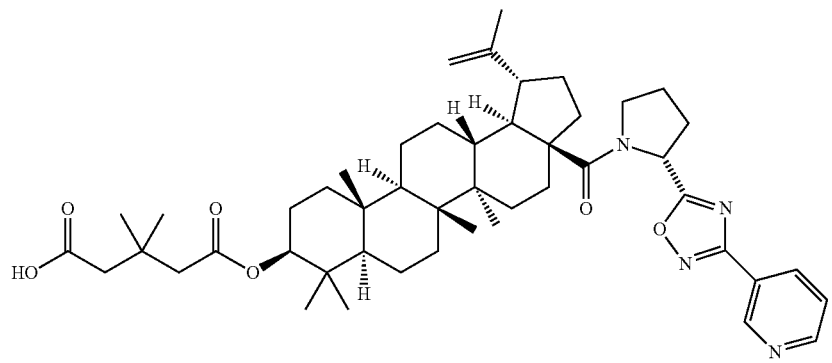 [SMILES: C=C(C)[C@@H]1CC[C@]2(C(=O)N3CCC[C@@H]3c3nc(-c4cccnc4)no3)CC[C@]3(C)[C@H](CC[C@@H]4[C@@]5(C)CC[C@H](OC(=O)CC(C)(C)CC(=O)O)C(C)(C)[C@@H]5CC[C@]43C)[C@@H]12]

3,3-Dimethyl glutaric anhydride (0.86 g, 6.11 mmol) was added to a stirred solution of (1R,3aS,5aR,5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yl acetate (Example 3-step 6, 0.50 g, 0.76 mmol) and DMAP (0.13 g, 1.13 mmol) in Toluene (10 mL) at room temperature and refluxed for about 24 hours. After completion of the reaction (monitored by TLC), the reaction mixture was diluted with EtOAc, washed with water, 1N HCl, brine and dried over $Na_2SO_4$, the solvent was evaporated and purified by silicagel column (100-200 mesh, elution 10% Acetone in DCM) to afford the title compound (Wt: 0.40 g) as an off white solid. $^1$H NMR (300 MHz, $CDCl_3$): δ 0.79-0.93 (m, 8H), 0.93 (s, 6H), 1.07-1.26 (m, 10H), 1.29-1.56 (m, 12H), 169-1.99 (m, 8H), 2.23-3.45 (m, 8H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 2H), 8.45 (s, 1H), 10.50 (s, 1H); Mass: 796 [M+1]$^+$ 797 (100%); HPLC Purity: 97.4%.

Example 5

Preparation of 2,2-dimethyl-4-oxo-4-((1R,3aS,5aR, 5bR,7aR,9S,11aR,11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yloxy) butanoic acid

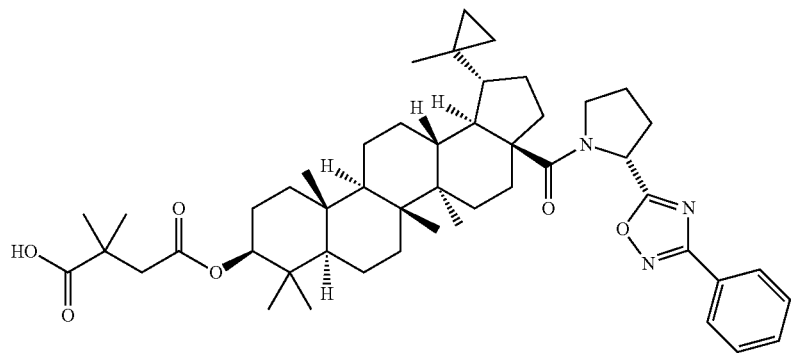 [SMILES: CC(C)(CC(=O)O[C@H]1CC[C@]2(C)[C@H]3CC[C@@H]4[C@H]5[C@H](C6(C)CC6)CC[C@]5(C(=O)N5CCC[C@@H]5c5nc(-c6ccccc6)no5)CC[C@@]4(C)[C@]3(C)CC[C@H]2C1(C)C)C(=O)O]

Step 1: Synthesis of (1R,3aS,5aR,5bR,7aR,9S,11aR, 11bR,13aR,13bR)-benzyl 9-acetoxy-5a,5b,8,8,11a-pentamethyl-1-(prop-1-en-2-yl)icosahydro-1H-cyclopenta[a]chrysene-3a-carboxylate

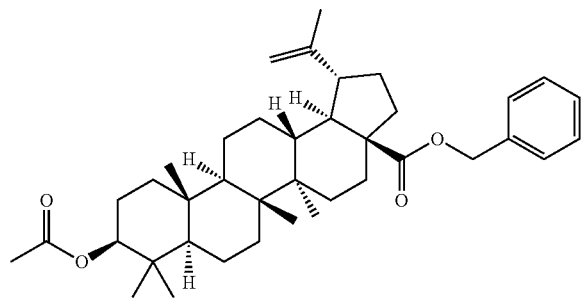 [SMILES: C=C(C)[C@@H]1CC[C@]2(C(=O)OCc3ccccc3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (7 g, 14.05 mmol) in DMF (60 mL) were added Potassium carbonate (3.9 g, 28.2 mmol) and benzyl bromide (2 mL, 11.69 mmol) at 0° C. and stirred at room temperature for about 12 hours. After completion of the reaction (monitored by TLC), the solvent was evaporated, the reaction mixture was diluted with ethyl acetate and washed with water, 1N HCl, water brine and dried over Na$_2$SO$_4$, the solvent was evaporated and purified by silicagel column (100-200 mesh, elution 15% EtOAc in hexane) to afford the title compound (Wt: 9 g) as an off white solid. $^1$H NMR (300 MHz, CDCl$_3$): δ 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 4.36-4.37 (m, 1H), 4.56 (s, 1H), 4.60 (s, 1H), 5.02-5.04 (m, 2H), 7.20-7.23 (m, 5H); Mass: 588 [M+1]$^+$ 589 (100%).

Step 2: Synthesis of 1R,3aS,5aR,5bR,7aR,9S,11aR, 11bR,13aR,13bR)-benzyl 9-acetoxy-5a,5b,8,8,11a-pentamethyl-1-(1-methylcyclopropyl)icosahydro-1H-cyclopenta[a]chrysene-3a-carboxylate

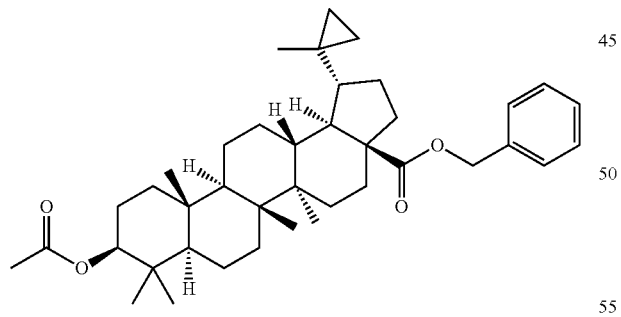

To a stirred solution of 1R,3aS,5aR,5bR,7aR,9S,11aR, 11bR,13aR,13bR)-benzyl 9-acetoxy-5a,5b,8,8,11a-pentamethyl-1-(prop-1-en-2-yl)icosahydro-1H-cyclopenta[a]chrysene-3a-carboxylate (step 1, 9 g, 15.30 mmol) in dry DCM (100 mL) was added diethyl zinc (40 mL, 234.1 mmol) at −20° C. and stirred for about one hour, then added Diiodomethane (5 mL, 18.7 mmol) at −20° c. and stir for about one hour. The reaction mixture was stirred at room temperature for about 12 hours. After completion of the reaction (monitored by TLC), the reaction mixture was quenched with saturated ammonium chloride, the reaction mixture was diluted with DCM and washed with water, 1N HCl, water brine and dried over Na$_2$SO$_4$, the solvent was evaporated and purified by silica gel column (100-200 mesh, elution 15% EtOAc in hexane to afford the title compound (Wt: 6.5 g) as an off white solid. $^1$H NMR (300 MHz, CDCl$_3$): δ 0.22-0.25 (m, 2H), 0.26-0.27 (m, 2H), 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 4.36-4.37 (m, 1H), 5.02-5.04 (m, 2H), 7.20-7.23 (m, 5H); Mass: 602[M+1]$^+$ 603 (100%).

Step 3: Synthesis of (1R,3aS,5aR,5bR,7aR,9S,11aR, 11bR,13aR,13bR)-9-acetoxy-5a,5b,8,8,11a-pentamethyl-1-(1-methylcyclopropyl)icosahydro-1H-cyclopenta[a]chrysene-3a-carboxylic acid

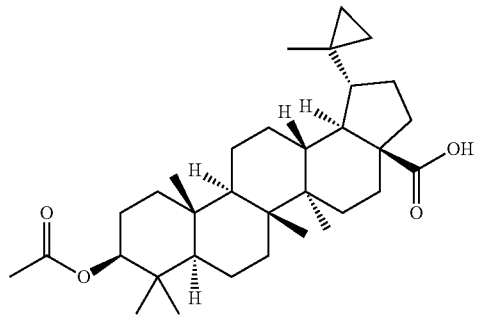 [SMILES: CC(=O)O[C@H]1CC[C@]2(C)[C@H]3CC[C@@H]4[C@H]5[C@H](C6(C)CC6)CC[C@]5(C(=O)O)CC[C@@]4(C)[C@]3(C)CC[C@H]2C1(C)C]

To a stirred solution of (1R,3aS,5aR,5bR,7aR,9S,11aR, 11bR,13aR,13bR)-benzyl 9-acetoxy-5a,5b,8,8,11a-pentamethyl-1-(1-methylcyclopropyl)icosahydro-1H-cyclopenta[a] chrysene-3a-carboxylate (step 2, 6.5 g, 10.7 mmol) in Ethyl acetate: Ethanol (300+200 mL) was added 10% pd/c (2 g) and stirred the reaction under H$_2$ atmosphere (60 psi) for about 12 hours. After completion of the reaction (monitored by TLC), the reaction mixture was filtered washed with ethanol, the solvent was evaporated and purified by silicagel column (100-200 mesh, elution 15% EtOAc in hexane to afford the title compound (Wt: 5.0 g) as an off white solid. $^1$H NMR (300 MHz, CDCl$_3$): δ 0.22-0.25 (m, 2H), 0.26-0.27 (m, 2H) 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 4.36-4.37 (m, 1H); Mass: 512 [M+1]$^+$ 513 (100%).

Step 4: Synthesis (1R,3aS,5aR,5bR,7aR,9S,11aR, 11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yl acetate

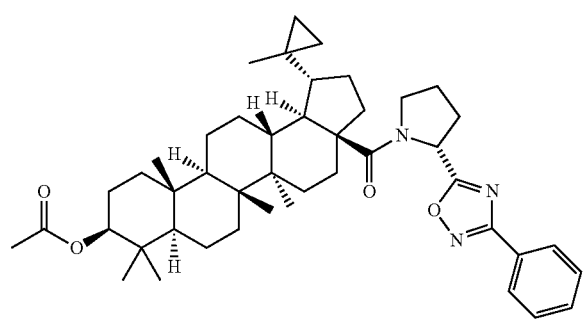 [SMILES: CC(=O)O[C@H]1CC[C@]2(C)[C@H]3CC[C@@H]4[C@H]5[C@H](C6(C)CC6)CC[C@]5(C(=O)N5CCC[C@@H]5c5nc(-c6ccccc6)no5)CC[C@@]4(C)[C@]3(C)CC[C@H]2C1(C)C]

To a stirred solution of (1R,3aS,5aR,5bR,7aR,9S,11aR,11bR,13aR,13bR)-9-acetoxy-5a,5b,8,8,11a-pentamethyl-1-(1-methylcyclopropyl)icosahydro-1H-cyclopenta[a]chrysene-3a-carboxylic acid (step 3, 4.0 g, 7.54 mmol) in DCM (50 mL), Oxolyl chloride (3.80 mL, 30.18 mmol) in DCM (5 mL) was added at 0° C. and stirred at room temperature for about 3 hours. After completion of the reaction (monitored by TLC), the solvent was evaporated under nitrogen atmosphere and dissolved in DCM (4 mL), which was added to the above stirred solution of (S)-3-phenyl-5-(pyrrolidin-2-yl)-1,2,4-oxadiazole (Example 3-step 4, 1.6 g 7.47 mmol) at 0° C. and allowed to stir at room temperature for about 16 hours. After completion of the reaction (monitored by TLC), the reaction mixture was diluted with DCM and washed with water, 1N HCl, water brine and dried over $Na_2SO_4$, the solvent was evaporated and purified by silicagel column (100-200 mesh, elution 15% EtOAc in hexane) to afford the title compound (Wt: 3.2 g) as an off white solid. $^1$H NMR (300 MHz, $CDCl_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 709[M+1]$^+$ 710 (100%).

Step 5: Synthesis of ((1R,3aS,5aR,5bR,7aR,9S,11aR,11bR,13aR,13bR)-9-hydroxy-5a,5b,8,8,11a-pentamethyl-1-(1-methylcyclopropyl)icosahydro-1H-cyclopenta[a]chrysen-3a-yl)((R)-2-(3-phenyl-1,2,4-oxadiazol-5-yl)pyrrolidin-1-yl)methanone

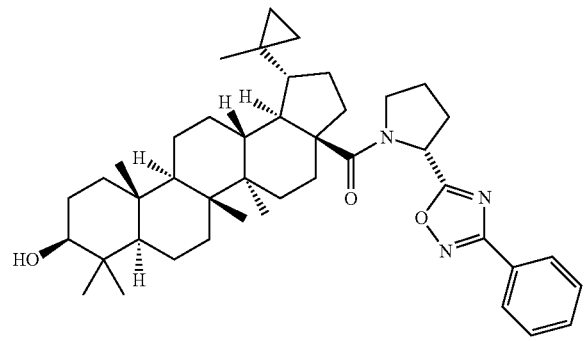 [SMILES: CC1([C@@H]2CC[C@]3(C(=O)N4CCC[C@@H]4c4nc(-c5ccccc5)no4)CC[C@]4(C)[C@H](CC[C@@H]5[C@@]6(C)CC[C@H](O)C(C)(C)[C@@H]6CC[C@]54C)[C@@H]23)CC1]

To a stirred solution of (1R,3aS,5aR,5bR,7aR,9S,11aR,11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yl acetate (step 4, 1.2 g, 1.69 mmol), in MeOH (40 mL) was added potassium carbonate (1.6 g, 11.59 mmol) at 0° C. and allowed to stir at room temperature for about 16 hours. After completion of the reaction (monitored by TLC), the volatile was evaporated and the aqueous layer was extracted with ethyl acetate and the organic layer was washed with water, brine and dried over $Na_2SO_4$, then the solvent was evaporated and the resulting crude was purified by silicagel column (100-200 mesh, elution 15% EtOAc in hexane) to afford the title compound (Wt: 0.70 g) as an off white solid. $^1$H NMR (300 MHz, $CDCl_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 667 [M+1]$^+$ 668 (100%).

Step 6: Synthesis of 2,2-dimethyl-4-oxo-4-((1R,3aS,5aR,5bR,7aR,9S,11aR,11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yloxy)butanoic acid 2,2-Dimethylsuccinic anhydride (0.48 mL, 3.75 mmol) was added to a stirred solution of ((1R,3aS,5aR,5bR,7aR,9S,11aR,11bR,13aR,13bR)-9-hydroxy-5a,5b,8,8,11a-pentamethyl-1-(1-methylcyclopropyl)icosahydro-1H-cyclopenta[a]chrysen-3a-yl)((R)-2-(3-phenyl-1,2,4-oxadiazol-5-yl)pyrrolidin-1-yl)methanone (step 5, 0.70 g, 1.04 mmol) and DMAP (0.15 g, 1.22 mmol) in Toluene (50 mL) at room temperature and refluxed for about 24 hours. After completion of the reaction (monitored by TLC), the reaction mixture was diluted with EtOAc, washed with water, 1N HCl, water, brine and dried over $Na_2SO_4$, the solvent was evaporated and purified by silicagel column (100-200 mesh, elution 20% EtOAc in hexane) to afford the title compound (Wt: 0.20 g) as an off white solid. $^1$H NMR (300 MHz, $CDCl_3$): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 795[M+1]$^+$ 796 (100%); HPLC Purity: 92.18%.

Example 6

Preparation of 3,3-dimethyl-5-oxo-5-((1R,3aS,5aR,5bR,7aR,9S,11aR,11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yloxy)pentanoic acid

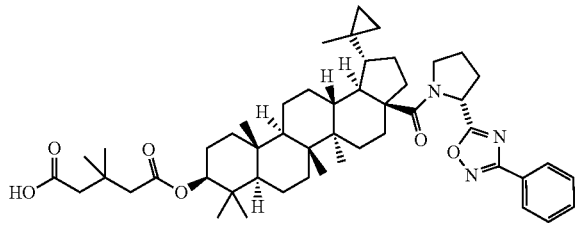 [SMILES: CC(C)(CC(=O)O)CC(=O)O[C@H]1CC[C@]2(C)[C@H]3CC[C@@H]4[C@H]5[C@H](C6(C)CC6)CC[C@]5(C(=O)N5CCC[C@@H]5c5nc(-c6ccccc6)no5)CC[C@@]4(C)[C@]3(C)CC[C@H]2C1(C)C]

3,3-Dimethyl glutaric anhydride (0.303 g, 2.365 mmol) was added to a stirred solution of ((1R,3aS,5aR,5bR,7aR,9S,11aR,11bR,13aR,13bR)-9-hydroxy-5a,5b,8,8,11a-pentamethyl-1-(1-methylcyclopropyl)icosahydro-1H-cyclopenta[a]chrysen-3a-yl)((R)-2-(3-phenyl-1,2,4-oxadiazol-5-yl)pyrrolidin-1-yl)methanone (Example 5-step 5, 0.150 g, 0.236 mmol) and DMAP (0.057 g, 0.473 mmol) in Toulene (10 mL) at room temperature and refluxed for about 24 hours. After completion of the reaction (monitored by TLC), the reaction mixture was diluted with EtOAc, washed with water, 1N HCl, water, brine and dried over $Na_2SO_4$, the solvent was evaporated and purified by silicagel column (100-200 mesh, elution 20% EtOAc in hexane) to afford the title compound (Wt: 0.045 g, Yield: 24.4%) as an off white solid. $^1$H NMR (300 MHz, $CDCl_3$): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H) 7.22-7.60 (m, 3H), 7.70-7.88 (m, 2H), 10.50 (s, 1H); Mass: 809[M+1] 810 (100%); HPLC Purity: 90%.

Example 7

Preparation of 2,2-dimethyl-3-(((1R,3aS,5aR,5bR, 7aR,9S,11aR,11bR,13aR,13bR)-5a,5b,8,8,11a-pentamethyl-3a-((R)-2-(3-phenyl-1,2,4-oxadiazol-5-yl) pyrrolidine-1-carbonyl)-1-(prop-1-en-2-yl) icosahydro-1H-cyclopenta[a]chrysen-9-yloxy) carbonyl)cyclobutanecarboxylic acid

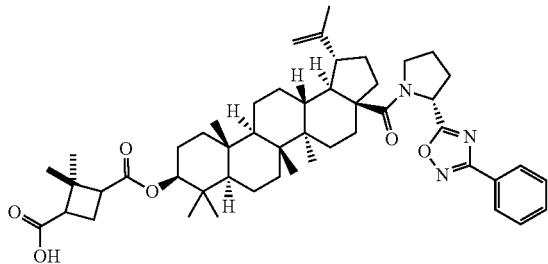

Step 1: Synthesis of (1S,3R)-3-(benzyloxycarbonyl)-2,2-dimethylcyclobutanecarboxylic 2,4,6-trichlorobenzoic anhydride

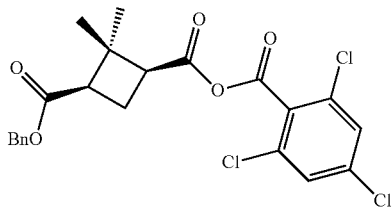

To a stirred solution of (1S,3R)-3-(benzyloxycarbonyl)-2,2-dimethylcyclobutanecarboxylic acid (0.700 g, 2.67 mmol, 1.0 eq) and triethylamine (0.809 g, 8.01 mmol, 3.0 eq) in THF (14 mL) at 0° C. was added 2,4,6-trichlorobenzoyl chloride (0.782 g, 3.20 mmol, 1.2 eq). The reaction mixture was allowed to stir at room temperature for about 4 hours. TLC indicated starting material was consumed and the desired product was observed. The reaction mixture was evaporated under reduced pressure obtained the crude and proceeded for next step without further purification.

Step 2: Synthesis of 1-benzyl 3-((1R,3aS,5aR,5bR, 7aR,9S,11aR,11bR,13aR,13bR)-5a,5b,8,8,11a-pentamethyl-3a-((R)-2-(3-phenyl-1,2,4-oxadiazol-5-yl) pyrrolidine-1-carbonyl)-1-(prop-1-en-2-yl) icosahydro-1H-cyclopenta[a]chrysen-9-yl) 2,2-dimethylcyclobutane-1,3-dicarboxylate

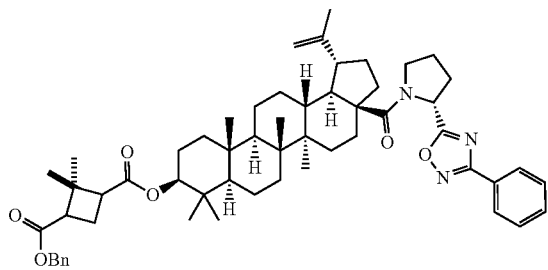

To a stirred solution of ((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(3-phenyl-1,2,4-oxadiazol-5-yl)pyrrolidin-1-yl) methanone (Example 1-step 6, 0.600 g, 1.05 mmol, 1.0 eq) in toluene (10 mL) was added DMAP (0.258 g, 2.11 mmol, 2.0 eq) and (1S,3R)-3-(benzyloxycarbonyl)-2,2-dimethylcyclobutanecarboxylic 2,4,6-trichlorobenzoic anhydride (step 1, 0.991 g, 2.11 mmol, 2.0 eq). The reaction mixture was heated to 90° C. for overnight. TLC indicated starting material was consumed and the desired product was observed. The reaction mixture was evaporated under reduced pressure and diluted with water. The aqueous layer was extracted with $CH_2Cl_2$ (2×50 mL). The combined organic layers were dried over $Na_2SO_4$, filtered and evaporated under reduced pressure. The crude residue was purified by silicagel column chromatography by using 1.5% methanol: dichloromethane as an eluent to obtain desired product (0.630 g, 73.4% yield) as a white solid. $^1$H NMR (300 MHz, $CDCl_3$): δ 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H) 7.01-7.11 (m, 3H), 7.12-7.13 (m, 2H), 7.22-7.60 (m, 3H), 7.70-7.88 (m, 2H), 10.50 (s, 1H); Mass: 897 [M+1]$^+$ 898 (100%); HPLC Purity: 92.21%.

Step 3: Synthesis of 2,2-dimethyl-3-((((1R,3aS,5aR, 5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl) icosahydro-1H-cyclopenta[a]chrysen-9-yl)oxy) carbonyl)cyclobutane-1-carboxylic acid To a solution of 1-benzyl 3-((1R,3aS,5aR,5bR,7aR,9S, 11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a] chrysen-9-yl) 2,2-dimethylcyclobutane-1,3-dicarboxylate (step 2, 0.630 g, 0.77 mmol, 1.0 eq) in dichloromethane (30 mL) was added palladium (II) acetate (0.0872 g, 0.388 mmol, 0.5 eq), triethyl amine (0.235 g, 2.33 mmol, 3.0 eq) and triethylsilane (0.271 g, 2.33 mmol, 3.0 eq). The mixture was flushed with $N_2$ and was heated to reflux for about 48 hours. The reaction mixture was cooled to room temperature, filtered through a pad of celite and was washed with dichloromethane (50 mL). The filtrate was evaporated under reduced pressure, cooled to 0° C., diluted with water (10 mL), acidified to pH 5.0 with 1N HCl and extracted with $CH_2Cl_2$ (2×200 mL). The combined organic layers were dried over $Na_2SO_4$, filtered and evaporated under reduced pressure. The crude residue was purified by silicagel column chromatography by using 6% methanol: dichloromethane as an eluent to gave the title compound (0.190 g, 33.9% yield) as a white solid. $^1$H NMR (300 MHz, Pyridine-d5): δ 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 807 [M+1]$^+$ 808 (100%); HPLC Purity: 92.21%.

Example 8

Preparation of 2,2-dimethyl-4-oxo-4-((1R,3aS,5aR, 5bR,7aR,9S,11aR,11bR,13aR,13bR)-5a,5b,8,8,11a-pentamethyl-3a-((S)-2-(5-phenyl-1H-imidazol-2-yl) pyrrolidine-1-carbonyl)-1-(prop-1-en-2-yl) icosahydro-1H-cyclopenta[a]chrysen-9-yloxy) butanoic acid

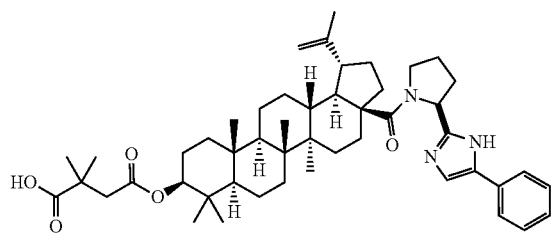

Step 1: Synthesis of 2-bromo-1-phenylethanone

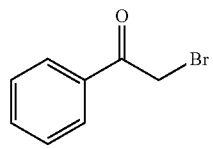

To the stirred solution of Acetophenone (15 g, 125 mmol) in 200 mL of diethyl ether at 0° C. was added Bromine (6.5 mL, 125 mmol) (dissolved in 12 mL diethyl ether), stirred for about 30 minutes and stirred for about 2 hours at room temperature. After completion of the reaction (monitored by TLC), the reaction mixture was concentrated and the crude product was dissolved in n-hexane and stirred for about 30 minutes. The obtained solid was filtered and washed with n-hexane then dried and proceeded for next step (Wt: 11.0 g).

Step 2: Synthesis of (S)-1-tert-butyl 2-(2-oxo-2-phenylethyl) pyrrolidine-1,2-dicarboxylate

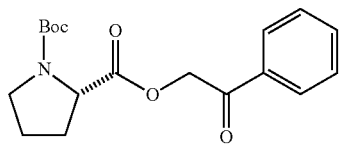 [SMILES: CC(C)(C)OC(=O)N1CCC[C@H]1C(=O)OCC(=O)c1ccccc1]

To a stirred solution of (S)-1-(tert-butoxycarbonyl) pyrrolidine-2-carboxylic acid (12 g, 55.8 mmol) in DCM (120 mL), DIPEA (17.6 mL, 105.4 mmol) was added at 0° C. temperature and after 10 minutes 2-bromo-1-phenylethanone (step 1, 11 g, 55.2 mmol) was added and the reaction mixture was allowed to stir at room temperature for about 12 hours. After completion of the reaction (monitored by TLC), the reaction mixture was diluted with DCM, washed with water, saturated brine and the organic layer was concentrated under reduced pressure. The resulting crude was proceeded for next step without further purification (Wt: 15.0 g).

Step 3: Synthesis of (S)-tert-butyl 2-(5-phenyl-1H-imidazol-2-yl) pyrrolidine-1-carboxylate

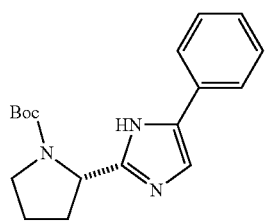

To a stirred solution of (S)-1-tert-butyl 2-(2-oxo-2-phenylethyl) pyrrolidine-1,2-dicarboxylate (step 2, 14.0 g, 42.04 mmol) in Toluene (120 mL), ammonium acetate (30 g, 389.6 mmol) was added at room temperature and refluxed for about 12 hours. After completion of the reaction (monitored by TLC), the reaction mixture was concentrated and the crude was diluted with EtOAc, washed with water, brine and dried over $Na_2SO_4$. The solvent was evaporated and purified by silicagel column (100-200 mesh, elution 20% EtOAc in hexane) to afford the title compound (Wt: 6.0 g) as an off white solid. $^1$H NMR (300 MHz, CDCl$_3$): δ 7.61-7.63 (m, 2H), 4.98-5.00 (d, 1H, j=6 Htz), 3.42 (s, 2H), 3.01 (s, 1H), 2.14-2.17 (m, 4H), 1.50 (s, 9H); Mass: 313 [M+1]$^+$ 314 (100%).

Step 4: Synthesis of (S)-5-phenyl-2-(pyrrolidin-2-yl)-1H-imidazole

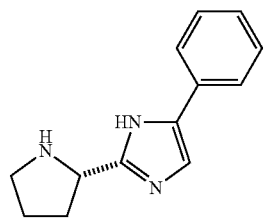

A solution of (S)-tert-butyl 2-(5-phenyl-1H-imidazol-2-yl)pyrrolidine-1-carboxylate (step 3, 2.0 g, 6.6 mmol) in TFA: DCM (1:2, 15 mL) stirred at 0° C.-room temperature for about 1 hour. After completion of the reaction (monitored by TLC), the solvent was evaporated and the crude was dissolved in DCM and proceeded for next step without further purification (Wt: 1.3 g).

Step 5: Synthesis (1R,3aS,5aR,5bR,7aR,9S,11aR, 11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl acetate

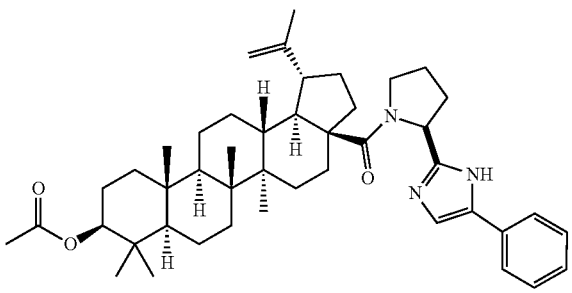

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in WO 2013/160810 A2, 3.0 g, 6.02 mmol) in DCM (30 mL), Oxolyl chloride (3 mL, 23.6 mmol) in DCM (5 mL) was added at 0° C. and stirred at room temperature for about 3 hours. After completion of the reaction (monitored by TLC), the solvent was evaporated under nitrogen atmosphere and dissolved in DCM (4 mL) which was added to the above stirred solution of (S)-5-phenyl-2-(pyrrolidin-2-yl)-1H-imidazole (step 4, 1.04 g, 0.66 mmol) at 0° C. and allowed to stir at room temperature for about 16 hours. After completion of the reaction (monitored by TLC), the reaction mixture was diluted with DCM, washed with water, 1N HCl, brine and dried over Na$_2$SO$_4$. The solvent was evaporated and purified by silicagel column (100-200 mesh, elution 30% EtOAc in hexane) to afford the title compound (Wt: 3.0 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 693 [M+1]$^+$ 694 (100%).

Step 6: Synthesis of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((S-2-(5-phenyl-1H-imidazol-2-yl)pyrrolidin-1-yl)methanone

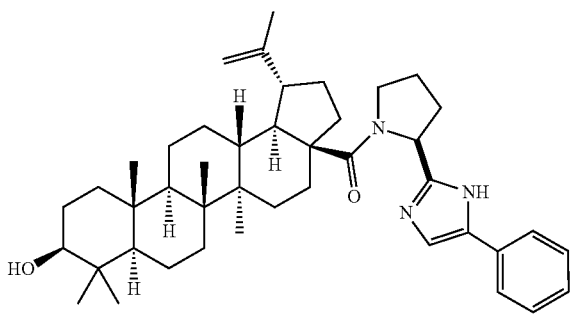

To a stirred solution of (1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl acetate (step 5, 2.4 g, 3.46 mmol) in MeOH (50 mL) was added potassium carbonate (3.3 g, 24.2 mmol) at 0° C. and allowed to stir at room temperature for about 16 hours. After completion of the reaction (monitored by TLC), the volatile was evaporated and the aqueous layer was extracted with ethyl acetate and the organic layer was washed with water, brine and dried over Na$_2$SO$_4$. Then the solvent was evaporated and the resulting crude was purified by silicagel column (100-200 mesh, elution 15% EtOAc in hexane) to afford the title compound (Wt: 1.8 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 651 [M+1]$^+$ 652 (100%).

Step 7: Synthesis of 2,2-dimethyl-4-oxo-4-((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)butanoic acid 2,2-Dimethylsuccinic anhydride (0.45 mL, 3.51 mmol) was added to a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(5-phenyl-1H-imidazol-2-yl)pyrrolidin-1-yl)methadone (step 6, 0.65 g, 0.99 mmol) and DMAP (0.18 g, 1.49 mmol) in Toluene (20 mL) at room temperature and refluxed for about 24 hours. After completion of the reaction (monitored by TLC), the reaction mixture was diluted with EtOAc, washed with water, 1N HCl, water, brine and dried over Na$_2$SO$_4$. The solvent was evaporated and purified by silicagel column (100-200 mesh, elution 5% MeOH/DCM) to afford the title compound (Wt: 0.5 g) as an off white solid. $^1$H NMR (300 MHz, CDCl$_3$): δ 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 779 [M+1]$^+$ 780 (100%); HPLC Purity: 90.21%.

Example 9

Preparation of 3,3-dimethyl-5-oxo-5-((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)pentanoic acid

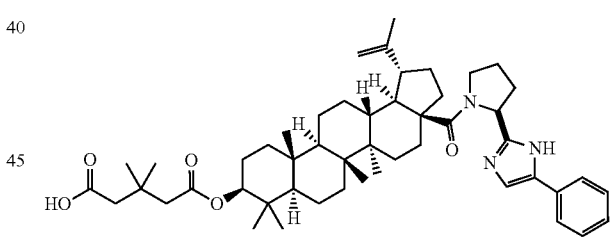

3,3-Dimethyl glutaric anhydride (0.5 g, 3.52 mmol) was added to a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(5-phenyl-1H-imidazol-2-yl)pyrrolidin-1-yl)methadone (Example 8-step 6, 0.5 g, 0.76 mmol) and DMAP (0.15 g, 1.22 mmol) in pyridine (15 mL) at room temperature and refluxed for about 24 hours. After completion of the reaction (monitored by TLC), the reaction mixture was diluted with EtOAc, washed with water, 1N HCl, water, brine and dried over Na$_2$SO$_4$. The solvent was evaporated and purified by silicagel column (100-200 mesh, elution 5% MeOH/DCM) to afford the title compound (Wt: 0.35 g) as an off white solid. $^1$H NMR (300 MHz, CDCl$_3$): δ 0.79-0.93 (m, 8H), 0.93 (s, 6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 793 [M+1]⁺ 794 (100%); HPLC Purity: 95.5%.

Example 10

2,2-dimethyl-4-oxo-4-((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yloxy)butanoic acid

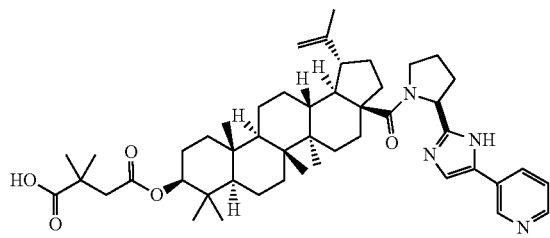 [SMILES: C=C(C)[C@@H]1CC[C@]2(C(=O)N3CCC[C@H]3c3ncc(-c4cccnc4)[nH]3)CC[C@]3(C)[C@H](CC[C@@H]4[C@@]5(C)CC[C@H](OC(=O)CC(C)(C)C(=O)O)C(C)(C)[C@@H]5CC[C@]43C)[C@@H]12]

Step 1: Synthesis of 2-bromo-1-(pyridin-3-yl)ethanone

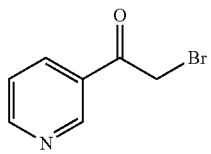

To the stirred solution of 1-(pyridin-3-yl) ethanone (10 g, 82.6 mmol) in 120 mL of diethyl ether at 0° C. was added Bromine (4.7 mL, 82.6 mmol) (dissolved in 20 mL diethyl ether) for about 15 minutes and stirred for about 2 hours at room temperature. After completion of the reaction (monitored by TLC), the reaction mixture was concentrated, the crude product was dissolved in n-hexane and stirred for about 30 minutes. The obtained solid was filtered and washed with n-hexane, dried and proceeded for next step (Wt: 11.0 g).

Step 2: Synthesis of (S)-1-tert-butyl 2-(2-oxo-2-(pyridin-3-yl)ethyl) pyrrolidine-1,2-dicarboxylate

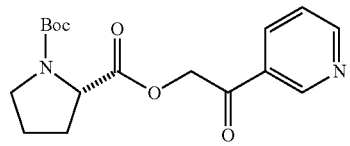

To a stirred solution of (S)-1-(tert-butoxycarbonyl)pyrrolidine-2-carboxylic acid (11.9 g, 55.5 mmol) in DCM (120 mL) was added DIPEA (20.3 mL, 110.9 mmol) at 0° C. temperature and after 10 minutes, 2-bromo-1-(pyridin-3-yl) ethanone (step 1, 11.0 g, 55.5 mmol) was added and the reaction mass was allowed to stir at room temperature for about 12 hours. After completion of the reaction (monitored by TLC), the reaction mixture was diluted with DCM, washed with water, saturated brine and the organic layer was concentrated under reduced pressure. The resulting crude was proceeded for next step without further purification (Wt: 13.0 g).

Step 3: Synthesis of (S)-tert-butyl 2-(5-(pyridin-3-yl)-1H-imidazol-2-yl)pyrrolidine-1-carboxylate

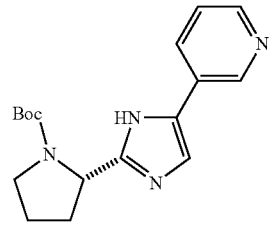 [SMILES: CC(C)(C)OC(=O)N1CCC[C@H]1c1ncc(-c2cccnc2)[nH]1]

To a stirred solution of (S)-1-tert-butyl 2-(2-oxo-2-(pyridin-3-yl)ethyl) pyrrolidine-1,2-dicarboxylate (step 2, 13 g, 38.9 mmol) in Toluene (130 mL) was added ammonium acetate (23.9 g, 311.2 mmol) at room temperature and refluxed for about 12 hours. After completion of the reaction (monitored by TLC), the reaction mixture was concentrated and the crude was diluted with EtOAc, washed with water, brine and dried over $Na_2SO_4$. The solvent was evaporated and purified by silicagel column (100-200 mesh, elution 20% EtOAc in hexane) to afford the title compound (Wt: 7 g) as an off white solid. ¹H NMR (300 MHz, CDCl₃): δ 7.61-7.63 (m, 2H), 4.98-5.00 (d, 1H, j=6 Htz), 3.42 (s, 2H), 3.01 (s, 1H), 2.14-2.17 (m, 4H), 1.50 (s, 9H); Mass: [M+1]⁺ 315 (100%).

Step 4: Synthesis of (S)-3-(2-(pyrrolidin-2-yl)-1H-imidazol-5-yl)pyridine

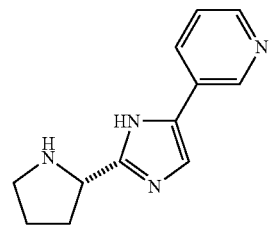 [SMILES: c1cncc(-c2cnc([C@@H]3CCCN3)[nH]2)c1]

A solution with (S)-tert-butyl 2-(5-(pyridin-3-yl)-1H-imidazol-2-yl)pyrrolidine-1-carboxylate (step 3, 7 g, 22.2 mmol) in TFA: DCM (1:4, 50 mL) stirred at 0° C.-room temperature for about 1 hour. After completion of the reaction (monitored by TLC), the solvent was evaporated and the crude was dissolved in DCM and proceeded for next step without further purification (Wt: 4.5 g).

Step 5: Synthesis of (1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yl acetate

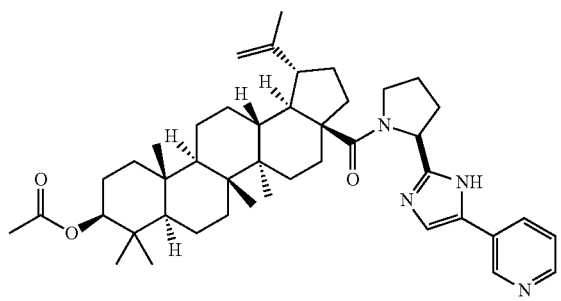 [SMILES: C=C(C)[C@@H]1CC[C@]2(C(=O)N3CCC[C@H]3c3ncc(-c4cccnc4)[nH]3)CC[C@]3(C)[C@H](CC[C@@H]4[C@@]5(C)CC[C@H](OC(C)=O)C(C)(C)[C@@H]5CC[C@]43C)[C@@H]12]

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in WO 2013/160810 A2, 3.8 g, 7.63 mmol) in DCM (35 mL), Oxolyl chloride (2.7 mL, 30.5 mmol) in DCM (4 mL) was added at 0° C. and stirred at room temperature for about 3 hours. After completion of the reaction (monitored by TLC), the solvent was evaporated under nitrogen atmosphere and dissolved in DCM (4 mL), which was added to the above stirred solution of (S)-3-(2-(pyrrolidin-2-yl)-1H-imidazol-5-yl)pyridine (step 4, 1.7 g, 7.94 mmol) at 0° C. and allowed to stir at room temperature for about 16 hours. After completion of the reaction (monitored by TLC), the reaction mixture was diluted with DCM, washed with water, 1N HCl, water brine and dried over Na$_2$SO$_4$. The solvent was evaporated and purified by silicagel column (100-200 mesh, elution 5% MeOH/DCM) to afford the title compound (Wt: 2.8 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.30-7.33 (m, 2H), 8.45 (s, 1H), 10.50 (s, 1H); Mass: 694 [M+1]$^+$ 695 (100%).

Step 6: Synthesis of (1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysen-3a-yl)((S)-2-(5-(pyridin-3-yl)-1H-imidazol-2-yl)pyrrolidin-1-yl)methanone

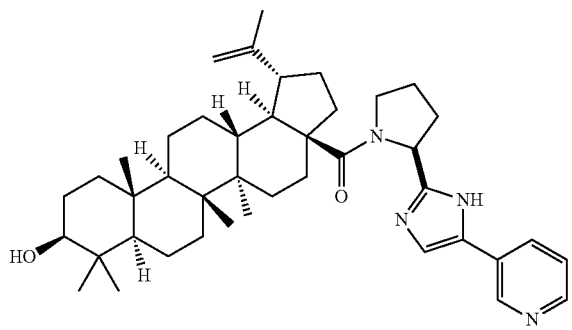 [SMILES: C=C(C)[C@@H]1CC[C@]2(C(=O)N3CCC[C@H]3c3ncc(-c4cccnc4)[nH]3)CC[C@]3(C)[C@H](CC[C@@H]4[C@@]5(C)CC[C@H](O)C(C)(C)[C@@H]5CC[C@]43C)[C@@H]12]

To a stirred solution of (1R,3aS,5aR,5bR,7aR,9S,11aR, 11bR,13aR,13bR)-5a,5b,8,8,11a-pentamethyl-1-(prop-1-en-2-yl)-3a-((R)-2-(5-(pyridin-3-yl)-1H-imidazol-2-yl)pyrrolidine-1-carbonyl)icosahydro-1H-cyclopenta[a]chrysen-9-yl acetate (step 5, 2.8 g, 4.06 mmol) in methanol (30 mL) was added potassium carbonate (4.4 g, 32 mmol) at room temperature, stir for about 16 hours. After completion of the reaction (monitored by TLC), the volatile was evaporated and the aqueous layer was extracted with ethyl acetate and the organic layer was washed with water, brine and dried over Na$_2$SO$_4$. Then the solvent was evaporated and the resulting crude was purified by silicagel column (100-200 mesh, elution 5% MeOH/DCM) to afford the title compound (Wt: 1.8 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H),7.22-7.60 (m, 2H), 8.45 (s, 1H), 10.50 (s, 1H); Mass: 652 [M+1]$^+$ 653 (100%).

Step 7: Synthesis of 2,2-dimethyl-4-oxo-4 ((1R, 3aS,5aR,5bR,7aR,9S,11aR,11bR,13aR,13bR)-5a,5b, 8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yloxy)butanoic acid 2,2-Dimethylsuccinic anhydride (0.7 mL, 6.13 mmol) was added to a stirred solution of ((1R,3aS,5aR,5bR,7aR, 9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(5-(pyridin-3-yl)-1H-imidazol-2-yl)pyrrolidin-1-yl)methanone (step 6, 1.0 g, 1.53 mmol) and DMAP (0.28 g, 2.30 mmol) in Toluene (10 mL) at room temperature and refluxed for about 24 hours. After completion of the reaction (monitored by TLC), the reaction mixture was diluted with EtOAc, washed with water, 1N HCl, water, brine and dried over Na$_2$SO$_4$. The solvent was evaporated and purified by silicagel column (100-200 mesh, elution 20% EtOAc in hexane) to afford the title compound (Wt: 0.78 g) as an off white solid. $^1$H NMR (300 MHz, CDCl$_3$): δ 0.79-0.93 (m, 8H), 0.93 (s, 6H), 1.07-1.26 (m, 10H), 1.29-1.56 (m, 12H), 1.69-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 2H), 8.45 (s, 1H), 10.50 (s, 1H); Mass: 780 [M+1]$^+$ 781 (100%); HPLC Purity: 90.5%.

Example 11

3,3-dimethyl-5-oxo-5-((1R,3aS,5aR,5bR,7aR,9S, 11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yloxy)pentanoic acid

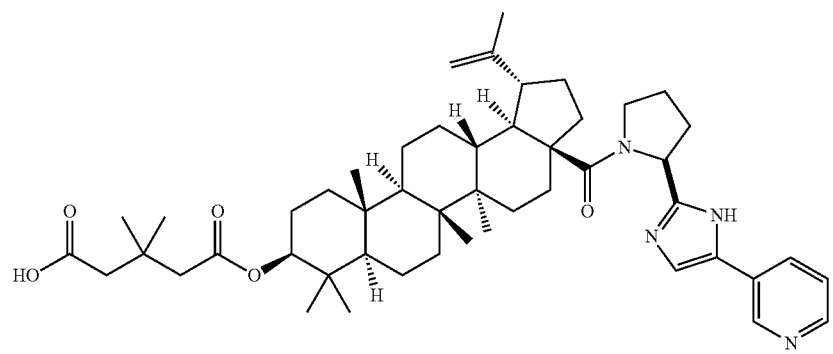 [SMILES: C=C(C)[C@@H]1CC[C@]2(C(=O)N3CCC[C@H]3c3ncc(-c4cccnc4)[nH]3)CC[C@]3(C)[C@H](CC[C@@H]4[C@@]5(C)CC[C@H](OC(=O)CC(C)(C)CC(=O)O)C(C)(C)[C@@H]5CC[C@]43C)[C@@H]12]

3,3-Dimethyl glutaric anhydride (1.39 g, 9.78 mmol) was added to a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((R)-2-(5-(pyridin-3-yl)-1H-imidazol-2-yl)pyrrolidin-1-yl)methanone (Example 10-step 6, 0.8 g, 1.22 mmol) and DMAP (0.2 g, 1.63 mmol) in Toluene (10 mL) at room temperature and refluxed for about 24 hours. After completion of the reaction (monitored by TLC), the reaction mixture was diluted with EtOAc, washed with water, 1N HCl, water, brine and dried over $Na_2SO_4$. The solvent was evaporated and purified by silicagel column (100-200 mesh, elution 20% EtOAc in hexane) to afford the title compound (Wt: 0.5 g) as an off white solid. $^1$H NMR (300 MHz, $CDCl_3$): δ 0.79-0.93 (m, 8H), 0.93 (s, 6H), 1.07-1.26 (m, 10H), 1.29-1.56 (m, 12H), 169-1.99 (m, 8H), 2.23-3.45 (m, 8H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 2H), 8.45 (s, 1H), 10.50 (s, 1H); Mass: 793 [M+1]$^+$ 794 (100%); HPLC Purity: 98.1%.

Example 12

2,2-dimethyl-4-oxo-4-((1R,3aS,5aR,5bR,7aR,9S,11aR,11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yloxy)butanoic acid mL, 11.69 mmol) at 0° C. and stirred at room temperature for about 12 hours. After completion of the reaction (monitored by TLC), the solvent was evaporated, the reaction mixture was diluted with ethyl acetate, washed with water, 1N HCl, water brine and dried over $Na_2SO_4$. The solvent was evaporated and purified by silicagel column (100-200 mesh, elution 15% EtOAc in hexane) to afford the title compound (Wt: 9 g) as an off white solid. $^1$H NMR (300 MHz, $CDCl_3$): δ 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 4.36-4.37 (m, 1H), 4.56 (s, 1H), 4.6 (s, 1H), 5.02-5.04 (m, 2H), 7.20-7.23 (m, 5H); Mass: 588 [M+1]$^+$ 589 (100%).

Step 2: synthesis of 1R,3aS,5aR,5bR,7aR,9S,11aR,11bR,13aR,13bR)-benzyl 9-acetoxy-5a,5b,8,8,11a-pentamethyl-1-(1-methylcyclopropyl)icosahydro-1H-cyclopenta[a]chrysene-3a-carboxylate

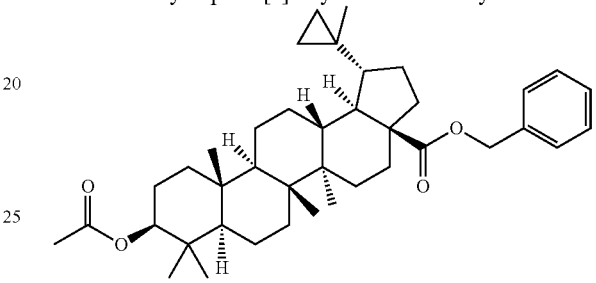

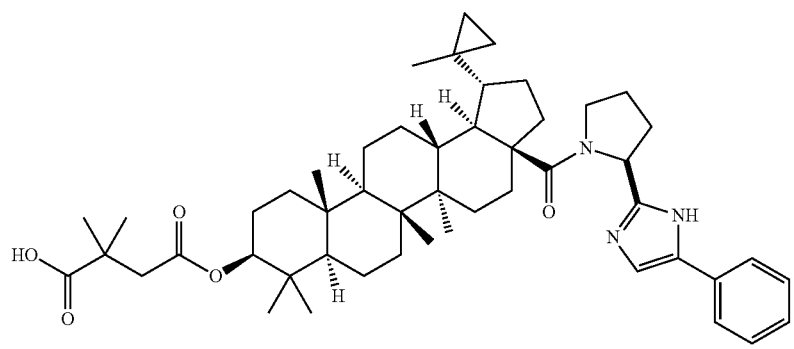 [SMILES: CC(C)(CC(=O)O[C@H]1CC[C@]2(C)[C@H]3CC[C@@H]4[C@H]5[C@H](C6(C)CC6)CC[C@]5(C(=O)N5CCC[C@H]5c5ncc(-c6ccccc6)[nH]5)CC[C@@]4(C)[C@]3(C)CC[C@H]2C1(C)C)C(=O)O]

Step 1: Synthesis of (1R,3aS,5aR,5bR,7aR,9S,11aR,11bR,13aR,13bR)-benzyl 9-acetoxy-5a,5b,8,8,11a-pentamethyl-1-(prop-1-en-2-yl)icosahydro-1H-cyclopenta[a]chrysene-3a-carboxylate To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-1H-cyclopenta[a]chrysene-3a-carboxylic acid (prepared as described in WO 2013/160810 A2, 7 g, 14.05 mmol) in DMF (60 mL) were added Potassium carbonate (3.9 g, 28.2 mmol) and benzyl bromide (2

To a stirred solution of 1R,3aS,5aR,5bR,7aR,9S,11aR,11bR,13aR,13bR)-benzyl 9-acetoxy-5a,5b,8,8,11a-pentamethyl-1-(prop-1-en-2-yl)icosahydro-1H-cyclopenta[a]chrysene-3a-carboxylate (step 1, 9 g, 15.30 mmol) in dry DCM (100 mL) was added diethyl zinc (40 mL, 234.1 mmol) at −20° C. and stirred for about one hour. Then added diiodomethane (5 mL, 18.7 mmol) at −20° C., stir for about one hour, then stirred at room temperature for about 12 hours. After completion of the reaction (monitored by TLC), the reaction mixture was quenched with saturated ammonium chloride, the reaction mixture was diluted with DCM, washed with water, 1N HCl, water brine and dried over $Na_2SO_4$. The solvent was evaporated and purified by silicagel column (100-200 mesh, elution 15% EtOAc in hexane to afford the title compound (Wt: 6.5 g) as an off white solid. $^1$H NMR (300 MHz, $CDCl_3$): δ 0.22-0.25 (m, 2H), 0.26-0.27 (m, 2H), 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 4.36-4.37 (m, 1H), 5.02-5.04 (m, 2H), 7.20-7.23 (m, 5H); Mass: 602[M+1]$^+$ 603 (100%).

Step 3: Synthesis of (1R,3aS,5aR,5bR,7aR,9S,11aR, 11bR,13aR,13bR)-9-acetoxy-5a,5b,8,8,11a-pentamethyl-1-(1-methylcyclopropyl)icosahydro-1H-cyclopenta[a]chrysene-3a-carboxylic acid

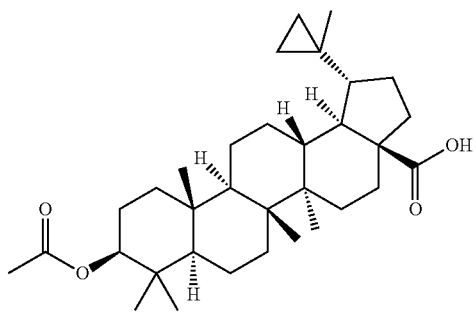 [SMILES: CC(=O)O[C@H]1CC[C@]2(C)[C@H]3CC[C@@H]4[C@H]5[C@H](C6(C)CC6)CC[C@]5(C(=O)O)CC[C@@]4(C)[C@]3(C)CC[C@H]2C1(C)C]

To a stirred solution of (1R,3aS,5aR,5bR,7aR,9S,11aR, 11bR,13aR,13bR)-benzyl 9-acetoxy-5a,5b,8,8,11a-pentamethyl-1-(1-methylcyclopropyl)icosahydro-1H-cyclopenta[a]chrysene-3a-carboxylate (step 2, 6.5 g, 10.7 mmol) in Ethyl acetate: Ethanol (300+200 mL) was added 10% pd/c (2 g) and stirred the reaction under hydrogen atmosphere (60 psi) for about 12 hours. After completion of the reaction (monitored by TLC), the reaction mixture was filtered, washed with ethanol. The solvent was evaporated and purified by silicagel column (100-200 mesh, elution 15% EtOAc in hexane to afford the title compound (Wt: 5.0 g) as an off white solid. $^1$H NMR (300 MHz, CDCl$_3$): δ 0.22-0.25 (m, 2H), 0.26-0.27 (m, 2H), 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 4.36-4.37 (m, 1H); Mass: 512 [M+1]$^+$ 513 (100%).

Step 4: Synthesis of (1R,3aS,5aR,5bR,7aR,9S,11aR, 11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl) icosahydro-1H-cyclopenta[a]chrysen-9-yl acetate

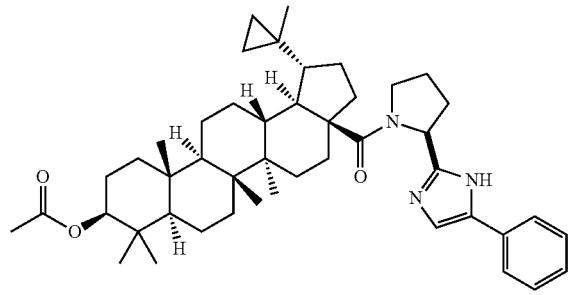 [SMILES: CC(=O)O[C@H]1CC[C@]2(C)[C@H]3CC[C@@H]4[C@H]5[C@H](C6(C)CC6)CC[C@]5(C(=O)N5CCC[C@H]5c5ncc(-c6ccccc6)[nH]5)CC[C@@]4(C)[C@]3(C)CC[C@H]2C1(C)C]

To a stirred solution of (1R,3aS,5aR,5bR,7aR,9S,11aR, 11bR,13aR,13bR)-9-acetoxy-5a,5b,8,8,11a-pentamethyl-1-(1-methylcyclopropyl)icosahydro-1H-cyclopenta[a]chrysene-3a-carboxylic acid (step 3, 4.0 g, 7.54 mmol) in DCM (30 mL) Oxolyl chloride (3 mL, 23.6 mmol) in DCM (50 mL) was added at 0° C. and stirred at room temperature for about 3 hours. After completion of the reaction (monitored by TLC), the solvent was evaporated under nitrogen atmosphere and dissolved in DCM (20 mL). The reaction mixture was added to the above stirred solution of (S)-5-phenyl-2-(pyrrolidin-2-yl)-1H-imidazole (Example 8-step 4, 1.6 g, 7.55 mmol) at 0° C. and allowed to stir at room temperature for about 16 hours. After completion of the reaction (monitored by TLC), the reaction mixture was diluted with DCM, washed with water, 1N HCl, brine solution and dried over Na$_2$SO$_4$. The solvent was evaporated and purified by silicagel column (100-200 mesh, elution 30% EtOAc in hexane) to afford the title compound (Wt: 3.2 g) as an off white solid. $^1$H NMR (300 MHz, CDCl$_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 707[M+1]$^+$ 708 (100%).

Step 5: Synthesis of ((1R,3aS,5aR,5bR,7aR,9S, 11aR,11bR,13aR,13bR)-9-hydroxy-5a,5b,8,8,11a-pentamethyl-1-(1-methylcyclopropyl)icosahydro-1H-cyclopenta[a]chrysen-3a-yl)((S)-2-(5-phenyl-1H-imidazol-2-yl)pyrrolidin-1-yl)methanone

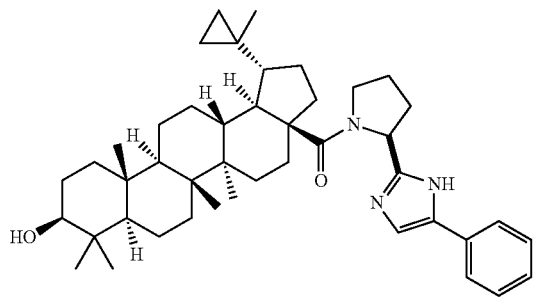 [SMILES: CC1([C@@H]2CC[C@]3(C(=O)N4CCC[C@H]4c4ncc(-c5ccccc5)[nH]4)CC[C@]4(C)[C@H](CC[C@@H]5[C@@]6(C)CC[C@H](O)C(C)(C)[C@@H]6CC[C@]54C)[C@@H]23)CC1]

To a stirred solution of (1R,3aS,5aR,5bR,7aR,9S,11aR, 11bR,13aR,13bR)-5a,5b,8,8,11a-pentamethyl-1-(1-methylcyclopropyl)-3a-((R)-2-(5-phenyl-1H-imidazol-2-yl)pyrrolidine-1-carbonyl)icosahydro-1H-cyclopenta[a]chrysen-9-yl acetate (step 4, 1.6 g, 2.26 mmol) in MeOH (20 mL) was added potassium carbonate (1.25 g, 9.05 mmol) at 0° C. and allowed to stir at room temperature for about 16 hours. After completion of the reaction (monitored by TLC), the volatile was evaporated and the aqueous layer was extracted with ethyl acetate. The organic layer was washed with water, brine and dried over Na$_2$SO$_4$, then the solvent was evaporated and the resulting crude was purified by silicagel column (100-200 mesh, elution 5% MeOH/DCM) to afford the title compound (Wt: 1.3 g) as an off white solid. $^1$H NMR (300 MHz, CDCl$_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 665 [M+1]$^+$ 666 (100%).

Step 6: Synthesis of 2,2-dimethyl-4-oxo-4-((1R, 3aS,5aR,5bR,7aR,9S,11aR,11bR,13aR,13bR)-5a,5b, 8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yloxy)butanoic acid 2,2-Dimethylsuccinic anhydride (0.53 g, 3.73 mmol) was added to a stirred solution of ((1R,3aS,5aR,5bR,7aR,9S, 11aR,11bR,13aR,13bR)-9-hydroxy-5a,5b,8,8,11a-pentamethyl-1-(1-methylcyclopropyl)icosahydro-1H-cyclopenta[a]chrysen-3a-yl)((R)-2-(5-phenyl-1H-imidazol-2-yl) pyrrolidin-1-yl)methanone (step 5, 0.5 g, 0.75 mmol) and DMAP (0.36 g, 2.95 mmol) in Toluene (30 mL) at room temperature and refluxed for about 24 hours. After completion of the reaction (monitored by TLC), the reaction mixture was diluted with EtOAc, washed with water, 1N HCl, water, brine and dried over Na$_2$SO$_4$. The solvent was evaporated and purified by silicagel column (100-200 mesh, elution 5% MeOH/DCM) to afford the title compound (Wt:

0.2 g) as an off white solid. $^1$H NMR (300 MHz, CDCl$_3$): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 793[M+1]$^+$ 794 (100%); HPLC Purity: 89.6%.

Example 13

Preparation of 33,3-dimethyl-5-oxo-5-((1R,3aS,5aR, 5bR,7aR,9S,11aR,11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl) icosahydro-1H-cyclopenta[a]chrysen-9-yloxy) pentanoic acid

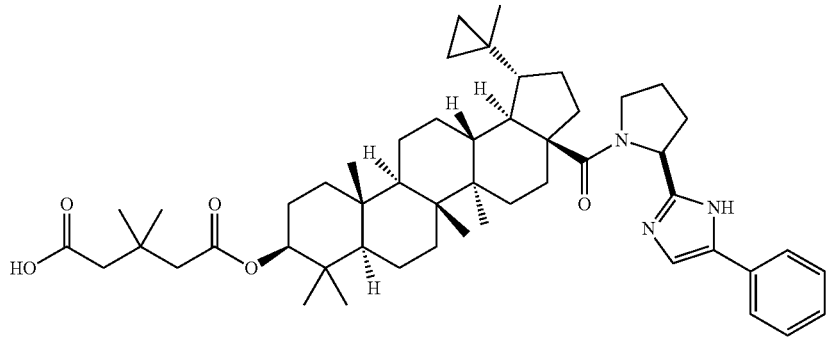 [SMILES: CC(C)(CC(=O)O)CC(=O)O[C@H]1CC[C@]2(C)[C@H]3CC[C@@H]4[C@H]5[C@H](C6(C)CC6)CC[C@]5(C(=O)N5CCC[C@H]5c5ncc(-c6ccccc6)[nH]5)CC[C@@]4(C)[C@]3(C)CC[C@H]2C1(C)C]

3,3-Dimethyl glutaric anhydride (0.85 g, 5.98 mmol) was added to a stirred solution of ((1R,3aS,5aR,5bR,7aR,9S, 11aR,11bR,13aR,13bR)-9-hydroxy-5a,5b,8,8,11a-pentamethyl-1-(1-methylcyclopropyl)icosahydro-1H-cyclopenta[a] chrysen-3a-yl)((R)-2-(5-phenyl-1H-imidazol-2-yl) pyrrolidin-1-yl)methanone (Example 12-step 5, 0.8 g, 1.20 mmol) and DMAP (0.6 g, 4.91 mmol) in pyridine (20 mL) at room temperature and refluxed for about 24 hours. After completion of the reaction (monitored by TLC), the reaction mixture was diluted with EtOAc, washed with water, 1N HCl, water, brine and dried over Na$_2$SO$_4$. The solvent was evaporated and purified by silicagel column (100-200 mesh, elution 5% MeOH/DCM) to afford the title compound (Wt: 0.5 g) as an off white solid. $^1$H NMR (300 MHz, CDCl$_3$): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.5 (s, 1H); Mass: 807[M+1]$^+$ 808 (100%); HPLC Purity: 96%.

Example 14

Preparation of (1R,3S)-2,2-dimethyl-3-((((1R,3aS, 5aR,5bR,7aR,9S,11aR,11bR,13aR,13bR)-5a,5b,8,8, 11a-pentamethyl-3a-((S)-2-(5-phenyl-1H-imidazol-2-yl)pyrrolidine-1-carbonyl)-1-(prop-1-en-2-yl) icosahydro-1H-cyclopenta[a]chrysen-9-yloxy) carbonyl)cyclobutanecarboxylic acid

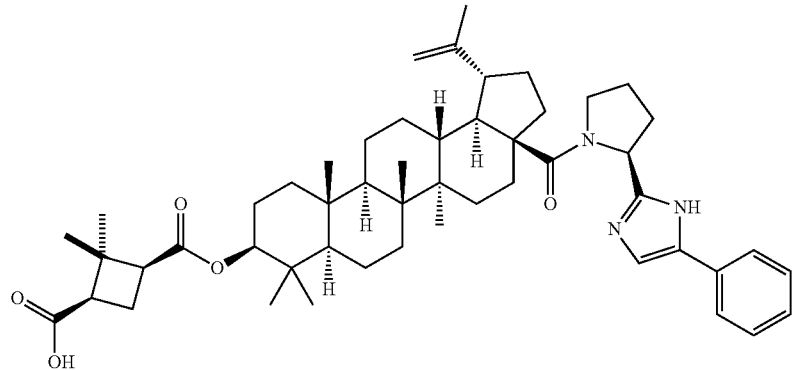

Step 1: Synthesis of (1S,3R)-3-(benzyloxycarbonyl)-2,2-dimethylcyclobutanecarboxylic 2,4,6-trichlorobenzoic anhydride

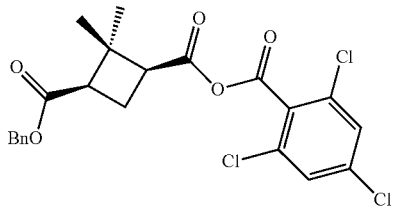

To a stirred solution of (1S,3R)-3-(benzyloxycarbonyl)-2,2-dimethylcyclobutanecarboxylic acid (0.37 g, 1.35 mmol, 1.0 eq) and DIPEA (0.86 g, 6.6 mmol, 3.0 eq) in THF (30 mL) at 0° C. was added 2,4,6-trichlorobenzoyl chloride (0.81 g, 3.33 mmol, 1.5 eq). The reaction mixture was allowed to stir at room temperature for about 4 hours. TLC indicated starting material was consumed and the desired product was observed. The reaction mixture was evaporated under reduced pressure obtained the crude and proceeded for next step without further purification.

Step 2: Synthesis of 1-benzyl 3-(1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl(1R,3S)-2,2-dimethylcyclobutane-1,3-dicarboxylate

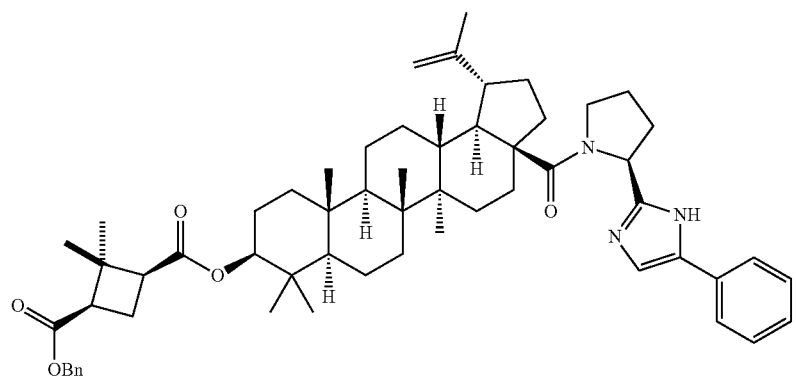

To a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)((S)-2-(5-phenyl-1H-imidazol-2-yl)pyrrolidin-1-yl)methanone (Example 8-step 6, 1.4 g, 2.24 mmol, 1.0 eq) in pyridine (50 mL) was added DMAP (0.54 g, 4.42 mmol, 2.0 eq) and (1S,3R)-3-(benzyloxycarbonyl)-2,2-dimethylcyclobutanecarboxylic 2,4,6-trichlorobenzoic anhydride (step 1, 1.6 g, 3.2 mmol). The reaction mixture was heated to 90° C. for overnight. TLC indicated starting material was consumed and the desired product was observed. The reaction mixture was evaporated under reduced pressure and diluted with water. The aqueous layer was extracted with CH$_2$Cl$_2$ (2×50 mL). The combined organic layers were dried over Na$_2$SO$_4$, filtered and evaporated under reduced pressure. The crude residue was purified by silicagel column chromatography by using 1.5% methanol: dichloromethane as an eluent to obtain the title compound (wt: 1.3 g) as a white solid. $^1$H NMR (300 MHz, CDCl$_3$): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.60 (m, 3H), 7.70-7.88 (m, 2H), 10.50 (s, 1H); Mass: 895 [M+1]$^+$ 896 (100%).

Step 3: Synthesis of (1R,3S)-2,2-dimethyl-3-((((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)carbonyl)cyclobutanecarboxylic acid To a solution of 1-benzyl 3-(1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl(1R,3S)-2,2-dimethylcyclobutane-1,3-dicarboxylate (step 2, 1.3 g, 1.45 mmol, 1.0 eq) in dichloromethane (30 mL) was added palladium (II) acetate (30 mg), triethyl amine (0.29 g, 2.87 mmol, 3.0 eq) and triethylsilane (0.56 g, 4.87 mmol, 3.0 eq). The mixture was flushed with N$_2$ and was heated to reflux for 48 hours. The reaction mixture was cooled to room temperature, filtered through a pad of celite and was washed with dichloromethane (50 mL). The filtrate was evaporated under reduced pressure, cooled to 0° C., diluted with water (10 mL), acidified to pH 5.0 with 1N HCl and extracted with CH$_2$Cl$_2$ (2×200 mL). The combined organic layers were dried over Na$_2$SO$_4$, filtered and evaporated under reduced pressure. The crude residue was purified by silicagel column chromatography by using 6% methanol: dichloromethane as an eluent gave the title compound (wt: 0.55 g) as a white solid. Mass: 805 [M+1]$^+$ 806 (100%); HPLC Purity: 92.6%.

Example 15

Preparation of (1R,3S)-3-(1R,3aS,5aR,5bR,7aR,9S,11aR,11bR,13aR,13bR)-3a-(2-(5-(4-methoxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethyl cyclobutane-1-carboxylic acid

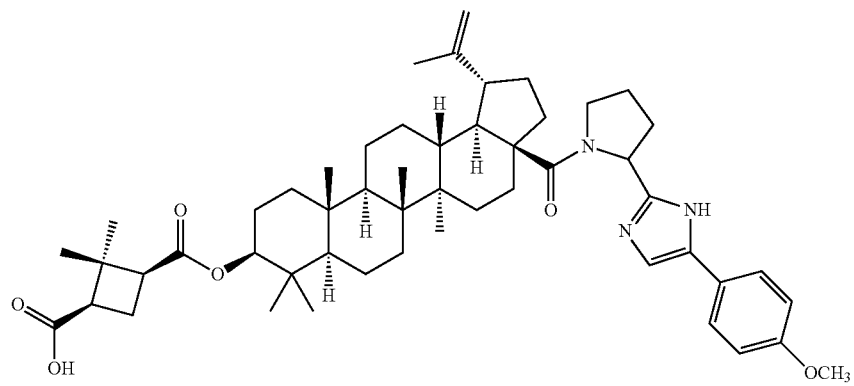

Step 1: Synthesis of (tert-butoxycarbonyl)-L-proline

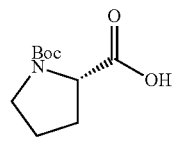

A solution of L-proline (30 g, 260.05 mmol) in 1,4-dioxane (240 mL) stirred at room temperature for 15 minutes. Then added saturated bicarbonate solution (66.4 g, 781.72 mmol, 3 eq), after stirring 10 minutes at room temperature then di-tert-butyl dicarbonate (69.5 mL, 312.69 mol) was added. The reaction mixture was stirred at room temperature for 12 hours. After completion of the reaction (monitored by TLC) the reaction mixture pH was adjusted to 2 to 3 by addition of 4N hydrochloric acid (Note: the temperature of reaction mixture should be 5-10° C.). The aqueous layer was extracted with dichloromethane combined organic layer was washed with water, dried over $Na_2SO_4$, filtered and solvent was evaporated under reduced pressure to provide a white solid (53 g, 94%).

Step 2: Synthesis of 1-(tert-butyl) 2-(2-(4-methoxyphenyl)-2-oxoethyl) (S)-pyrrolidine-1,2-dicarboxylate

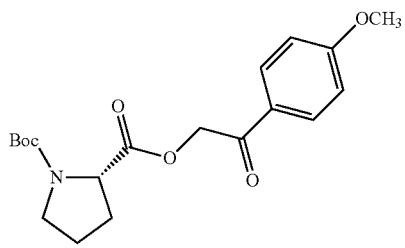 [SMILES: COc1ccc(C(=O)COC(=O)[C@@H]2CCCN2C(=O)OC(C)(C)C)cc1]

To a stirred solution of (tert-butoxycarbonyl)-L-proline (step 1, 5.0 g, 23.36 mmol) in DCM (75 mL), DIPEA (8.1 mL, 46.72 mmol, 1.0 eq) was added at 0° C. After 10 minutes 2-bromo-1-(4-methoxyphenyl)ethan-1-one (5.3 g, 23.36 mmol, 1.0 eq) was added and the reaction mixture was allowed to stir at room temperature for about 12 hours. After completion of the reaction (monitored by TLC), the reaction mixture was diluted with DCM and washed with water, saturated brine and the organic layer was concentrated under reduced pressure to afford the title compound (7.5 g, 89%). The crude product was used in the next step without further purification.

Step 3: Synthesis of tert-butyl (S)-2-(5-(4-methoxyphenyl)-1H-imidazol-2-yl)pyrrolidine-1-carboxylate

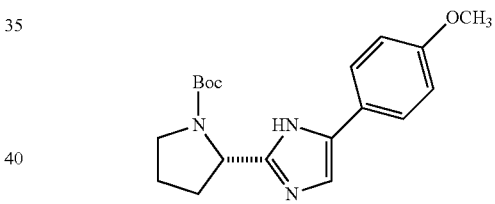

To a stirred solution of 1-(tert-butyl) 2-(2-(4-methoxyphenyl)-2-oxoethyl) (S)-pyrrolidine-1,2-dicarboxylate (step 2, 7.5 g, 20.71 mmol, 1.0 eq) in toluene (75 mL) and ammonium acetate (12.76 g, 165.74 mmol, 8.0 eq) was added at room temperature and refluxed for about 16 hours. After completion of the reaction (monitored by TLC), diluted with EtOAc and the organic layer was washed with 0.5 N hydrochloric acid. Aqueous layer was basified with 2N NaOH (pH 10-11) and extracted with ethyl acetate. The organic layer was washed with water, dried over $Na_2SO_4$, filtered and solvent was evaporated under reduced pressure to provide a light yellow solid was taken in to hexane stirred for one hour and filtered (4.0 g, yield 59.0%)

Step 4: Synthesis of (S)-5-(4-methoxyphenyl)-2-(pyrrolidin-2-yl)-1H-imidazole

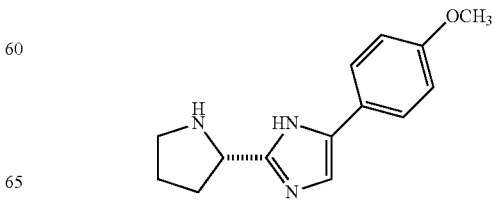

A solution of tert-butyl (S)-2-(5-(4-methoxyphenyl)-1H-imidazol-2-yl)pyrrolidine-1-carboxylate (step 3, 2.8 g, 8.4 mmol, 1.0 eq) in Dioxane in HCl (25 mL), stirred at room temperature for about 3 hours. After completion of the reaction, the solvent was evaporated and proceed for next step without further purification (1.8 g, 95.0%) as a semi solid.

Step 5: Synthesis of (1R,3aS,5aR,5bR,7aR,9S,11aR, 11bR,13aR,13bR)-3a-(2-(5-(4-methoxy phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl acetate

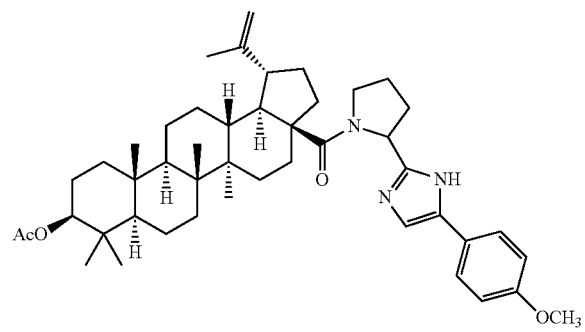

To a stirred solution of (S)-5-(4-methoxyphenyl)-2-(pyrrolidin-2-yl)-1H-imidazole (step 4, 1.87 g, 8.13 mmol, 2.1 eq) and triethylamine (2.6 mL, 19.37 mmol, 5.0 eq) in CH$_2$Cl$_2$ (30 mL) at 0° C. was added (1R,3aS,5aR,5bR,7aR, 9S,11aR,11bR,13aR,13bR)-3a-(chlorocarbonyl)-5a,5b,8,8, 11a-pentamethyl-1-(1-methylcyclopropyl)icosahydro-1H-cyclopenta[a]chrysen-9-yl acetate ((prepared as described in WO 2013/160810 A2, 2.0 g, 3.87 mmol, 1.0 eq) in CH$_2$Cl$_2$ (20 mL). The reaction mixture was allowed to stir at room temperature for overnight. The reaction mixture was diluted with water and extracted with CH$_2$Cl$_2$. The combined organic extracts were dried over Na$_2$SO$_4$, filtered and evaporated under reduced pressure. The residue was purified by column chromatography by using 5% ethylacetate and hexane as an eluent gave the desired product (2.0 g, 74.0%) as a semi solid. H$^1$ NMR (DMSO-D$_6$, 300 MHz): δ 11.48 (s, 1H), 7.64 (d, 2H), 7.28 (s, 1H), 6.88 (d, 2H), 5.06 (d, 1H), 4.54 (d, 2H), 4.25 (d, 1H), 3.74 (s, 4H), 3.63 (d, 1H), 3.41 (q, 1H), 2.96 (d, 1H), 2.77-2.63 (m, 2H), 2.36-2.12 (m, 4H), 1.99 (s, 3H), 1.86 (m, 1H), 1.57 (s, 6H), 1.42-1.31 (m, 9H), 1.11 (q, 4H), 0.91 (d, 11H), 0.79 (s, 4H) and 0.47 (q, 4H); Mass: [M]$^+$ 724.75 (100%).

Step 6: Synthesis of (1R,3aS,5aR,5bR,7aR,9S,11aR, 11bR,13aR,13bR)-9-hydroxy-5a,5b,8,8,11a-pentamethyl-1-(prop-1-en-2-yl)icosahydro-3aH-cyclopenta [a]chrysen-3a-yl)(2-(5-(4-methoxy phenyl)-1H-imidazol-2-yl)pyrrolidin-1-yl)methanone

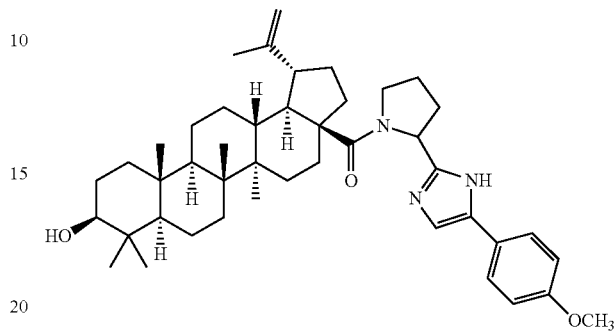

To a stirred solution of (1R,3aS,5aR,5bR,7aR,9S,11aR, 11bR,13aR,13bR)-3a-(2-(5-(4-methoxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a] chrysen-9-yl acetate (step 5, 2.0 g, 2.81 mmol, 1.0 eq) in THF (20 mL) and Methanol (20 mL) was added potassium carbonate (2.5 g, 19.69 mmol, 7.0 eq). The reaction mixture was stirred at room temperature for 48 hours. TLC indicated starting material was consumed and the desired product was observed. The reaction mixture was filtered through a pad of celite and washed with CH$_2$Cl$_2$. The filtrate was evaporated under reduced pressure and the crude was purified by column chromatography by using 5% methanol: dichloromethane as an eluent gave the desired product (1.7 g, 94.0%) as a white solid. H$^1$ NMR (CDCl$_3$, 300 MHz): δ 11.90 (s, 1H), 11.50 (s, 1H), 7.64 (d, 2H), 7.28 (s, 1H), 6.88 (d, 2H), 5.05 (d, 1H), 4.54 (d, 2H), 4.25 (d, 1H), 3.74 (s, 4H), 3.63 (d, 1H), 3.41 (q, 1H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 4H), 0.91 (d, 11H), 0.79 (s, 4H) and 0.47 (q, 4H); Mass: [M]$^+$ 682.63 (100%).

Step 7: Synthesis of 1-benzyl 3-((1R,3aS,5aR,5bR, 7aR,9S,11aR,11bR,13aR,13bR)-3a-(2-(5-(4-methoxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)(1R, 3S)-2,2-dimethylcyclobutane-1,3-dicarboxylate

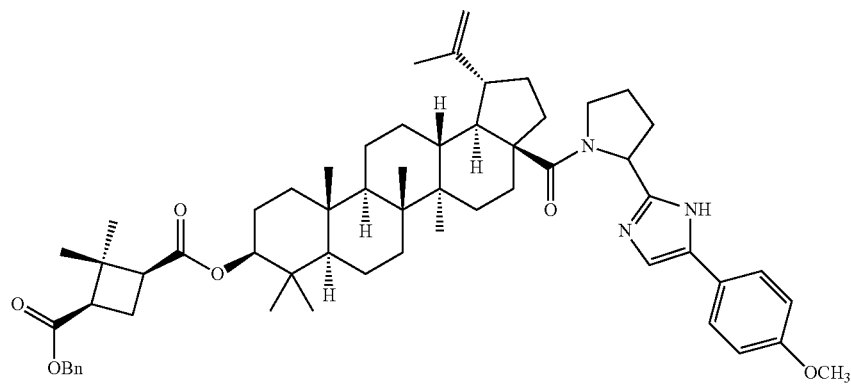

To a stirred solution of (1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)(2-(5-(4-methoxyphenyl)-1H-imidazol-2-yl)pyrrolidin-1-yl)methanone (step 6, 0.700 g, 1.04 mmol, 1.0 eq) in DCM (10 mL) was added (1S,3R)-3-(benzyloxy)carbonyl)-2,2-dimethylcyclobutane-1-carboxylic acid (prepared as described in WO 2013/160810 A2, 0.412 g, 1.56 mmol, 1.5 eq) in DCM (10 mL). This reaction mixture was cooled to 0° C. and added DCC (0.430 g, 2.09 mmol, 2.0 eq) followed by DMAP (0.025 g, 0.20 mmol, 0.2 eq). The reaction mixture was raised to room temperature stirred for overnight. TLC indicated starting material was consumed and the desired product was observed. The reaction mixture was evaporated under reduced pressure and diluted with water. The aqueous layer was extracted with $CH_2Cl_2$. The organic layer was washed with water and brine solution. The combined organic layers were dried over $Na_2SO_4$, filtered and evaporated under reduced pressure. The crude residue was purified by column chromatography by using 2% methanol: DCM as an eluent to obtain the desired product (0.500 g, 55.0% yield) as a white solid. $H^1$ NMR (DMSO-$d_6$, 300 MHz): –δ 11.48 (s, 1H), 7.64 (d, 2H), 7.36 (s, 5H), 7.28 (s, 1H), 6.88 (d, 2H), 5.10 (q, 3H), 4.55 (d, 2H), 4.33 (t, 1H), 3.76 (s, 3H), 3.60 (bs, 1H), 2.81-2.69 (m, 5H), 2.34-2.11 (m, 4H), 1.91-1.85 (m, 3H), 1.59-1.46 (m, 9H), 1.42-1.32 (m, 5H), 1.26 (s, 6H), 1.13 (d, 3H), 0.93-0.86 (m, 13H) and 0.80 (s, 10H); Mass: $[M]^+$ 926.78 (40%).

Step 8: Synthesis of (1R,3S)-3-(1R,3aS,5aR,5bR,7aR,9S,11aR,11bR,13aR,13bR)-3a-(2-(5-(4-methoxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid To a solution of 1-benzyl 3-(1R,3aS,5aR,5bR,7aR,9S,11aR,11bR,13aR,13bR)-3a-(2-(5-(4-methoxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)(1R,3S)-2,2-dimethylcyclobutane-1,3-dicarboxylate (step 7, 0.500 g, 0.54 mmol, 1.0 eq) in ethylacetate (10 mL) and methanol (2.5 mL) was added palladium carbon (0.03 g, 0.27 mmol, 0.5 eq). The reaction mixture was stirred in hydrogen atmosphere at room temperature for overnight. After completion of the reaction (monitored by TLC), the reaction mixture was filtered through a pad of celite and washed with MeOH and DCM. The filtrate was evaporated under reduced pressure, the crude residue was purified by column chromatography by using 5% methanol: DCM as an eluent gave the desired compound (0.086 g, 20%) as a white solid. $H^1$ NMR (DMSO-$d_6$, 300 MHz): δ 12.15 (bs, 1H), 11.48 (s, 1H), 7.64 (d, 2H), 7.28 (s, 1H), 6.88 (d, 2H), 5.04 (s, 1H), 4.55 (d, 2H), 4.33 (t, 1H), 3.76 (s, 3H), 3.60 (bs, 1H), 2.81-2.69 (m, 5H), 2.34-2.11 (m, 4H), 1.91-1.85 (m, 3H), 1.59-1.46 (m, 9H), 1.42-1.32 (m, 5H), 1.26 (s, 6H), 1.13 (d, 3H), 0.93-0.86 (m, 13H) and 0.80 (s, 10H); Mass: $[M]^+$ 836.68 (100%); HPLC: 90.30%.

Example 16

Preparation of (1R,3S)-2,2-dimethyl-3-((((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-4-yl)-1H-imidazol-2-yl) pyrrolidine-1-carbonyl)icosahydro-1H-cyclopenta[a]chrysen-9-yl)oxy)carbonyl)cyclobutane-1-carboxylic acid

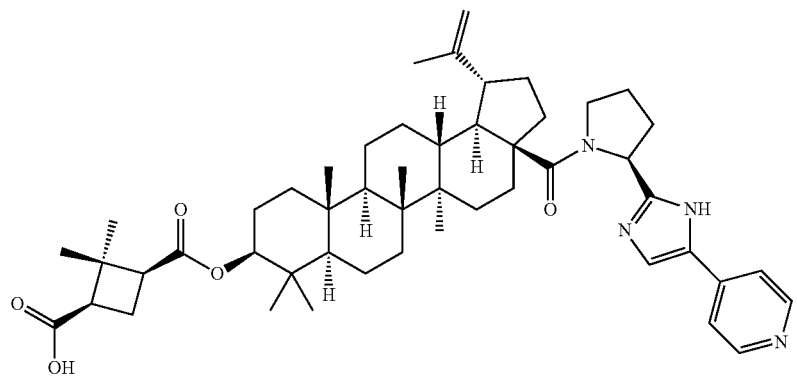

Step 1: Synthesis of 1-(tert-butyl) 2-(2-oxo-2-(pyridin-4-yl)ethyl) (S)-pyrrolidine-1,2-dicarboxylate

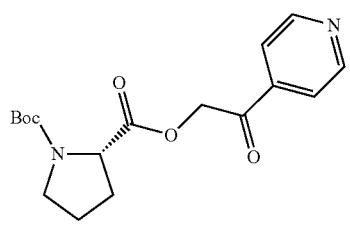 [SMILES: CC(C)(C)OC(=O)N1CCC[C@H]1C(=O)OCC(=O)c1ccncc1]

To a stirred solution of (tert-butoxycarbonyl)-L-proline (Example 15-step 1, 2.0 g, 9.3 mmol, 1.0 eq) in DCM (30 mL), DIPEA (3.2 mL, 18.69 mmol) was added at 0° C. After 10 minutes 2-bromo-1-(pyridin-4-yl)ethan-1-one (2.6 g, 9.3 mmol) was added and the reaction mixture was allowed to stir at room temperature for about 12 hours. After completion of the reaction (monitored by TLC), the reaction mixture was diluted with DCM, washed with water, saturated brine and the organic layer was concentrated under reduced pressure to afford the title compound (1.0 g, 32%). The crude product was used in the next step without further purification.

Step 2: Synthesis of tert-butyl (S)-2-(5-(pyridin-4-yl)-1H-imidazol-2-yl)pyrrolidine-1-carboxylate

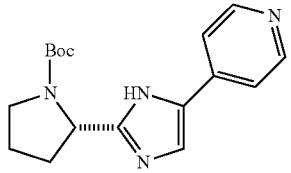 [SMILES: CC(C)(C)OC(=O)N1CCC[C@H]1c1ncc(-c2ccncc2)[nH]1]

To a stirred solution of 1-(tert-butyl) 2-(2-oxo-2-(pyridin-4-yl)ethyl) (S)-pyrrolidine-1,2-dicarboxylate (step 1, 4.0 g, 12.00 mmol) in toluene (30 mL), ammonium acetate (7.3 g, 96 mmol) was added at room temperature and refluxed for about 16 hours. After completion of the reaction (monitored by TLC), diluted with EtOAc and the organic layer was washed with 0.5 N hydrochloric acid. Aqueous layer was basified with 2N NaOH (pH 10-11) and extracted with ethyl acetate. The organic layer was washed with water, dried over $Na_2SO_4$, filtered and solvent was evaporated under reduced pressure to provide a light yellow solid. The solid was taken in to hexane, stirred for one hour and filtered to afford the title compound (2.0 g, yield 54%).

Step 3: Synthesis of (S)-4-(2-(pyrrolidin-2-yl)-1H-imidazol-5-yl)pyridine

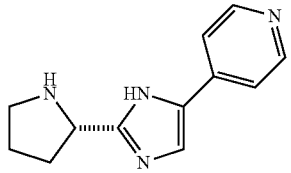 [SMILES: c1cc(-c2cnc([C@@H]3CCCN3)[nH]2)ccn1]

A solution of tert-butyl (S)-2-(5-(pyridin-4-yl)-1H-imidazol-2-yl)pyrrolidine-1-carboxylate (step 2, 1.2 g, 3.83 mmol) in Dioxane in HCl (20 mL) stirred at room temperature for about 3 hours. After completion of the reaction (monitored by TLC), the solvent was evaporated and proceed for next step without further purification.

Step 4: Synthesis of (1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-4-yl)-1H-imidazol-2-yl)pyrrolidine-1-carbonyl)icosahydro-1H-cyclopenta[a]chrysen-9-yl acetate

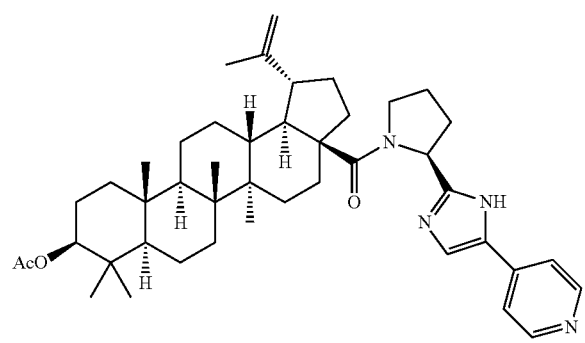

To a stirred solution of (S)-4-(2-(pyrrolidin-2-yl)-1H-imidazol-5-yl)pyridine (step 3, 0.82 g, 3.87 mmol, 2.0 eq) and triethylamine (1.3 mL, 9.65 mmol, 5.0 eq) in $CH_2Cl_2$ (15 mL) at 0° C. was added (1R,3aS,5aR,5bR,7aR,9S,11aR,11bR,13aR,13bR)-3a-(chlorocarbonyl)-5a,5b,8,8,11a-pentamethyl-1-(1-prop-1-en-2-yl)icosahydro-1H-cyclopenta[a]chrysen-9-yl acetate (prepared as described in WO 2013/160810 A2, 1.0 g, 1.93 mmol, 1.0 eq) in $CH_2Cl_2$ (15 mL). The reaction mixture was allowed to stir at room temperature for overnight. The reaction mixture was diluted with water and extracted with $CH_2Cl_2$. The combined organic extracts were dried over $Na_2SO_4$, filtered and evaporated under reduced pressure. The residue was purified by column chromatography by using 5% MeOH and DCM as an eluent gave the desired product (0.600 g, 46.0%) as a semi solid. $H^1$ NMR (DMSO-$D_6$, 300 MHz): δ 11.89 (s, 1H), 8.45 (d, 2H), 7.73 (s, 1H), 7.70 (d, 2H), 5.06 (d, 1H), 4.53 (d, 2H), 4.36 (d, 1H), 3.80 (s, 1H), 3.63 (d, 1H), 3.41 (q, 1H), 2.96 (d, 1H), 2.86 (s, 3H), 2.77-2.63 (m, 2H), 2.36-2.12 (m, 3H), 1.86 (m, 1H), 1.57 (s, 6H), 1.42-1.31 (m, 9H), 1.11 (q, 4H), 0.91 (d, 12H), 0.79 (s, 4H) and 0.47 (q, 4H); Mass: $[M]^+$ 695.54 (100%).

Step 5: Synthesis of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(5-(pyridin-4-yl)-1H-imidazol-2-yl)pyrrolidin-1-yl)methanone

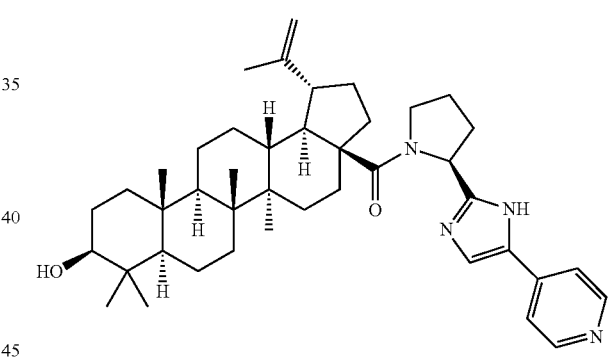

To a stirred solution of (1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-4-yl)-1H-imidazol-2-yl)pyrrolidine-1-carbonyl)icosahydro-1H-cyclopenta[a]chrysen-9-yl acetate (step 4, 0.600 g, 0.86 mmol, 1.0 eq) in THF (8 mL) and Methanol (8 mL) was added potassium carbonate (0.82 g, 6.06 mmol, 7.0 eq). The reaction mixture was stirred at room temperature for 48 hours. TLC indicated starting material was consumed and the desired product was observed. The reaction mixture was filtered through a pad of celite and washed with $CH_2Cl_2$. The filtrate was evaporated under reduced pressure and the crude was purified by column chromatography by using 6% MeOH and DCM as an eluent gave the desired product (0.500 g, 89.0%) as a white solid. $H^1$ NMR ($CDCl_3$, 300 MHz): δ 11.89 (s, 1H), 8.45 (d, 2H), 7.73 (s, 1H), 7.65 (d, 2H), 5.04 (d, 1H), 4.52 (d, 2H), 4.27 (d, 1H), 3.80 (s, 1H), 3.63 (d, 1H), 3.41 (q, 1H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 4H), 0.91 (d, 12H), 0.79 (s, 4H) and 0.47 (q, 4H); Mass: $[M]^+$ 653.49 (100%).

Step 6: Synthesis of (1S,3R)-3-((benzyloxy)carbonyl)-2,2-dimethylcyclobutane-1-carboxylic 2,4,6-trichlorobenzoic anhydride

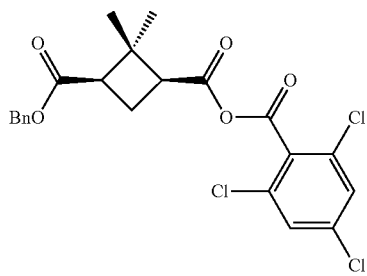

To a stirred solution of (1S,3R)-3-(benzyloxycarbonyl)-2,2-dimethyl cyclobutane carboxylic acid (prepared as described in WO 2013/160810 A2, 0.350 g, 1.33 mmol, 1.0 eq) and triethylamine (0.55 mL, 3.99 mmol, 3.0 eq) in THF (15 mL) at 0° C. was added 2,4,6-trichlorobenzoyl chloride (0.386 g, 1.6 mmol, 1.2 eq). The reaction mixture was allowed to stir at room temperature for 4 hours. TLC indicated starting material was consumed and the desired product was observed. The reaction mixture was evaporated under reduced pressure to obtain the crude compound (0.576 g, 90.0% yield) was used as such for next step.

Step 7: Synthesis of 1-benzyl 3-((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-4-yl)-1H-imidazol-2-yl)pyrrolidine-1-carbonyl) icosahydro-1H-cyclopenta[a]chrysen-9-yl)(1R,3S)-2,2-dimethylcyclobutane-1,3-dicarboxylate To a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(5-(pyridin-4-yl)-1H-imidazol-2-yl)pyrrolidin-1-yl)methanone (step 5, 0.400 g, 0.61 mmol, 1.0 eq) in toluene (20 mL) was added DMAP (0.14 g, 1.22 mmol, 2.0 eq) and ((1S,3R)-3-(benzyloxy)carbonyl)-2,2-dimethylcyclobutane-1-carboxylic 2,4,6-trichlorobenzoic anhydride (step 6, 0.576 g, 1.22 mmol, 2.0 eq). The reaction mixture was heated to 90° C. for overnight. TLC indicated starting material was consumed and the desired product was observed. The reaction mixture was evaporated under reduced pressure and diluted with water. The aqueous layer was extracted with $CH_2Cl_2$. The combined organic layers were dried over $Na_2SO_4$, filtered and evaporated under reduced pressure. The crude residue was purified by column chromatography by using 5% MeOH and DCM as an eluent to obtain desired product (0.300 g, 54.0% yield) as a white solid. $H^1$ NMR (DMSO-$d_6$, 300 MHz): –δ 11.90 (s, 1H), 8.46 (d, 2H), 7.73 (s, 1H), 7.68 (d, 2H), 7.35 (s, 5H), 5.13 (q, 3H), 4.54 (d, 2H), 4.45 (t, 1H), 3.81 (d, 1H), 3.64 (d, 1H), 2.81 (t, 3H), 2.63 (m, 2H), 2.41-2.15 (m, 4H), 1.91-1.83 (m, 3H), 1.58-1.46 (m, 8H), 1.42-1.32 (m, 5H), 1.26 (s, 6H), 1.13 (d, 3H), 0.93-0.86 (m, 13H) and 0.80 (s, 10H); Mass: $[M]^+$ 897.67 (100%).

Step 8: Synthesis of (1R,3S)-2,2-dimethyl-3-((((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-4-yl)-1H-imidazol-2-yl) pyrrolidine-1-carbonyl)icosahydro-1H-cyclopenta[a]chrysen-9-yl)oxy)carbonyl)cyclobutane-1-carboxylic acid To a solution of 1-benzyl 3-((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-4-yl)-1H-imidazol-2-yl)pyrrolidine-1-carbonyl)icosahydro-1H-cyclopenta[a]chrysen-9-yl)(1R,3S)-2,2-dimethylcyclobutane-1,3-dicarboxylate (step 7, 0.300 g, 0.33 mmol, 1.0 eq) in ethylacetate (30 mL) and MeOH. Then added ammoniumformate (0.10 g, 1.67 mmol, 5 eq) followed by palladium carbon (0.035 g, 0.32 mmol, 0.5 eq). The reaction mixture was stirred at room temperature for overnight. After completion of the reaction (monitored by TLC), the reaction mix-

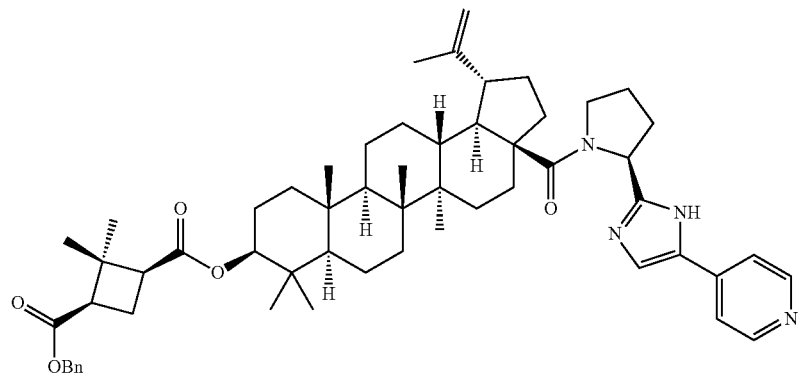

ture was filtered through a pad of celite and was washed with MeOH and DCM. The filtrate was evaporated under reduced pressure, the crude residue was purified by column chromatography by using 6% MeOH and DCM as an eluent gave the desired compound (0.085 g, 32%) as a white solid. $H^1$ NMR (DMSO-$d_6$, 300 MHz): δ 12.15 (bs, 1H), 11.90 (s, 1H), 8.45 (d, 2H), 7.72 (s, 1H), 7.65 (d, 2H), 5.05 (d, 1H), 4.53 (d, 2H), 4.32 (t, 1H), 3.79 (d, 1H), 3.60 (d, 1H), 2.81 (t, 3H), 2.63 (m, 2H), 2.41-2.15 (m, 4H), 1.91-1.83 (m, 3H), 1.58-1.46 (m, 8H), 1.42-1.32 (m, 5H), 1.26 (s, 6H), 1.13 (d, 3H), 0.93-0.86 (m, 13H) and 0.80 (s, 10H); Mass: $[M]^+$ 807.57 (40%); HPLC: 89.62%.

Example 17

Preparation of (1R,3S)-2,2-dimethyl-3-(1R,3aS,5aR,5bR,7aR,9S,11aR,11bR,13aR,13bR)-5a,5b,8,8,11a-pentamethyl-3a-(2-(5-(4-nitrophenyl)-1H-imidazol-2-yl)pyrrolidine-1-carbonyl)-1-(prop-1-en-2-yl)icosahydro-1H-cyclopenta[a]chrysen-9-yl)oxy)carbonyl) cyclobutane-1-carboxylic acid

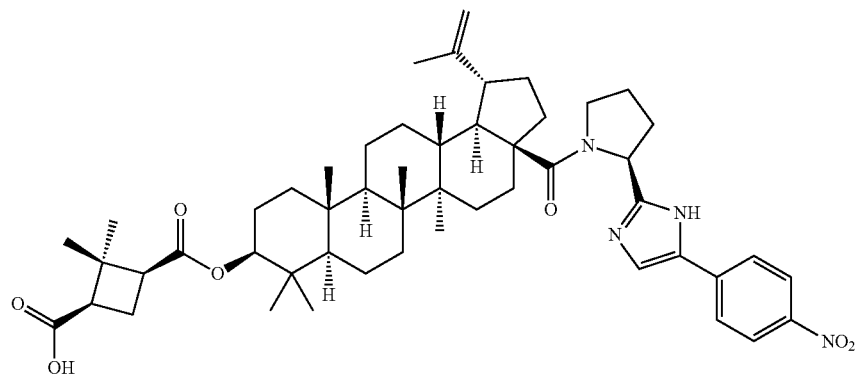

Step 1: Synthesis of 1-(tert-butyl) 2-(2-(4-nitrophenyl)-2-oxoethyl) (S)-pyrrolidine-1,2-dicarboxylate

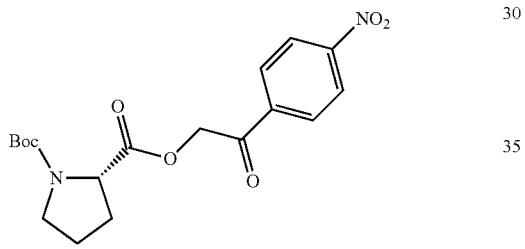

To a stirred solution of (tert-butoxycarbonyl)-L-proline (Example 15-step 1, 4.5 g, 21.0 mmol) in DCM (45 mL), DIPEA (6.98 mL, 42.0 mmol, 2.0 eq) was added at 0° C. After 10 minutes 2-bromo-1-(4-nitrophenyl)ethan-1-one (5.1 g, 21.0 mmol, 1.0 eq) was added and the reaction mixture was allowed to stir at room temperature for about 12 hours. After completion of the reaction (monitored by TLC), the reaction mixture was diluted with DCM, washed with water, saturated brine and the organic layer was concentrated under reduced pressure to afford the title compound (7.92 g, 100%). The crude product was used in the next step without further purification.

Step 2: Synthesis of tert-butyl (S)-2-(5-(4-nitrophenyl)-1H-imidazol-2-yl)pyrrolidine-1-carboxylate

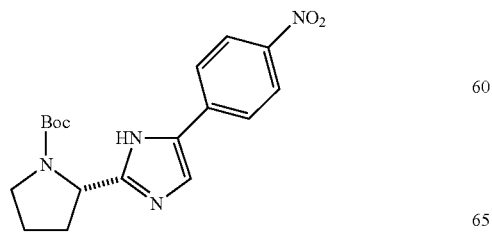

To a stirred solution of 1-(tert-butyl) 2-(2-(4-nitrophenyl)-2-oxoethyl) (S)-pyrrolidine-1,2-dicarboxylate (step 1, 7.92 g, 21.2 mmol) in toluene (80 mL), ammonium acetate (13.0 g, 169.6 mmol, 8 eq) was added at room temperature and refluxed for about 16 hours. After completion of the reaction (monitored by TLC), the reaction mixture was diluted with EtOAc and the organic layer was washed with 0.5 N hydrochloric acid. Aqueous layer was basified with 2N NaOH (pH 10-11) and extracted with ethyl acetate. The organic layer was washed with water, dried over Na$_2$SO$_4$, filtered and solvent was evaporated under reduced pressure to afford a light yellow solid. The solid was taken in to hexane stirred for one hour and filtered (5.3 g, 69.0%).

Step 3: Synthesis of (S)-5-(4-nitrophenyl)-2-(pyrrolidin-2-yl)-1H-imidazole

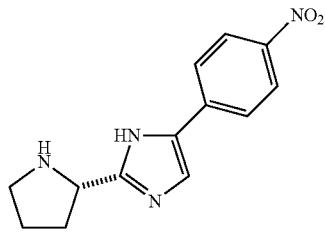 [SMILES: O=[N+]([O-])c1ccc(-c2cnc([C@@H]3CCCN3)[nH]2)cc1]

A solution of tert-butyl (S)-2-(5-(4-nitrophenyl)-1H-imidazol-2-yl)pyrrolidine-1-carboxylate (step 2, 1.0 g, 3.1 mmol) in Dioxane in HCl (20 mL) stirred at room temperature for about 3 hours. After completion of the reaction (monitored by TLC), the solvent was evaporated and proceed for next step without further purification.

Step 4: Synthesis of (1R,3aS,5aR,5bR,7aR,9S,11aR, 11bR,13aR,13bR)-5a,5b,8,8,11a-pentamethyl-3a-(2-(5-(4-nitrophenyl)-1H-imidazol-2-yl)pyrrolidine-1-carbonyl)-1-(prop-1-en-2-yl) icosahydro-1H-cyclopenta[a]chrysen-9-yl acetate Step 5: Synthesis of (1R,3aS,5aR,5bR,7aR,9S,11aR, 11bR,13aR,13bR)-9-hydroxy-5a,5b,8,8,11a-pentamethyl-1-(prop-1-en-2-yl)icosahydro-3aH-cyclopenta[a]chrysen-3a-yl)(2-(5-(4-nitrophenyl)-1H-imidazol-2-yl)pyrrolidin-1-yl)methanone

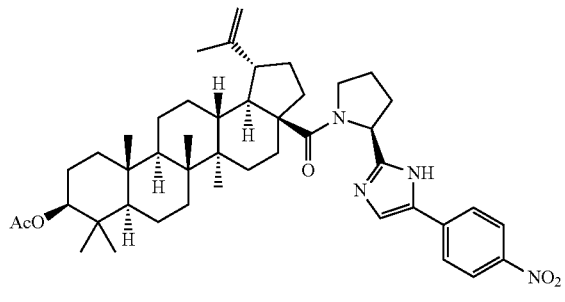

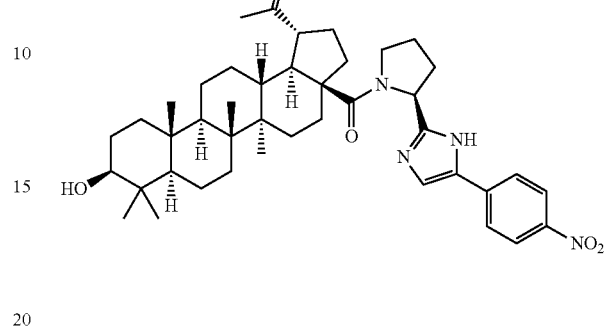

To a stirred solution of (S)-5-(4-nitrophenyl)-2-(pyrrolidin-2-yl)-1H-imidazole (step 3, 0.620 g, 2.07 mmol, 1 eq) and triethylamine (10.0 mL, 18.79 mmol, 5.0 eq) in $CH_2Cl_2$ (150 mL) at 0° C. was added (1R,3aS,5aR,5bR,7aR,9S, 11aR,11bR,13aR,13bR)-3a-(chlorocarbonyl)-5a,5b,8,8,11a-pentamethyl-1-(1-methylcyclopropyl)icosahydro-1H-cyclopenta[a]chrysen-9-yl acetate (prepared as described in WO 2013/160810 A2, 1.5 g, 2.07 mmol, 1.0 eq) in $CH_2Cl_2$ (10 mL). The reaction mixture was allowed to stir at room temperature for overnight. After completion of the reaction (monitored by TLC), the reaction mixture was diluted with water and extracted with $CH_2Cl_2$. The combined organic extracts were dried over $Na_2SO_4$, filtered and evaporated under reduced pressure. The residue was purified by column chromatography by using 40% ethylacetate and hexane as an eluent gave the desired product (1.1 g, 52.0%) as a solid. $H^1$ NMR (DMSO-$D_6$, 300 MHz): δ 11.97 (s, 1H), 8.20 (d, 2H), 7.97 (d, 2H), 7.79 (s, 1H), 5.07 (d, 1H), 4.52 (d, 2H), 4.27 (d, 1H), 3.80 (s, 1H), 3.63 (d, 1H), 3.41 (q, 1H), 2.96 (d, 1H), 2.86 (s, 3H), 2.77-2.63 (m, 2H), 2.36-2.12 (m, 3H), 1.86 (m, 1H), 1.57 (s, 6H), 1.42-1.31 (m, 9H), 1.11 (q, 4H), 0.91 (d, 12H), 0.79 (s, 4H) and 0.47 (q, 4H); Mass: [M]⁺ 739.59 (30%).

To a stirred solution of (1R,3aS,5aR,5bR,7aR,9S,11aR, 11bR,13aR,13bR)-5a,5b,8,8,11a-pentamethyl-3a-(2-(5-(4-nitrophenyl)-1H-imidazol-2-yl)pyrrolidine-1-carbonyl)-1-(prop-1-en-2-yl)icosahydro-1H-cyclopenta[a]chrysen-9-yl acetate (step 4, 1.1 g, 1.52 mmol, 1.0 eq) in THF (15 mL) and Methanol (15 mL), was added potassium carbonate (1.47 g, 10.06 mmol, 7.0 eq). The reaction mixture was stirred at room temperature for 48 hours. TLC indicated starting material was consumed and the desired product was observed. The reaction mixture was filtered through a pad of celite and washed with $CH_2Cl_2$. The filtrate was evaporated under reduced pressure, the crude was purified by column chromatography by using 40% ethylacetate and hexane as an eluent gave the desired product (0.650 g, 67.0%) as a white solid. $H^1$ NMR (CDCl₃, 300 MHz): δ 11.97 (s, 1H), 8.20 (d, 2H), 7.97 (d, 2H), 7.79 (s, 1H), 5.07 (d, 1H), 4.52 (d, 2H), 4.27 (d, 1H), 3.80 (s, 1H), 3.63 (d, 1H), 3.41 (q, 1H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 4H), 0.91 (d, 12H), 0.79 (s, 4H) and 0.47 (q, 4H); Mass: [M]⁺ 697.37 (100%).

Step 6: Synthesis of 1-benzyl 3-((1R,3aS,5aR,5bR, 7aR,9S,11aR,11bR,13aR,13bR)-5a,5b,8,8,11a-pentamethyl-3a-(2-(5-(4-nitrophenyl)-1H-imidazol-2-yl) pyrrolidine-1-carbonyl)-1-(prop-1-en-2-yl) icosahydro-1H-cyclopenta[a]chrysen-9-yl)(1R,3S)-2, 2-dimethylcyclobutane-1,3-dicarboxylate

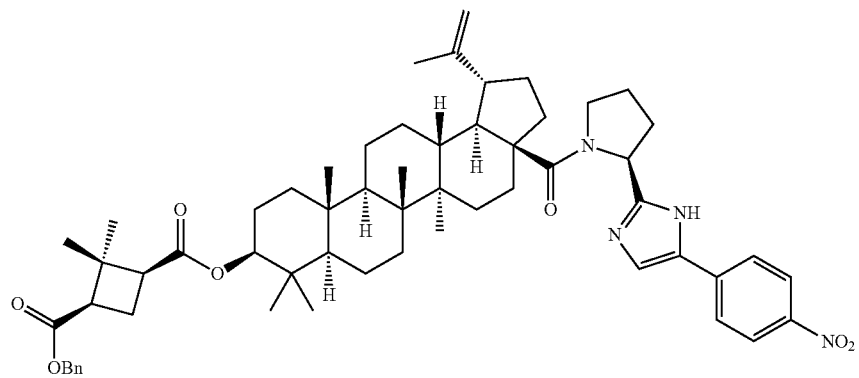

To a stirred solution of (1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)(2-(5-(4-methoxyphenyl)-1H-imidazol-2-yl)pyrrolidin-1-yl)methanone (step 5, 0.650 g, 0.93 mmol, 1.0 eq) in DCM (20 mL), then added (1S,3R)-3-(benzyloxy)carbonyl)-2,2-dimethylcyclobutane-1-carboxylic acid (prepared as described in WO 2013/160810 A2, 0.367 g, 1.39 mmol, 1.5 eq). This reaction mixture was cooled to 0° C. and then added DCC (0.383 g, 1.86 mmol, 2.0 eq) followed by DMAP (0.022 g, 0.18 mmol, 0.2 eq). The reaction mixture was raised to room temperature stirred for overnight. TLC indicated starting material was consumed and the desired product was observed. The reaction mixture was evaporated under reduced pressure and diluted with water. The aqueous layer was extracted with $CH_2Cl_2$. The organic layer was washed with water and brine solution. The combined organic layers were dried over $Na_2SO_4$, filtered and evaporated under reduced pressure. The crude residue was purified by column chromatography by using 5% methanol: DCM as an eluent to obtain the desired product (0.380 g, 43.0% yield) as a white solid. $H^1$ NMR (DMSO-$d_6$, 300 MHz): –δ 11.97 (s, 1H), 8.20 (d, 2H), 7.97 (d, 2H), 7.79 (s, 1H), 7.34 (s, 5H), 5.09 (q, 3H), 4.53 (d, 2H), 4.35 (t, 1H), 3.81 (d, 1H), 3.64 (d, 1H), 2.81 (t, 3H), 2.63 (m, 2H), 2.41-2.15 (m, 4H), 1.91-1.83 (m, 3H), 1.58-1.46 (m, 8H), 1.42-1.32 (m, 5H), 1.26 (s, 6H), 1.13 (d, 3H), 0.93-0.86 (m, 13H) and 0.80 (s, 10H); Mass: $[M]^+$ 941.67 (100%).

Step 7: Synthesis of (1R,3S)-2,2-dimethyl-3-(1R,3aS,5aR,5bR,7aR,9S,11aR,11bR,13aR,13bR)-5a,5b,8,8,11a-pentamethyl-3a-(2-(5-(4-nitrophenyl)-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid To a solution of 1-benzyl 3-(1R,3aS,5aR,5bR,7aR,9S,11aR,11bR,13aR,13bR)-5a,5b,8,8,11a-pentamethyl-3a-(2-(5-(4-nitrophenyl)-1H-imidazol-2-yl)pyrrolidine-1-carbonyl)-1-(prop-1-en-2-yl)icosahydro-1H-cyclopenta[a]chrysen-9-yl)(1R,3S)-2,2-dimethylcyclobutane-1,3-dicarboxylate (step 6, 0.600 g, 0.74 mmol, 1.0 eq) in ethylacetate (14 mL) was added palladium carbon (0.06 g, 0.5 mmol, 0.5 eq). The reaction mixture was stirred in hydrogen atmosphere at room temperature for overnight. After completion of the reaction (monitored by TLC), the reaction mixture was filtered through a pad of celite and was washed with MeOH and DCM. The filtrate was evaporated under reduced pressure, the crude residue was purified by column chromatography by using 0.5% methanol: DCM as an eluent gave the desired compound (0.025 g, 4.5%) as a white solid. $H^1$ NMR (DMSO-$d_6$, 300 MHz): δ 12.15 (bs, 1H), 11.97 (s, 1H), 8.20 (d, 2H), 7.97 (d, 2H), 7.79 (s, 1H), 5.07 (d, 1H), 4.53 (d, 2H), 4.35 (t, 1H), 3.81 (d, 1H), 3.64 (d, 1H), 2.81 (t, 3H), 2.63 (m, 2H), 2.41-2.15 (m, 4H), 1.91-1.83 (m, 3H), 1.58-1.46 (m, 8H), 1.42-1.32 (m, 5H), 1.26 (s, 6H), 1.13 (d, 3H), 0.93-0.86 (m, 13H) and 0.80 (s, 10H); Mass: $[M]^+$ 852.57 (40%); HPLC: 90.13%.

Example 18

Preparation of (1R,3S)-2,2-dimethyl-3-(1R,3aS,5aR,5bR,7aR,9S,11aR,11bR,13aR,13bR)-5a, 5b,8,8,11a-pentamethyl-1-(prop-1-en-2-yl)-3a-(2-(5-(p-tolyl)-1H-imidazol-2-yl)pyrrolidine-1-carbonyl)icosahydro-1H-cyclopenta[a]chrysen-9-yl)oxy)carbonyl)cyclobutane-1-carboxylic acid

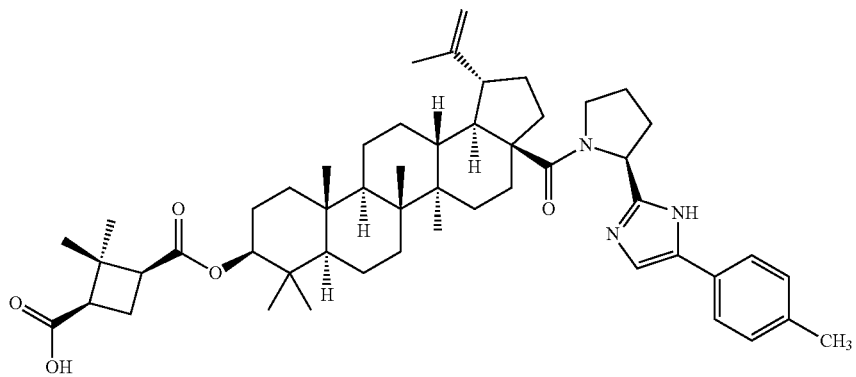

Step 1: Synthesis of 1-(tert-butyl) 2-(2-oxo-2-(p-tolyl)ethyl) (S)-pyrrolidine-1,2-dicarboxylate

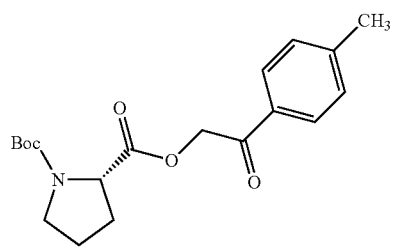

To a stirred solution of (tert-butoxycarbonyl)-L-proline (Example 15-step 1, 5.0 g, 23.36 mmol) in DCM (50), DIPEA (8.05 mL, 46.72 mmol) was added at 0° C. After 10 minutes 2-bromo-1-(p-tolyl)ethan-1-one (5.02 g, 23.36 mmol) was added and the reaction mixture was allowed to stir at room temperature for about 12 hours. After completion of the reaction (monitored by TLC), the reaction mixture was diluted with DCM, washed with water, saturated brine and the organic layer was concentrated under reduced pressure to afford the title compound (8.0 g, 98%). The crude product was used in the next step without further purification.

Step 2: Synthesis of tert-butyl (S)-2-(5-(p-tolyl)-1H-imidazol-2-yl)pyrrolidine-1-carboxylate

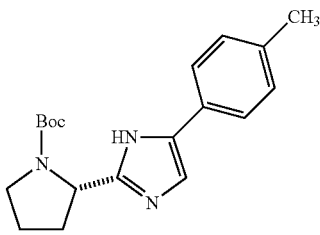 [SMILES: Cc1ccc(-c2cnc([C@@H]3CCCN3C(=O)OC(C)(C)C)[nH]2)cc1]

To a stirred solution of 1-(tert-butyl) 2-(2-oxo-2-(p-tolyl) ethyl) (S)-pyrrolidine-1,2-dicarboxylate (step 1, 8.0 g, 22.92 mmol) in toluene (8 mL), ammonium acetate (14.12 g, 183.38 mmol) was added at room temperature and refluxed for about 16 hours. After completion of the reaction (monitored by TLC), the reaction mixture was diluted with EtOAc and the organic layer was washed with 0.5 N hydrochloric acid. Aqueous layer was basified with 2N NaOH (pH 10-11) and extracted with ethyl acetate. The organic layer was washed with water, dried over $Na_2SO_4$, filtered and solvent was evaporated under reduced pressure to obtain the title compound (5.2 g, 69.4%) as a solid.

Step 3: Synthesis of (S)-2-(pyrrolidin-2-yl)-5-(p-tolyl)-1H-imidazole

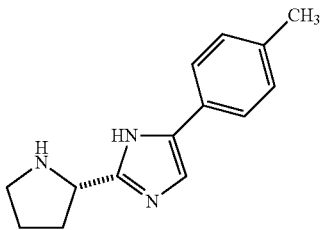 [SMILES: Cc1ccc(-c2cnc([C@@H]3CCCN3)[nH]2)cc1]

A solution of tert-butyl (S)-2-(5-(p-tolyl)-1H-imidazol-2-yl)pyrrolidine-1-carboxylate (step 2, 2.6 g, 7.95 mmol) in Dioxane. HCl (20 mL) stirred at room temperature for about 3 hours. After completion of the reaction (monitored by TLC) solvent was evaporated, crude was dissolved in DCM and proceeds for next step without further purification (0.8 g, 63.0%).

Step 4: Synthesis (1R,3aS,5aR,5bR,7aR,9S,11aR, 11bR,13aR,13bR)-5a,5b,8,8,11a-pentamethyl-1-(prop-1-en-2-yl)-3a-(2-(5-(p-tolyl)-1H-imidazol-2-yl)pyrrolidine-1-carbonyl)icosahydro-1H-cyclopenta[a]chrysen-9-yl acetate

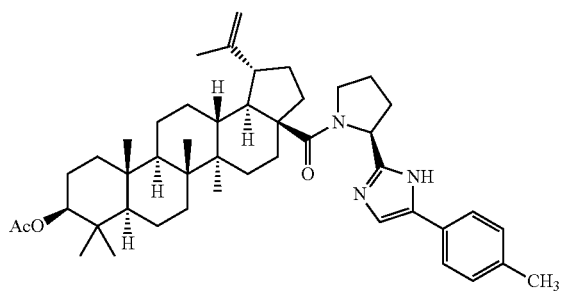

To a stirred solution of (S)-2-(pyrrolidin-2-yl)-5-(p-tolyl)-1H-imidazole (step 3, 0.79 g, 3.48 mmol, 1.5 eq) and triethylamine (1.61 mL, 11.62 mmol, 5.0 eq) in $CH_2Cl_2$ (12 mL) at 0° C. was added (1R,3aS,5aR,5bR,7aR,9S,11aR, 11bR,13aR,13bR)-3a-(chlorocarbonyl)-5a,5b,8,8,11a-pentamethyl-1-(1-methylcyclopropyl)icosahydro-1H-cyclopenta[a]chrysen-9-yl acetate (prepared as described in WO 2013/160810 A2, 1.2 g, 2.32 mmol, 1.0 eq) in DCM (12 mL). The reaction mixture was allowed to stir at room temperature for overnight. After completion of the reaction (monitored by TLC), the reaction mixture was diluted with water and extracted with $CH_2Cl_2$. The combined organic extracts were dried over $Na_2SO_4$, filtered and evaporated under reduced pressure. The residue was purified by column chromatography by using 15% ethylacetate and hexane as an eluent gave the desired product (0.9 g, 56.0%) as a solid. $H^1$ NMR (DMSO-$D_6$, 300 MHz): δ 11.53 (s, 1H), 7.61 (d, 2H), 7.35 (s, 1H), 7.11 (d, 2H), 5.06 (d, 1H), 4.54 (d, 2H), 4.36 (d, 1H), 3.77 (d, 1H), 3.60 (d, 1H), 3.00 (q, 1H), 2.07 (s, 3H), 2.27 (s, 3H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 5H), 0.91 (d, 10H), 0.79 (s, 4H) and 0.47 (q, 4H); Mass: $[M]^+$ 708.75 (100%).

Step 5: Synthesis of ((1R,3aS,5aR,5bR,7aR,9S, 11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)(2-(5-(p-tolyl)-1H-imidazol-2-yl)pyrrolidin-1-yl)methanone

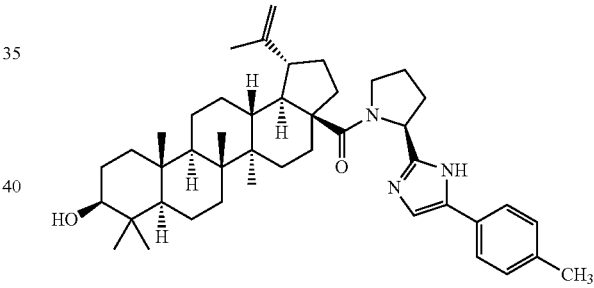

To a stirred solution of (1R,3aS,5aR,5bR,7aR,9S,11aR, 11bR,13aR,13bR)-5a,5b,8,8,11a-pentamethyl-1-(prop-1-en-2-yl)-3a-(2-(5-(p-tolyl)-1H-imidazol-2-yl)pyrrolidine-1-carbonyl) icosahydro-1H-cyclopenta[a]chrysen-9-yl acetate (step 4, 0.9 g, 1.27 mmol, 1.0 eq) in THF (10 mL) and Methanol (10 mL) was added potassium carbonate (1.75 g, 12.72 mmol, 10.0 eq). The reaction mixture was stirred at room temperature for 48 hours. TLC indicated starting material was consumed and the desired product was observed. The reaction mixture was filtered through a pad of celite and washed with $CH_2Cl_2$. The filtrate was evaporated under reduced pressure and the crude was purified by column chromatography by using 2% MeOH and DCM as an eluent gave the desired product (0.55 g, 65.0%) as a white solid. $H^1$ NMR (CDCl$_3$, 300 MHz): δ 11.53 (s, 1H), 7.58 (d, 2H), 7.36 (s, 1H), 7.13 (d, 2H), 5.06 (d, 1H), 4.54 (d, 2H), 4.27 (d, 1H), 3.77 (d, 1H), 3.60 (d, 1H), 3.00 (q, 1H), 2.27 (s, 3H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 5H), 0.91 (d, 11H), 0.79 (s, 4H) and 0.47 (q, 4H); Mass: $[M]^+$ 666.60 (100%).

Step 6: Synthesis of 1-benzyl 3-((1R,3aS,5aR,5bR, 7aR,9S,11aR,11bR,13aR,13bR)-5a,5b,8,8,11a-pentamethyl-1-(prop-1-en-2-yl)-3a-(2-(5-(p-tolyl)-1H-imidazol-2-yl)pyrrolidine-1-carbonyl) icosahydro-1H-cyclopenta[a]chrysen-9-yl) (1R,3S)-2,2-dimethylcyclobutane-1,3-dicarboxylate

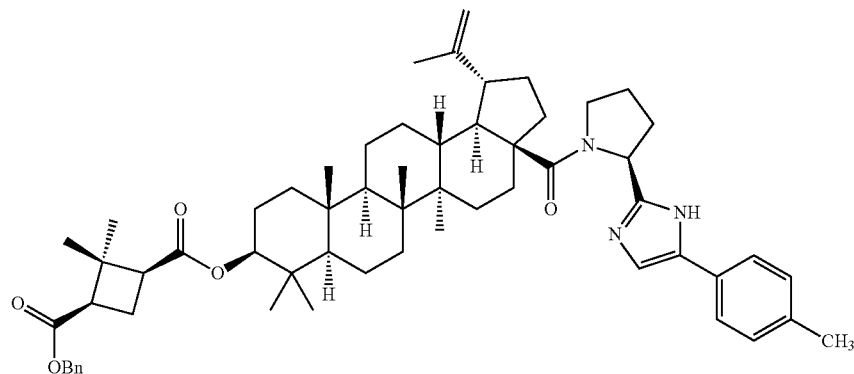

To a stirred solution of (1R,3aS,5aR,5bR,7aR,9S,11aR, 11bR,13aR,13bR)-9-hydroxy-5a,5b,8,8,11a-pentamethyl-1-(prop-1-en-2-yl)icosahydro-3aH-cyclopenta[a]chrysen-3a-yl)(2-(5-(p-tolyl)-1H-imidazol-2-yl)pyrrolidin-1-yl) methanone (step 5, 0.550 g, 0.82 mmol, 1.0 eq) in DCM (15 mL), added (1S,3R)-3-(benzyloxy)carbonyl)-2,2-dimethyl-cyclobutane-1-carboxylic acid (prepared as described in WO 2013/160810 A2, 0.33 g, 1.24 mmol, 1.5 eq). This reaction mixture was cooled to 0° C. and then added DCC (0.34 g, 1.65 mmol, 2.0 eq) followed by DMAP (0.020 g, 0.16 mmol, 0.2 eq). The reaction mixture was raised to room temperature stirred for overnight. TLC indicated starting material was consumed and the desired product was observed. The reaction mixture was evaporated under reduced pressure and diluted with water. The aqueous layer was extracted with $CH_2Cl_2$. The organic layer was washed with water and brine solution. The combined organic layers were dried over $Na_2SO_4$, filtered and evaporated under reduced pressure. The crude residue was purified by column chromatography by using 2% MeOH and DCM as an eluent to obtain (0.500 g, 73.0% yield) as a white solid. $H^1$ NMR (DMSO-$d_6$, 300 MHz): −δ 11.48 (s, 1H), 7.61 (d, 2H), 7.36 (s, 5H), 7.28 (s, 1H), 6.88 (d, 2H), 5.14 (q, 4H), 4.55 (d, 2H), 4.33 (t, 1H), 3.76 (s, 3H), 3.60 (bs, 1H), 2.81-2.69 (m, 5H), 2.37-2.18 (m, 6H), 1.91-1.85 (m, 3H), 1.59-1.46 (m, 9H), 1.42-1.32 (m, 5H), 1.26 (s, 6H), 1.13 (d, 3H), 0.93-0.86 (m, 10H) and 0.80 (s, 10H); Mass: [M]$^+$ 910.60 (20%).

Step 7: Synthesis of (1R,3S)-2,2-dimethyl-3-(1R, 3aS,5aR,5bR,7aR,9S,11aR,11bR,13aR,13bR)-5a,5b, 8,8,11a-pentamethyl-1-(prop-1-en-2-yl)-3a-(2-(5-(p-tolyl)-1H-imidazol-2-yl)pyrrolidine-1-carbonyl) icosahydro-1H-cyclopenta[a]chrysen-9-yl)oxy) carbonyl)cyclobutane-1-carboxylic acid To a solution of 1-benzyl 3-((1R,3aS,5aR,5bR,7aR,9S, 11aR,11bR,13aR,13bR)-5a,5b,8,8,11a-pentamethyl-1-(prop-1-en-2-yl)-3a-(2-(5-(p-tolyl)-1H-imidazol-2-yl)pyrrolidine-1-carbonyl)icosahydro-1H-cyclopenta[a]chrysen-9-yl)(1R,3S)-2,2-dimethylcyclobutane-1,3-dicarboxylate (step 6, 0.500 g, 0.54 mmol, 1.0 eq) in ethylacetate (10 mL) was added palladium carbon (0.120 g, 1.09 mmol, 2 eq). The reaction mixture was stirred in hydrogen atmosphere at room temperature for overnight. After completion of the reaction (monitored by TLC), the reaction mixture was filtered through a pad of celite and was washed with MeOH and DCM. The filtrate was evaporated under reduced pressure, the crude residue was purified by column chromatography by using 3% MeOH and DCM as an eluent gave the desired compound (0.130 g, 29%) as a white solid. $H^1$ NMR (DMSO-$d_6$, 300 MHz): δ 12.16 (bs, 1H), 11.53 (s, 1H), 7.61 (d, 2H), 7.35 (s, 1H), 7.11 (d, 2H), 5.05 (s, 1H), 4.54 (d, 2H), 4.33 (t, 1H), 3.77 (s, 3H), 3.59 (bs, 1H), 2.81-2.72 (m, 3H), 2.27 (m, 5H), 2.12 (m, 2H), 1.91-1.85 (m, 3H), 1.59-1.46 (m, 8H), 1.42-1.32 (m, 8H), 1.26 (s, 5H), 1.15 (d, 4H), 0.93-0.87 (m, 10H) and 0.80 (s, 12H); Mass: [M]$^+$ 820.59 (100%); HPLC: 91.32%.

Example 19

Preparation of (1R,3S)-3-(1R,3aS,5aR,5bR,7aR,9S,11aR,11bR,13aR,13bR)-3a-(2-(5-(4-cyano phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid

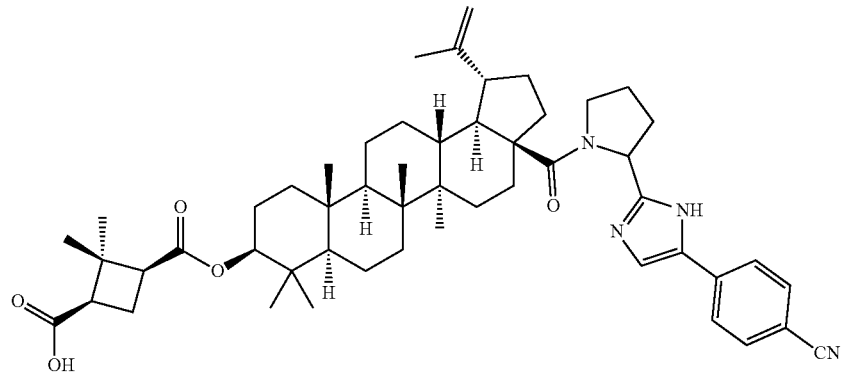

Step 1: Synthesis of 1-(tert-butyl) 2-(2-(4-cyanophenyl)-2-oxoethyl) (S)-pyrrolidine-1,2-dicarboxylate

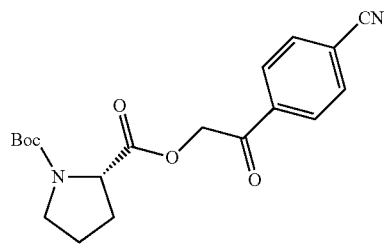 [SMILES: CC(C)(C)OC(=O)N1CCC[C@H]1C(=O)OCC(=O)c1ccc(C#N)cc1]

To a stirred solution of (tert-butoxycarbonyl)-L-proline (Example 15-step 1, 5.0 g, 23.36 mmol, 1.0 eq) in DCM (50 mL), DIPEA (6.2 mL, 46.60 mmol, 2.0 eq) was added at 0° C. After 10 minutes 4-(2-bromoacetyl)benzonitrile (5.2 g, 23.36 mmol, 1.0 eq) was added and the reaction mixture was allowed to stir at room temperature for about 12 hours. After completion of the reaction (monitored by TLC), the reaction mixture was diluted with DCM, washed with water, saturated brine and the organic layer was concentrated under reduced pressure to afford the title compound (8.0 g, 97%). The crude product was used in the next step without further purification.

Step 2: Synthesis of tert-butyl (S)-2-(5-(4-cyanophenyl)-1H-imidazol-2-yl)pyrrolidine-1-carboxylate

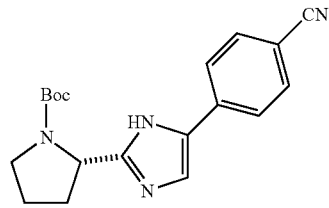

To a stirred solution of 1-(tert-butyl) 2-(2-(4-cyanophenyl)-2-oxoethyl) (S)-pyrrolidine-1,2-dicarboxylate (step 1, 8.0 g, 22.4 mmol, 1 eq) in toluene (19.0 mL), ammonium acetate (14.0 g, 179.2 mmol, 8 eq) was added at room temperature and refluxed for about 16 hours. After completion of the reaction (monitored by TLC), the reaction mixture was diluted with EtOAc and the organic layer was washed with 0.5 N hydrochloric acid. Aqueous layer was basified with 2N NaOH (pH 10-11) and extracted with ethyl acetate. The organic layer was washed with water, dried over Na₂SO₄, filtered and solvent was evaporated under reduced pressure to provide a white solid was taken in to hexane stirred for one hour and filtered (6.0 g, yield 80%).

Step 3: Synthesis of (S)-4-(2-(pyrrolidin-2-yl)-1H-imidazol-5-yl)benzonitrile

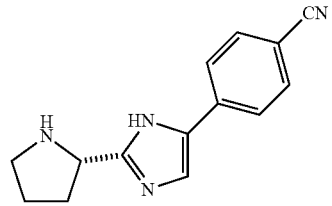

A solution of tert-butyl (S)-2-(5-(4-cyanophenyl)-1H-imidazol-2-yl)pyrrolidine-1-carboxylate (step 2, 2.0 g, 5.9 mmol) in Dioxane. HCl (20 mL) stirred at room temperature for about 3 hours. After completion of the reaction (monitored by TLC), the solvent was evaporated, crude was dissolved in DCM and proceeds for next step without further purification.

Step 4: Synthesis of (1R,3aS,5aR,5bR,7aR,9S,11aR,11bR,13aR,13bR)-3a-(2-(5-(4-cyanophenyl)-1H-imidazol-2-yl)pyrrolidine-1-carbonyl)-5a,5b,8,8,11a-pentamethyl-1-(prop-1-en-2-yl) icosahydro-1H-cyclopenta[a]chrysen-9-yl acetate

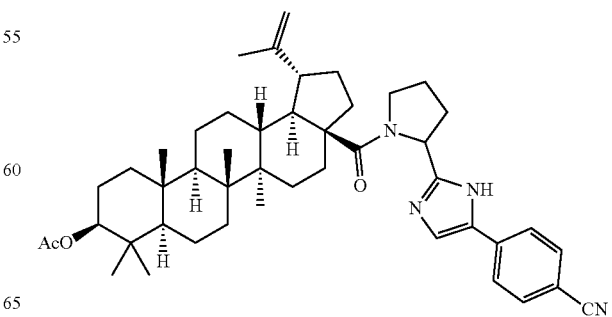

To a stirred solution of (S)-4-(2-(pyrrolidin-2-yl)-1H-imidazol-5-yl)benzonitrile (step 3, 1.4 g, 6.0 mmol, 2.0 eq) and triethylamine (5.0 mL, 18.79 mmol, 5.0 eq) in CH$_2$Cl$_2$ (20 mL) at 0° C. was added (1R,3aS,5aR,5bR,7aR,9S,11aR,11bR,13aR,13bR)-3a-(chlorocarbonyl)-5a,5b,8,8,11a-pentamethyl-1-(1-methylcyclopropyl)icosahydro-1H-cyclopenta[a]chrysen-9-yl acetate (prepared as described in WO 2013/160810 A2, 1.5 g, 3.0 mmol, 1.0 eq) in CH$_2$Cl$_2$ (20 mL). The reaction mixture was allowed to stir at room temperature for overnight. After completion of the reaction (monitored by TLC), the reaction mixture was diluted with water and extracted with CH$_2$Cl$_2$. The combined organic extracts were dried over Na$_2$SO$_4$, filtered and evaporated under reduced pressure. The residue was purified by column chromatography by using 20% ethylacetate: hexane as an eluent gave the desired product (1.1 g, 55.0%) as a semi solid. H$^1$ NMR (DMSO-D$_6$, 300 MHz): δ 11.89 (s, 1H), 7.90 (d, 2H), 7.76 (d, 2H), 7.70 (s, 1H), 5.06 (d, 1H), 4.53 (d, 2H), 4.27 (d, 1H), 3.80 (s, 1H), 3.63 (d, 1H), 3.41 (q, 1H), 2.96 (d, 1H), 2.77-2.63 (m, 2H), 2.36-2.12 (m, 4H), 1.99 (s, 3H), 1.86 (m, 1H), 1.57 (s, 5H), 1.42-1.31 (m, 9H), 1.11 (q, 4H), 0.91 (d, 12H), 0.79 (s, 4H) and 0.47 (q, 4H); Mass: [M]$^+$ 719.56 (60%).

2-yl)pyrrolidine-1-carbonyl)-5a,5b,8,8,11a-pentamethyl-1-(prop-1-en-2-yl)icosahydro-1H-cyclopenta[a]chrysen-9-yl acetate (step 4, 1.1 g, 1.5 mmol, 1.0 eq) in THF (8.8 mL) and Methanol (8.8 mL) was added potassium carbonate (2.1 g, 15.03 mmol, 7.0 eq). The reaction mixture was stirred at room temperature for 48 hours. TLC indicated starting material was consumed and the desired product was observed. The reaction mixture was filtered through a pad of celite and washed with CH$_2$Cl$_2$. The filtrate was evaporated under reduced pressure and the crude was purified by column chromatography by using 25% ethylacetate and hexane as an eluent gave the desired product (0.910 g, 91.0%) as a white solid. H$^1$ NMR (CDCl$_3$, 300 MHz): δ 11.88 (s, 1H), 7.90 (d, 2H), 7.76 (d, 2H), 7.36 (s, 1H), 5.07 (q, 1H), 4.53 (d, 2H), 4.27 (d, 1H), 3.80 (s, 1H), 3.63 (d, 1H), 3.41 (q, 1H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 4H), 0.91 (d, 12H), 0.79 (s, 4H) and 0.47 (q, 4H); Mass: [M]$^+$ 677.51 (50%).

Step 6: Synthesis of 1-benzyl 3-(1R,3aS,5aR,5bR,7aR,9S,11aR,11bR,13aR,13bR)-3a-(2-(5-(4-cyanophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)(1R,3S)-2,2-dimethylcyclobutane-1,3-dicarboxylate

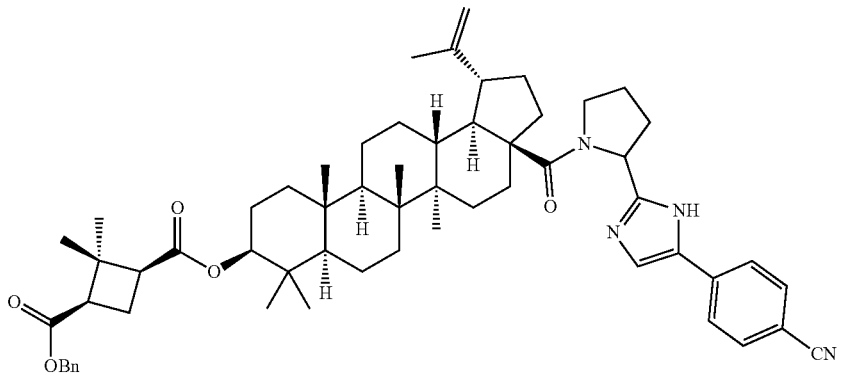

Step 5: Synthesis of 4-(2-(1-(1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl) pyrrolidin-2-yl)-1H-imidazol-5-yl)benzonitrile

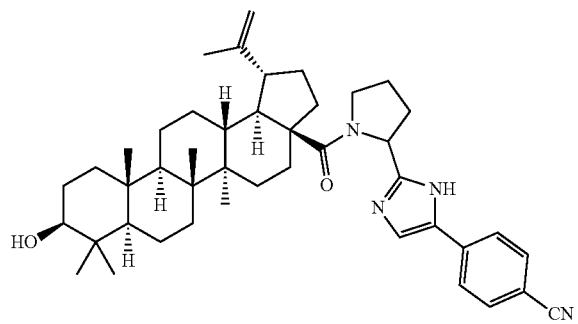

To a stirred solution of (1R,3aS,5aR,5bR,7aR,9S,11aR,11bR,13aR,13bR)-3a-(2-(5-(4-cyanophenyl)-1H-imidazol- To a stirred solution of 4-(2-(1-(1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysene-3a-carbonyl)pyrrolidin-2-yl)-1H-imidazol-5-yl)benzonitrile (step 5, 0.900 g, 1.36 mmol, 1.0 eq) in DCM (10 mL) then added (1S,3R)-3-((benzyloxy)carbonyl)-2,2-dimethylcyclobutane-1-carboxylic acid (prepared as described in WO 2013/160810 A2, 0.530 g, 1.7 mmol, 1.5 eq). This reaction mixture was cooled to 0° C. then added DCC (0.560 g, 2.3 mmol, 2.0 eq) followed by DMAP (0.033 g, 0.27 mmol, 0.2 eq). The reaction mixture was raised to room temperature and stirred for overnight. TLC indicated starting material was consumed and the desired product was observed. The reaction mixture was evaporated under reduced pressure and diluted with water. The aqueous layer was extracted with CH$_2$Cl$_2$. The organic layer was washed with water and brine solution. The combined organic layers were dried over Na$_2$SO$_4$, filtered and evaporated under reduced pressure. The crude residue was purified by column chromatography by using 20% ethylacetate and hexane as an eluent to obtain the desired product (0.700 g, 59.0% yield) as a white solid. H$^1$ NMR (DMSO-d$_6$, 300 MHz): −δ 11.88 (s, 1H), 7.90 (d, 2H), 7.76 (d, 2H), 7.70 (s, 1H), 7.36 (d, 5H), 5.09 (q, 3H), 4.53 (d, 2H), 4.35 (t, 1H), 3.81 (d, 1H), 3.64 (d, 1H), 2.81 (t, 3H), 2.63 (m, 2H), 2.41-2.15 (m, 4H), 1.91-1.83 (m, 3H), 1.58-1.46 (m, 8H), 1.42-1.32 (m, 5H), 1.26 (s, 6H), 1.13 (d, 3H), 0.93-0.86 (m, 13H) and 0.80 (s, 10H); Mass: [M]$^+$921.66 (30%).

Step 7: Synthesis of (1R,3S)-3-(1R,3aS,5aR,5bR, 7aR,9S,11aR,11bR,13aR,13bR)-3a-(2-(5-(4-cyanophenyl)-1H-imidazol-2-yl)pyrrolidine-1-carbonyl)-5a,5b,8,8,11a-pentamethyl-1-(prop-1-en-2-yl) icosahydro-1H-cyclopenta[a]chrysen-9-yl)oxy) carbonyl)-2,2-dimethylcyclobutane-1-carboxylic acid To a solution of 1-benzyl 3-(1R,3aS,5aR,5bR,7aR,9S, 11aR,11bR,13aR,13bR)-3a-(2-(5-(4-cyanophenyl)-1H-imidazol-2-yl)pyrrolidine-1-carbonyl)-5a,5b,8,8,11a-pentamethyl-1-(prop-1-en-2-yl)icosahydro-1H-cyclopenta[a] chrysen-9-yl)(1R,3S)-2,2-dimethylcyclobutane-1,3-dicarboxylate (step 6, 0.300 g, 0.92 mmol, 1.0 eq) in ethylacetate (20 mL) added palladium carbon (0.022 g, 0.2 mmol, 0.6 eq) and ammonium formate (0.102 g, 1.6 mmol, 5 eq). The reaction mixture was stirred at room temperature, for overnight. TLC indicated starting material was consumed and the desired product was observed. The reaction mixture was filtered through a pad of celite and was washed with MeOH and DCM. The filtrate was evaporated under reduced pressure, the crude residue was purified by column chromatography by using 0.3% methanol: DCM as an eluent gave the desired compound (0.120 g, 44%) as a white solid. H$^1$ NMR (DMSO-d$_6$, 300 MHz): δ 12.15 (bs, 1H), 11.53 (s, 1H), 7.61 (d, 2H), 7.35 (s, 1H), 7.11 (d, 2H), 5.04 (s, 1H), 4.54 (d, 2H), 4.33 (t, 1H), 3.78 (s, 1H), 3.60 (d, 1H), 2.81-2.65 (m, 5H), 2.41-2.15 (m, 4H), 1.91-1.83 (m, 3H), 1.58-1.46 (m, 8H), 1.42-1.32 (m, 5H), 1.26 (s, 6H), 1.13 (d, 3H), 0.93-0.86 (m, 13H) and 0.80 (s, 10H); Mass: [M]$^+$ 831.50 (40%); HPLC: 89.19%.

Example 20

Preparation of 2,2-dimethyl-5-oxo-5-(((1R,3aS,5aR, 5bR,7aR,9S,11aR,11bR,13aR,13bR)-5a,5b,8,8,11a-pentamethyl-3a-((S)-2-(5-phenyl-1H-imidazol-2-yl) pyrrolidine-1-carbonyl)-1-(prop-1-en-2-yl) icosahydro-1H-cyclopenta[a]chrysen-9-yl)oxy) pentanoic acid

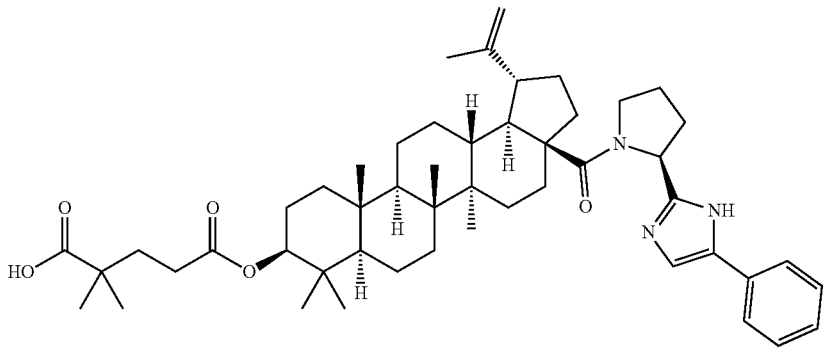

To a stirred solution of ((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(5-phenyl-1H-imidazol-2-yl)pyrrolidin-1-yl) methanone (Example 8-step 6, 0.4 g, 0.63 mmol, 1.0 eq) in Toluene (4 mL) was added 2,2-dimethyl glutaric anhydride (0.36 g, 2.52 mmol, 4 eq), DMAP (0.154 g, 1.26 mmol, 2 eq) and reaction mixture was refluxed for 12 hours. TLC indicated starting material was consumed and the desired product was observed. The reaction mixture was concentrated under reduced pressure, cooled to 0° C., acidified to pH=6-7 with 1N HCl and extracted with CH$_2$Cl$_2$. The combined organic extracts were washed with water, brine and dried over Na$_2$SO$_4$, filtered and evaporated under reduced pressure. The crude residue was purified by silicagel column chromatography by using 60% EtOAc: n-Hexane as an eluent gave the desired product (0.105 g, 20% yield) as an orange color solid. $^1$H NMR (300 MHz, DMSO): δ12.18 (s, 1H), 11.59 (s, 1H), 7.73-7.68 (m, 2H), 7.39 (s, 1H), 7.33-7.28 (m, 2H), 7.18-7.09 (m, 1H), 5.07 (bs, 1H), 4.55 (s, 1H), 4.47 (s, 1H), 4.38-4.34 (m, 1H), 3.82-3.73 (m, 1H), 3.66-3.58 (m, 1H), 2.88-2.63 (m, 3H), 2.38-2.05 (m, 7H), 1.92-1.81 (m, 3H), 1.78-1.68 (m, 3H), 1.68-1.03 (m, 20H), 0.98-0.73 (m, 21H); ES Mass: [M+1]$^+$ 794.64; HPLC purity: 94%.

Example 21

Preparation of (1R,3S)-3-(((((1 S,3aS,5aR,5bR,7aR, 9S,11aR,11bR,13aR,13bR)-1-isopropyl-5a,5b,8,8, 11a-pentamethyl-3a-((S)-2-(5-phenyl-1H-imidazol-2-yl)pyrrolidine-1-carbonyl)icosahydro-1H-cyclopenta[a]chrysen-9-yl)oxy)carbonyl)-2,2-dimethylcyclobutane-1-carboxylic acid

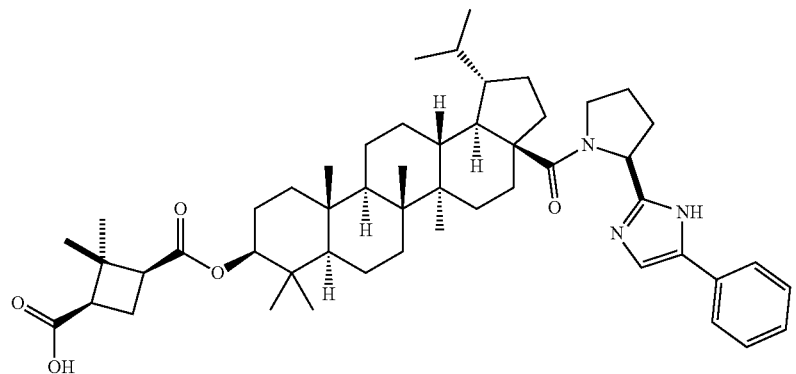

Step 1: Synthesis of (1 S,3aS,5aR,5bR,7aR,9S, 11aR,11bR,13aR,13bR)-9-acetoxy-1-isopropyl-5a, 5b,8,8,11a-penta methylicosahydro-3aH-cyclopenta[a]chrysene-3a-carboxylic acid Step 2: Synthesis of (1 S,3aS,5aR,5bR,7aR,9S, 11aR,11bR,13aR,13bR)-1-isopropyl-5a,5b,8,8,11a-pentamethyl-3a-((S)-2-(5-phenyl-1H-imidazol-2-yl) pyrrolidine-1-carbonyl) icosahydro-1H-cyclopenta[a]chrysen-9-yl acetate

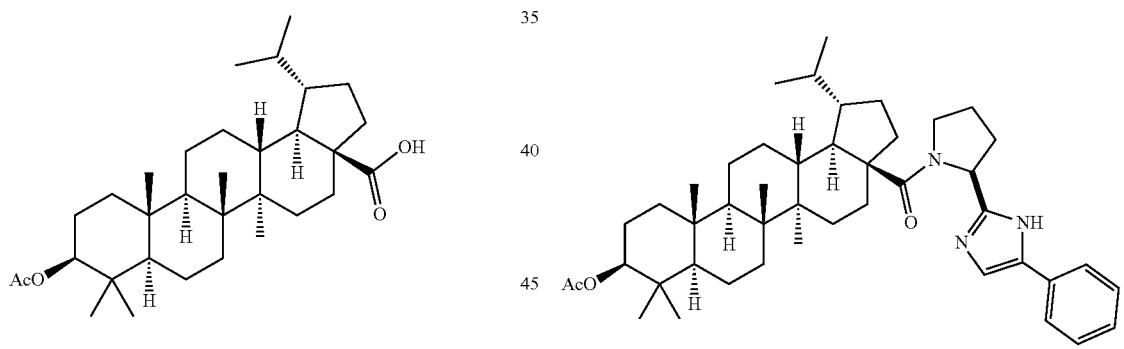

To a stirred solution of (1R,3aS,5aR,5bR,7aR,9S,11aR, 11bR,13aR,13bR)-9-acetoxy-5a,5b,8,8,11a-pentamethyl-1-(prop-1-en-2-yl)icosahydro-3aH-cyclopenta[a]chrysene-3a-carboxylic acid (prepared as described in WO 2013/160810 A2, 5 g, 10.66 mmol) in ethyl acetate (100 mL) was added 10% Pd/C (0.5 g) and purged with nitrogen. The Reaction mixture was stirred for 4 hours under hydrogen atmosphere. After completion of the reaction (monitored by TLC), the reaction mixture was filtered and filtrate was concentrated to give the desired compound (4.5 g, Yield 89.6%) as a white solid. $^1$H-NMR (CDCl$_3$, 300 MHz): δ 4.50-4.45 (m, 1H), 2.26-2.16 (m, 3H), 2.04 (s, 3H), 1.91-1.76 (m, 2H), 1.71-1.46 (m, 12H), 1.41-1.14 (m, 9H), 1.04-1.00 (m, 1H), 0.95 (s, 3H), 0.93 (s, 3H), 0.85-0.83 (m, 12H), 0.76 (d, J=6.6 Hz, 3H).

To a stirred solution of (1S,3aS,5aR,5bR,7aR,9S,11aR, 11bR,13aR,13bR)-9-acetoxy-1-isopropyl-5a,5b,8,8,11a-penta methylicosahydro-3aH-cyclopenta[a]chrysene-3a-carboxylic acid (step 1, 6 g, 13.1 mmol) in DCM (60 mL) were added oxalyl chloride (8.3 mL, 65.5 mmol) at 0° C. drop wise and DMF (0.2 mL, cat). The reaction mixture was stirred at room temperature for about 3 hours. After completion of the reaction (monitored by TLC), the solvent was evaporated under nitrogen atmosphere and redissolved in DCM (30 mL), which was added to the stirred solution of (S)-5-phenyl-2-(pyrrolidin-2-yl)-1H-imidazole (Example 8-step 4, 3.8 g, 15.6 mmol) in DCM (25 mL) and Triethylamine (12.4 mL) mixture at 0° C. and allowed to stir at room temperature for about 16 hours. After completion of the reaction (monitored by TLC), the reaction mixture was diluted with DCM and washed with water, 1N HCl, saturated sodium bicarbonate solution, brine and dried over Na$_2$SO$_4$. The solvent was evaporated and purified by silica gel column (elution 30% EtOAc in hexane) to afford the title compound (5.1 g, Yield 62%) as an off white solid. ¹H-NMR (CDCl₃, 300 MHz): δ 10.93 (brs, 0.5H), 10.49 (brs, 0.5H), 7.77-7.75 (m, 1H), 7.39-7.31 (m, 3H), 7.18 (m, 2H), 5.41-5.30 (m, 1H), 4.51-4.46 (m, 1H), 3.69-3.50 (m, 2H), 3.08-2.96 (m, 2H), 2.30-2.19 (m, 3H), 2.04 (s, 3H), 1.18-1.14 (m, 25H), 1.00 (s, 3H), 0.97 (s, 3H), 0.92-0.88 (m, 12H), 0.74 (d, J=6.8 Hz, 3H); ESI MS: 696.6 (M+H).

Step 3: Synthesis of ((1 S,3aS,5aR,5bR,7aR,9S, 11aR,11bR,13aR,13bR)-9-hydroxy-1-isopropyl-5a, 5b,8,8,11a-pentamethylicosahydro-3aH-cyclopenta [a]chrysen-3a-yl)((S)-2-(5-phenyl-1H-imidazol-2-yl) pyrrolidin-1-yl)methanone

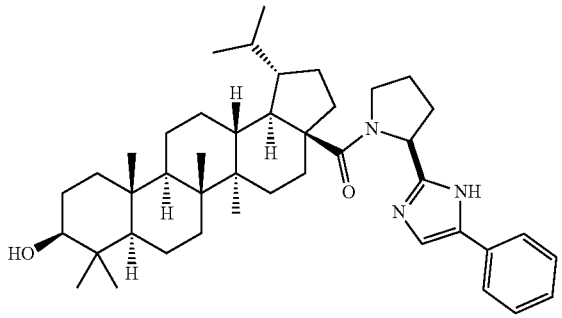

To a stirred solution of (1S,3aS,5aR,5bR,7aR,9S,11aR, 11bR,13aR,13bR)-1-isopropyl-5a,5b,8,8,11a-pentamethyl-3a-((S)-2-(5-phenyl-1H-imidazol-2-yl)pyrrolidine-1-carbonyl)icosahydro-1H-cyclopenta[a]chrysen-9-yl acetate (step 2, 1 g, 1.5 mmol) in MeOH:THF (10 mL:10 mL) was added NaOH (0.18 g, 4.6 mmol) in H₂O at 0° C. and allowed to stir at room temperature for about 12 hours. After completion of the reaction (monitored by TLC), the reaction mixture was concentrated under reduced pressure. The reaction mixture was diluted with DCM, washed with water, brine and dried over Na₂SO₄. The solvent was evaporated, the resulting solid was taken in hexane and stirred for one hour, filtered to afford the title compound (0.7 g, yield 75%) as a white solid. ¹H-NMR (CDCl₃, 300 MHz): δ 10.93 (brs, 0.5H), 10.49 (brs, 0.5H), 7.78-7.75 (m, 1H), 7.42-7.39 (m, 1H), 7.36-7.31 (m, 2H), 7.21-7.16 (m, 2H), 5.42-5.31 (m, 1H), 3.74-3.49 (m, 2H), 3.21-3.19 (m, 1H), 2.97-2.94 (m, 2H), 2.31-2.04 (m, 5H), 1.83-1.08 (m, 24H), 1.01-0.97 (m, 9H), 0.94-0.85 (m, 6H), 0.77 (s, 3H), 0.73 (d, J=6.9 Hz, 3H); ESI MS:654.6 (M+H).

Step 4: Synthesis of 1-benzyl 3-((1 S,3aS,5aR,5bR, 7aR,9S,11aR,11bR,13aR,13bR)-1-isopropyl-5a,5b,8, 8,11a-pentamethyl-3a-((S)-2-(5-phenyl-1H-imidazol-2-yl)pyrrolidine-1-carbonyl) icosahydro-1H-cyclopenta[a]chrysen-9-yl) (1R,3S)-2,2-dimethylcyclobutane-1,3-dicarboxylate

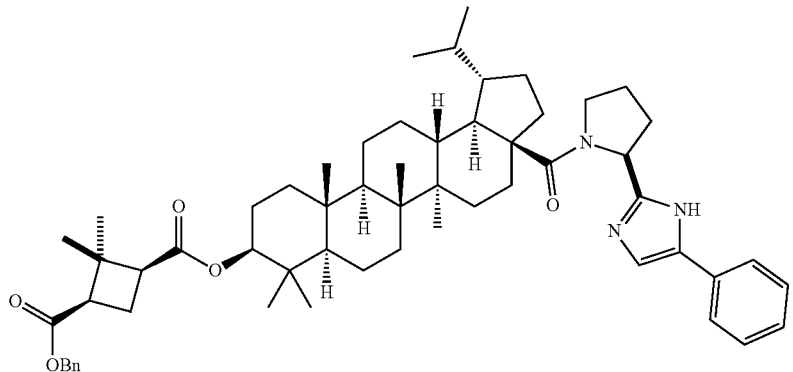

To a stirred solution of ((1S,3aS,5aR,5bR,7aR,9S,11aR, 11bR,13aR,13bR)-9-hydroxy-1-isopropyl-5a,5b,8,8,11a-pentamethylicosahydro-3aH-cyclopenta[a]chrysen-3a-yl) ((S)-2-(5-phenyl-1H-imidazol-2-yl)pyrrolidin-1-yl) methanone (step 3, 0.3 g, 0.5 mmol) and (1S,3R)-3-((benzyloxy)carbonyl)-2,2-dimethylcyclobutane-1-carboxylic acid (prepared as described in WO 2013/160810 A2, 0.19 g, 0.73 mmol) and DMAP (0.012 g, 0.09 mmol) in DCM (5 mL) was added DCC (0.2 g, 0.9 mmol) in DCM (2 mL) slowly at 0° C. and allowed to stir at room temperature for about 12 hours. After completion of the reaction (monitored by TLC), the reaction mixture was diluted with DCM, washed with water, saturated with aq. NaHCO₃ solution, brine and dried over Na₂SO₄. The solvent was evaporated, the resulting solid DCM (3 mL) was added and stirred for one hour and filtered. The filtrate was concentrated under reduced pressure to afford the title compound (0.35 g, yield 79%) as a white solid. ¹H-NMR (DMSO-d₆, 300 MHz): δ 10.92 (brs, 0.5H), 10.52 (brs, 0.5H), 7.74 (m, 1H), 7.35-7.31 (m, 9H), 7.18 (s, 1H), 5.38 (m, 1H), 5.18-5.08 (m, 2H), 4.51-4.40 (m, 1H), 3.82-3.41 (m, 2H), 3.06-2.58 (m, 5H), 2.32-2.29 (m, 2H), 2.11-1.08 (m, 27H), 1.00-0.78 (m, 24H), 0.73 (d, J=6.0 Hz, 3H); ESI MS: 895.5 (M+H).

Step 5: Synthesis of (1R,3S)-3-((((1S,3aS,5aR,5bR,7aR,9S,11aR,11bR,13aR,13bR)-1-isopropyl-5a,5b,8,8,11a-pentamethyl-3a-((S)-2-(5-phenyl-1H-imidazol-2-yl)pyrrolidine-1-carbonyl)icosahydro-1H-cyclopenta[a]chrysen-9-yl)oxy)carbonyl)-2,2-dimethylcyclobutane-1-carboxylic acid To a stirred solution of 1-benzyl 3-((1S,3aS,5aR,5bR,7aR,9S,11aR,11bR,13aR,13bR)-1-isopropyl-5a,5b,8,8,11a-pentamethyl-3a-((S)-2-(5-phenyl-1H-imidazol-2-yl)pyrrolidine-1-carbonyl)icosahydro-1H-cyclopenta[a]chrysen-9-yl) (1R,3S)-2,2-dimethylcyclobutane-1,3-dicarboxylate (step 4, 0.35 g, 0.39 mmol) in ethyl acetate and methanol (2:2 mL) was added 10% Pd/C (0.05 g) and purged with nitrogen. The Reaction mixture was stirred for 12 hours under hydrogen atmosphere. After completion of the reaction (monitored by TLC), the reaction mixture was filtered, filtrate was concentrated and recrystallized from MeOH to give the title compound (0.25 g, Yield 82%) as a white solid. $^1$H-NMR (DMSO-d$_6$, 300 MHz): δ 12.15 (s, 1H), 11.56 (s, 1H), 7.72-7.70 (m, 2H), 7.40 (s, 1H), 7.32-7.27 (m, 2H), 7.15-7.13 (m, 1H), 5.07-5.05 (m, 1H), 4.36-4.31 (m, 1H), 3.78 (m, 1H), 3.59-3.57 (m, 1H), 2.82-2.76 (m, 2H), 2.34-1.85 (m, 8H), 1.62-1.09 (m, 25H), 0.90-0.81 (m, 20H), 0.69 (d, J=6.0 Hz, 6H); ESI MS: 808.5 (M+H).

Example 22

Preparation of (1R,3S)-3-((((1S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl)oxy)carbonyl)-2,2-dimethylcyclobutane-1-carboxylic acid To a stirred solution of (1S,3aS,5aR,5bR,7aR,9S,11aR,11bR,13aR,13bR)-9-acetoxy-1-isopropyl-5a,5b,8,8,11a-penta methylicosahydro-3aH-cyclopenta[a]chrysene-3a-carboxylic acid (Example 21-step 1, 1 g, 2.1 mmol) in DCM (10 mL) were added oxalyl chloride (1.4 mL, 10.9 mmol) at 0° C. drop wise and DMF (0.1 mL, cat). The reaction mixture was stirred at room temperature for about 3 hours and completion of the reaction (monitored by TLC), the solvent was evaporated under nitrogen atmosphere and redissolved in DCM (6 mL), which was added to the stirred solution of (S)-5-(4-fluorophenyl)-2-(pyrrolidin-2-yl)-1H-imidazole (Example 33-step 4, 0.8 g, 3.0 mmol) in DCM (10 mL) and Triethylamine (2.2 mL) mixture at 0° C. and allowed to stir at room temperature for about 16 hours. After completion of the reaction (monitored by TLC), the reaction mixture was diluted with DCM, washed with water, 1N HCl, saturated sodium bicarbonate solution, brine and dried over Na$_2$SO$_4$. The solvent was evaporated and purified by silica gel column (elution 25% EtOAc in hexane) to afford the title compound (1.2 g, Yield 80%) as an off white solid.

$^1$H-NMR (CDCl$_3$, 300 MHz): δ 10.93 (brs, 0.3H), 10.51 (brs, 0.7H), 7.74-7.70 (m, 1H), 7.38-7.33 (m, 1H), 7.13 (s, 1H), 7.05-7.00 (m, 2H), 5.42-5.28 (m, 1H), 4.51-4.46 (m, 1H), 3.77-3.50 (m, 2H), 3.05-2.94 (m, 2H), 2.33-2.01 (m, 5H), 2.04 (s, 3H), 1.81-1.12 (m, 23H), 0.99 (s, 3H), 0.96 (s, 3H), 0.92-0.80 (m, 12H), 0.74 (d, J=6.6 Hz, 3H); ESI MS: 714.4 (M+H).

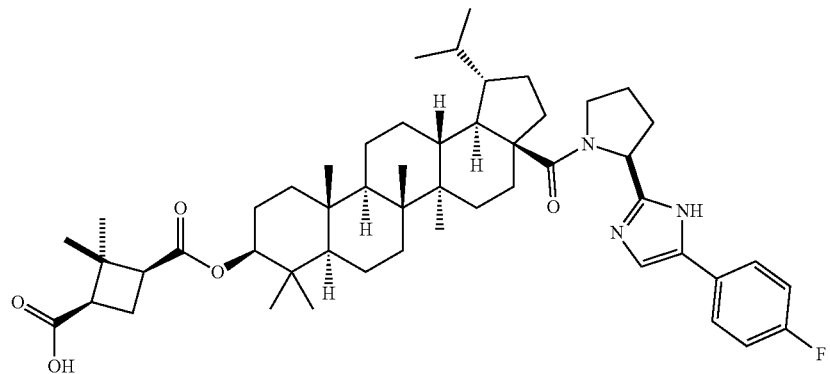

Step 1: Synthesis of (1S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl acetate Step 2: Synthesis of ((S)-2-(5-(4-fluorophenyl)-1H-imidazol-2-yl)pyrrolidin-1-yl)((1S,3aS,5aR,5bR,7aR,9S,11aR,11bR,13aR,13bR)-9-hydroxy-1-isopropyl-5a,5b,8,8,11a-pentamethylicosahydro-3aH-cyclopenta[a]chrysen-3a-yl)methanone

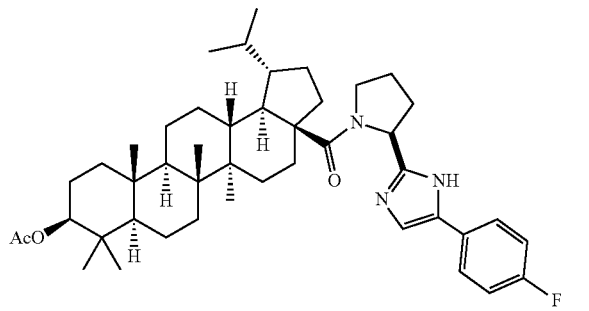
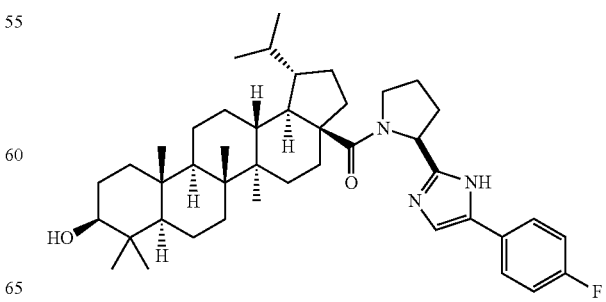

To a stirred solution of (1S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl acetate (step 1, 1 g, 1.4 mmol) in MeOH:THF (10 mL:10 mL) was added NaOH (0.17 g, 4.2 mmol) in H$_2$O (3 mL) at 0° C. and allowed to stir at room temperature for about 12 hours. After completion of the reaction (monitored by TLC), the reaction mixture was concentrated under reduced pressure. The reaction mixture was diluted with DCM, washed with water, brine and dried over Na$_2$SO$_4$. Then the solvent was evaporated, the resulting solid was taken in hexane and stirred for one hour, filtered to afford the title compound (0.75 g, yield 79%) as a white solid. $^1$H-NMR (CDCl$_3$, 300 MHz): δ 10.93 (brs, 0.3H), 10.51 (brs, 0.7H), 7.74-7.70 (m, 1H), 7.35 (m, 1H), 7.13 (s, 1H), 7.05-7.00 (m, 2H), 5.37-5.31 (m, 1H), 3.74-3.52 (m, 2H), 3.23-3.17 (m, 1H), 3.02-2.94 (m, 2H), 2.37-2.01 (m, 5H), 1.82-1.08 (m, 22H), 0.99-0.97 (m, 11H), 0.86-0.85 (m, 6H), 0.77 (s, 3H), 0.73 (d, J=6.6 Hz, 3H).

Step 3: Synthesis of 1-benzyl 3-((1S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl) (1R,3S)-2,2-dimethylcyclobutane-1,3-dicarboxylate for about 12 hours. After completion of the reaction (monitored by TLC), the reaction mixture was diluted with DCM, washed with water, saturated aq. NaHCO$_3$ solution, brine and dried over Na$_2$SO$_4$. Then the solvent was evaporated and to the resulting solid DCM (3 mL) was added and stirred for one hour, filtered. The filtrate was concentrated under reduced pressure to afford the title compound (0.34 g, yield 79%) as a white solid. $^1$H-NMR (CDCl$_3$, 300 MHz): δ 10.91 (brs, 0.5H), 10.51 (brs, 0.5H), 7.79-7.72 (m, 1H), 7.35 (m, 5H), 7.13 (s, 1H), 7.05-7.00 (m, 2H), 5.42-5.29 (m, 1H), 5.13-5.11 (m, 2H), 4.49-4.40 (m, 1H), 3.71-3.50 (m, 2H), 3.09-2.62 (m, 5H), 2.43-1.12 (m, 33H), 0.99-0.84 (m, 21H), 0.73 (d, J=6.6 Hz, 3H).

Step 4: Synthesis of (1R,3S)-3-(((((1S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl)oxy)carbonyl)-2,2-dimethylcyclobutane-1-carboxylic acid To a stirred solution of 1-benzyl 3-((1 S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl) (1R,3S)-2,2-dimethylcyclobutane-1,3-dicarboxylate (step 3, 0.34 g, 0.37 mmol) in ethyl acetate and methanol (2:2 mL) was added 10% Pd/C (0.05 g) and

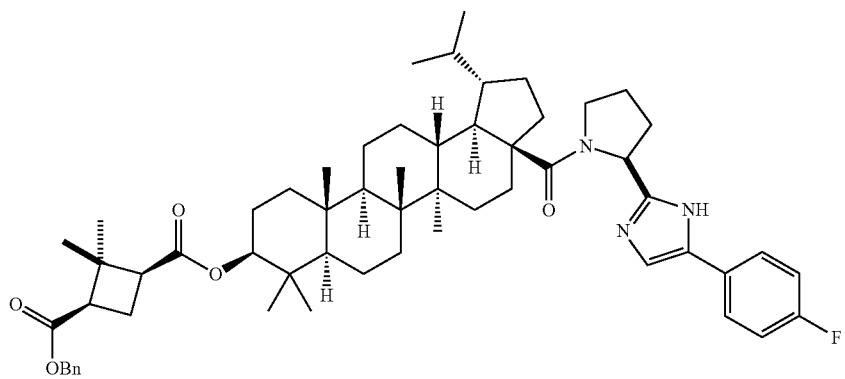

To a stirred solution of ((S)-2-(5-(4-fluorophenyl)-1H-imidazol-2-yl)pyrrolidin-1-yl)((1 S,3aS,5aR,5bR,7aR,9S,11aR,11bR,13aR,13bR)-9-hydroxy-1-isopropyl-5a,5b,8,8,11a-pentamethylicosahydro-3aH-cyclopenta[a]chrysen-3a-yl)methanone (step 2, 0.3 g, 0.4 mmol) and (1S,3R)-3-((benzyloxy)carbonyl)-2,2-dimethylcyclobutane-1-carboxylic acid (prepared as described in WO 2013/160810 A2, 0.19 g, 0.71 mmol) and DMAP (0.012 g, 0.09 mmol) in DCM (5 mL) was added DCC (0.2 g, 0.9 mmol) in DCM (2 mL) slowly at 0° C. and allowed to stir at room temperature purged with nitrogen. The Reaction mixture was stirred for 12 hours under hydrogen atmosphere. After completion of the reaction (monitored by TLC), reaction mixture was filtered, filtrate was concentrated and recrystallized from MeOH to give the title compound (0.23 g, Yield 76%) as a white solid. $^1$H-NMR (DMSO-d$_6$, 300 MHz): δ 12.14 (s, 1H), 11.57 (1H), 7.73 (m, 2H), 7.39 (s, 1H), 7.16-7.13 (m, 2H), 5.04 (m, 1H), 4.34-4.31 (m, 1H), 3.78 (m, 1H), 3.59 (m, 1H), 2.82-2.72 (m, 3H), 2.39-1.86 (m, 9H), 1.63-1.11 (m, 22H), 0.90-0.82 (m, 21H), 0.69 (d, J=6.0 Hz, 6H); ESI MS: 826.5 (M+H).

Example 23

Preparation of 4-((((1S,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl)oxy)-2,2-dimethyl-4-oxobutanoic acid

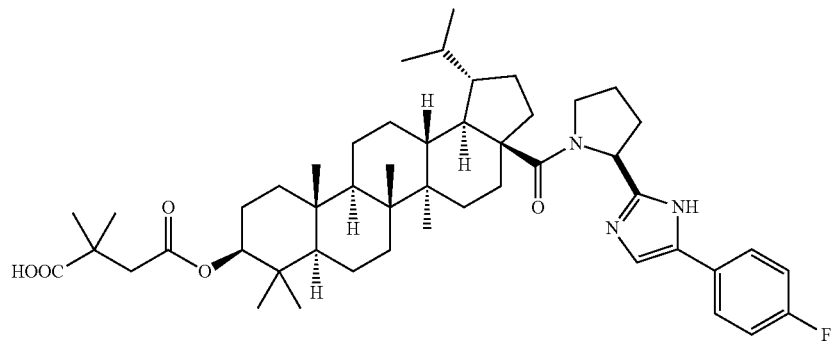

To a stirred solution of ((S)-2-(5-(4-fluorophenyl)-1H-imidazol-2-yl)pyrrolidin-1-yl)((1S,3aS,5aR,5bR,7aR,9S,11aR,11bR,13aR,13bR)-9-hydroxy-1-isopropyl-5a,5b,8,8,11a-pentamethylicosahydro-3aH-cyclopenta[a]chrysen-3a-yl)methanone (Example 22-step 2, 0.15 g, 0.22 mmol) and 2,2-dimethyl succinicanhydride (0.12 g, 0.8 mmol) in toluene (8 mL) was added DMAP (0.06 g, 0.44 mmol). The reaction mixture was heated at 90° C. for 12 hours. After completion of the reaction (monitored by TLC), the reaction mixture was concentrated under reduced pressure, cooled to 0° C., acidified to pH=6 with 1N HCl and extracted with DCM. The combined organic extracts was washed with water, brine, dried over $Na_2SO_4$, then the solvent was evaporated and to the resulting solid was recrystalised from ACN to give the title compound (0.08 g, Yield 47%) as a white solid. $^1$H-NMR (CDCl$_3$, 300 MHz): δ 7.57 (m, 2H), 7.15 (s, 1H), 7.03 (t, J=6.9 Hz, 2H), 5.35-5.32 (m, 1H), 4.54-4.48 (m, 1H), 3.71-3.69 (m, 1H), 3.55 (m, 1H), 2.97-2.93 (m, 2H), 2.71-2.60 (m, 3H), 2.29-1.13 (m, 36H), 0.99-0.82 (m, 15H), 0.73 (d, J=6.6 Hz, 3H); ESI MS: 800.5 (M+H).

Example 24

Preparation of (1R,3S)-3-(((((1S,3aS,5aR,5bR,7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl)oxy)carbonyl)-2,2-dimethylcyclobutane-1-carboxylic acid

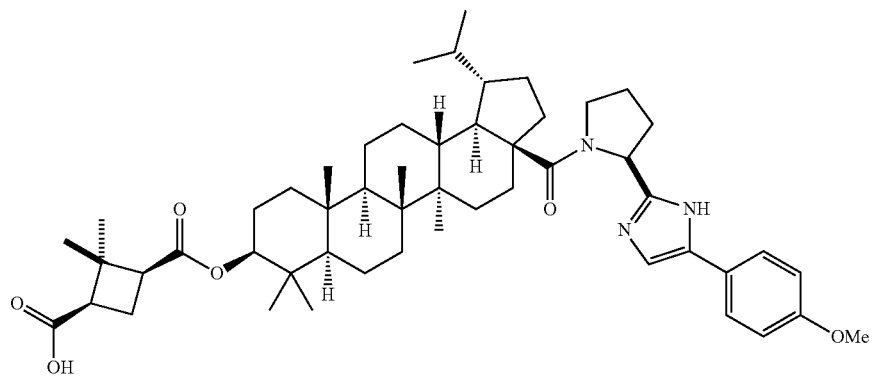

Step 1: Synthesis of (1 S,3aS,5aR,5bR,7aR,9S, 11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl acetate Step 2: Synthesis of ((1S,3aS,5aR,5bR,7aR,9S, 11aR,11bR,13aR,13bR)-9-hydroxy-1-isopropyl-5a, 5b,8,8,11a-pentamethylicosahydro-3aH-cyclopenta[a]chrysen-3a-yl)((S)-2-(5-(4-methoxyphenyl)-1H-imidazol-2-yl)pyrrolidin-1-yl)methanone

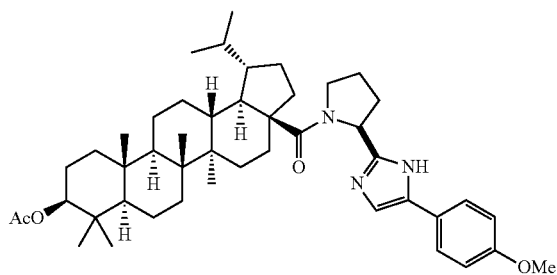

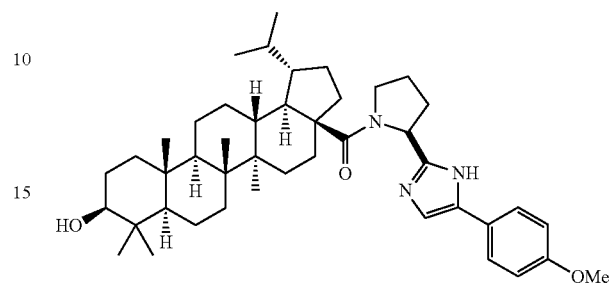

To a stirred solution of (1S,3aS,5aR,5bR,7aR,9S,11aR, 11bR,13aR,13bR)-9-acetoxy-1-isopropyl-5a,5b,8,8,11a-penta methylicosahydro-3aH-cyclopenta[a]chrysene-3a-carboxylic acid (Example 21-step 1, 2.8 g, 2.1 mmol) in DCM (10 mL) were added oxalyl chloride (3.9 mL, 30.3 mmol) at 0° C. drop wise and DMF (0.1 mL, cat). The reaction mixture was stirred at room temperature for about 3 hours. After completion of the reaction (monitored by TLC), the solvent was evaporated under nitrogen atmosphere and redissolved in DCM (15 mL), which was added to the stirred solution of (S)-5-(4-methoxyphenyl)-2-(pyrrolidin-2-yl)-1H-imidazole (Example 15-step 4, 2.1 g, 7.6 mmol) in DCM (15 mL) and Triethylamine (5.8 mL) mixture at 0° C. and allowed to stir at room temperature for about 14 hours. After completion of the reaction (monitored by TLC), the reaction mixture was diluted with DCM, washed with water, 1N HCl, saturated sodium bicarbonate solution, brine and dried over $Na_2SO_4$. The solvent was evaporated and purified by silica gel column (elution 30% EtOAc in hexane) to afford the title compound (3.3 g, Yield 76%) as an off white solid. $^1$H-NMR (CDCl$_3$, 300 MHz): δ 10.93 (brs, 0.5H), 10.51 (brs, 0.5H), 7.80 (m, 1H), 7.37 (m, 1H), 7.08 (s, 1H), 6.88 (d, J=8.7 Hz, 2H), 5.34 (m, 1H), 4.51-4.46 (m, 1H), 3.81 (s, 3H), 3.70-3.66 (m, 1H), 3.57 (m, 1H), 2.98-2.91 (m, 2H), 2.33-2.01 (m, 5H), 2.04 (s, 3H), 1.89-1.06 (m, 23H), 1.00 (s, 3H), 0.97 (s, 3H), 0.88-0.76 (m, 12H), 0.74 (d, J=6.6 Hz, 3H).

To a stirred solution of (1S,3aS,5aR,5bR,7aR,9S,11aR, 11bR,13aR,13bR)-1-isopropyl-3a-((S)-2-(5-(4-methoxyphenyl)-1H-imidazol-2-yl)pyrrolidine-1-carbonyl)-5a,5b,8, 8,11a-pentamethylicosahydro-1H-cyclopenta[a]chrysen-9-yl acetate (step 1, 1 g, 1.3 mmol) in MeOH:THF (10 mL:10 mL) was added NaOH (0.16 g, 4.1 mmol) in H$_2$O (3 mL) at 0° C. and allowed to stir at room temperature for about 12 hours. After completion of the reaction (monitored by TLC), the reaction mixture was concentrated under reduced pressure. The reaction mixture was diluted with DCM and washed with water, brine and dried over Na$_2$SO$_4$. Then the solvent was evaporated and the resulting solid was taken in hexane and stirred for one hour, filtered to afford the title compound (0.72 g, yield 76%) as a white solid.
$^1$H-NMR (CDCl$_3$, 300 MHz): δ 10.82 (brs, 0.5H), 10.44 (brs, 0.5H), 7.69-7.67 (m, 1H), 7.34-7.31 (m, 1H), 7.07 (s, 1H), 6.88 (d, J=8.4 Hz, 2H), 5.37-5.30 (m, 1H), 3.81 (s, 3H), 3.81-3.57 (m, 2H), 3.23-3.17 (m, 1H), 2.95 (m, 2H), 2.39-2.01 (m, 5H), 1.83-1.12 (m, 24H), 1.00-0.97 (m, 9H), 0.87-0.85 (m, 6H), 0.77 (s, 3H), 0.74 (d, J=6.6 Hz, 3H); ESI MS: 683.5 (M+H).

Step 3: Synthesis of 1-benzyl 3-((1 S,3aS,5aR,5bR, 7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl) (1R,3S)-2,2-dimethylcyclobutane-1,3-dicarboxylate

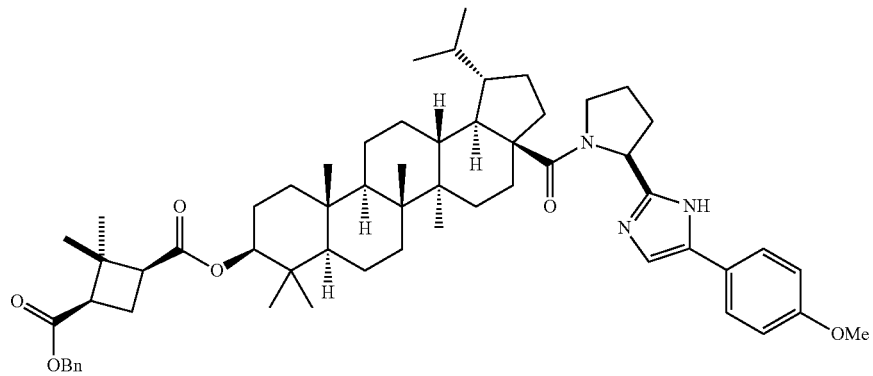

To a stirred solution of ((1S,3aS,5aR,5bR,7aR,9S,11aR, 11bR,13aR,13bR)-9-hydroxy-1-isopropyl-5a,5b,8,8,11a-pentamethylicosahydro-3aH-cyclopenta[a]chrysen-3a-yl) ((S)-2-(5-(4-methoxyphenyl)-1H-imidazol-2-yl)pyrrolidin-1-yl)methanone (step 2, 0.4 g, 0.62 mmol) and (1S,3R)-3-((benzyloxy)carbonyl)-2,2-dimethylcyclobutane-1-carboxylic acid (prepared as described in WO 2013/160810 A2, 0.25 g, 0.93 mmol) and DMAP (0.015 g, 0.12 mmol) in DCM (5 mL) was added DCC (0.25 g, 1.2 mmol) in DCM (2 mL) slowly at 0° C. and allowed to stir at room temperature for about 12 hours. After completion of the reaction (monitored by TLC), the reaction mixture was diluted with DCM, washed with water, saturated aq. NaHCO$_3$ solution, brine and dried over Na$_2$SO$_4$. Then the solvent was evaporated and to the resulting solid was added DCM (3 mL) and stirred for one hour, filtered. The filtrate was concentrated under reduced pressure to afford the title compound (0.45 g, yield 82%) as a white solid. $^1$H-NMR (DMSO-d$_6$, 300 MHz): δ1.45 (s, 1H), 8.09 (d, J=6.3 Hz, 2H), 7.36 (m, 6H), dicarboxylate (step 3, 0.45 g, 0.48 mmol) in ethyl acetate and methanol (3:3 mL) was added 10% Pd/C (0.06 g) and purged with nitrogen. The Reaction mixture was stirred for 12 hours under hydrogen atmosphere. After completion of the reaction (monitored by TLC), reaction mixture was filtered and filtrate was concentrated and recrystallized from ACN to give the title compound (0.30 g, Yield 74%) as a white solid. $^1$H-NMR (DMSO-d$_6$, 300 MHz): δ12.15 (s, 1H), 11.44 (s, 1H), 7.63 (d, J=8.1 Hz, 2H), 7.27 (s, 1H), 6.88 (d, J=8.1 Hz, 2H), 5.03 (m, 1H), 4.36-4.30 (m, 1H), 3.74 (s, 3H), 3.59 (m, 2H), 2.82-2.76 (m, 3H), 2.34-1.01 (m, 34H), 0.90-0.70 (m, 24H); ESI MS: 838.6 (M+H).

Example 25

Preparation of 4-(((1S,3aS,5aR,5bR,7aR,9S,11aR, 11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl)oxy)-2,2-dimethyl-4-oxobutanoic acid

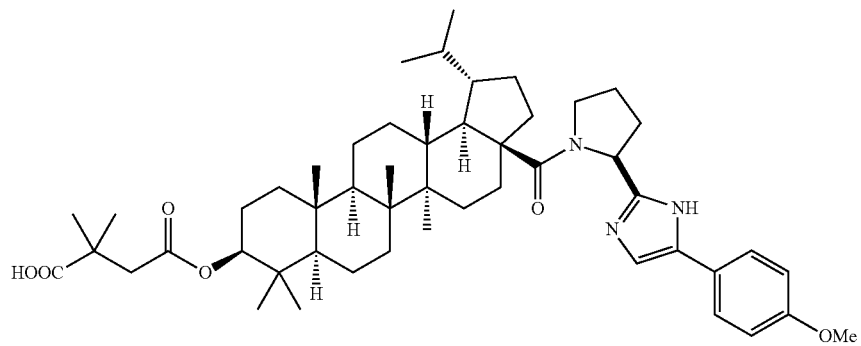

6.59 (d, J=6.3 Hz, 2H), 5.14-5.03 (m, 3H), 4.32 (m, 1H), 3.74 (s, 3H), 3.54 (m, 2H), 2.94-2.72 (m, 3H), 2.41-1.08 (m, 37H), 0.91-0.68 (m, 21H); ESI MS: 928.5 (M+H).

Step 4: Synthesis of (1R,3S)-3-((((1 S,3aS,5aR, 5bR,7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl)oxy)carbonyl)-2,2-dimethylcyclobutane-1-carboxylic acid To a stirred solution of 1-benzyl 3-((1 S,3aS,5aR,5bR, 7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl) (1R,3S)-2,2-dimethylcyclobutane-1,3-

To a stirred solution of ((1S,3aS,5aR,5bR,7aR,9S,11aR, 11bR,13aR,13bR)-9-hydroxy-1-isopropyl-5a,5b,8,8,11a-pentamethylicosahydro-3aH-cyclopenta[a]chrysen-3a-yl) ((S)-2-(5-(4-methoxyphenyl)-1H-imidazol-2-yl)pyrrolidin-1-yl)methanone (Example 24-step 2, 0.2 g, 0.29 mmol) and 2,2-dimethyl succinicanhydride (0.14 g, 1.17 mmol) in toluene (6 mL) was added DMAP (0.07 g, 0.58 mmol). The reaction mixture was heated at 90° C. for 12 hours. After completion of the reaction (monitored by TLC), reaction mixture was concentrated under reduced pressure, cooled to 0° C., acidified to pH=6 with 1N HCl and extracted with DCM. The combined organic extracts were washed with water, brine, dried over Na$_2$SO$_4$. Then the solvent was evaporated and to the resulting solid was recrystalised from ACN to give the title compound (0.09 g, Yield 26%) as a white solid. $^1$H-NMR, CDCl$_3$, 300 MHz): δ 7.49-7.47 (m, 2H), 7.12 (s, 1H), 6.89 (d, J=8.7 Hz, 2H), 5.36-5.34 (m, 1H), 4.54-4.49 (m, 1H), 3.81 (s, 3H), 3.68-3.56 (m, 2H), 2.94-2.90 (m, 2H), 2.71-1.12 (m, 36H), 0.99-0.84 (m, 18H), 0.72 (d, J=6.6 Hz, 3H); ESI MS: 812.5 (M+H).

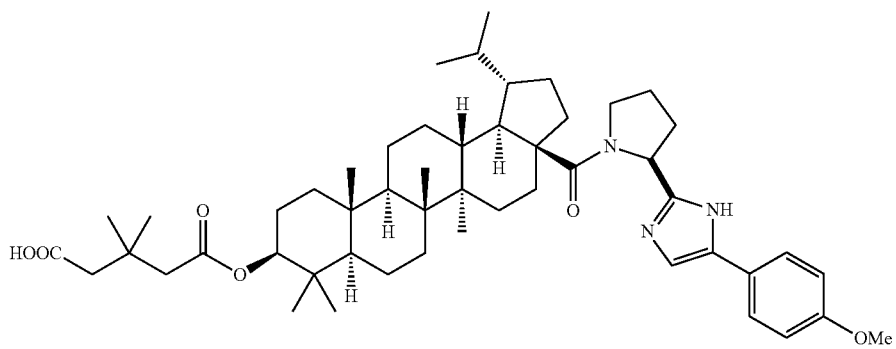

To a stirred solution of (((1S,3aS,5aR,5bR,7aR,9S,11aR,11bR,13aR,13bR)-9-hydroxy-1-isopropyl-5a,5b,8,8,11a-pentamethylicosahydro-3aH-cyclopenta[a]chrysen-3a-yl) ((S)-2-(5-(4-methoxyphenyl)-1H-imidazol-2-yl)pyrrolidin-1-yl)methanone (Example 24-step 2, 0.1 g, 0.14 mmol) and 3,3-dimethyl glutaricanhydride (0.083 g, 0.58 mmol) in toluene (5 mL) was added DMAP (0.035 g, 0.29 mmol). The reaction mixture was heated at 90° C. for 12 hours. After completion of the reaction (monitored by TLC), the reaction mixture was concentrated under reduced pressure, cooled to 0° C., acidified to pH=6 with 1N HCl and extracted with DCM. The combined organic extracts were washed with water, brine, dried over Na$_2$SO$_4$. Then the solvent was evaporated and to the resulting solid was recrystallized from ACN to give the title compound (0.07 g, Yield 58.3%) as a white solid. $^1$H-NMR (CDCl$_3$, 300 MHz): δ7.49-7.47 (m, 2H), 7.18 (s, 1H), 6.91 (d, J=8.4 Hz, 2H), 5.40-5.38 (m, 1H), 4.54-4.49 (m, 1H), 3.82 (s, 3H), 3.75-3.68 (m, 2H), 2.99-2.81 (m, 2H), 2.51-1.15 (m, 38H), 1.02 (s, 6H), 0.92-0.83 (m, 12H), 0.73 (d, J=6.6 Hz, 3H); ESI MS: 826.5 (M+H).

Example 27

Preparation of (1S,3R)-2,2-dimethyl-3-((((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl) icosahydro-1H-cyclopenta[a]chrysen-9-yl)oxy) carbonyl)cyclobutane-1-carboxylic acid Step 1: Synthesis of (1R,3S)-3-acetyl-2,2-dimethyl-cyclobutane-1-carboxylic acid

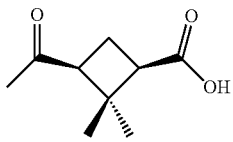

To a stirred solution of (+)-Verbenone (55 g, 366.6 mmol) in Acetone (550 mL, 10 vol) followed by added aq.KMnO$_4$ solution (115.8 g, 733.3 mmol) dissolved in water (825 mL, 15 vol) at 0° C. and allowed to stir for about 3 hours at same temperature. The reaction mass was then acidified with 2N HCl (pH-3-4) and allowed to stir overnight at room temperature. After completion of the reaction as monitored by TLC, added NaHSO$_3$ to get colorless solution. Then the reaction mixture was diluted with CH$_2$Cl$_2$ (2×500 mL) and the organic layers were separated. The combined organic layers were dried with Na$_2$SO$_4$ and concentrated under reduced to get the residue. The resulting crude solid material was washed with EtOAc:hexane (1:9, 500 mL) to get the desired product (wt: 40 g; yield 64%). $^1$H NMR (300 MHz, CDCl$_3$): δ 2.94-2.79 (m, 2H), 2.63 (q, 1H, J=10.8 Hz), 2.07 (s, 3H), 1.86-1.95 (m, 1H), 1.40 (s, 3H), 0.97 (s, 3H); Mass: [M+1]$^+$ 171 (10%), [M+Na]$^+$ 193 (72%).

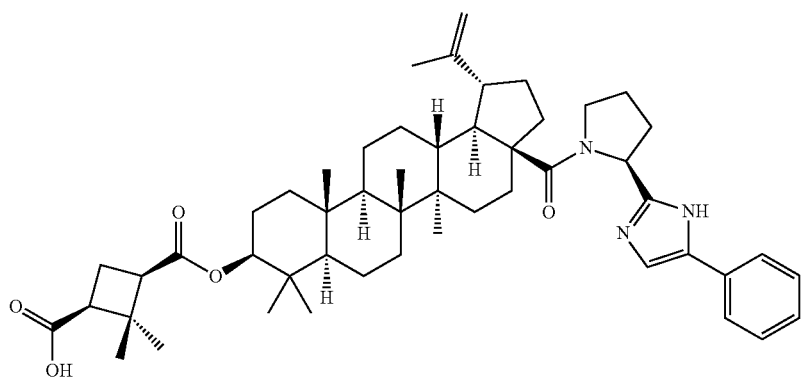

Step 2: Synthesis of tert-butyl (1R,3S)-3-acetyl-2,2-dimethylcyclobutane-1-carboxylate

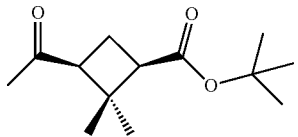

To a stirred ice cold solution of (1R,3S)-3-acetyl-2,2-dimethylcyclobutane-1-carboxylic acid (step 1, 40 g, 235.3 mmol) in DCM (400 mL), DMAP (2.86 g, 23.5 mmol), t-BuOH (92 mL, 940 mmol) were added followed by DCC (63 g, 305 mmol) was added portion wise. After addition the reaction mixture was stirred at room temperature for about 12 hours. After completion of the reaction (monitored by TLC), the reaction mixture was diluted with DCM, filtered through celite bed and washed with DCM. The filtrate was as such concentrated and purified by silica gel column chromatography to afford the desired compound (wt: 50 g; yield 94%) as a liquid. $^1$H NMR (300 MHz, CDCl$_3$): δ 2.86-2.80 (m, 1H), 2.70-2.50 (m, 2H), 2.05 (s, 3H), 1.89-1.79 (m, 1H), 1.43, 1.41 (2s, 12H), 0.92 (s, 3H); Mass: [M+Na]$^+$ 249 (10%).

Step 3: Synthesis of (1S,3R)-3-(tert-butoxycarbonyl)-2,2-dimethylcyclobutane-1-carboxylic acid

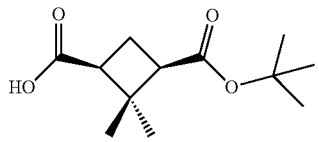

To a stirred solution of tert-butyl (1R,3S)-3-acetyl-2,2-dimethylcyclobutane-1-carboxylate (step 2, 50 g, 220.92 mmol) in dioxane (500 mL, 10 vol) at 0° C., NaOBr solution (bromine: 34.2 mL, 662.7 mmol; NaOH: 79.5 gr, 1988.3 mmol; water: 1500 mL, 30 vol) were added drop wise and stirred at the same temperature for about 3 hours. After that the reaction mass stirred at room temperature for about 10 hours. After completion of the reaction (monitored by TLC), the reaction mixture was washed with DCM, the aqueous layer was adjusted P$^H$ with 2N HCl solution and extracted with DCM. The organic layer washed with water, brine solution, dried with Na$_2$SO$_4$ and the solvent was evaporated to afford the desired compound (wt: 43 g; yield 85%) as off white solid. $^1$H NMR (300 MHz, DMSO): δ 12.1 (s, 1H), 2.76-2.68 (m, 2H), 2.3-2.23 (m, 1H), 1.88-1.82 (m, 1H), 1.40 (s, 9H), 1.23 (s, 1H), 0.93 (s, 3H); Mass: [M+Na]$^+$ 251 (10%).

Step 4: Synthesis of 1-benzyl 3-(tert-butyl) (1S,3R)-2,2-dimethylcyclobutane-1,3-dicarboxylate

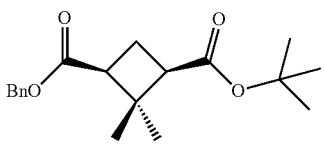

To a stirred solution of (1S,3R)-3-(tert-butoxycarbonyl)-2,2-dimethylcyclobutane-1-carboxylic acid (step 3, 43 g, 188.35 mmol) in DCM (215 mL, 5 vol) at 0° C., aq.Na$_2$CO$_3$ solution (39.9 g, 376.7 mmol, dissolved in 215 mL water) followed by added TBAB (1.51 gr, 47 mmol) and Benzyl bromide (23.7 mmol, 188.35 mmol, 1.0 eq.) at 0° C. After that the reaction mass stirred at room temperature for about 12 hours. After completion of the reaction (monitored by TLC), the reaction mixture was diluted with water and DCM. Then the reaction mixture was stirred for about 30 minutes. The organic layer was separated, washed with water, brine and dried over Na$_2$SO$_4$, then the solvent was evaporated to afford the desired product (wt: 18 g; yield: 30%). $^1$H NMR (300 MHz, CDCl$_3$): δ 7.42-7.31 (m, 5H), 5.13 (s, 2H), 2.93-2.81 (m, 2H), 2.68 (q, 1H, J=10.5 Hz), 2.05 (s, 3H), 1.97-1.88 (m, 1H), 1.43 (s, 3H), 0.87 (s, 3H); Mass: [M+Na]$^+$ 341.2 (100%).

Step 5: Synthesis of (1R,3S)-3-((benzyloxy)carbonyl)-2,2-dimethylcyclobutane-1-carboxylic acid

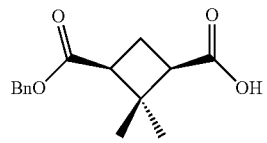

1-benzyl 3-(tert-butyl) (1S,3R)-2,2-dimethylcyclobutane-1,3-dicarboxylate (step 4, 18 g, 56.5 mmol) was dissolved in 6N HCl in Dioxane (216 mL) at 0° C., after that the reaction mass was stirred at room temperature for about 4 hours. After completion of the reaction (monitored by TLC), the reaction mixture was diluted with water and extracted with DCM (2×200 mL). The combined organic layers were washed with water, brine and dried over Na$_2$SO$_4$, then the solvent was evaporated and concentrate to afford the desired product (wt: 14 g: yield: 95%). $^1$H NMR (300 MHz, DMSO): δ 11.39 (bs, 1H), 7.41-7.28 (m, 5H), 5.14-5.04 (m, 2H), 2.93-2.87 (m, 1H), 2.81-2.75 (m, 1H), 2.32 (q, J=10.8 Hz, 1H), 1.96-1.87 (m, 1H), 1.25 (s, 1H), 0.83 (s, 3H); Mass: [M+Na]$^+$ 283 (87%).

Step 6: Synthesis of (1R,3S)-3-((benzyloxy)carbonyl)-2,2-dimethylcyclobutane-1-carboxylic acid

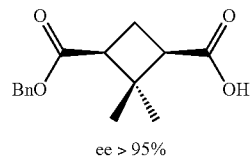

ee > 95%

To a stirred solution of (1S,3R)-3-(benzyloxycarbonyl)-2,2-dimethyl cyclobutanecarboxylic acid (ee:88, major and minor ratio is 94:6) (step 5, 14 gr, 53.4 mmol) in Diisopropyl ether (140 mL, 10 vol) slowly added (S)-(+)-1-Phenylethylamine (6.5 mL, 53.4 mmol) at room temperature and stirred the reaction mixture for about 12 hours at room temperature. The reaction mixture was filtered and collected solid (11 gr) was redissolved in CH$_2$Cl$_2$ (200 mL) and acidified with 1N HCl (P$^H$=4-5). The organic layer was separated, aqueous layer was extracted with CH$_2$Cl$_2$ (200 mL). The combined organic extracts were washed with water, brine, dried over Na$_2$SO$_4$, filtered and evaporated under reduced pressure to get the acid (wt: 8 gr; yield: 73%; Enantiomeric excess: 95% (Major isomer optical purity 97.5% and minor isomer 2.5%)) as a light brown syrup.

Step 7: Synthesis of 1-benzyl 3-((1R,3aS,5aR,5bR, 7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl) (1S,3R)-2,2-dimethylcyclobutane-1,3-dicarboxylate

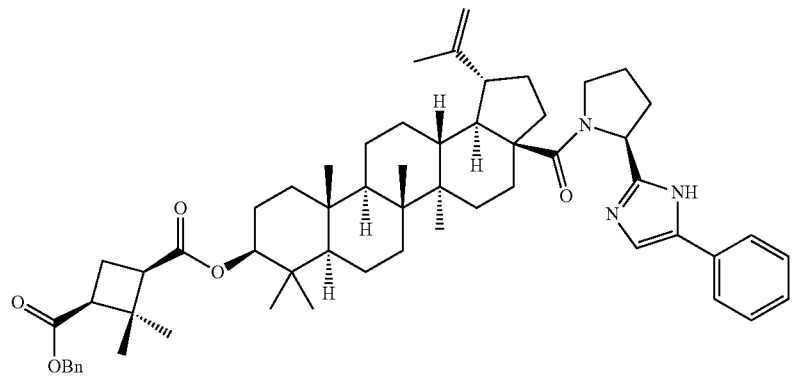

To a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(5-phenyl-1H-imidazol-2-yl)pyrrolidin-1-yl)methanone (Example 8-step 6, 2.0 g, 3.14 mmol, 1.0 eq) in CH$_2$Cl$_2$ (20 mL) was added (1R,3S)-3-((benzyloxy)carbonyl)-2,2-dimethylcyclobutane-1-carboxylic acid (step 6, 1.15 g, 4.72 mmol, 1.5 eq), DMAP (0.077 mg, 0.63 mmol, 0.2 eq) and DCC (1.3 g, 6.29 mmol, 2.0 eq) at 0° C. The reaction mixture was stirred for about 12 hours at room temperature. TLC indicated starting material was consumed and the desired product was observed. The reaction mixture was filtered through celite and the collected solid was washed with CH$_2$Cl$_2$ (10 mL). The filtrate was washed with water, the aqueous layer was extracted with CH$_2$Cl$_2$ (2×50 mL). The combined organic layers were dried over Na$_2$SO$_4$, filtered and evaporated under reduced pressure. The crude residue was purified by silicagel column chromatography by using 20% EtOAc in n-Hexane as an eluent to obtain the desired product (1.5 g, 54.5% yield) as an off-white solid. $^1$H NMR (300 MHz, CDCl$_3$): δ10.91 (s, 0.5H), 10.48 (s, 0.5H), 7.78-7.74 (m, 1H), 7.48-7.18 (m, 10H), 5.43-5.39 (m, 0.5H), 5.36-5.29 (m, 0.5H), 4.75 (s, 1H), 4.61 (s, 1H), 4.48-4.43 (m, 1H), 3.78-3.66 (m, 1H), 3.62-3.45 (m, 1H), 3.18-2.73 (m, 5H), 2.68-2.56 (m, 1H), 2.36-2.23 (m, 2H), 2.13-1.86 (m, 5H), 1.82-1.11 (m, 25H), 1.06-0.68 (m, 21H); ES Mass: [M+1]$^+$ 896.7.

Step 8: Synthesis of (1S,3R)-2,2-dimethyl-3-((((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid To a solution of 1-benzyl 3-((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl) (1S,3R)-2,2-dimethylcyclobutane-1,3-dicarboxylate (step 7, 1.5 g, 1.71 mmol, 1.0 eq) in EtOAc: MeOH (1:1, 30 mL) added ammonium formate (0.54 g, 8.53 mmol) and 10% Pd—C (181 mg, 0.17, 0.1 eq) at room temperature and stirred for about 2 hours. TLC indicated starting material was consumed and the desired product was observed. The reaction mixture was filtered through celite and the collected solid was washed with EtOAc: MeOH (1:1, 20 mL). The filtrate was concentrated under reduced pressure to afford the residue. The residue was redissolved in CH$_2$Cl$_2$ (20 mL), diluted with water, the organic layer was separated and the aqueous layer was extracted with CH$_2$Cl$_2$ (2×20 mL). The combined organic layers were dried over Na$_2$SO$_4$, filtered and evaporated under reduced pressure. The crude residue was purified by silicagel column chromatography by using 30% EtOAc in n-Hexane as an eluent to obtain the desired product (0.6 g, 43.5% yield) as an off-white solid. $^1$H NMR (300 MHz, DMSO): δ12.15 (bs, 1H), 11.6 (s, 1H), 7.36-7.58 (m, 2H), 7.42 (s, 1H), 7.34-7.26 (m, 2H), 7.18-7.09 (m, 1H), 5.06 (bs, 1H), 4.56 (s, 1H), 4.47 (s, 1H), 4.36-4.29 (m, 1H), 3.83-3.73 (m, 1H), 3.65-3.58 (m, 1H), 2.88-2.63 (m, 5H), 2.39-2.05 (m, 6H), 1.93-1.78 (m, 4H), 1.64-1.07 (m, 21H), 0.98-0.74 (m, 21H); ES Mass: [M+1]$^+$ 806.67; HPLC: 95.09%.

Example 28

Preparation of 4-(1R,3aS,5aR,5bR,7aR,9S,11aR,11bR,13aR,13bR)-3a-((R)-2-(5-(4-chlorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid

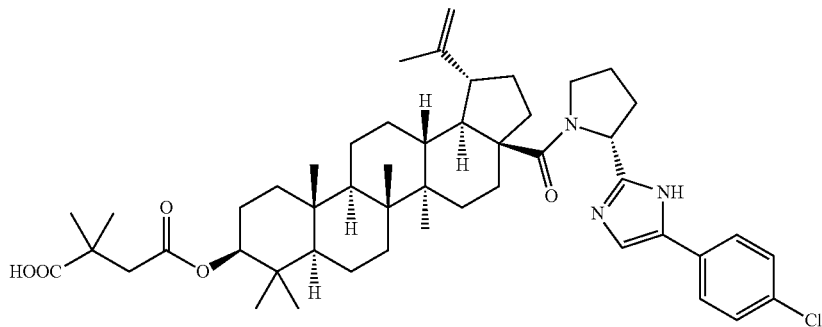

Step 1: Synthesis of 1-(tert-butyl) 2-(2-(4-chlorophenyl)-2-oxoethyl) (S)-pyrrolidine-1,2-dicarboxylate

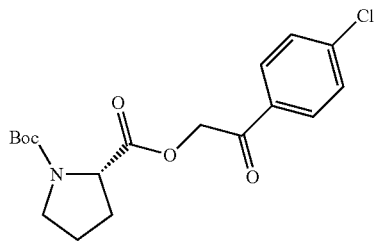 [SMILES: CC(C)(C)OC(=O)N1CCC[C@H]1C(=O)OCC(=O)c1ccc(Cl)cc1]

To a stirred solution of (tert-butoxycarbonyl)-L-proline (Example 15-step 1, 5 g, 23.36 mmol) in DCM (50 mL), DIPEA (8.05 mL, 46.72 mmol) was added at 0° C. and after 10 minutes 2-bromo-1-(4-chlorophenyl)ethan-1-one (5.4 g, 23.36 mmol) was added. Then the reaction mixture was allowed to stir at room temperature for about 12 hours. After completion of the reaction (monitored by TLC), the reaction mixture was diluted with DCM, washed with water, saturated brine and the organic layer was concentrated under reduced pressure to afford the title compound (8.0 g, 94%). The crude product was used in the next step without further purification.

Step 2: Synthesis of tert-butyl (S)-2-(5-(4-chlorophenyl)-1H-imidazol-2-yl)pyrrolidine-1-carboxylate

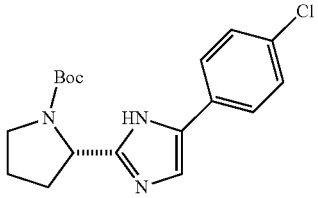

To a stirred solution of 1-(tert-butyl) 2-(2-(4-chlorophenyl)-2-oxoethyl) (S)-pyrrolidine-1,2-dicarboxylate (step 1, 8.0 g, 21.85 mmol) in toluene (8 mL), ammonium acetate (13.4 g, 174.8 mmol) was added at room temperature and refluxed for about 16 hours. After completion of the reaction (monitored by TLC), the reaction mixture was diluted with EtOAc and the organic layer was washed with 0.5 N hydrochloric acid. Aqueous layer was basified with 2N NaOH (pH 10-11) and extracted with ethyl acetate. The organic layer was washed with water, dried over Na₂SO₄, filtered and solvent was evaporated under reduced pressure to afford the title compound (5.0 g, 67.0%).

Step 3: Synthesis of (S)-5-(4-chlorophenyl)-2-(pyrrolidin-2-yl)-1H-imidazole

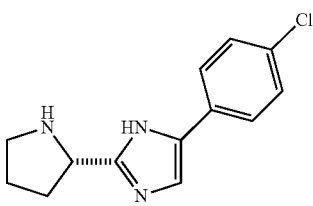

A solution of tert-butyl (S)-2-(5-(4-chlorophenyl)-1H-imidazol-2-yl)pyrrolidine-1-carboxylate (step 2, 3.0 g, 8.64 mmol) in Dioxane. HCl (20 mL) stirred at room temperature for about 3 hours. After completion of the reaction (monitored by TLC), the solvent was evaporated and the crude was dissolved in DCM and proceeds for next step without further purification (2.0 g, 95.0%).

Step 4: Synthesis of (1R,3aS,5aR,5bR,7aR,9S,11aR,11bR,13aR,13bR)-3a-(2-(5-(4-chlorophenyl)-1H-imidazol-2-yl)pyrrolidine-1-carbonyl)-5a,5b,8,8,11a-pentamethyl-1-(prop-1-en-2-yl)icosahydro-1H-cyclopentaialchrysen-9-yl acetate

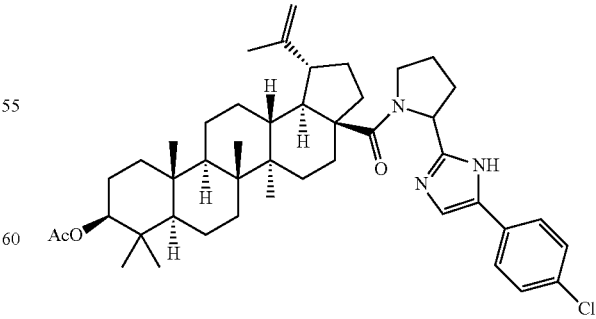

To a stirred solution of (S)-2-(pyrrolidin-2-yl)-5-(4-chlorophenyl)-1H-imidazole (step 3, 2.00 g, 8.13 mmol, 2.1 eq) and triethylamine (2.60 mL, 19.37 mmol, 5.0 eq) in CH₂Cl₂

(20 mL) at 0° C. was added (1R,3aS,5aR,5bR,7aR,9S,11aR, 11bR,13aR,13bR)-3a-(chlorocarbonyl)-5a,5b,8,8,11a-pentamethyl-1-(1-methylcyclopropyl)icosahydro-1H-cyclopenta[a]chrysen-9-yl acetate (prepared as described in WO 2013/160810 A2, 2.0 g, 3.87 mmol, 1.0 eq) in DCM (12 mL). The reaction mixture was allowed to stir at room temperature for overnight. The reaction mixture was diluted with water and extracted with $CH_2Cl_2$. The combined organic extracts were dried over $Na_2SO_4$, filtered and evaporated under reduced pressure. The residue was purified by column chromatography by using 12% ethylacetate and hexane as an eluent to gave the desired product (1.4 g, 50.0%) as a solid. $H^1$ NMR (DMSO-$D_6$, 300 MHz): δ 11.53 (s, 1H), 7.61 (d, 2H), 7.35 (s, 1H), 7.11 (d, 2H), 5.06 (d, 1H), 4.54 (d, 2H), 4.36 (d, 1H), 3.77 (d, 1H), 3.60 (d, 1H), 3.00 (q, 1H), 2.27 (s, 3H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 5H), 0.91 (d, 10H), 0.79 (s, 4H) and 0.47 (q, 4H); Mass: $[M]^+$ 728.51 (100%).

Step 5: Synthesis of (2-(5-(4-chlorophenyl)-1H-imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)methanone

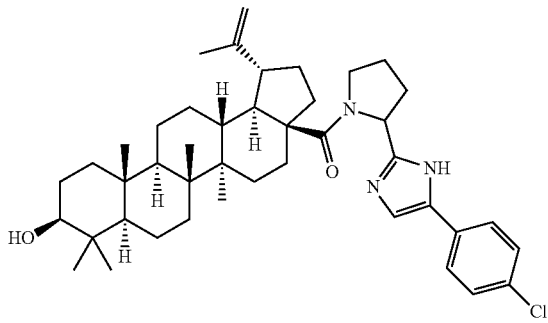

To a stirred solution of (1R,3aS,5aR,5bR,7aR,9S,11aR,11bR,13aR,13bR)-3a-(2-(5-(4-chlorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl acetate (step 4, 1.4 g, 1.92 mmol, 1.0 eq) in THF (14 mL) and Methanol (14 mL) was added potassium carbonate (1.7 g, 13.48 mmol, 10.0 eq). The reaction mixture was stirred at room temperature for about 48 hours. TLC indicated starting material was consumed and the desired product was observed. The reaction mixture was filtered through a pad of celite and washed with $CH_2Cl_2$. The filtrate was evaporated under reduced pressure and the crude was purified by column chromatography by using 20% ethylacetate and hexane as an eluent to gave the desired product (0.8 g, 61.0%) as a white solid. $H^1$ NMR ($CDCl_3$, 300 MHz): δ 11.53 (s, 1H), 7.58 (d, 2H), 7.36 (s, 1H), 7.13 (d, 2H), 5.06 (d, 1H), 4.54 (d, 2H), 4.27 (d, 1H), 3.77 (d, 1H), 3.60 (d, 1H), 3.00 (q, 1H), 2.96 (d, 1H), 2.77-2.63 (m, 2H), 2.36-2.12 (m, 4H), 1.86 (m, 1H), 1.57 (s, 6H), 1.42-1.31 (m, 9H), 1.11 (q, 5H), 0.91 (d, 11H), 0.79 (s, 4H) and 0.47 (q, 4H); Mass: $[M]^+$ 686.46 (100%).

Step 6: Synthesis of 4-(1R,3aS,5aR,5bR,7aR,9S,11aR,11bR,13aR,13bR)-3a-((R)-2-(5-(4-chlorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid To a stirred solution of (R)-2-(5-(4-chlorophenyl)-1H-imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)methanone (step 5, 0.300 g, 0.43 mmol, 1.0 eq) and 2,2-dimethyl succinicanhydride (0.22 g, 1.75 mmol, 4.0 eq) in toluene (7.5 mL) was added DMAP (0.10 g, 0.87 mmol, 2.0 eq). The reaction mixture was heated at 90° C. for overnight. TLC indicated starting material was consumed and the desired product was observed. The mixture was concentrated under reduced pressure, cooled to 0° C., acidified to pH=5 with 1N HCl and extracted with $CH_2Cl_2$. The combined organic extracts were washed with water, dried over $Na_2SO_4$, filtered and evaporated under reduced pressure. The crude residue was purified by column chromatography by using 2% methanol: dichloromethane as an eluent to gave the desired product (0.150 g, 43.0%) as a white solid. $H^1$ NMR (DMSO-$d_6$, 300 MHz): δ 12.16 (s, 1H), 11.67 (s, 1H), 7.74 (d, 2H), 7.48 (s. 1H), 7.36 (d, 2H), 5.04 (s, 1H), 4.54 (d, 2H), 4.36 (t, 1H), 3.78 (s, 1H), 3.56 (bs, 2H), 2.08 (m 1H), 2.38-1.85 (m, 9H), 1.58-1.32 (m, 15H), 1.16 (m, 7H), 0.93-0.87 (m, 10H) and 0.83-0.78 (m, 12H); Mass: $[M]^+$ 814.53 (100%); HPLC: 89.00%.

Example 29

Preparation of 2,2-dimethyl-3-((((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yl)oxy)carbonyl) cyclobutane-1-carboxylic acid

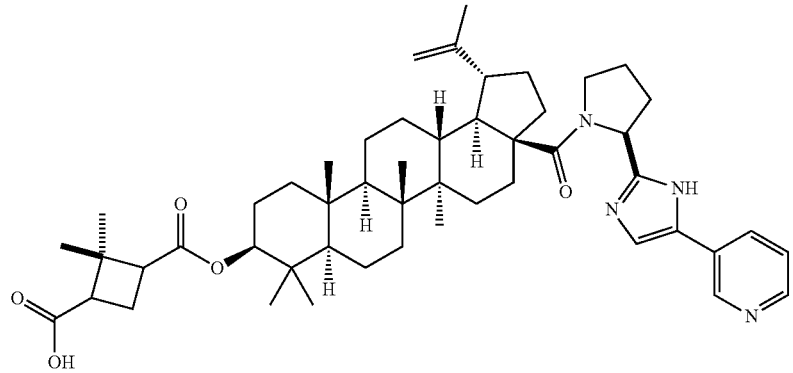

Step 1: synthesis of 1-benzyl 3-((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yl)-2,2-dimethylcyclobutane-1,3-dicarboxylate

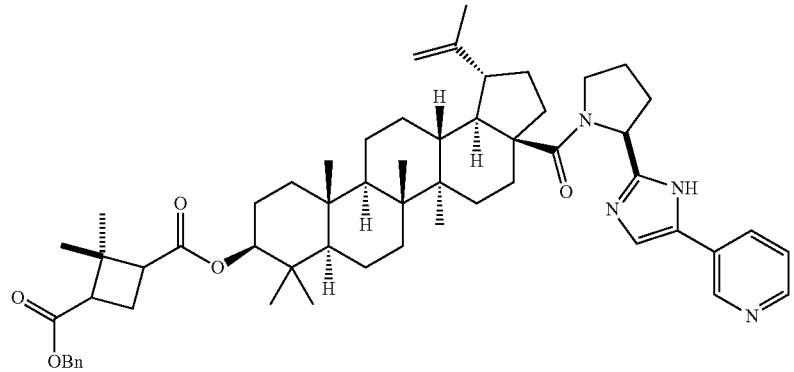

To a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((S)-2-(5-(pyridin-3-yl)-1H-imidazol-2-yl)pyrrolidin-1-yl)methanone (Example 10-step 6, 0.6 g, 0.9 mmol, 1.0 eq) in pyridine (10 mL) was added DMAP (0.2 g, 1.8 mmol, 2.0 eq) and (1S,3R)-3-(benzyloxycarbonyl)-2,2-dimethylcyclobutanecarboxylic 2,4,6-trichlorobenzoic anhydride (Example 14-step 1, 0.64 g, 1.3 mmol). The reaction mixture was heated at 90° C. for overnight. TLC indicated starting material was consumed and the desired product was observed. The reaction mixture was evaporated under reduced pressure and diluted with water. The aqueous layer was extracted with $CH_2Cl_2$ (2×50 mL) and the DCM layer was washed with 1N HCl, followed by water and brine solution. The organic layers were dried over $Na_2SO_4$, filtered and evaporated under reduced pressure. The crude residue was purified by silicagel column chromatography by using 1.5% methanol: dichloromethane as an eluent to obtain the title compound (wt: 0.5 g,) as a white solid. $^1$H NMR (300 MHz, $CDCl_3$): δ 1.17-1.26 (m, 29H), 1.29-1.56 (m, 4H), 1.59-1.82 (m, 18H), 1.82-1.89 (m, 13H), 2.09-2.18 (m, 5H), 2.23-2.8 (m, 8H), 3.52-4.13 (m, 3H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.60 (m, 3H), 7.70-7.88 (m, 2H), 10.50 (s, 1H); Mass: [M+1]$^+$ 896 (100%).

Step 2: synthesis of 2,2-dimethyl-3-((((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yl)oxy)carbonyl) cyclobutane-1-carboxylic acid To a solution of 1-benzyl 3-((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yl)-2,2-dimethylcyclobutane-1,3-dicarboxylate (step 1, 0.5 g, 0.55 mmol, 1.0 eq) dissolved in EtOAc:MeOH (1:1) was added 0.25 g of Pd/C (Wet: 10%) under $N_2$ atmosphere and was added (0.17 g, 2.7 mmol) of ammonium acetate at room temperature, stirred for about 4 hours. TLC indicated starting material was consumed and the desired product was observed. The reaction mixture was filtered through a pad of celite and was washed with hot EtOAc: MeOH (1:1, 50 mL). The filtrate was evaporated under reduced pressure, diluted with water (10 mL) and extracted with $CH_2Cl_2$ (2×200 mL). The organic layer was washed with brine solution, dried over $Na_2SO_4$, filtered and evaporated under reduced pressure. The crude residue was purified by silicagel column chromatography by using 6% methanol: dichloromethane as an eluent to gave the title compound (wt: 0.065 g) as a white solid. $^1$H NMR (300 MHz, DMSO-d6): δ 1.17-1.26 (m, 29H), 1.29-1.56 (m, 4H), 1.59-1.82 (m, 18H), 1.82-1.89 (m, 13H), 2.09-2.18 (m, 5H), 2.23-2.8 (m, 8H), 3.52-4.13 (m, 3H), 4.20-4.24 (m, 1H), 4.61-4.75 (m, 1H), 4.77 (s, 1H), 4.80 (s, 1H), 5.31-5.35 (m, 1H), 7.31-7.34 (s, 1H), 7.58 (m, 1H), 7.62-7.70 (d, 1H), 8.0 (m, 2H), 10.50 (s, 1H); Mass: 806 [M+1]$^+$ (100%); HPLC Purity: 91.4%.

Example 30

Preparation of 2,2-dimethyl-4-oxo-4-(((1R,3aS,5aR,5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)butanoic acid

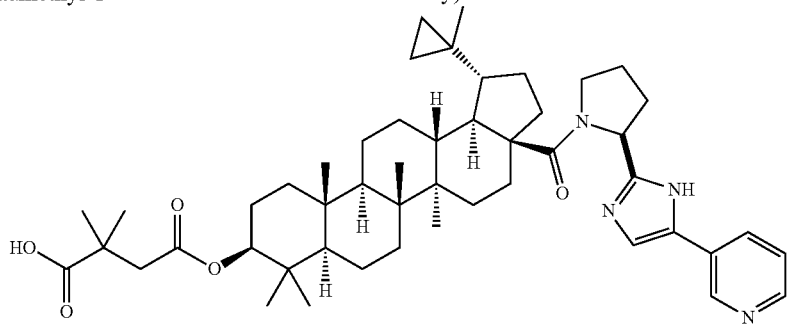

Step 1: Synthesis of (1R,3aS,5aR,5bR,7aR,9S,11aR, 11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl acetate

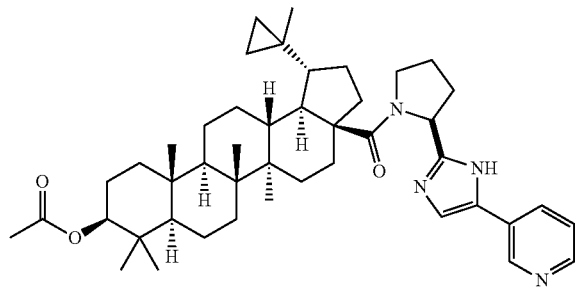

To a stirred solution of (1R,3aS,5aR,5bR,7aR,9S,11aR, 11bR,13aR,13bR)-9-acetoxy-5a,5b,8,8,11a-pentamethyl-1-(1-methylcyclopropyl)icosahydro-1H-cyclopenta[a]chrysene-3a-carboxylic acid (Example 12-step 3, 2.3 g, 4.4 mmol) in DCM (30 mL) Oxalyl chloride (1.6 mL, 12.8 mmol) in DCM (50 mL) was added at 0° C. and stirred at room temperature for about 3 hours. After completion of the reaction (monitored by TLC), the solvent was evaporated under nitrogen atmosphere and dissolved in DCM (20 mL), which was added to the above stirred solution of (S)-3-(2-(pyrrolidin-2-yl)-1H-imidazol-5-yl)pyridine (Example 10-step 4, 1.5 g, 6.9 mmol) at 0° C. and allowed to stir at room temperature for about 16 hours. After completion of the reaction (monitored by TLC), the reaction mixture was diluted with DCM, washed with water, 1N HCl, and brine solution and dried over $Na_2SO_4$. The solvent was evaporated and purified by silica gel column (100-200 mesh, elution 30% EtOAc in hexane) to afford the title compound (Wt: 3 g) as an off white solid. $^1$H NMR (300 MHz, $CDCl_3$): δ 0.22-0.25 (m, 2H), 0.26-0.27 (m, 2H), 0.79-0.93 (m, 8H), 1.07-1.26 (m, 10H), 1.29-1.56 (m, 12H), 1.69-1.99 (m, 8H), 2.09 (s, 3H), 2.23-3.45 (m, 6H), 3.82-4.13 (m, 5H), 4.20-4.24 (s, 1H), 5.31-5.35 (m, 1H), 7.22-7.60 (m, 3H), 7.70-7.88 (m, 2H), 10.50 (s, 1H); Mass: 708 [M+1]$^+$ 709 (100%).

Step 2: Synthesis of ((1R,3aS,5aR,5bR,7aR,9S, 11aR,11bR,13aR,13bR)-9-hydroxy-5a,5b,8,8,11a-pentamethyl-1-(1-methylcyclopropyl)icosahydro-3aH-cyclopenta[a]chrysen-3a-yl)((S)-2-(5-(pyridin-3-yl)-1H-imidazol-2-yl)pyrrolidin-1-yl)methanone

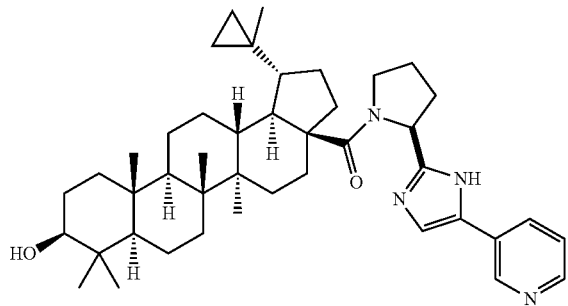

To a stirred solution of (1R,3aS,5aR,5bR,7aR,9S,11aR, 11bR,13aR,13bR)-5a,5b,8,8,11a-pentamethyl-1-(1-methylcycloprop yl)-3a-((S)-2-(5-(pyridin-3-yl)-1H-imidazol-2-yl) pyrrolidine-1-carbonyl)icosahydro-1H-cyclopenta[a]chrysen-9-yl acetate (step 1, 2.5 g, 3.5 mmol) in MeOH (40 mL) was added potassium carbonate (3.8 g, 28.24 mmol) at 0° C. and allowed to stir at room temperature for about 16 hours. After completion of the reaction (monitored by TLC), the volatile was evaporated and the aqueous layer was extracted with ethyl acetate. The organic layer was washed with water, brine and dried over $Na_2SO_4$, then the solvent was evaporated and the resulting crude was purified by silica gel column (100-200 mesh, elution 5% MeOH/DCM) to afford the title compound (wt: 1.3 g) as an off white solid. $^1$H NMR (300 MHz, $CDCl_3$): δ 0.22-0.25 (m, 2H), 0.26-0.27 (m, 2H), 0.79-0.93 (m, 8H), 1.07-1.26 (m, 10H), 1.29-1.56 (m, 12H), 1.69-1.99 (m, 8H), 2.23-3.45 (m, 6H), 3.82-4.13 (m, 5H), 4.20-4.24 (m, 1H), 5.31-5.35 (m, 1H), 7.22-7.60 (m, 3H), 7.70-7.88 (m, 2H), 10.50 (s, 1H); Mass: 666 [M+1]$^+$ 667 (100%).

Step 3: Synthesis of 2,2-dimethyl-4-oxo-4-(((1R, 3aS,5aR,5bR,7aR,9S,11aR,11bR,13aR,13bR)-5a,5b, 8,8,11a-pentamethyl-1-(1-methylcyclopropyl)-3a-((S)-2-(5-(pyridin-3-yl)-1H-imidazol-2-yl) pyrrolidine-1-carbonyl)icosahydro-1H-cyclopenta[a] chrysen-9-yl)oxy) butanoic acid 2,2-Dimethylsuccinic anhydride (0.53 g, 4.2 mmol) was added to a stirred solution of ((1R,3aS,5aR,5bR,7aR,9S, 11aR,11bR,13aR,13bR)-9-hydroxy-5a,5b,8,8,11a-pentamethyl-1-(1-methylcyclopropyl)icosahydro-3aH-cyclopenta [a]chrysen-3a-yl)((S)-2-(5-(pyridin-3-yl)-1H-imidazol-2-yl) pyrrolidin-1-yl)methanone (step 2, 0.7 g, 1.0 mmol) and DMAP (0.19 g, 1.5 mmol) in toluene (30 mL) at room temperature and refluxed for about 24 hours. After completion of the reaction (monitored by TLC), the reaction mixture was diluted with EtOAc, washed with water, 1N HCl, water, brine and dried over $Na_2SO_4$. The solvent was evaporated and purified by silica gel column (100-200 mesh, elution 5% MeOH/DCM) to afford the title compound (Wt: 0.2 g) as an off white solid. $^1$H NMR (300 MHz, $CDCl_3$): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H),4.20-4.24 (m, 1H), 5.31-5.35 (m, 1H), 7.22-7.60 (m, 3H), 7.70-7.88 (m, 2H),10.50 (s, 1H); Mass: 794 [M+1]$^+$ 795 (100%); HPLC Purity: 91.3%.

Example 31

Preparation of 3,3-dimethyl-5-oxo-5-((((1R,3aS,5aR, 5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)pentanoic acid

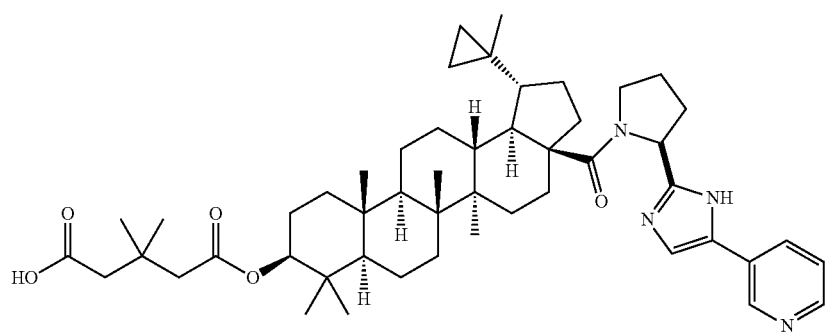

3,3-Dimethyl glutaric anhydride (0.42 g, 3.0 mmol) was added to a stirred solution of ((1R,3aS,5aR,5bR,7aR,9S,11aR,11bR,13aR,13bR)-9-hydroxy-5a,5b,8,8,11a-pentamethyl-1-(1-methylcyclopropyl)icosahydro-3aH-cyclopenta[a]chrysen-3a-yl)((S)-2-(5-(pyridin-3-yl)-1H-imidazol-2-yl)pyrrolidin-1-yl)methanone (Example 30-step 2, 0.5 g, 0.7 mmol) and DMAP (0.13 g, 1.1 mmol) in pyridine (20 mL) at room temperature and refluxed for about 24 hours. After completion of the reaction (monitored by TLC), the reaction mixture was diluted with EtOAc, washed with water, 1N HCl, brine and dried over $Na_2SO_4$. The solvent was evaporated and purified by silica gel column (100-200 mesh, elution 5% MeOH/DCM) to afford the title compound (Wt: 0.2 g) as an off white solid. $^1$H NMR (300 MHz, DMSO-d6): δ 0.22-0.25 (m, 2H), 0.26-0.27 (m, 2H), 0.79-0.93 (m, 17H), 0.93 (6H), 1.07-1.26 (m, 2H), 1.29-1.56 (m, 13H), 1.69-1.99 (m, 8H), 2.09-2.18 (m, 4H), 2.23-3.45 (m, 6H), 3.82-4.13 (m, 5H), 4.20-4.24 (m, 1H), 5.31-5.35 (m, 1H), 7.22-7.60 (m, 3H), 7.70-7.88 (m, 2H), 10.5 (s, 1H); Mass: 808 [M+1]$^+$ 809 (100%); HPLC Purity: 90%.

Example 32

Preparation of 2,2-dimethyl-3-(((((1R,3aS,5aR,5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)carbonyl)cyclobutane-1-carboxylic acid

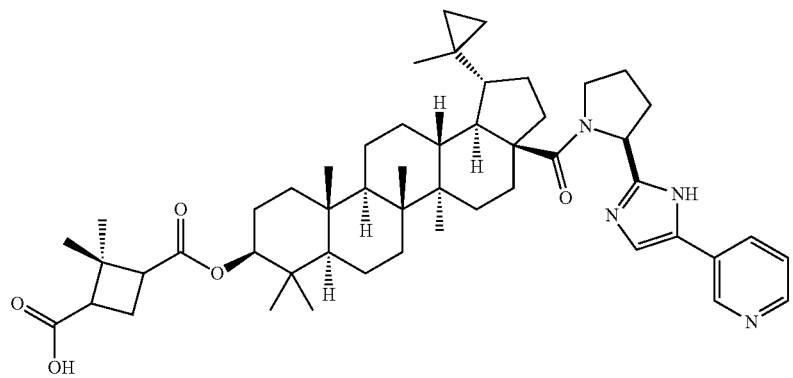

Step 1: synthesis of 1-benzyl 3-((1R,3aS,5aR,5bR, 7aR,9S,11aR,11bR,13aR,13bR)-5a,5b,8,8,11a-pentamethyl-1-(1-methylcycloprop yl)-3a-((S)-2-(5-(pyridin-3-yl)-1H-imidazol-2-yl)pyrrolidine-1-carbonyl)icosahydro-1H-cyclopenta[a]chrysen-9-yl) 2,2-dimethylcyclobutane-1,3-dicarboxylate

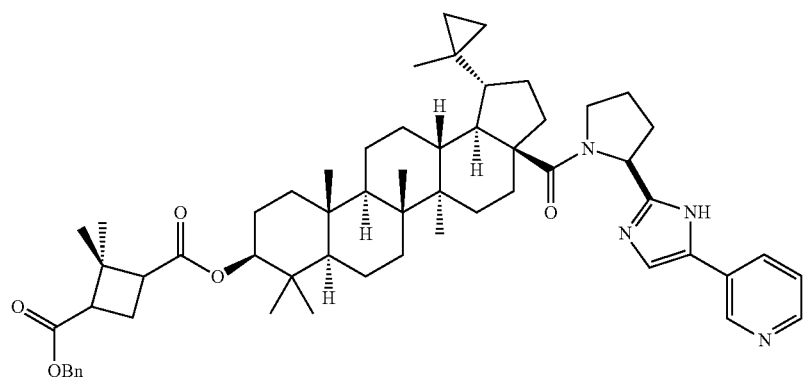

To a stirred solution of ((1R,3aS,5aR,5bR,7aR,9S,11aR, 11bR,13aR,13bR)-9-hydroxy-5a,5b,8,8,11a-pentamethyl-1-(1-methylcycloprop yl)icosahydro-3aH-cyclopenta[a]chrysen-3a-yl)((S)-2-(5-(pyridin-3-yl)-1H-imidazol-2-yl) pyrrolidin-1-yl)methanone (Example 30-step 2, 0.6 g, 0.9 mmol, 1.0 eq) in pyridine (10 mL) was added DMAP (0.2 g, 1.8 mmol, 2.0 eq) and (1S,3R)-3-(benzyloxycarbonyl)-2,2-dimethylcyclobutanecarboxylic 2,4,6-trichlorobenzoic anhydride (Example 14-step 1, 0.62 g, 1.2 mmol). The reaction mixture was heated to 90° C. for overnight. TLC indicated starting material was consumed and the desired product was observed. The reaction mixture was evaporated under reduced pressure and diluted with water. The aqueous layer was extracted with CH$_2$Cl$_2$ (2×50 mL), 1N HCl, water wash and brine wash. The combined organic layers were dried over Na$_2$SO$_4$, filtered and evaporated under reduced pressure. The crude residue was purified by silicagel column chromatography by using 1.5% methanol: dichloromethane as an eluent to obtain the title compound (wt: 0.5 g) as a white solid. $^1$H NMR (300 MHz, CDCl$_3$): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 5.31-5.35 (m, 1H), 7.01-7.11 (m, 3H), 7.12-7.13 (m, 2H), 7.22-7.60 (m, 3H), 7.70-7.88 (m, 2H), 10.50 (s, 1H); Mass 910: [M+1]$^+$ 911 (100%).

Step 2: synthesis of 2,2-dimethyl-3-(((((1R,3aS,5aR, 5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl) oxy)carbonyl)cyclobutane-1-carboxylic acid To a solution of 1-benzyl 3-((1R,3aS,5aR,5bR,7aR,9S, 11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta [a]chrysen-9-yl) 2,2-dimethylcyclobutane-1,3-dicarboxylate (step 1, 0.5 g, 0.55 mmol, 1.0 eq) dissolved in EtOAc:MeOH (1:1) was added 0.25 g of Pd/C (Wet 10%) under N$_2$ atmosphere and (0.17 g 2.7 mmol) of ammonium formate at room temperature for about 4 hours. TLC indicated starting material was consumed and the desired product was observed. The reaction mixture was filtered through a pad of celite and was washed with hot EtOAc:MeOH (1:1, 50 mL). The filtrate was evaporated under reduced pressure, diluted with water (10 mL), extracted with CH$_2$Cl$_2$ (2×200 mL) and brine wash. The combined organic layers were dried over Na$_2$SO$_4$, filtered and evaporated under reduced pressure. The crude residue was purified by silicagel column chromatography by using 6% methanol: dichloromethane as an eluent to gave the title compound (0.065 g) as a white solid. $^1$H-NMR (300 MHz, DMSO-d6): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.70-7.88 (m, 3H), 10.50 (s, 1H); Mass: 820 [M+1]$^+$ 821 (100%); HPLC Purity: 87.5%.

Example 33

Preparation of 4-((((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl)oxy)-2,2-dimethyl-4-oxobutanoic acid

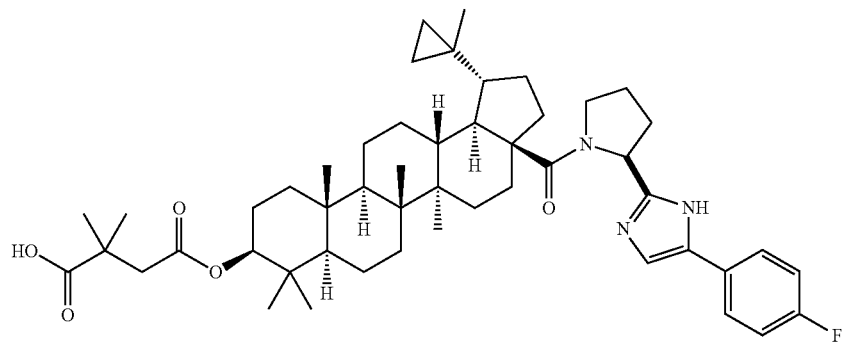

Step 1: Synthesis of 2-bromo-1-(4-fluorophenyl)ethan-1-one

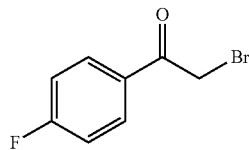 [SMILES: O=C(CBr)c1ccc(F)cc1]

To the stirred solution of 4-Fluoroacetophenone (10 g, 71.9 mmol) in 200 mL of MeOH at 0° C. was added Bromine (3.7 mL, 23.1 mmol) (dropwise addition) and stirred for about 30 minutes and stirred for about 2 hours at room temperature. After completion of the reaction (monitored by TLC), the reaction mixture was concentrated and the crude product was dissolved in n-hexane and stirred for about 30 minutes. The obtained solid was filtered and washed with n-hexane then dried and proceeded for next step (wt: 14.0 g).

Step 2: Synthesis of 1-(tert-butyl) 2-(2-(4-fluorophenyl)-2-oxoethyl) (S)-pyrrolidine-1,2-dicarboxylate

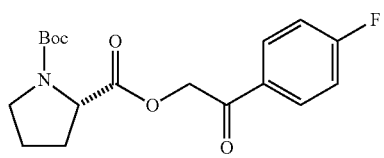 [SMILES: CC(C)(C)OC(=O)N1CCC[C@H]1C(=O)OCC(=O)c1ccc(F)cc1]

To a stirred solution of (S)-1-(tert-butoxycarbonyl)pyrrolidine-2-carboxylic acid (13.8 g, 64.1 mmol) in DCM (120 mL), DIPEA (22.19 mL, 172.01 mmol) was added at 0° C. temperature and after 10 minutes 2-bromo-1-(4-fluorophenyl)ethan-1-one (step 1, 14 g, 64.5 mmol) was added. Then the reaction mixture was allowed to stir at room temperature for about 12 hours. After completion of the reaction (monitored by TLC), the reaction mixture was diluted with DCM, washed with water, saturated brine and the organic layer was concentrated under reduced pressure, the resulting crude was proceeded to next step without further purification (wt: 18.0 g).

Step 3: tert-butyl (S)-2-(5-(4-fluorophenyl)-1H-imidazol-2-yl)pyrrolidine-1-carboxylate

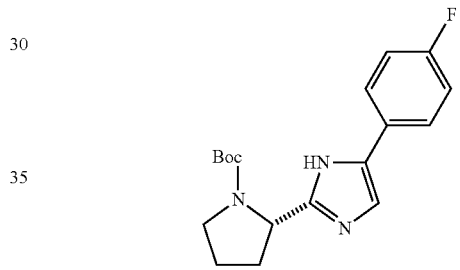

To a stirred solution of 1-(tert-butyl) 2-(2-(4-fluorophenyl)-2-oxoethyl)-(S)-pyrrolidine-1,2-dicarboxylate (step 2, 18.0 g, 51.1 mmol) in Toulene (180 mL) ammonium acetate (39.3 g, 51.03 mmol) was added at room temperature and refluxed for about 12 hours. After completion of the reaction (monitored by TLC), the reaction mixture was concentrated and the crude was diluted with EtOAc, washed with water, brine and dried over $Na_2SO_4$. The solvent was evaporated and purified by silica gel column (100-200 mesh, elution 20% EtOAc in hexane) to afford the title compound (wt: 8.0 g) as an off white solid. $^1$H NMR (300 MHz, CDCl$_3$): δ 7.1-7.5 (m, 3H), 7.61-7.63 (m, 2H), 4.98-5.00 (d, 1H, j=6 Htz), 3.42 (s, 2H), 3.01 (s, 1H), 2.14-2.17 (m, 4H), 1.50 (s, 9H); Mass: 331 [M+1]$^+$ 332 (100%).

Step 4: Synthesis of (S)-5-(4-fluorophenyl)-2-(pyrrolidin-2-yl)-1H-imidazole

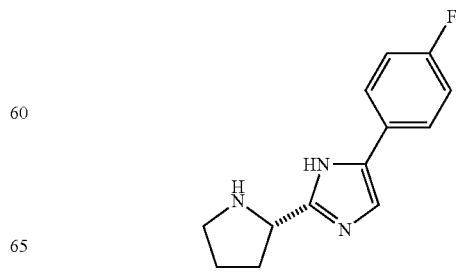

A solution of tert-butyl (S)-2-(5-(4-fluorophenyl)-1H-imidazol-2-yl)pyrrolidine-1-carboxylate (step 3, 2.1 g, 6.4 mmol) in TFA:DCM (1:2, 30 mL) stirred at 0° C.-room temperature for about 1 hour. After completion of the reaction, the solvent was evaporated and the crude was dissolved in DCM and proceeded for next step without further purification (wt: 1.4 g).

Step 5: Synthesis of (1R,3aS,5aR,5bR,7aR,9S,11aR, 11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl acetate

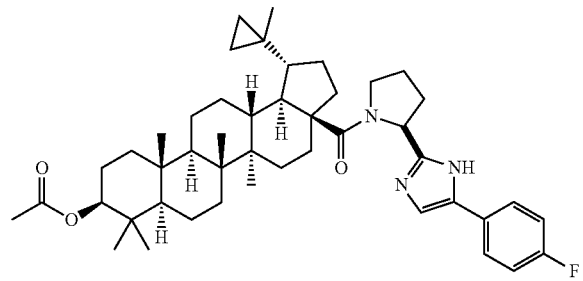

To a stirred solution of (1R,3aS,5aR,5bR,7aR,9S,11aR, 11bR,13aR,13bR)-9-acetoxy-5a,5b,8,8,11a-pentamethyl-1-(1-methylcyclopropyl)icosahydro-1H-cyclopenta[a]chrysene-3a-carboxylic acid (Example 12-step 3, 3.3 g, 60.34 mmol) in DCM (30 mL), Oxalyl chloride (2.28 mL, 17.9 mmol) in DCM (50 mL) was added at 0° C. and stirred at room temperature for about 3 hours. After completion of the reaction (monitored by TLC), the solvent was evaporated under nitrogen atmosphere and dissolved in DCM (50 mL), which was added to the above stirred solution of (S)-5-(4-fluorophenyl)-2-(pyrrolidin-2-yl)-1H-imidazole (step 4, 1.6 g, 7.55 mmol) at 0° C. and allowed to stir at room temperature for about 16 hours. After completion of the reaction (monitored by TLC), the reaction mixture was diluted with DCM, washed with water, 1N HCl, brine solution and dried over Na$_2$SO$_4$. The solvent was evaporated and purified by silica gel column (100-200 mesh, elution 30% EtOAc in hexane) to afford the title compound (Wt: 2.5 g) as an off white solid. $^1$H NMR (300 MHz, CDCl$_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (s, 1H), 5.31-5.35 (m, 1H), 7.22-7.60 (m, 3H), 7.70-7.88 (m, 2H), 10.50 (s, 1H); Mass: 725 [M+1]$^+$ 726 (100%).

Step 6: Synthesis of ((S)-2-(5-(4-fluorophenyl)-1H-imidazol-2-yl)pyrrolidin-1-yl)((1R,3aS,5aR,5bR, 7aR,9S,11aR,11bR,13aR)-9-hydroxy-5a,5b,8,8,11a-pentamethyl-1-(1-methylcyclopropyl)icosahydro-3aH-cyclopenta[a]chrysen-3a-yl)methanone

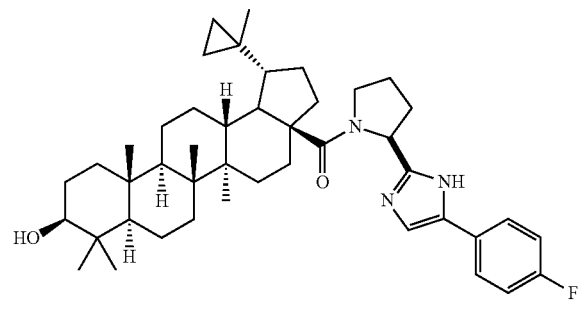

To a stirred solution of (1R,3aS,5aR,5bR,7aR,9S,11aR, 11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl acetate (step 5, 2.2 g, 30.34 mmol) in MeOH (30 mL) was added potassium carbonate (3.35 g, 24.27 mmol) at 0° C. and allowed to stir at room temperature for about 16 hours. After completion of the reaction (monitored by TLC), the volatile was evaporated and the aqueous layer was extracted with ethyl acetate and the organic layer was washed with water, brine and dried over Na$_2$SO$_4$. Then the solvent was evaporated and the resulting crude was purified by silica gel column (100-200 mesh, elution 5% MeOH/DCM) to afford the title compound (wt: 1.8 g) as an off white solid. $^1$H NMR (300 MHz, CDCl$_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 5.31-5.35 (m, 1H), 7.22-7.60 (m, 3H), 7.70-7.88 (m, 2H), 10.50 (s, 1H); Mass: 683 [M+1]$^+$ 684 (100%).

Step 7: Synthesis of 4-(((1R,3aS,5aR,5bR,7aR,9S, 11aR,11bR,13aR,13bR)-3a-((S)-2-(5-(4-fluorophenyl)-1H-imidazol-2-yl)pyrrolidine-1-carbonyl)-5a, 5b,8,8,11a-pentamethyl-1-(1-methylcyclopropyl) icosahydro-1H-cyclopenta[a]chrysen-9-yl)oxy)-2,2-dimethyl-4-oxobutanoic acid 2,2-Dimethylsuccinic anhydride (0.16 g, 1.3 mmol) was added to a stirred solution of ((S)-2-(5-(4-fluorophenyl)-1H-imidazol-2-yl)pyrrolidin-1-yl)((1R,3aS,5aR,5bR,7aR,9S, 11aR,11bR,13aR,13bR)-9-hydroxy-5a,5b,8,8,11a-pentamethyl-1-(1-methylcyclopropyl) icosahydro-3aH-cyclopenta [a]chrysen-3a-yl)methanone (step 6, 0.5 g, 0.75 mmol) and DMAP (0.4 g, 3.3 mmol) in toluene (30 mL) at room temperature and refluxed for about 24 hours. After completion of the reaction (monitored by TLC), the reaction mixture was diluted with EtOAc, washed with water, 1N HCl, water, brine and dried over Na$_2$SO$_4$. The solvent was evaporated and purified by silica gel column (100-200 mesh, elution 5% MeOH/DCM) to afford the title compound (Wt: 0.1 g) as an off white solid. $^1$H NMR (300 MHz, CDCl$_3$): δ 0.22-0.25 (m, 2H), 0.26-0.27 (m, 2H), 0.79-0.93 (m, 13H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 5.31-5.35 (m, 1H), 7.22-7.60 (m, 3H), 7.70-7.88 (m, 2H), 10.50 (s, 1H); Mass: 811[M+1]$^+$ 812 (100%); HPLC Purity: 90%.

Example 34

Preparation of 4-(((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid compound (Wt: 2.5 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (s, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 711[M+1]$^+$ 712 (100%).

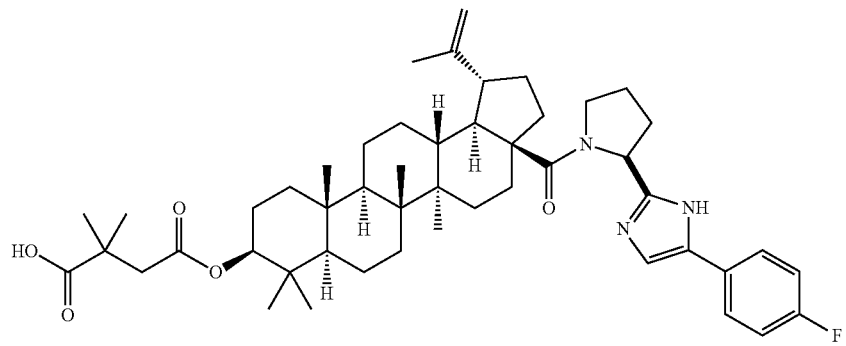

Step 1: Synthesis of (1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl acetate Step 2: Synthesis of ((S)-2-(5-(4-fluorophenyl)-1H-imidazol-2-yl)pyrrolidin-1-yl)((1R,3aS,5aR,5bR,7aR,9S,11aR,11bR,13aR)-9-hydroxy-5a,5b,8,8,11a-pentamethyl-1-(prop-1-en-2-yl)icosahydro-3aH-cyclopenta[a]chrysen-3ayl)methanone

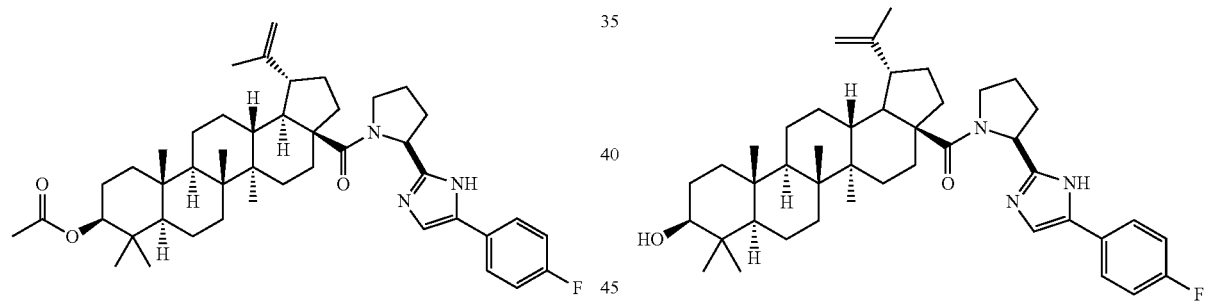

To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a]chrysene-3a-carboxylic acid (prepared as described in WO 2013/160810 A2, 3.3 g, 6.62 mmol) in DCM (30 mL), Oxalyl chloride (2.4 mL, 18.9 mmol) in DCM (50 mL) was added at 0° C. and stirred at room temperature for about 3 hours. After completion of the reaction (monitored by TLC), the solvent was evaporated under nitrogen atmosphere and dissolved in DCM (50 mL), which was added to the above stirred solution of (S)-5-(4-fluorophenyl)-2-(pyrrolidin-2-yl)-1H-imidazole (Example 33-step 4, 1.6 g, 7.55 mmol) at 0° C. and allowed to stir at room temperature for about 16 hours. After completion of the reaction (monitored by TLC), the reaction mixture was diluted with DCM, washed with water, 1N HCl, brine solution and dried over Na$_2$SO$_4$. The solvent was evaporated and purified by silica gel column (100-200 mesh, elution 30% EtOAc in hexane) to afford the title To a stirred solution of (1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl acetate (step 1, 2.2 g, 3.3 mmol) in MeOH (30 mL) was added potassium carbonate (2.9 g, 21.65 mmol) at 0° C. and allowed to stir at room temperature for about 16 hours. After completion of the reaction (monitored by TLC), the volatile was evaporated and the aqueous layer was extracted with ethyl acetate. The organic layer was washed with water, brine and dried over Na$_2$SO$_4$, then the solvent was evaporated and the resulting crude was purified by silica gel column (100-200 mesh, elution 5% MeOH/DCM) to afford the title compound (wt: 1.8 g) as an off white solid. $^1$H NMR (300 MHz, CDCl$_3$): δ 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 669 [M+1]$^+$ 670 (100%).

Step 3: Synthesis of 4-((((1R,3aS,5aR,5bR,7aR,9S, 11aR,11bR,13aR,13bR)-3a-((S)-2-(5-(4-fluorophenyl)-1H-imidazol-2-yl)pyrrolidine-1-carbonyl)-5a, 5b,8,8,11a-pentamethyl-1-(prop-1-en-2-yl) icosahydro-1H-cyclopenta[a]chrysen-9-yl)oxy)-2,2-dimethyl-4-oxobutanoic acid 2,2-Dimethylsuccinic anhydride (0.3 g, 2.7 mmol) was added to a stirred solution of ((S)-2-(5-(4-fluorophenyl)-1H-imidazol-2-yl)pyrrolidin-1-yl)((1R,3aS,5aR,5bR,7aR,9S, 11aR,11bR,13aR)-9-hydroxy-5a,5b,8,8,11a-pentamethyl-1-(prop-1-en-2-yl)icosahydro-3aH-cyclopenta[a]chrysen-3ayl)methanone (step 2, 0.5 g, 0.75 mmol) and DMAP (0.14 g, 1.14 mmol) in toluene (30 mL) at room temperature and refluxed for about 24 hours. After completion of the reaction (monitored by TLC), the reaction mixture was diluted with EtOAc, washed with water, 1N HCl, water, brine and dried over Na$_2$SO$_4$. The solvent was evaporated and purified by silica gel column (100-200 mesh, elution 5% MeOH/DCM) to afford the title compound (Wt: 0.22 g) as an off white solid. $^1$H NMR (300 MHz, DMSO-d6): δ 0.79-0.93 (m, 8H), 0.93 (6H), 1.07-1.26 (m, 10H), 1.29-1.56 (m, 12H), 169-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 797 [M+1]$^+$ 798 (100%); HPLC Purity: 90%.

Example 35

Preparation of 3-(((((1R,3aS,5aR,5bR,7aR,9S,11aR, 11bR,13aR,13bR)-3a-((S)-2-(5-(4-fluorophenyl)-1H-imidazol-2-yl)pyrrolidine-1-carbonyl)-5a, 5b,8,8, 11a-pentamethyl-1-(prop-1-en-2-yl)icosahydro-1H-cyclopenta[a]chrysen-9-yl)oxy)carbonyl)-2,2-dimethylcyclobutane-1-carboxylic acid

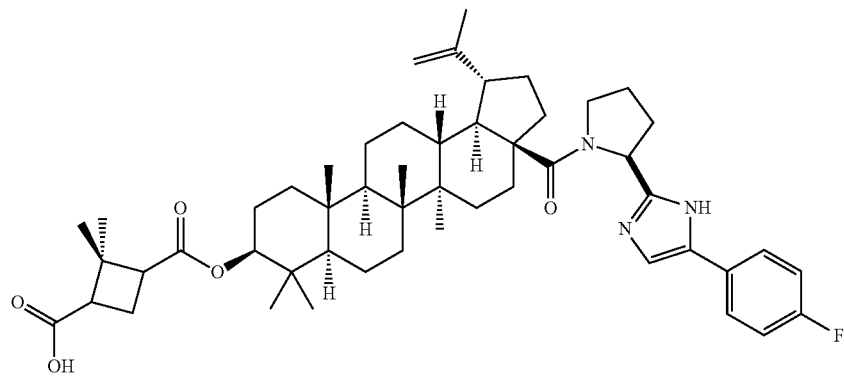

Step 1: Synthesis of 1-benzyl 3-((1R,3aS,5aR,5bR, 7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl) icosahydro-1H-cyclopenta[a]chrysen-9-yl)-2,2-dimethyl cyclobutane-1,3-dicarboxylate

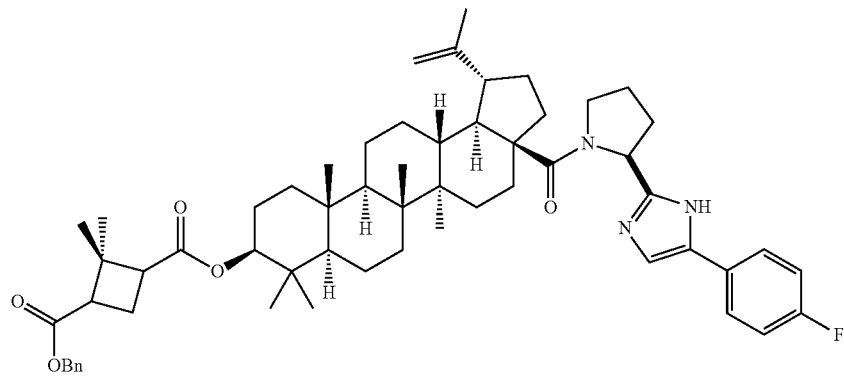

To a stirred solution of ((S)-2-(5-(4-fluorophenyl)-1H-imidazol-2-yl)pyrrolidin-1-yl)((1R,3aS,5aR,5bR,7aR,9S,11aR,11bR,13aR,13bR)-9-hydroxy-5a,5b,8,8,11a-pentamethyl-1-(1-methylcyclopropyl)icosahydro-3aH-cyclopenta[a]chrysen-3a-yl)methanone (example 34-step 2, 6.5 g, 9.68 mmol, 1.0 eq) in pyridine (100 ml) was added DMAP (3.5 g, 28.68 mmol, 2.0 eq) and (1S,3R)-3-(benzyloxycarbonyl)-2,2-dimethylcyclobutanecarboxylic 2,4,6-trichlorobenzoic anhydride (Example 14-step 1, 6.6 g, 13.2 mmol). The reaction mixture was heated to 90° C. for overnight. TLC indicated starting material was consumed and the desired product was observed. The reaction mixture was evaporated under reduced pressure and diluted with water. The aqueous layer was extracted with $CH_2Cl_2$ (2×500 ml). The combined organic layers were dried over $Na_2SO_4$, filtered and evaporated under reduced pressure. The crude residue was purified by silicagel column chromatography by using 1.5% methanol: dichloromethane as an eluent to obtain the title compound (wt: 4.5 g) as a white solid. $^1$H NMR (300 MHz, $CDCl_3$): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.60 (m, 3H), 7.8-8.1 (s, 1H), 10.50 (s, 1H); Mass: 913 [M+1]$^+$ 914 (100%).

Step 2: Synthesis of 3-(((((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid To a solution of 1-benzyl 3-((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)-2,2-dimethylcyclobutane-1,3-dicarboxylate (step 1, 4.5 g, 4.9 mmol, 1.0 eq) dissolved in EtOAc:MeOH (1:1) and was added 2 g of Pd/C (Wet 10%) under $N_2$ atmosphere and was added (1.5 g, 24.61 mmol) of ammonium formate at room temperature, filtered through a pad of celite and was washed with hot EtOAc:MeOH (1:1, 50 mL). The filtrate was evaporated under reduced pressure, diluted with water (10 ml), extracted with $CH_2Cl_2$ (2×200 ml) and brine wash. The combined organic layers were dried over $Na_2SO_4$, filtered and evaporated under reduced pressure. The crude residue was purified by silicagel column chromatography by using 6% methanol: dichloromethane as an eluent to gave the title compound (wt: 1.8 g) as a white solid. $^1$H NMR (300 MHz, DMSO-d6): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.70 (m, 3H), 10.50 (s, 1H); Mass: 823 [M+1]$^+$ 824 (100%); HPLC Purity: 96%.

Example 36

Preparation of 3-(((((1R,3aS,5aR,5bR,7aR,9S,11aR,11bR,13aR,13bR)-3a-((S)-2-(5-(4-hydroxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid

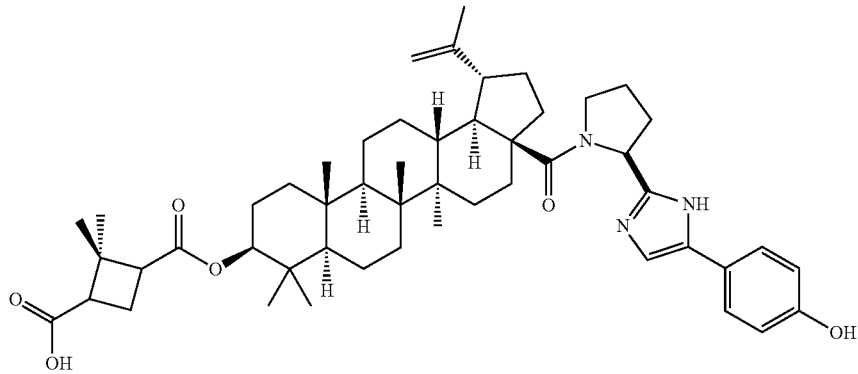

Step 1: Synthesis of 1-(4-(benzyloxy)phenyl)ethan-1-one

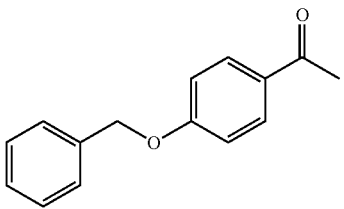 [SMILES: CC(=O)c1ccc(OCc2ccccc2)cc1]

To a stirred solution of 1-(4-(benzyloxy)phenyl)ethan-1-one (25 g, 183.62 mmol) in DMF (250 ml) were added potassium carbonate (25 g, 181.1 mmol) and benzyl bromide (26.9 ml, 157.3 mmol) at 0° C. and stirred at room temperature for about 12 hours. After completion of the reaction (monitored by TLC), the solvent was evaporated, the reaction mixture was diluted with ethyl acetate, washed with water, brine and dried over $Na_2SO_4$. The solvent was evaporated and purified by silica gel column (100-200 mesh, elution 5% EtOAc in hexane) to afford the title compound (Wt: 25 g) as an off white solid. $^1$H NMR (300 MHz, $CDCl_3$): δ 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 7.1-7.2 (m, 2H), 7.3-7.6 (m, 3H); Mass: 226.

Step 2: Synthesis of 1-(4-(benzyloxy)phenyl)-2-bromoethan-1-one

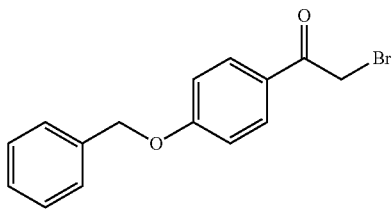 [SMILES: O=C(CBr)c1ccc(OCc2ccccc2)cc1]

To the stirred solution of 1-(4-(benzyloxy)phenyl)ethan-1-one (step 1, 25 g, 110.5 mmol) in 200 ml of MeOH at 0° C. was added Bromine (4.5 ml, 28.5 mmol) (dropwise addition), stirred for about 30 minutes and stirred for about 4 hours at room temperature. After completion of the reaction (monitored by TLC), the reaction mixture was concentrated and the crude product was dissolved in n-hexane and stirred for about 30 minutes. The obtained solid was filtered and washed with n-hexane then dried and proceeded for next step (wt: 16.0 g). M. Wt: 305.

Step 3: Synthesis of 2-(2-(4-(benzyloxy)phenyl)-2-oxoethyl) 1-(tert-butyl) (S)-pyrrolidine-1,2-dicarboxylate

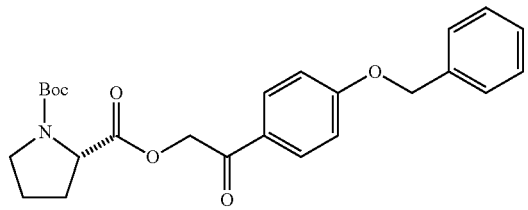

To a stirred solution of (S)-1-(tert-butoxycarbonyl)pyrrolidine-2-carboxylic acid (15 g, 69.76 mmol) in DCM (160 ml), DIPEA (25 ml, 193.7 mmol) was added at 0° C. temperature and after 10 minutes 1-(4-(benzyloxy)phenyl)-2-bromoethan-1-one (step 2, 22 g, 72.09 mmol) was added and the reaction mixture was allowed to stir at room temperature for about 12 hours. After completion of the reaction (monitored by TLC), the reaction mixture was diluted with DCM, washed with water, saturated brine and the organic layer was concentrated under reduced pressure. The resulting crude was proceeded to next step without further purification (wt: 32 g). M. Wt: 439.

Step 4: tert-butyl (S)-2-(5-(4-(benzyloxy)phenyl)-1H-imidazol-2-yl)pyrrolidine-1-carboxylate

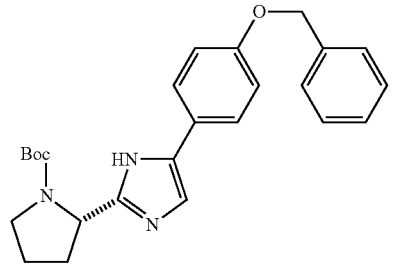

To a stirred solution of 2-(2-(4-(benzyloxy)phenyl)-2-oxoethyl) 1-(tert-butyl) (S)-pyrrolidine-1,2-dicarboxylate (step 3, 32 g, 72.89 mmol) in toulene (450 ml), ammonium acetate (56 g, 727.2 mmol) was added at room temperature and refluxed for about 12 hours. After completion of the reaction (monitored by TLC), the reaction mixture was concentrated and the crude was diluted with EtOAc, washed with water, brine and dried over $Na_2SO_4$. The solvent was evaporated and purified by silica gel column (100-200 mesh, elution 20% EtOAc in hexane) to afford the title compound as an off white solid (wt: 6.0 g). $^1$H NMR (300 MHz, $CDCl_3$): δ 7.1-7.2 (m, 2H), 7.3-7.6 (m, 3H) 7.61-7.63 (m, 2H), 4.98-5.00 (d, 1H, j=6 Htz), 3.42 (s, 2H), 3.01 (s, 1H), 2.14-2.17 (m, 4H), 1.50 (s, 9H); M. Wt: 419.

Step 5: Synthesis of tert-butyl (S)-2-(5-(4-hydroxyphenyl)-1H-imidazol-2-yl)pyrrolidine-1-carboxylate

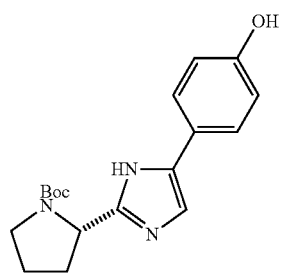

A solution of tert-butyl (S)-2-(5-(4-(benzyloxy)phenyl)-1H-imidazol-2-yl)pyrrolidine-1-carboxylate (step 4, 0.5 g, 1.19 mmol) dissolved in EtOAc: MeOH (1:1) and was added 0.25 g of Pd/C (Wet 10%) under $N_2$ atmosphere and was added (0.3 g, 4.7 mmol) of ammonium formate at room temperature. After completion of the reaction (monitored by TLC), the reaction mixture was filtered through a pad of celite and was washed with hot EtOAc:MeOH (1:1, 50 ml). The filtrate was evaporated under reduced pressure, diluted with water (10 ml), extracted with $CH_2Cl_2$ (2×200 ml) and brine wash. The combined organic layers were dried over $Na_2SO_4$, filtered and evaporated under reduced pressure. The crude residue was purified by hexane wash.

Step 6: Synthesis of (S)-4-(2-(pyrrolidin-2-yl)-1H-imidazol-5-yl)phenol

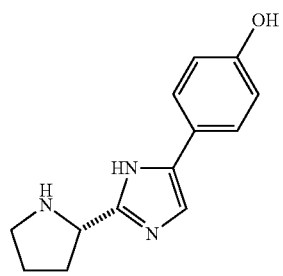

A solution of tert-butyl (S)-2-(5-(4-(benzyloxy)phenyl)-1H-imidazol-2-yl)pyrrolidine-1-carboxylate (step 5, 0.5 g, 3.0 mmol) in TFA: DCM (1:2, 15 ml) stirred at 0° C.-room temperature for about 1 hour. After completion of the reaction (monitored by TLC), the solvent was evaporated and the crude was dissolved in DCM and proceeded for next step without further purification (wt: 0.7 g).

Step 7: Synthesis of (1R,3aS,5aR,5bR,7aR,9S,11aR, 11bR,13aR,13bR)-9-((3-((benzyloxy)carbonyl)-2,2-dimethylcyclobutane-1-carbonyl)oxy)-5a,5b,8,8,11a-pentamethyl-1-(prop-1-en-2-yl)icosahydro-3aH-cyclopenta[a]chrysene-3a-carboxylic acid

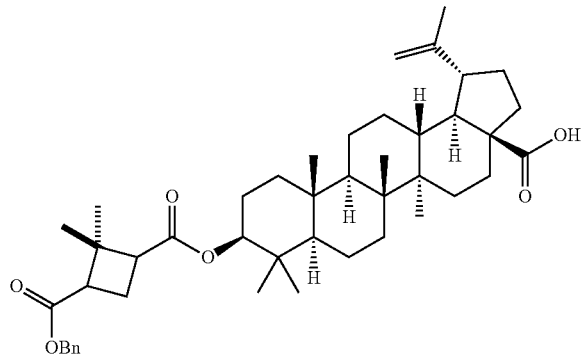

To a stirred solution of (1R,3aS,5aR,5bR,7aR,9S,11aR, 11bR,13aR,13bR)-9-hydroxy-5a,5b,8,8,11a-pentamethyl-1-(prop-1-en-2-yl)icosahydro-3aH-cyclopenta[a]chrysene-3a-carboxylic acid (prepared as described in WO 2013/160810 A2, 5 g, 10.9 mmol, 1.0 eq) in pyridine (50 ml) was added DMAP (2.6 mL, 21.31 mmol, 2.0 eq) and (1S,3R)-3-(benzyloxycarbonyl)-2,2-dimethylcyclobutanecarboxylic 2,4,6-trichlorobenzoic anhydride (Example 14-step 1, 6.1 g, 13.03 mmol). The reaction mixture was heated for overnight at 90° C. TLC indicated starting material was consumed and the desired product was observed. The reaction mixture was evaporated under reduced pressure and diluted with water. The aqueous layer was extracted with $CH_2Cl_2$ (2×50 ml). The combined organic layers were dried over $Na_2SO_4$, filtered and evaporated under reduced pressure. The crude residue was purified by silicagel column chromatography by using 20% ethyl acetate in hexane as an eluent to obtained the title compound (wt: 6.8 g) as a white solid. $^1$H NMR (300 MHz, $CDCl_3$): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 10.50 (s, 1H); Mass: 701 [M+1]$^+$.

Step 8: Synthesis of 1-benzyl 3-((1R,3aS,5aR,5bR, 7aR,9S,11aR,11bR,13aR,13bR)-3a-((S)-2-(5-(4-(2-methoxyethoxy)phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl) 2,2-dimethylcyclobutane-1,3-dicarboxylate

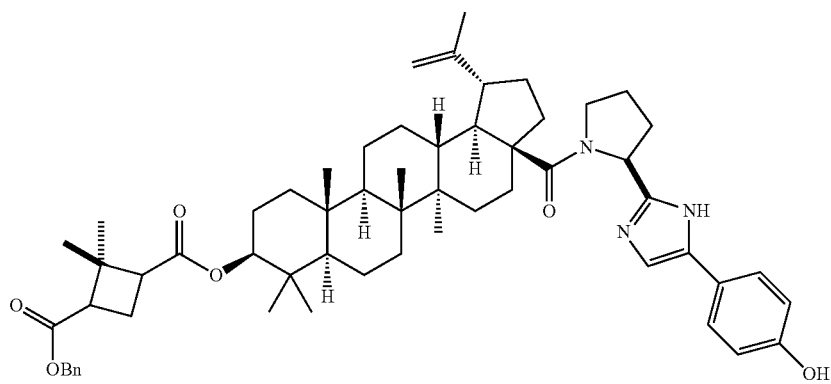

To a stirred solution of (1R,3aS,5aR,5bR,7aR,9S,11aR, 11bR,13aR,13bR)-9-((3-((benzyloxy)carbonyl)-2,2-dimethylcyclobutane-1-carbonyl)oxy)-5a,5b,8,8,11a-pentamethyl-1-(prop-1-en-2-yl)icosahydro-3aH-cyclopenta[a]chrysene-3a-carboxylic acid (step 7, 6.8 g, 9.4 mmol) in DCM (30 ml), Oxalyl chloride (3.4 ml, 26.77 mmol) in DCM (50 ml) was added at 0° C. and stirred at room temperature for about 3 hours. After completion of the reaction (monitored by TLC), the solvent was evaporated under nitrogen atmosphere and dissolved in DCM (20 ml), which was added to the above stirred solution of (S)-4-(2-(pyrrolidin-2-yl)-1H-imidazol-5-yl)phenol (Example 36-step 6, 1.2 g, 9.3 mmol) at 0° C. and TEA (3 ml, 29.7) allowed to stir at room temperature for about 16 hours. After completion of the reaction (monitored by TLC), the reaction mixture was diluted with DCM, washed with water, 1N HCl, brine solution and dried over $Na_2SO_4$. The solvent was evaporated and purified by silica gel column (100-200 mesh, elution 30% EtOAc in hexane) to afford the title compound (Wt: 1 g) as an off white solid. $^1$H NMR (300 MHz, $CDCl_3$): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.60 (m, 2H), 7.62-7.72 (m, 3H), 10.50 (s, 1H); Mass: 970 [M+1]$^+$.

Step 9: Synthesis of 3-(((((1R,3aS,5aR,5bR,7aR,9S,11aR,11bR,13aR,13bR)-3a-((S)-2-(5-(4-hydroxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid To a solution of 1-benzyl 3-((1R,3aS,5aR,5bR,7aR,9S,11aR,11bR,13aR,13bR)-3a-((S)-2-(5-(4-hydroxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)-2,2-dimethyl cyclobutane-1,3-dicarboxylate (step 8, 1.0 g, 1.0 mmol, 1.0 eq) dissolved in EtOAc:MeOH (1:1) and was added 0.6 g of Pd/C (Wet 10%) under N$_2$ atmosphere and was added (0.3 g 4.7 mmol) of ammonium formate at room temperature. After completion of the reaction (monitored by TLC), the reaction mixture was filtered through a pad of celite and was washed with hot EtOAc:MeOH (1:1, 25 ml). The filtrate was evaporated under reduced pressure, diluted with water (10 ml), extracted with CH$_2$Cl$_2$ (2×200 ml) and brine wash. The combined organic layers were dried over Na$_2$SO$_4$, filtered and evaporated under reduced pressure. The crude residue was purified by silicagel column chromatography by using 6% methanol: dichloromethane as an eluent to gave the title compound (wt: 0.2 g) as a white solid. $^1$H NMR (300 MHz, DMSO-d6): δ 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 1H), 7.22-7.60 (m, 2H), 10.50 (s, 1H); Mass: 821 [M+1]$^+$; HPLC Purity: 95.3%.

Example 37

Preparation of 3-((((1R,3aS,5aR,5bR,7aR,9S,11aR,11bR,13aR,13bR)-3a-((S)-2-(5-(4-(2-methoxyethoxy)phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid

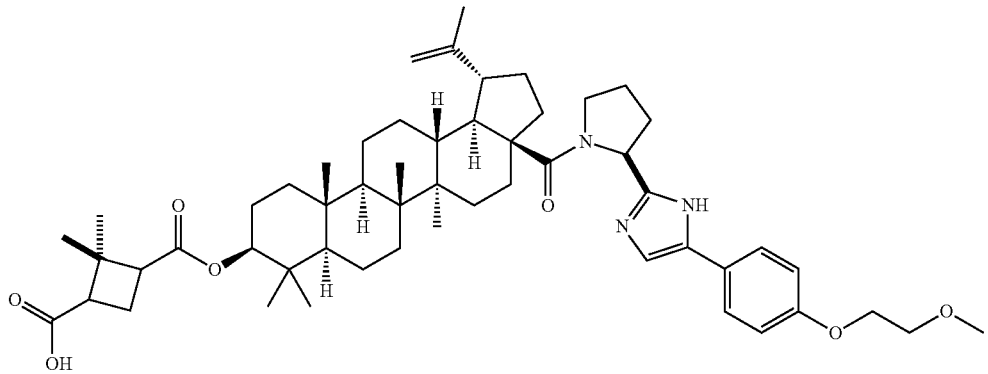

Step 1: Synthesis of 1-benzyl 3-((1R,3aS,5aR,5bR,7aR,9S,11aR,11bR,13aR,13bR)-3a-((S)-2-(5-(4-(2-methoxyethoxy)phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl) 2,2-dimethylcyclobutane-1,3-dicarboxylate

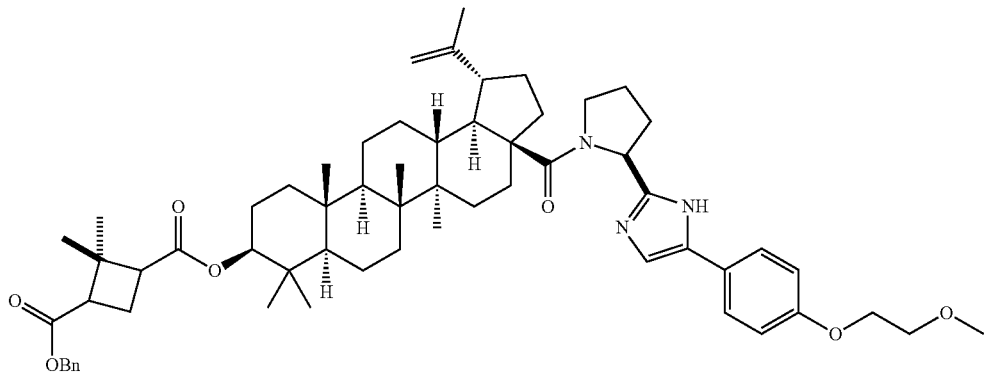

To a stirred solution of 1-benzyl 3-((1R,3aS,5aR,5bR,7aR,9S,11aR,11bR,13aR,13bR)-3a-((S)-2-(5-(4-hydroxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)-2,2-dimethyl cyclobutane-1,3-dicarboxylate (Example 36-step 8, 0.2 g, 0.21 mmol) in acetonitrile (15 ml) were added Potassium carbonate (0.060 g, 0.43 mmol) and BrCH$_2$CH$_2$OCH$_3$ (0.02 ml, 0.14 mmol) at 0° C. and stirred at reflux for about 12 hours. After completion of the reaction (monitored by TLC), the solvent was evaporated, the reaction mixture was diluted with ethyl acetate, washed with water, 1N HCl, water brine and dried over Na$_2$SO$_4$. The solvent was evaporated and purified by silica gel column (100-200 mesh, elution 22% acetone: hexane) to afford the title compound as an off white solid (Wt: 0.15 g). $^1$H NMR (300 MHz, CDCl$_3$): δ 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 3.57-3.57 (s, 1H) 3.64-3.66 (d, 2H) 3.77 (s, 1H) 4.0-4.14 (m, 3H) 4.36-4.37 (m, 1H), 4.56 (s, 1H), 4.6 (s, 1H), 5.02-5.04 (m, 2H), 7.01-7.11 (m, 3H), 7.12-7.13 (m, 2H), 7.22-7.60 (m, 2H), 7.62-7.72 (m, 3H), 10.50 (s, 1H); Mass: 970 [M+1]$^+$.

Step 2: Synthesis of 3-(((((1R,3aS,5aR,5bR,7aR,9S,11aR,11bR,13aR,13bR)-3a-((S)-2-(5-(4-(2-methoxyethoxy)phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid To a solution of 1-benzyl 3-((1R,3aS,5aR,5bR,7aR,9S,11aR,11bR,13aR,13bR)-3a#S)-2-(5-(4-(2-methoxyethoxy)phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl) 2,2-dimethylcyclobutane-1,3-dicarboxylate (step 1, 0.15 g, 0.15 mmol, 1.0 eq) dissolved in EtOAc:MeOH (1:1) and was added 0.06 g of Pd/C (Wet 10%) under N2 atmosphere and was added (0.04 g, 0.7 mmol) of ammonium formate at room temperature. After completion of the reaction (monitored by TLC), the reaction mixture was filtered through a pad of celite and was washed with Hot EtOAc:MeOH (1:1, 25 ml). The filtrate was evaporated under reduced pressure, diluted with water (10 ml), extracted with CH$_2$Cl$_2$ (2×200 ml) and brine wash. The combined organic layers were dried over Na$_2$SO$_4$, filtered and evaporated under reduced pressure. The crude residue was purified by silicagel column chromatography by using 4% methanol: dichloromethane as an eluent to gave the title compound (wt: 0.2 g) as a white solid. $^1$H NMR (300 MHz, DMSO-d6): δ 0.08-0.91 (m, 11H), 1.12-1.28 (m, 3H), 1.30-1.33 (m, 10H), 1.50-1.58 (m, 2H), 2.01 (s, 3H), 2.03-2.04 (m, 1H), 2.11-2.13 (m, 1H), 3.01-3.13 (m, 1H), 3.57-3.57 (s, 1H), 3.64-3.66 (d, 2H), 3.77 (s, 1H), 4.0-4.14 (m, 3H), 4.36-4.37 (m, 1H), 4.56 (s, 1H), 4.6 (s, 1H), 5.02-5.04 (m, 2H), 7.01-7.11 (m, 3H), 7.12-7.13 (m, 1H), 7.22-7.70 (m, 2H), 10.50 (s, 1H); Mass: 880 [M+1]$^+$; HPLC Purity: 94.1%.

Example 38

Preparation of 2,2-dimethyl-4-oxo-4-(((1R,3aS,5aR,5bR,7aR,9S,11aR,11bR,13aR,13bR)-5a,5b,8,8,11a-pentamethyl-1-(1-methylcyclopropyl)-3a-((S)-2-(5-(thiophen-2-yl)-1H-imidazol-2-yl)pyrrolidine-1-carbonyl)icosahydro-1H-cyclopenta[a]chrysen-9-yl)oxy)butanoic acid

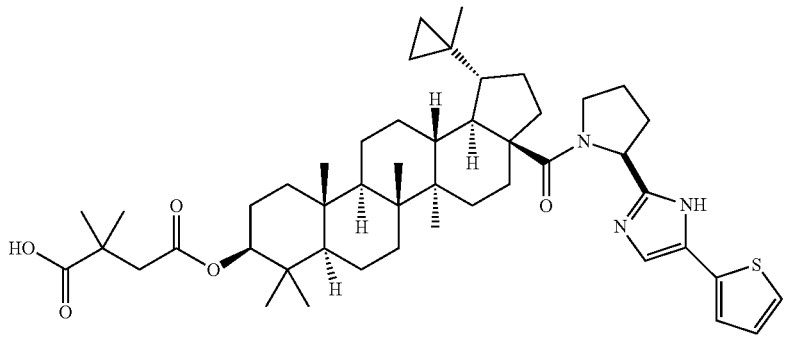
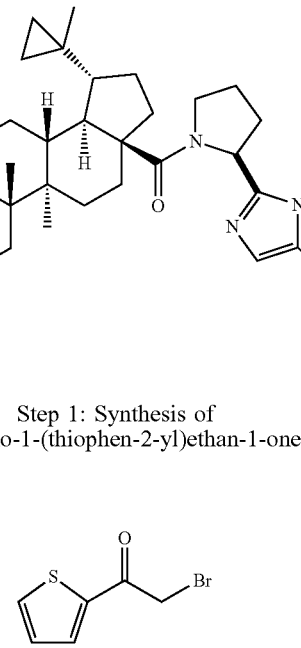

Step 1: Synthesis of 2-bromo-1-(thiophen-2-yl)ethan-1-one

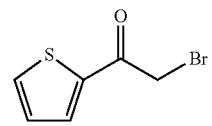

To the stirred solution of 1-(thiophen-2-yl)ethan-1-one (10 g, 68.9 mmol) in 110 ml of MeOH at 0° C. was added Bromine (2.8 ml, 17.7 mmol) (dropwise addition), stirred for about 30 minutes and stirred for about 2 hours at room temperature. After completion of the reaction (monitored by TLC), the reaction mixture was concentrated and the crude product was dissolved in n-hexane and stirred for about 30 minutes. The obtained solid was filtered and washed with n-hexane then dried and proceeded for next step (wt: 14.0 g).

Step 2: Synthesis of 1-(tert-butyl) 2-(2-oxo-2-(thiophen-2-yl)ethyl) (S)-pyrrolidine-1,2-dicarboxylate

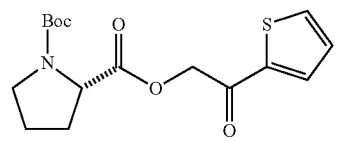 [SMILES: CC(C)(C)OC(=O)N1CCC[C@H]1C(=O)OCC(=O)c1cccs1]

To a stirred solution of (S)-1-(tert-butoxycarbonyl)pyrrolidine-2-carboxylic acid (13.8 g, 64.18 mmol) in DCM (140 ml), DIPEA (11.5 ml, 89.4 mmol) was added at 0° C. temperature and after 10 minutes 2-bromo-1-(thiophen-2-yl)ethan-1-one (step 1, 13.8 g, 31.2 mmol) was added and the reaction mixture was allowed to stir at room temperature for about 12 hours. After completion of the reaction (monitored by TLC), the reaction mixture was diluted with DCM, washed with water, saturated brine and the organic layer was concentrated under reduced pressure, the resulting crude was proceeded to next step without further purification (wt: 18.0 g).

Step 3: tert-butyl (5)-2-(5-(thiophen-2-yl)-1H-imidazol-2-yl)pyrrolidine-1-carboxylate

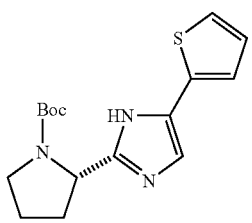 [SMILES: CC(C)(C)OC(=O)N1CCC[C@H]1c1ncc(-c2cccs2)[nH]1]

To a stirred solution of 1-(tert-butyl) 2-(2-oxo-2-(thiophen-2-yl)ethyl) (S)-pyrrolidine-1,2-dicarboxylate (step 2, 18.0 g, 52.9 mmol) in Toulene (180 ml), ammonium acetate (40 g, 529.4 mmol) was added at room temperature and refluxed for about 12 hours. After completion of the reaction (monitored by TLC), the reaction mixture was concentrated, the crude was diluted with EtOAc, washed with water, brine and dried over $Na_2SO_4$. The solvent was evaporated and purified by silica gel column (100-200 mesh, elution 20% EtOAc in hexane) to afford the title compound (wt: 8.0 g) as an off white solid. $^1$H NMR (300 MHz, $CDCl_3$): δ 7.1-7.5 (m, 3H), 7.61-7.63 (m, 2H), 4.98-5.00 (d, 1H, j=6 Htz), 3.42 (s, 2H), 3.01 (s, 1H), 2.14-2.17 (m, 4H), 1.50 (s, 9H); Mass: 319 [M+1]$^+$ 320 (100%).

Step 4: Synthesis of (5)-2-(pyrrolidin-2-yl)-5-(thiophen-2-yl)-1H-imidazole

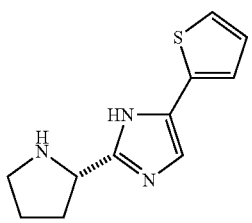 [SMILES: c1csc(-c2cnc([C@@H]3CCCN3)[nH]2)c1]

A solution of tert-butyl (5)-2-(5-(thiophen-2-yl)-1H-imidazol-2-yl)pyrrolidine-1-carboxylate (step 3, 2.1 g, 6.5 mmol) in TFA: DCM (1:2, 30 ml) stirred at 0° C.-room temperature for about 1 hour. After completion of the reaction, the solvent was evaporated, the crude was dissolved in DCM and proceeded for next step without further purification (wt: 1.4 g).

Step 5 Synthesis of (1R,3aS,5aR,5bR,7aR,9S,11aR,11bR,13aR,13bR)-5a,5b,8,8,11a-pentamethyl-1-(prop-1-en-2-yl)-3a-((S)-2-(5-(thiophen-2-yl)-1H-imidazol-2-yl) pyrrolidine-1-carbonyl)icosahydro-1H-cyclopenta[a]chrysen-9-yl acetate

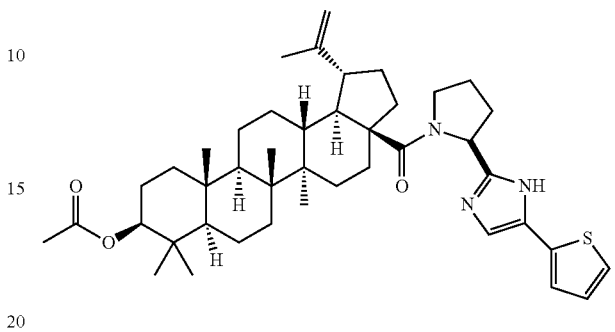

To a stirred solution of (1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a]chrysene-3a-carboxylic acid (prepared as described in WO 2013/160810 A2, 3.3 g, 6.6 mmol) in DCM (30 ml), Oxalyl chloride (2.4 ml, 18.9 mmol) in DCM (50 ml) was added at 0° C. and stirred at room temperature for about 3 hours. After completion of the reaction (monitored by TLC), the solvent was evaporated under nitrogen atmosphere and dissolved in DCM (50 ml), which was added to the above stirred solution of (S)-2-(pyrrolidin-2-yl)-5-(thiophen-2-yl)-1H-imidazole (step 4, 1.6 g, 7.2 mmol) at 0° C. and allowed to stir at room temperature for about 16 hours. After completion of the reaction (monitored by TLC), the reaction mixture was diluted with DCM, washed with water, 1N HCl, brine solution and dried over $Na_2SO_4$. The solvent was evaporated and purified by silica gel column (100-200 mesh, elution 30% EtOAc in hexane) to afford the title compound (Wt: 2.5 g) as an off white solid. $^1$H NMR (300 MHz, $CDCl_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.09 (s, 3H), 2.23-3.45 (m, 6H), 3.82-4.13 (m, 5H), 4.20-4.24 (s, 1H), 5.31-5.35 (m, 1H), 7.22-7.60 (m, 3H), 7.70-7.88 (m, 2H), 10.50 (s, 1H); Mass: 699 [M+1]$^+$ 700 (100%).

Step 6: Synthesis of ((1R,3aS,5aR,5bR,7aR,9S,11aR,11bR,13aR)-9-hydroxy-5a,5b,8,8,11a-pentamethyl-1-(prop-1-en-2-yl)icosahydro-3aH-cyclopenta[a]chrysen-3a-yl)((S)-2-(5-(thiophen-2-yl)-1H-imidazol-2-yl)pyrrolidin-1-yl)methanone

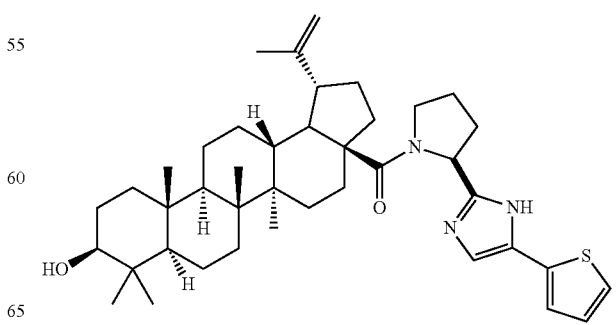

To a stirred solution of (1R,3aS,5aR,5bR,7aR,9S,11aR, 11bR,13aR,13bR)-5a,5b,8,8,11a-pentamethyl-1-(prop-1-en-2-yl)-3a-((S)-2-(5-(thiophen-2-yl)-1H-imidazol-2-yl)pyrrolidine-1-carbonyl)icosahydro-1H-cyclopenta[a]chrysen-9-yl acetate (step 5, 2.2 g, 3.3 mmol) in MeOH (30 ml) was added potassium carbonate (3.5 g, 25.3 mmol) at 0° C. and allowed to stir at room temperature for about 16 hours. After completion of the reaction (monitored by TLC), the volatile was evaporated and the aqueous layer was extracted with ethyl acetate. The organic layer was washed with water, brine and dried over $Na_2SO_4$, then the solvent was evaporated and the resulting crude was purified by silica gel column (100-200 mesh, elution 5% MeOH/DCM) to afford the title compound (wt: 1.8 g) as an off white solid. $^1$H NMR (300 MHz, $CDCl_3$): δ 0.22-0.25 (m, 2H), 0.26-0.27 (m, 2H), 0.79-0.93 (m, 8H), 1.07-1.26 (m, 10H), 1.29-1.56 (m, 12H), 169-1.99 (m, 8H), 2.23-3.45 (m, 6H), 3.82-4.13 (m, 5H), 4.20-4.24 (m, 1H), 5.31-5.35 (m, 1H), 7.22-7.60 (m, 3H), 7.70-7.88 (m, 2H), 10.50 (s, 1H); Mass: 657 $[M+1]^+$ 658 (100%).

Step 7: Synthesis of 2,2-dimethyl-4-oxo-4-(((1R,3aS,5aR,5bR,7aR,9S,11aR,11bR,13aR,13bR)-5a,5b,8,8,11a-pentamethyl-1-(prop-1-en-2-yl)-3a-((S)-2-(5-(thiophen-2-yl)-1H-imidazol-2-yl)pyrrolidine-1-carbonyl)icosahydro-1H-cyclopenta[a]chrysen-9-yl)oxy)butanoic acid

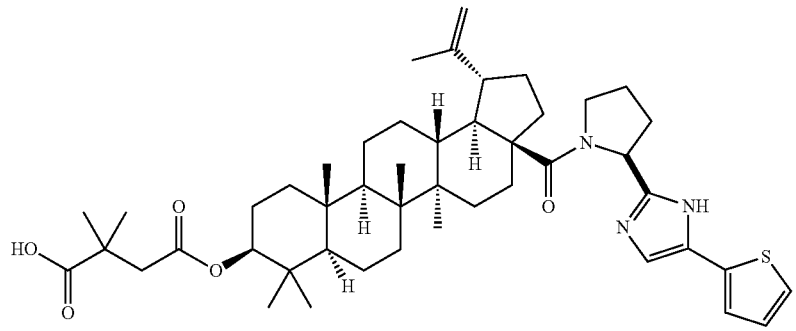

2,2-Dimethylsuccinic anhydride (1 g, 1.5 mmol) was added to a stirred solution of ((1R,3aS,5aR,5bR,7aR,9S,11aR,11bR,13aR)-9-hydroxy-5a,5b,8,8,11a-pentamethyl-1-(prop-1-en-2-yl)icosahydro-3aH-cyclopenta[a]chrysen-3a-yl)((S)-2-(5-(thiophen-2-yl)-1H-imidazol-2-yl)pyrrolidin-1-yl)methanone (step 6, 0.217 g, 15.3 mmol) and DMAP (0.03 g, 0.3 mmol) in toluene (30 ml) at room temperature and refluxed for about 24 hours. After completion of the reaction (monitored by TLC), the reaction mixture was diluted with EtOAc, washed with water, 1N HCl, water, brine and dried over $Na_2SO_4$. The solvent was evaporated and purified by silica gel column (100-200 mesh, elution 5% MeOH/DCM) to afford the title compound (Wt: 0.1 g) as an off white solid. $^1$H NMR (300 MHz, $CDCl_3$): δ 0.22-0.25 (m, 2H), 0.26-0.27 (m, 2H), 0.79-0.93 (m, 13H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 5.31-5.35 (m, 1H), 7.22-7.60 (m, 3H), 7.70-7.88 (m, 2H), 10.50 (s, 1H); Mass: 785 $[M+1]^+$ 786 (100%); HPLC Purity: 90%.

Example 39

Preparation of 2,2-dimethyl-4-oxo-4-(((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)butanoic acid

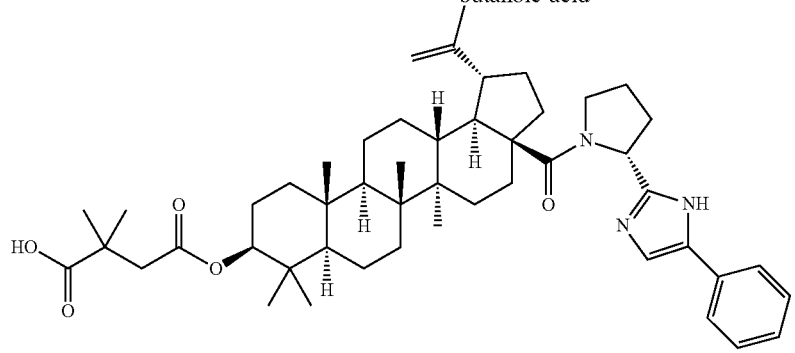

Step-1: Synthesis of N-tert-butoxycarbonyl-(D)-Proline

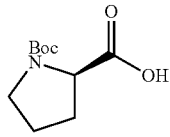 [SMILES: CC(C)(C)OC(=O)N1CCC[C@@H]1C(=O)O]

To a stirred solution of D-proline (100 g, 868.58 mmol) in dioxane (400 mL, 8 vol) was added $NaHCO_3$ (182.4 g, 2.5 eq.) and water (800 mL, 8 vol) at room temperature and stirred the reaction mixture for about 30 minutes. The reaction mixture was cooled to 0-5° C. temperature and Di-tert-butyl dicarbonate $(BOC)_2O$ (224.26 g, 1.2 eq.) was added and stirred for 1 h at 0-5° C. Then the reaction mixture was warmed to room temperature and stirred for over night (12-16 hours). Reaction mixture was monitored by TLC, after completion of reaction, solvent dioxane was evaporated. The aqueous layer was acidified with 4N HCl solution to $P^H$ 2 to 3 at 0-5° C. The Aqueous layer was extracted with ethyl acetate (4×200 mL) and combined organic layer was washed with water and dried over $Na_2SO_4$. Organic layer was evaporated under reduced pressure to provide a white solid. The obtained white solid was taken in to heptane (200 mL) and stirred for about 2 hours at room temperature. Filtered the solid and dried the compound under vacuum at 45-50° C. temperature (Wt.: 125 g, Yield: 90-95%). $^1H$ NMR (300 MHz, $CDCl_3$): δ 9.20 (br, 1H), 4.34 (t, 1H), 3.54-3.13 (m, 2H), 2.31-2.25 (m, 1H), 2.09-1.88 (m, 3H), 1.48-1.42 (b, 9H); Mass: $[M+Na]^+$ 238 (100%).

Step 2: Synthesis of 1-(tert-butyl) 2-(2-oxo-2-phenylethyl) (R)-pyrrolidine-1,2-dicarboxylate

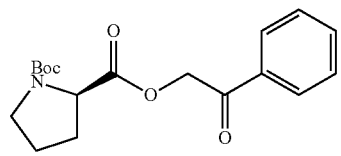 [SMILES: CC(C)(C)OC(=O)N1CCC[C@@H]1C(=O)OCC(=O)c1ccccc1]

To a stirred solution of (R)-1-(tert-butoxycarbonyl)pyrrolidine-2-carboxylic acid (step 1, 100 g, 464.5 mmol) in DCM (1000 ml, 10 vol) and DIPEA (161.14 ml, 929.2 mmol) was added slowly 2-bromo-1-phenylethanone (93 g, 473.83 mmol) at 0° C. for about 1 hour and the reaction mixture was allowed to stir at room temperature for about 12 hours. After completion of the reaction (monitored by TLC), the reaction mixture was diluted with DCM (200 ml, 2 vol), washed with water and saturated brine solution. The organic layer was dried over $Na_2SO_4$ and concentrated under reduced pressure to provide crude compound. To the compound added three volumes of heptane, stirred for about 4 hours, filter the solid, washed with one volumes of heptane and dried under vacuum at 45-50° C. to provide the pure compound (144 g, 93% yield). $^1H$ NMR (300 MHz, $CDCl_3$): δ 7.92-7.88 (m, 2H), 7.62-7.59 (m, 1H), 7.52-7.47 (m, 2H), 5.36-5.31 (dd, 2H, J=15 Hz), 4.51-4.38 (m, 1H), 3.61-3.38 (m, 2H), 3.42-3.38 (m, 1H), 2.35-2.29 (m, 1H), 2.10-2.09 (m, 1H), 2.08-2.06 (m, 1H), 1.45 (s, 9H); 1.31; Mass: $[M+Na]^+$ 356 (95%).

Step 3: (R)-tert-butyl 2-(5-phenyl-1H-imidazol-2-yl)pyrrolidine-1-carboxylate

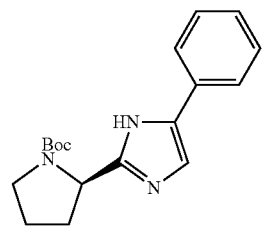 [SMILES: CC(C)(C)OC(=O)N1CCC[C@@H]1c1ncc(-c2ccccc2)[nH]1]

To a stirred solution of (R)-1-tert-butyl 2-(2-oxo-2-phenylethyl) pyrrolidine-1,2-dicarboxylate (step 2, 144 g, 432.43 mmol) in Toluene (120 ml), ammonium acetate (125 g) was added at room temperature and refluxed for about 12 hours. After completion of the reaction (monitored by TLC), the reaction mixture was concentrated, the crude was diluted with EtOAc, washed with water, brine and dried over $Na_2SO_4$. A crude compound was dissolved in 5 volumes of methanol and 5 volumes of water and stir for about 4 hours at room temperature. Filter the solid and washed with 2 volumes of methanol and dried to afford the compound (Wt: 172.8 g, Yield: 90%) at 45-50° C. $^1H$ NMR (300 MHz, $CDCl_3$): δ 10.71 (m, 1H), 7.67-7.60 (m, 2H), 7.38-7.33 (m, 2H), 7.22-7.20 (m, 2H), 4.99-4.95 (m, 1H), 3.52-3.48 (m, 2H), 3.42-3.38 (m, 1H), 2.15 (m, 2H), 1.31 (m, 1H), 1.49 (s, 9H); Mass: $[M+1]^+$ 314 (100%), $[M+Na]^+$ 336 (40%); HPLC Purity: 97.5%.

Step 4: Synthesis of (S)-5-phenyl-2-(pyrrolidin-2-yl)-1H-imidazole

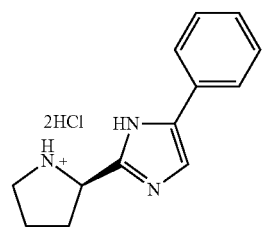 [SMILES: c1ccc(-c2cnc([C@H]3CCCN3)[nH]2)cc1]

A solution of (R)-tert-butyl-2-(5-phenyl-1H-imidazol-2-yl)-pyrrolidine-1-carboxylate (step 3, 50 g) in TFA: DCM (1:2, 27 ml) stirred at 0° C.-room temperature for about 3 hours. After completion of the reaction (monitored by TLC), the solvent was evaporated and the crude compound was dissolved in DCM and carried to next step without further purification.

Step 5: Synthesis of (1R,3aS,5aR,5bR,7aR,9S,11aR, 11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl acetate

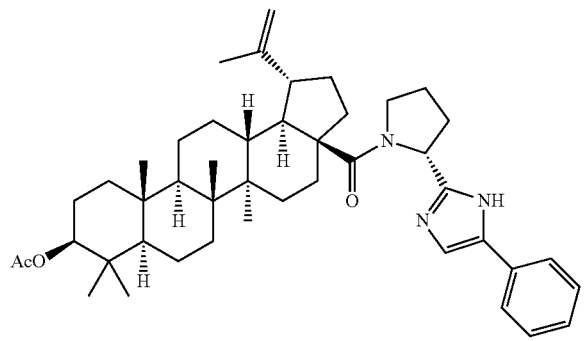

To a stirred solution of (S)-4-(2-(pyrrolidin-2-yl)-1H-imidazol-5-yl)pyridine (step 4, 16.4 g, 77.4 mmol, 2.0 eq) and triethylamine (26 mL, 193 mmol, 5.0 eq) in CH$_2$Cl$_2$ (300 ml) at 0° C. was added slowly (1R,3aS,5aR,5bR,7aR, 9S,11aR,11bR,13aR,13bR)-3a-(chlorocarbonyl)-5a,5b,8,8, 11a-pentamethyl-1-(prop-1-en-2-yl)icosahydro-1H-cyclopenta[a]chrysen-9-yl acetate (prepared as described in WO 2013/160810 A2, 20 g, 38.6 mmol, 1.0 eq) in CH$_2$Cl$_2$ (300 ml) for about 30 minutes. The reaction mixture was allowed to stir at room temperature for overnight. The reaction mixture was diluted with water and extracted with CH$_2$Cl$_2$. The combined organic extracts were dried over Na$_2$SO$_4$, filtered and evaporated under reduced pressure. The residue was purified by column chromatography using 5% MeOH in DCM as an eluent to gave the desired product (wt: 12.0 g, 69.0%) as a semi solid. H$^1$ NMR (DMSO-D$_6$, 300 MHz): δ 10.49 (s, 1H), 7.78 (d, 2H), 7.49 (d, 1H), 7.38-7.36 (m, 2H), 7.23-7.18 (m, 1H), 5.32 (d, 1H), 5.01-4.91 (d, 2H) 4.78-4.73 (d, 1H), 4.62-4.44 (m, 3H), 4.16-4.04 (m, 1H), 3.49-3.29 (m, 6H), 2.84-2.78 (m, 3H), 2.50-2.48 (m, 6H), 2.21 (s, 3H), 2.04 (s, 3H), 2.0 (s, 3H), 1.69-1.67 (m, 6H), 1.52-1.1.28 (m, 6H), 1.05-0.95 (m, 3H), 0.91-0.70 (m, 9H); Mass: [M]$^+$ 695.54 (100%).

Step 6: Synthesis of ((1R,3aS,5aR,5bR,7aR,9S, 11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((R)-2-(5-phenyl-1H-imidazol-2-yl)pyrrolidin-1-yl)methanone

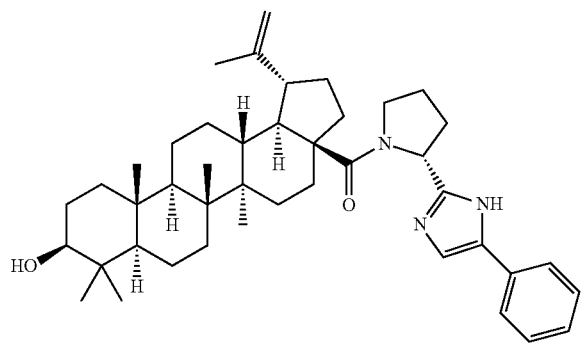

To a stirred solution of (1R,3aS,5aR,5bR,7aR,9S,11aR, 11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl acetate (step 5, 12 g, 17.2 mmol, 1.0 eq) in THF (160 ml) and Methanol (160 ml) was added potassium carbonate (16.4 g, 121.2 mmol, 7.0 eq). The reaction mixture was stirred at room temperature for about 48 hours. After completion of reaction TLC indicated the starting material consumption and the formation of desired product was observed. The reaction mixture was filtered through a pad of celite and washed with CH$_2$Cl$_2$. The filtrate was evaporated under reduced pressure and the crude was purified by column chromatography by using 6% MeOH and DCM as an eluent to gave the desired product (10.44 g, 93.0%) as a white solid. $^1$H NMR (300 MHz, CDCl$_3$): 0.92 (s, 3H), 0.96 (s, 3H), 1.16-1.14 (m, 12H), 1.46-1.28 (m, 9H), 1.70 (s, 3H), 1.97-1.90 (m, 2H), 2.04 (s, 1H) (m, 5H), 2.28-2.10 (m, 6H), 3.17-3.06 (m, 3H), 3.40 (m, 1H), 3.48-3.35 (m, 1H), 3.60 (m, 1H), 3.90-3.88 (m, 1H), 4.61 (s, 1H), 4.77 (s, 1H), 5.34-5.28 (m, 1H), 7.22-7.19 (m, 2H), 7.39-7.36 (m, 2H), 7.51 (m, 1H), 7.79 (s, 1H), 10.50 (s, 1H); Mass: 651 [M+1]$^+$ 652 (100%).

Step 7: Synthesis of 2,2-dimethyl-4-oxo-4-(((1R, 3aS,5aR,5bR,7aR,9S,11aR,11bR,13aR,13bR)-5a,5b, 8,8,11a-pentamethyl-3a-((R)-2-(5-phenyl-1H-imidazol-2-yl)pyrrolidine-1-carbonyl)-1-(prop-1-en-2-yl) icosahydro-1H-cyclopenta[a]chrysen-9-yl)oxy) butanoic acid 2,2-Dimethylsuccinic anhydride (983 mg, 7.60 mmol) was added to a stirred solution of ((1R,3aS,5aR,5bR,7aR, 9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((R)-2-(5-phenyl-1H-imidazol-2-yl) pyrrolidin-1-yl)methanone (step 6, 1.0 g, 1.53 mmol) and DMAP (0.366 g, 3.0 mmol) in Pyridine (10 ml) at room temperature and refluxed for about 24 hours. After completion of the reaction (monitored by TLC), the reaction mixture was diluted with ethyl acetate, washed with water followed by 1N HCl, water and brine solution. The residue was dried over Na$_2$SO$_4$ and the solvent was evaporated under vacuum and purified by silica gel column (100-200 mesh, elution 5% MeOH/DCM) to afford the title compound (Wt: 0.61 g, Yield: 51%) as an off white solid. $^1$H NMR (300 MHz, CDCl$_3$): δ 0.79-0.93 (m, 8H), 0.93 (s, 6H), 1.07-1.26 (m, 9H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.22-7.60 (m, 3H), 7.70-7.88 (m, 2H), 10.50 (s, 1H); Mass: 779 [M+1]$^+$ 780 (100%). HPLC Purity: 90.21%.

Example 40

Preparation of 3,3-dimethyl-5-oxo-5-((((1R,3aS,5aR, 5bR,7aR,9S,11aR,11bR,13aR,13bR)-5a,5b,8,8,11a-pentamethyl-3a-((R)-2-(5-phenyl-1H-imidazol-2-yl) pyrrolidine-1-carbonyl)-1-(prop-1-en-2-yl) icosahydro-1H-cyclopenta[a]chrysen-9-yl)oxy) pentanoic acid

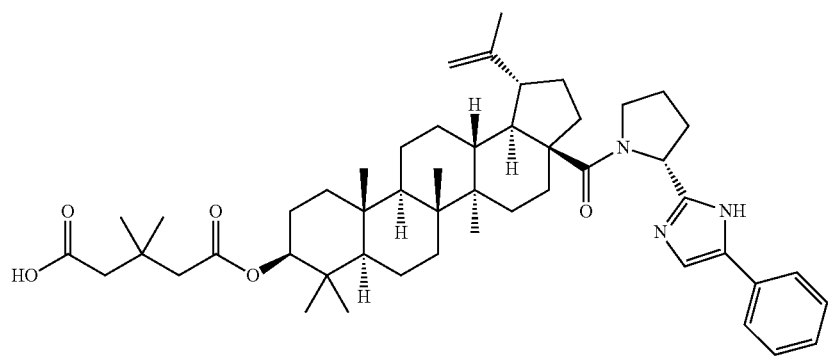

3,3-Dimethylglutaric anhydride (1.1 g, 7.6 mmol) was added to a stirred solution of ((1R,3aS,5aR,5bR,7aR,9S, 11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((R)-2-(5-phenyl-1H-imidazol-2-yl)pyrrolidin-1-yl)methanone (Example 39-step 6, 1.0 g, 1.5 mmol) and DMAP (366 mg, 3.0 mmol) in pyridine (10 ml) at room temperature and refluxed for about 24 hours. After completion of the reaction (monitored by TLC), the reaction mixture was diluted with ethyl acetate, washed with water followed by 1N HCl, water and brine solution. The residue was dried over $Na_2SO_4$, the solvent was evaporated and purified by silica gel column (100-200 mesh, elution 5% MeOH/DCM) to afford the title compound (Wt: 0.60 g, Yield: 50%) as an off white solid. $^1$H NMR (300 MHz, CDCl$_3$): δ 0.89-0.71 (m, 6H), 0.98-0.91 (m, 6H), 1.15-1.14 (m, 8H), 1.29-1.16 (m, 8H), 1.69-1.38 (m, 9H), 1.69-1.75 (m, 4H), 2.01-1.95 (m, 4H), 2.23-2.17 (m, 6H), 2.50-2.39 (m, 3H), 3.40-3.19 (m, 3H), 3.69-3.60 (m, 2H), 3.93-3.87 (m, 1H), 4.51 (s, 1H), 4.61 (s, 1H), 4.78 (s, 1H), 5.33-5.28 (m, 1H), 7.21-7.19 (m, 2H), 7.38-7.32 (m, 3H), 7.75-7.60 (m, 1H), 10.50 (s, 1H); Mass: 793 [M+1]$^+$ 794 (100%); HPLC Purity: 91.5%.

Example 41

Preparation of 2,2-dimethyl-3-((((1R,3aS,5aR,5bR, 7aR,9S,11aR,11bR,13aR,13bR)-5a,5b,8,8,11a-pentamethyl-3a-((R)-2-(5-phenyl-1H-imidazol-2-yl) pyrrolidine-1-carbonyl)-1-(prop-1-en-2-yl) icosahydro-1H-cyclopenta[a]chrysen-9-yl)oxy) carbonyl)cyclobutane-1-carboxylic acid

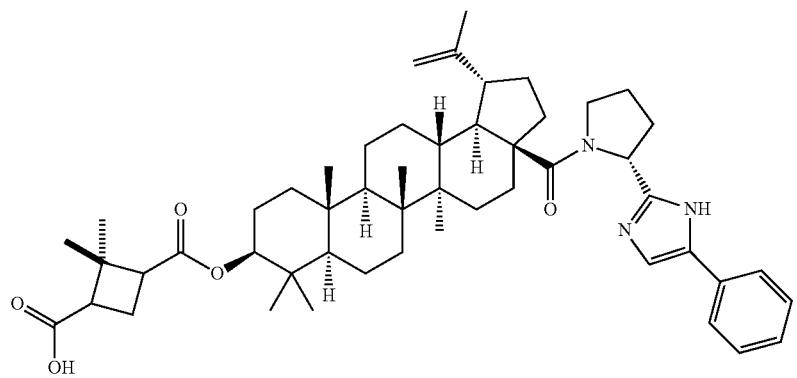

Step 1: Synthesis of 1-benzyl 3-((1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl) 2,2-dimethylcyclobutane-1,3-dicarboxylate

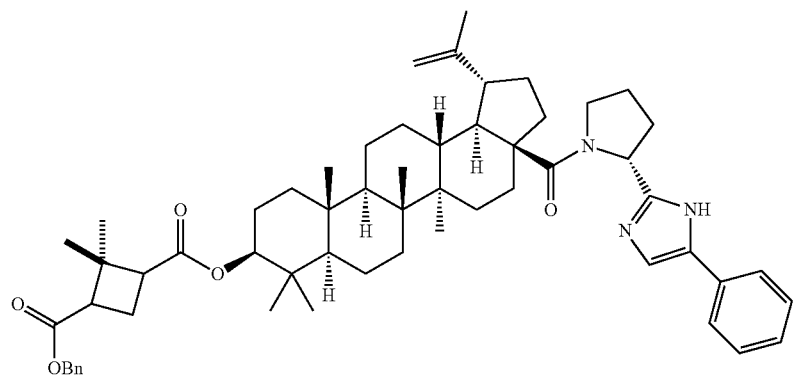

To a stirred solution of ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-3aH-cyclopenta[a]chrysen-3a-yl)((R)-2-(5-phenyl-1H-imidazol-2-yl)pyrrolidin-1-yl)methanone (Example 39-step 6, 38 g, 58.19 mmol, 1.0 eq) in pyridine (400 ml) was added DMAP (14.19 g, 116.3 mmol, 2.0 eq) and (1S,3R)-3-(benzyloxycarbonyl)-2,2-dimethylcyclobutanecarboxylic 2,4,6-trichlorobenzoic anhydride (Example 14-step 1, 40.85 g, 87.28 mmol). The reaction mixture was heated to 90° C. for overnight. TLC indicated starting material was consumed and the desired product was observed. The reaction mixture was evaporated under reduced pressure and diluted with water. The aqueous layer was extracted with $CH_2Cl_2$ (2×500 ml) and washed with 1N HCl followed by water and brine solution. The organic layer were dried over $Na_2SO_4$, filtered and evaporated under reduced pressure. The crude residue was purified by silicagel column chromatography by using 1.5% methanol: dichloromethane as an eluent to obtain the title compound (30 g) as a white solid. $^1$H NMR (300 MHz, $CDCl_3$): δ 0.79-0.93 (m, 8H), 0.93 (s, 6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H), 7.22-7.60 (m, 3H), 7.70-7.88 (m, 2H), 10.50 (s, 1H); Mass 895: $[M+1]^+$ 896 (100%).

Step 2: Synthesis of 2,2-dimethyl-3-(((((1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid To a solution of 1-benzyl 3-((1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl) 2,2-dimethylcyclobutane-1,3-dicarboxylate (step 1, 30 g, 33.5 mmol, 1.0 eq) dissolved in EtOAc:MeOH (1:1, 300 ml and was added 20 g of Pd/C (Wet 10%) under $N_2$ atmosphere and was added (10.5, 166.5 mmol) of ammonium formate at room temperature for about 4 hours. TLC indicated starting material was consumed and the desired product was observed. The reaction mixture was filtered through a pad of celite and was washed with Hot EtOAc:MeOH (1:1, 500 ml). The filtrate was evaporated under reduced pressure, diluted with water (10 ml), extracted with $CH_2Cl_2$ (2×800 ml) and brine wash. The combined organic layers were dried over $Na_2SO_4$, filtered and evaporated under reduced pressure. The crude residue was purified by silicagel column chromatography by using 2% methanol: dichloromethane as an eluent to gave the title compound (25 g) as a white solid. $^1$H NMR (300 MHz, DMSO-d6): δ 0.79-0.93 (m, 8H), 0.93 (s, 6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 4.61-4.75 (m, 1H), 4.77 (s, 1H), 4.80 (s, 1H), 5.31-5.35 (m, 1H), 7.01-7.11 (m, 3H), 7.12-7.13 (m, 2H) 7.70-7.88 (m, 3H), 10.50 (s, 1H); Mass: 805 $[M+1]^+$ 806 (100%); HPLC Purity: 95.6%.

Example 42

Preparation of 3-((((1R,3aS,5aR,5bR,7aR,9S,11aR, 11bR,13aR,13bR)-3a-((S)-2-(5-(4-fluorophenyl)-1H-imidazol-2-yl)pyrrolidine-1-carbonyl)-5a, 5b,8,8, 11a-pentamethyl-1-(1-methylcyclopropyl) icosahydro-1H-cyclopenta[a]chrysen-9-yl)oxy) carbonyl)-2,2-dimethylcyclobutane-1-carboxylic acid

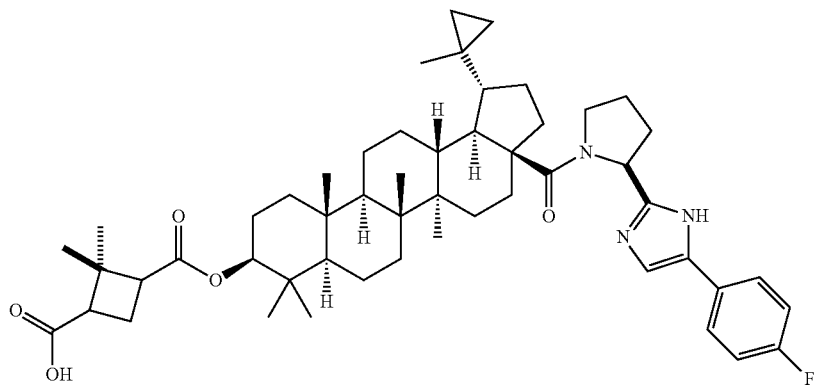

To a solution of 1-benzyl 3-((1R,3aS,5aR,5bR,7aR,9S, 11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(1-methylcyclopropyl)icosahydro-1H-cyclopenta[a]chrysen-9-yl)-2,2-dimethylcyclobutane-1,3-dicarboxylate (Example 33-step 6, 1 g, 1.0 mmol, 1.0 eq) dissolved in EtOAc:MeOH (1:1) and was added 0.5 g of Pd/C (Wet 10%) under $N_2$ atmosphere and was added (0.34 g, 5.3 mmol) of ammonium formate at room temperature. After completion of the reaction (monitored by TLC), the reaction mixture was filtered through a pad of celite and was washed with Hot EtOAc:MeOH (1:1, 50 ml). The filtrate was evaporated under reduced pressure, diluted with water (10 ml), extracted with $CH_2Cl_2$ (2×200 ml) and brine wash. The combined organic layers were dried over $Na_2SO_4$, filtered and evaporated under reduced pressure. The crude residue was purified by silicagel column chromatography by using 6% methanol: dichloromethane as an eluent to gave the title compound (wt: 1.8 g) as a white solid. $^1$H NMR (300 MHz, DMSO-d6): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 5.31-5.35 (m, 1H), 7.01-7.11 (m, 2H), 7.12-7.13 (m, 1H), 7.22-7.70 (m, 2H), 10.50 (s, 1H); Mass:837 [M+1]$^+$ 838 (100%); HPLC Purity: 94.7%.

Example 43

Preparation of 2,2-dimethyl-3-((((1R,3aS,5aR,5bR, 7aR,9S,11aR,11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl) icosahydro-1H-cyclopenta[a]chrysen-9-yl)oxy) carbonyl)cyclobutane-1-carboxylic acid

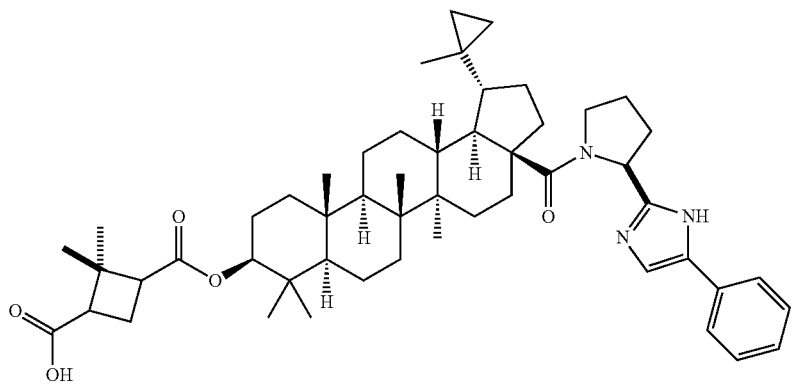

Step 1: Synthesis of 1-benzyl 3-((1R,3aS,5aR,5bR, 7aR,9S,11aR,11bR,13aR,13bR)-5a,5b,8,8,11a-pentamethyl-1-(1-methylcycloprop yl)-3a-((S)-2-(5-phenyl-1H-imidazol-2-yl)pyrrolidine-1-carbonyl) icosahydro-1H-cyclopenta[a]chrysen-9-yl) 2,2-dimethylcyclobutane-1,3-dicarboxylate

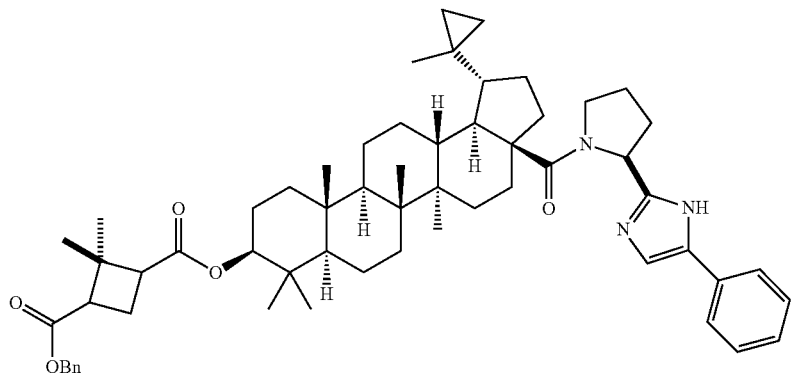

To a stirred solution of ((1R,3aS,5aR,5bR,7aR,9S,11aR, 11bR,13aR,13bR)-9-hydroxy-5a,5b,8,8,11a-pentamethyl-1-(1-methylcyclopropyl)icosahydro-3aH-cyclopenta[a]chrysen-3a-yl)((S)-2-(5-phenyl-1H-imidazol-2-yl)pyrrolidin-1-yl)methanone (Example 12-step 5, 3.5 g, 5.2 mmol, 1.0 eq) in pyridine (40 ml) was added DMAP (1.2 g, 10.4 mmol, 2.0 eq) and (1S,3R)-3-(benzyloxycarbonyl)-2,2-dimethylcyclobutanecarboxylic 2,4,6-trichlorobenzoic anhydride (Example 14-step 1, 3.6 g, 7.8 mmol). The reaction mixture was heated to 90° C. for overnight. TLC indicated starting material was consumed and the desired product was observed. The reaction mixture was evaporated under reduced pressure and diluted with water. The aqueous layer was extracted with $CH_2Cl_2$ (2×500 ml), washed with 1N HCl followed by water and brine solution. The organic layer were dried over $Na_2SO_4$, filtered and evaporated under reduced pressure. The crude residue was purified by silicagel column chromatography by using 1.5% methanol: dichloromethane as an eluent to obtain the title compound (1.5 g,) as a white solid. $^1$H NMR (300 MHz, $CDCl_3$): δ 0.22-0.25 (m, 2H), 0.26-0.27 (m, 2H), 0.79-0.93 (m, 8H), 0.93 (s, 6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 5.31-5.35 (m, 1H), 7.01-7.11 (m, 3H), 7.12-7.13 (m, 2H), 7.22-7.60 (m, 3H), 7.70-7.88 (m, 2H), 10.50 (s, 1H); Mass 909: [M+1]$^+$ 910 (100%).

Step 2: Synthesis of 2,2-dimethyl-3-(((((1R,3aS,5aR, 5bR,7aR,9S,11aR,11bR,13aR,13bR)-5a,5b,8,8,11a-pentamethyl-1-(1-methylcycloprop yl)-3a-((S)-2-(5-phenyl-1H-imidazol-2-yl)pyrrolidine-1-carbonyl) icosahydro-1H-cyclopenta[a]chrysen-9-yl)oxy) carbonyl)cyclobutane-1-carboxylic acid To a solution of 1-benzyl 3-((1R,3aS,5aR,5bR,7aR,9S, 11aR,11bR,13aR,13bR)-5a,5b,8,8,11a-pentamethyl-1-(1-methylcyclopropyl)-3a-((S)-2-(5-phenyl-1H-imidazol-2-yl) pyrrolidine-1-carbonyl)icosahydro-1H-cyclopenta[a] chrysen-9-yl)-2,2-dimethylcyclobutane-1,3-dicarboxylate (step 1, 1 g, 1.1 mmol, 1.0 eq) dissolved in EtOAc:MeOH (1:1) and was added 0.5 g of Pd/C (Wet 10%) under $N_2$ atmosphere and was added (0.3 g, 5.5 mmol) of ammonium formate at room temperature. TLC indicated starting material was consumed and the desired product was observed. The reaction mixture was filtered through a pad of celite and was washed with Hot EtOAc:MeOH (1:1, 50 ml). The filtrate was evaporated under reduced pressure, diluted with water (10 ml), extracted with $CH_2Cl_2$ (2×20 ml) and brine wash. The combined organic layers were dried over $Na_2SO_4$, filtered and evaporated under reduced pressure. The crude residue was purified by silicagel column chromatography by using 6% methanol: dichloromethane as an eluent to gave the title compound (1.8 g) as a white solid. $^1$H NMR (300 MHz, DMSO-d6): δ 0.22-0.25 (m, 2H), 0.26-0.27 (m, 2H), 0.79-0.93 (m, 8H), 0.93 (6H), 1.07-1.26 (m, 10H), 1.29-1.56 (m, 12H), 1.69-1.99 (m, 8H), 2.09-2.18 (m, 4H), 2.23-3.45 (m, 6H), 3.82-4.13 (m, 5H), 4.20-4.24 (m, 1H), 5.31-5.35 (m, 1H), 7.01-7.11 (m, 3H), 7.12-7.13 (m, 1H), 7.22-7.70 (m, 2H), 10.50 (s, 1H); Mass:819 [M+1]$^+$ 820 (100%); HPLC Purity: 95.6%.

Pharmacological Activity

The compounds described herein can be tested for their antiviral activity following procedures known to a person of ordinary skill in the art. For example, the following protocols can be employed for testing the compounds. These protocols are illustrative and do not limit to the scope of the invention.

Example 44

Evaluation of Compounds Antiviral Activity

MT2 cells were infected with HIV-1 strain 92HT599 (10 TCID 50/30000 cells). The infected cells were plated at the concentration of ~30 000 cells per well in 96 well plate. Test compound was added to the micro plate in defined format with the final concentration of DMSO (vehicle) is not more than 1%. Incubation was carried out in CO2 incubator for ~96 hours for viral infection. At the end of incubation period an aliquot from each well was taken for p24 estimation. The quantitation of p24 is an index for antiviral activity of the compound. Percent inhibition was calculated with reference to control values (vehicle controls).

p-24 estimation was carried out using Advance biosciences kit as per the procedure detailed by supplier.

Results:

TABLE 1

| Compound No. | Antiviral activity % inhibition | |
|---|---|---|
| | 1000 nM | 100 nM |
| 2 | 90 | 30 |
| 3 | 100 | 100 |
| 4 | 96 | 84 |
| 5 | 99 | 64 |
| 8 | 100 | 100 |
| 9 | 98 | 81 |
| 10 | 100 | 100 |
| 11 | 100 | 99 |
| 12 | 100 | 100 |
| 13 | 100 | 78 |
| 14 | 100 | 94 |
| 15 | 97 | 98 |
| 17 | 100 | 96 |
| 19 | 100 | 86 |
| 32 | 100 | 100 |
| 41 | 99 | 98 |

TABLE 1A

| Compound No. | Antiviral activity $IC_{50}$ (nM) |
|---|---|
| 1 | 5.02 |
| 3 | 3.34 |
| 4 | 8.64 |
| 8 | 12.92 |
| 10 | 0.80 |
| 11 | 1.51 |
| 12 | 4.59 |
| 14 | 15.29 |
| 27 | 11.03 |
| 30 | 3.83 |
| 31 | 1.62 |
| 33 | 9.5 |
| 34 | 17 |
| 35 | 74 |
| 38 | 8.4 |
| 42 | <0.3 |
| 43 | 4.4 |

Example 45

Evaluation of Compounds Cyto-Toxicity

For cyto-toxicity assay the same amount of MT2 cells as in antiviral assay without virus was added to the 96 well plates. The cyto-toxicity was measured using MTT reagent in parallel with p24 estimation. The percent viability is calculated in comparison with vehicle control.

Results:

TABLE 2

| Compound No. | Cytotoxicity % viability | |
|---|---|---|
| | 1000 nM | 1000 nM |
| 2 | 90 | 92 |
| 3 | 97 | 100 |
| 5 | 91 | 100 |
| 8 | 96 | 88 |
| 9 | 100 | 99 |
| 10 | 82 | 81 |
| 11 | 80 | 84 |
| 12 | 85 | 85 |
| 13 | 74 | 72 |
| 14 | 82 | 86 |

Example 46

Evaluation of Compounds Single Dose Oral Pharmacokinetic Study

The test item was administered through oral route to animals (rat/mice) at 30 mg/kg dose in a suitable vehicle at 10 ml/kg dose volume. Blood samples (~50 uL at each time point) were collected from retro-orbital plexus using K3 EDTA as anticoagulant in eppendorf tubes at defined time intervals under light ether anesthesia. The samples were centrifuged at 3500×g to separate plasma and stored at −80° C. until analysis.

Sample analysis: Test samples were analyzed using LC-MS-MS after developing fit-for-purpose method for each of test compound.

Results:

TABLE 3

| Compound No. | Mice oral PK @30 mg/kg | | | |
|---|---|---|---|---|
| | Cmax µg/mL | AUC 0-t µg · hr/mL | AUC 0-inf µg · hr/mL | Tmax hrs |
| 1 | 12.66 | 125.15 | — | 6.0 |
| 3 | 7.43 | 66.49 | — | 1.75 |
| 4 | 4.83 | 36.92 | — | 2.50 |
| 8 | 11.12 | 143.11 | — | 3.75 |
| 9 | 5.46 | 57.95 | — | 6.0 |
| 10 | 5.84 | 40.46 | — | 1.13 |
| 11 | 7.62 | 59.52 | — | 1.25 |
| 12 | 7.26 | 69.31 | — | 3.0 |
| 13 | 11.13 | 156.20 | — | 4.0 |
| 14 | 10.99 | 171.37 | — | 5.0 |

TABLE 4

| Compound No. | Mice oral PK @30 mg/kg | | | |
|---|---|---|---|---|
| | Cmax µg/mL | AUC 0-t µg · hr/mL | AUC 0-inf µg · hr/mL | $t_{1/2}$ hrs |
| 15 | 11.4 | 286.2 | 445.9 | 30.9 |
| 27 | 10.1 | 231.05 | 534.6 | 38.1 |
| 30 | 6.4 | 54.6 | 57.8 | 1.7 |
| 31 | 9.3 | 135.8 | 144.6 | 10.9 |
| 33 | 4.4 | 88.7 | 151.8 | 32.1 |
| 34 | 13.3 | 223.9 | 262.9 | 16.1 |
| 35 | 16 | 410.2 | 654.7 | 34.25 |
| 36 | 10.9 | 333.96 | 517.64 | 30.3 |
| 38 | 7 | 110 | 119 | 12.3 |
| 42 | 9.3 | 253.9 | 448.1 | 37.3 |
| 43 | 13.9 | 293.5 | 776.04 | 55.6 |

REFERENCES

1. Antiviral methods and protocols (Eds: D Kinchington and R F Schinazi) Humana Press Inc., 2000
2. HIV protocols (Eds: N L Michael and J H Kim) Humana Press Inc, 1999

3. DAIDS Virology manual fro HIV laboratories, Publication NIH-97-3838, 1997
4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

The invention claimed is:
1. A compound of the formula (1):

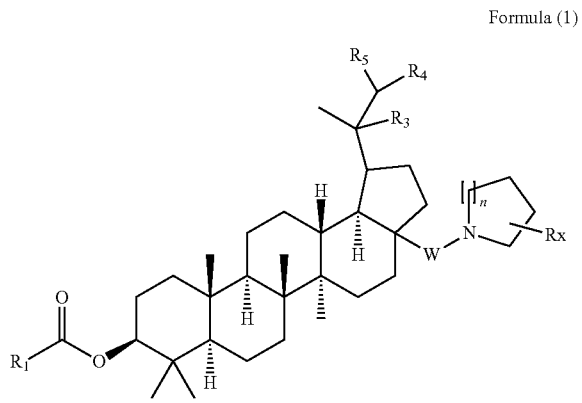

wherein,
$R_1$ is H, substituted or unsubstituted alkyl,

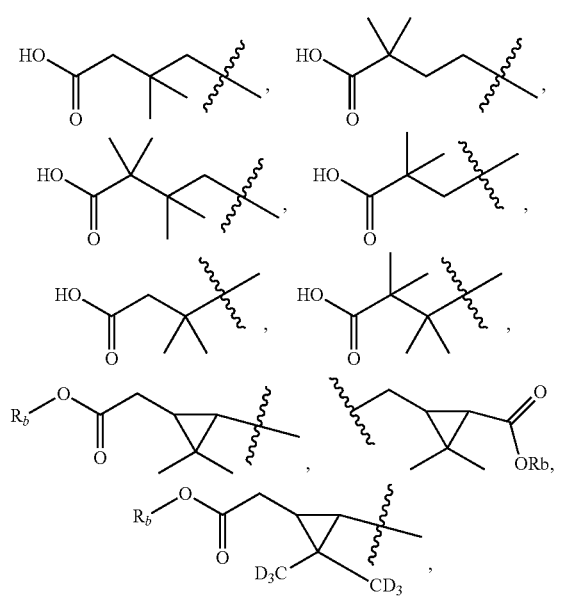

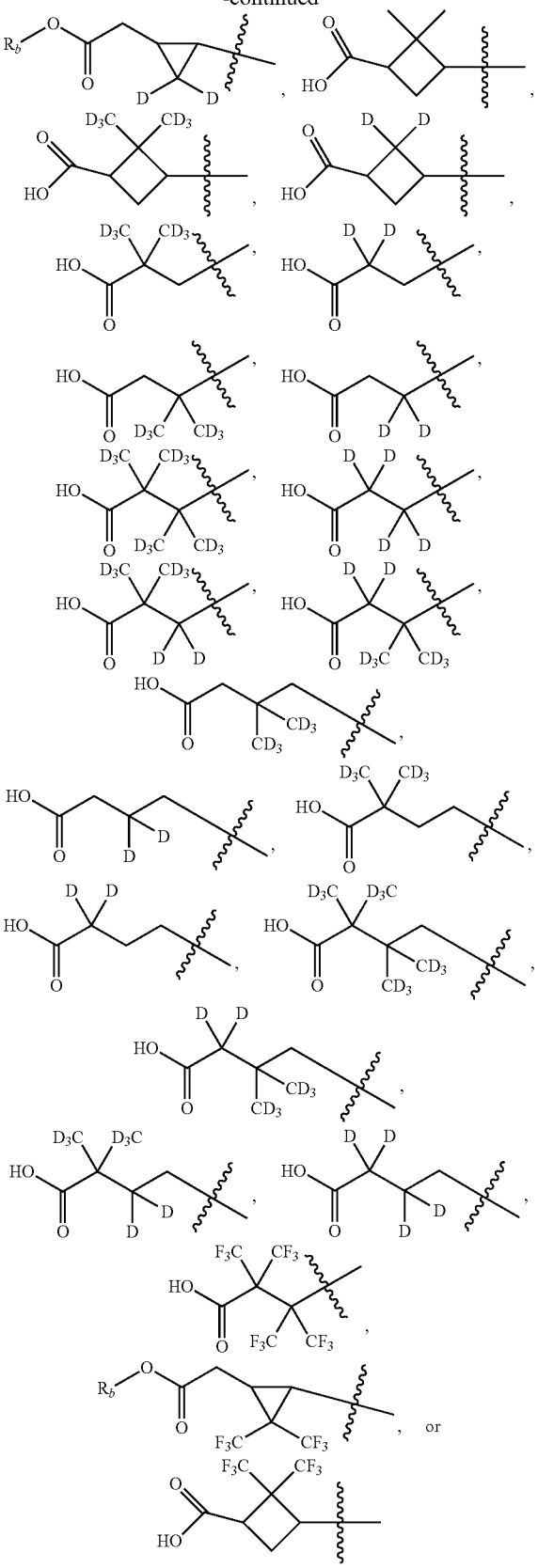

(wherein Rb is H, substituted or unsubstituted alkyl, or substituted or unsubstituted cycloalkyl);

R₃ and R₄ are independently selected from H, OH, substituted or unsubstituted alkyl, substituted or unsubstituted alkoxy, substituted or unsubstituted alkoxylalkoxy, or R₃ and R₄ together with their adjacent carbons to form a bond or R₃ and R₄ together with their adjacent carbons to form cyclopropyl or epoxide;

W is a bond, C(O), or CR₆R₇;

Rx is substituted or unsubstituted heteroaryl;

R₅, R₆ and R₇ are independently selected from H, D, CD₃, CH₂CD₃, CH(CD₃)₂, CO₂R$_d$ (wherein R$_d$ is H, substituted or unsubstituted alkyl, or substituted or unsubstituted cycloalkyl), or substituted or unsubstituted alkyl;

n is an integer from 1 to 3;

pharmaceutically acceptable salts, tautomers, stereoisomers, or esters thereof.

2. The compound of claim 1, wherein W is —C(O)—.

3. The compound of claim 1, wherein Rx is imidazole, oxazole, oxadiazole, thiazole, thiadiazole, isothiazole, isothiadiazole, pyridine, pyrazine, pyrimidine, or pyridazine.

4. A compound of the formula (1A):

Formula (1A)

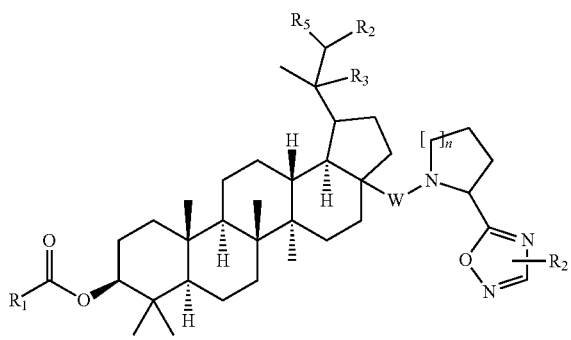

wherein,

R₁ is H, substituted or unsubstituted alkyl,

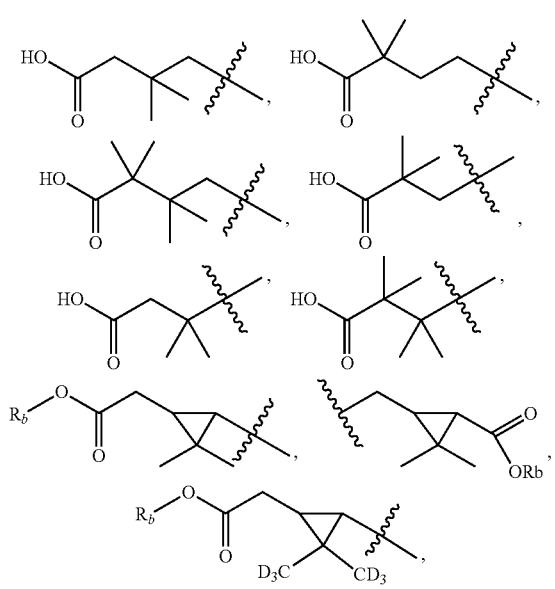

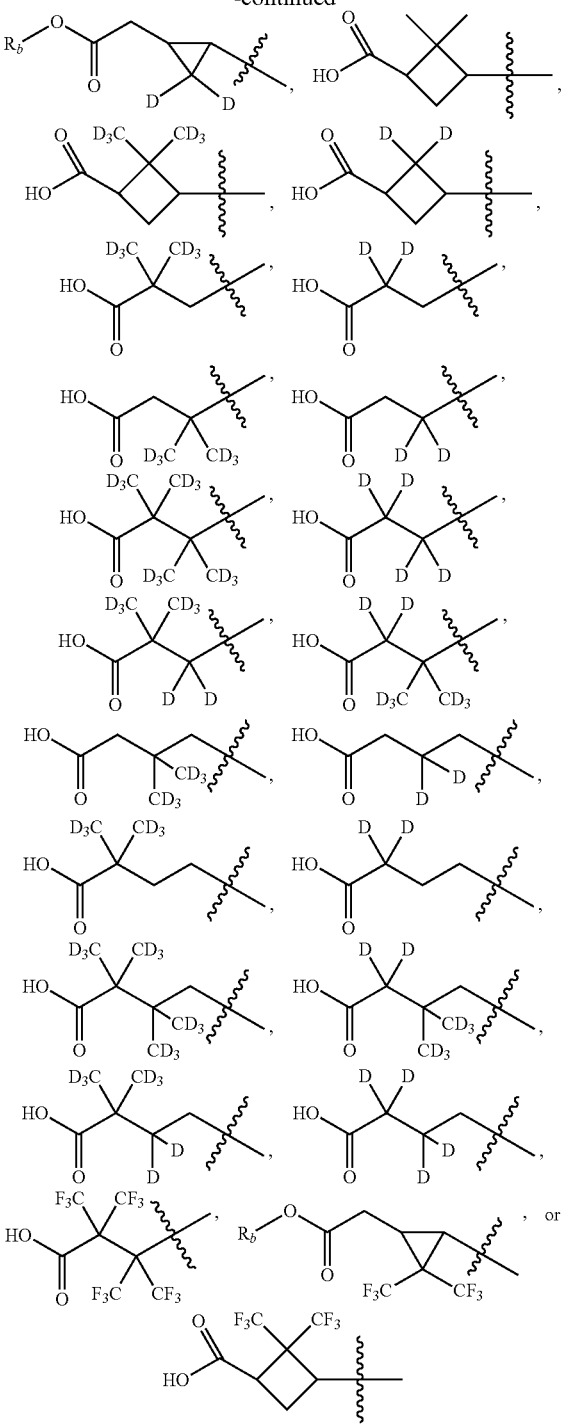

(wherein Rb is H, substituted or unsubstituted alkyl, or substituted or unsubstituted cycloalkyl);

R₂ is H, substituted or unsubstituted alkyl, substituted or unsubstituted cycloalkyl, substituted or unsubstituted aryl, substituted or unsubstituted heterocyclyl, or substituted or unsubstituted heteroaryl;

R₃ and R₄ are independently selected from H, OH, substituted or unsubstituted alkyl, substituted or unsubstituted alkoxy, substituted or unsubstituted alkoxylalkoxy, or R₃ and R₄ can be together with their adjacent carbons to form a bond or $R_3$ and $R_4$ together with their adjacent carbons to form cyclopropyl or epoxide;

W is a bond, C(O), or $CR_6R_7$;

$R_5$, $R_6$ and $R_7$ are independently selected from H, D, $CD_3$, $CH_2CD_3$, $CH(CD_3)_2$, $CO_2R_d$ (wherein $R_d$ is H, substituted or unsubstituted alkyl, or substituted or unsubstituted cycloalkyl), or substituted or unsubstituted alkyl;

n is an integer from 1 to 3; pharmaceutically acceptable salts, tautomers, stereoisomers, or esters thereof.

5. The compound of claim 4, wherein W is —C(O)—.
6. The compound of claim 4, wherein $R_2$ is isopropyl, t-butyl, phenyl, pyridine, pyrazine, thiophene or chromene.
7. A compound of the formula (1B):

Formula (1B)

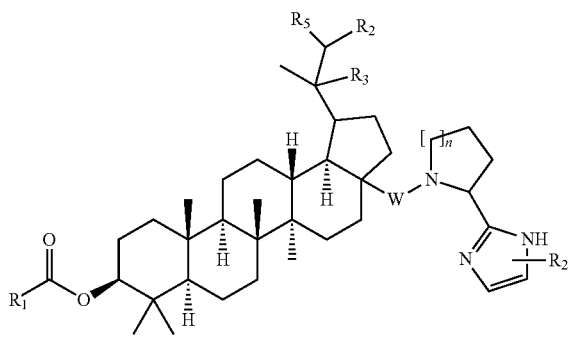

wherein,
$R_1$ is H, substituted or unsubstituted alkyl,

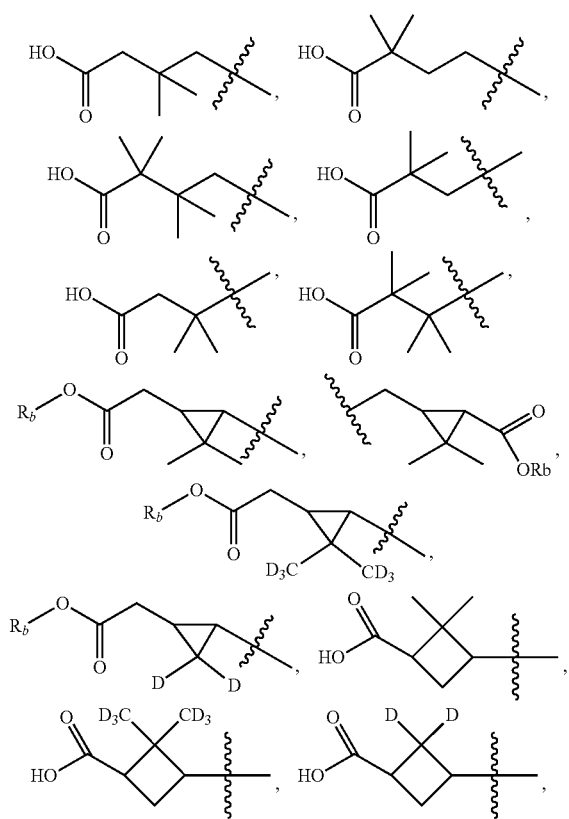

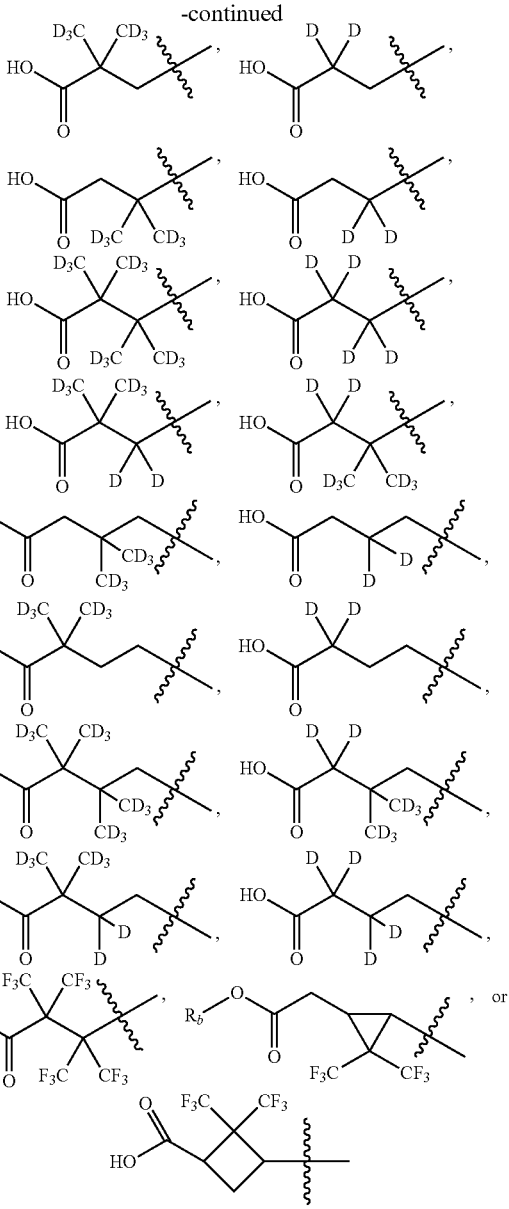

(wherein Rb is H, substituted or unsubstituted alkyl, or substituted or unsubstituted cycloalkyl);

$R_2$ is H, substituted or unsubstituted alkyl, substituted or unsubstituted cycloalkyl, substituted or unsubstituted aryl, substituted or unsubstituted heterocyclyl, or substituted or unsubstituted heteroaryl;

$R_3$ and $R_4$ are independently selected from H, OH, substituted or unsubstituted alkyl, substituted or unsubstituted alkoxy, substituted or unsubstituted alkoxylalkoxy, or $R_3$ and $R_4$ together with their adjacent carbons to form a bond or $R_3$ and $R_4$ together with their adjacent carbons to form cyclopropyl or epoxide;

W is a bond, C(O), or $CR_6R_7$;

$R_5$, $R_6$ and $R_7$ are independently selected from H, D, $CD_3$, $CH_2CD_3$, $CH(CD_3)_2$, $CO_2R_d$ (wherein $R_d$ is H, substituted or unsubstituted alkyl, or substituted or unsubstituted cycloalkyl), or substituted or unsubstituted alkyl;

n is an integer from 1 to 3; pharmaceutically acceptable salts, tautomers, stereoisomers, or esters thereof.

8. The compound of claim 7, wherein W is —C(O)—.

9. The compound of claim 7, wherein $R_2$ is isopropyl, t-butyl, phenyl, pyridine, pyrazine, thiophene or chromene.

10. A compound selected from the group consisting of:

2,2-dimethyl-4-oxo-4-((1R,3aS,5aR,5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy)butanoic acid, 3,3-dimethyl-5-oxo-5-((1R,3aS,5aR,5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy)pentanoic acid, 2,2-dimethyl-4-oxo-4-((1R,3aS,5aR,5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yloxy)butanoic acid, 3,3-dimethyl-5-oxo-5-((1R,3aS,5aR,5bR,7aR,9S,11aR,11bR,13aR,13bR)-5a,5b,8,8,11a-pentamethyl-1-(prop-1-en-2-yl)-3a-((R)-2-(3-(pyridin-3-yl)-1,2,4-oxadiazol-5-yl)pyrrolidine-1-carbonyl)icosahydro-1H-cyclopenta[a]chrysen-9-yloxy)pentanoic acid, 2,2-dimethyl-4-oxo-4-((1R,3aS,5aR,5bR,7aR,9S,11aR,11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yloxy)butanoic acid, 3,3-dimethyl-5-oxo-5-((1R,3aS,5aR,5bR,7aR,9S,11aR,11bR,13aR,13bR)-5a,5b,8,8,11a-pentamethyl-1-(1-methylcyclopropyl)-3a-((R)-2-(3-phenyl-1,2,4-oxadiazol-5-yl)pyrrolidine-1-carbonyl)icosahydro-1H-cyclopenta[a]chrysen-9-yloxy)pentanoic acid, 2,2-dimethyl-3-(((1R,3aS,5aR,5bR,7aR,9S,11aR,11bR,13aR,13bR)-5a,5b,8,8,11a-pentamethyl-3a-((R)-2-(3-phenyl-1,2,4-oxadiazol-5-yl)pyrrolidine-1-carbonyl)-1-(prop-1-en-2-yl)icosahydro-1H-cyclopenta[a]chrysen-9-yloxy)carbonyl)cyclobutanecarboxylic acid, 2,2-dimethyl-4-oxo-4-((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)butanoic acid, 3,3-dimethyl-5-oxo-5-((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)pentanoic acid, 2,2-dimethyl-4-oxo-4-((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yloxy)butanoic acid, 3,3-dimethyl-5-oxo-5-((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yloxy)pentanoic acid, 2,2-dimethyl-4-oxo-4-((1R,3aS,5aR,5bR,7aR,9S,11aR,11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yloxy)butanoic acid, 3,3-dimethyl-5-oxo-5-((1R,3aS,5aR,5bR,7aR,9S,11aR,11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yloxy)pentanoic acid, (1R,1S)-2,2-dimethyl-3-((((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yloxy)carbonyl)cyclobutanecarboxylic acid, (1R,3S)-3-((((1R,3aS,5aR,5bR,7aR,9S,11aR,11bR,13aR,13bR)-3a-(2-(5-(4-methoxyphenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethyl cyclobutane-1-carboxylic acid, (1R,3S)-2,2-dimethyl-3-(1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-4-yl)-1H-imidazol-2-yl) pyrrolidine-1-carbonyl)icosahydro-1H-cyclopenta[a]chrysen-9-yl)oxy)carbonyl)cyclobutane-1-carboxylic acid, (1R,3S)-2,2-dimethyl-3-(1R,3aS,5aR,5bR,7aR,9S,11aR,11bR,13aR,13bR)-5a,5b,8,8,11a-pentamethyl-3a-(2-(5-(4-nitrophenyl)-1H-imidazol-2-yl)pyrrolidine-1-carbonyl)-1-(prop-1-en-2-yl)icosahydro-1H-cyclopenta[a]chrysen-9-yl)oxy)carbonyl) cyclobutane-1-carboxylic acid, (1R,3S)-2,2-dimethyl-3-(1R,3aS,5aR,5bR,7aR,9S,11aR,11bR,13aR,13bR)-5a,5b,8,8,11a-pentamethyl-1-(prop-1-en-2-yl)-3a-(2-(5-(p-tolyl)-1H-imidazol-2-yl)pyrrolidine-1-carbonyl)icosahydro-1H-cyclopenta[a]chrysen-9-yl)oxy)carbonyl)cyclobutane-1-carboxylic acid, (1R,3S)-3-(1R,3aS,5aR,5bR,7aR,9S,1aR,11bR,13aR,13bR)-3a-(2-(5-(4-cyano phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, 2,2-dimethyl-5-oxo-5-(((1R,3aS,5aR,5bR,7aR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)pentanoic acid, (1R,3S)-3-((((1 S,3aS,5aR,5bR,7aR,9S,11aR,11bR,13aR,13bR)-1-isopropyl-5a,5b,8,8,11a-pentamethyl-3a-((S)-2-(5-phenyl-1H-imidazol-2-yl)pyrrolidine-1-carbonyl)icosahydro-1H-cyclopenta[a]chrysen-9-yl)oxy) carbonyl)-2,2-dimethylcyclobutane-1-carboxylic acid, (1R,3 S)-3-((((1 S,3 aS,5aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl)oxy)carbonyl)-2,2-dimethylcyclobutane-1-carboxylic acid, 4-(((1 S,3aS,5 aR,5bR,7aR,9S,11aR,11bR,13aR,13bR)-3a-((S)-2-(5-(4-fluorophenyl)-1H-imidazol-2-yl)pyrrolidine-1-carbonyl)-1-isopropyl-5a,5b,8,8,11a-pentamethylicosahydro-1H-cyclopenta[a]chrysen-9-yl)oxy)-2,2-dimethyl-4-oxobutanoic acid, (1R,3 S)-3-((((1 S,3 aS,5aR,5bR,7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b, 8,8,11a-pentamethylicosahydro-1H-cyclopenta[a]
chrysen-9-yl)oxy)carbonyl)-2,2-dimethylcyclobutane-1-carboxylic acid, 4-(((1S,3aS,5aR,5bR,7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl)oxy)-2,2-dimethyl-4-oxobutanoic acid, 5-(((1S,3aS,5aR,5bR,7aR,9S,11aR,11bR,13aR,13bR)-1-isopropyl-3a-((S)-2-(5-(4-methoxyphenyl)-1H-imidazol-2-yl)pyrrolidine-1-carbonyl)-5a,5b,8,8,11a-pentamethylicosahydro-1H-cyclopenta[a]chrysen-9-yl)oxy)-3,3-dimethyl-5-oxopentanoic acid, (1S,3R)-2,2-dimethyl-3-(((((1R,3aS,5aR,5bR,9S,11aR,11bR,13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid, 4-(1R,3aS,5aR,5bR,7aR,9S,11aR,11bR,13aR,13bR)-3a-((R)-2-(5-(4-chloro phenyl)-1H-imidazol-2-yl)pyrrolidine-1-carbonyl)-5a,5b,8,8,8,11a-pentamethyl-1-(prop-1-en-2-yl)icosahydro-1H-cyclopenta[a]chrysen-9-yl)oxy)-2,2-dimethyl-4-oxobutanoic acid, 2,2-dimethyl-3-((((1R,3aS,5aR,5bR,7aR,9S,11aR,11bR,13aR,13bR)-5a,5b,8,8,11a-pentamethyl-1-(prop-1-en-2-yl)-3a-((S)-2-(5-(pyridin-3-yl)-1H-imidazol-2-yl)pyrrolidine-1-carbonyl)icosahydro-1H-cyclopenta[a]chrysen-9-yl)oxy)carbonyl) cyclobutane-1-carboxylic acid, 2,2-dimethyl-4-oxo-4-(((1R,3aS,5aR,5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)butanoic acid, 3,3-dimethyl-5-oxo-5-(((1R,3aS,5aR,5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)pentanoic acid, 2,2-dimethyl-3-((((1R,3aS,5aR,5bR,7aR,9S,11aR,11bR,13aR,13bR)-5a,5b,8,8,11a-pentamethyl-1-(1-methylcyclopropyl)-3a-((S)-2-(5-(pyridin-3-yl)-1H-imidazol-2-yl)pyrrolidine-1-carbonyl)icosahydro-1H-cyclopenta[a]chrysen-9-yl)oxy)carbonyl)cyclobutane-1-carboxylic acid, 4-(((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,8,11a-pentamethyl-1-(1-methylcyclopropyl)icosahydro-1H-cyclopenta[a]chrysen-9-yl)oxy)-2,2-dimethyl-4-oxobutanoic acid, 4-(((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)-2,2-dimethyl-4-oxobutanoic acid, 3-((((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, 3-((((1R,3aS,5aR,5bR,7aR,9S,11aR,11bR,13aR,13bR)-3a-((S)-2-(5-(4-hydroxyphenyl)-1H-imidazol-2-yl)pyrrolidine-1-carbonyl)-5a,5b,8,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, 3-((((1R,3aS,5aR,5bR,7aR,9S,11aR,11bR,13aR,13bR)-3a-((S)-2-(5-(4-(2-methoxyethoxy)phenyl)-1H-imidazol-2-yl)pyrrolidine-1-carbonyl)-5a,5b,8,8,11a-pentamethyl-1-(prop-1-en-2-yl)icosahydro-1H-cyclopenta[a]chrysen-9-yl)oxy)carbonyl)-2,2-dimethylcyclobutane-1-carboxylic acid, 2,2-dimethyl-4-oxo-4-(((1R,3aS,5aR,5bR,7aR,9S,11aR,11bR,13aR,13bR)-5a,5b,8,8,11a-pentamethyl-1-(1-methylcyclopropyl)-3a-((S)-2-(5-(thiophen-2-yl)-1H-imidazol-2-yl)pyrrolidine-1-carbonyl)icosahydro-1H-cyclopenta[a]chrysen-9-yl)oxy)butanoic acid, 2,2-dimethyl-4-oxo-4-(((1R,3aS,5aR,5bR,7aR,9S,11aR,11bR,-13aR,13bR)-5a,5b,8,8,11a-pentamethyl-3a-((S)-2-(5-phenyl-1H-imidazol-2-yl)pyrrolidine-1-carbonyl)-1-(prop-1-en-2-yl)icosahydro-1H-cyclopenta[a]chrysen-9-yl)oxy)butanoic acid, 3,3-dimethyl-5-oxo-5-(((1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl)oxy)pentanoic acid, 2,2-dimethyl-3-((((1R,3aS,5aR,5bR,7aR,9S,11aR,11bR,13aR,13bR)-5a,5b,8,8,11a-pentamethyl-3a-((R)-2-(5-phenyl-1H-imidazol-2-yl)pyrrolidine-1-carbonyl)-1-(prop-1-en-2-yl)icosahydro-1H-cyclopenta[a]chrysen-9-yl)oxy)carbonyl)cyclobutane-1-carboxylic acid, 3-((((1R,3aS,5aR,5bR,7aR,9S,11aR,11bR,13aR,13bR)-3a-((S)-2-(5-(4-fluorophenyl)-1H-imidazol-2-yl)pyrrolidine-1-carbonyl)-5a,5b,8,8,8,11a-pentamethyl-1-(1-methylcyclopropyl)icosahydro-1H-cyclopenta[a]chrysen-9-yl)oxy) carbonyl)-2,2-dimethylcyclobutane-1-carboxylic acid, 2,2-dimethyl-3-((((1R,3aS,5aR,5bR,7aR,9S,11aR,11bR,13aR,13bR)-5a,5b,8,8,11a-pentamethyl-1-(1-methylcyclopropyl)-3a-((S)-2-(5-phenyl-1H-imidazol-2-yl)pyrrolidine-1-carbonyl)icosahydro-1H-cyclopenta[a]chrysen-9-yl)oxy)carbonyl)cyclobutane-1-carboxylic acid, pharmaceutically acceptable salts, tautomers, stereoisomers, or esters thereof.

11. A pharmaceutical composition comprising a compound according to claim 1 and at least one pharmaceutically acceptable excipient.

12. The pharmaceutical composition according to claim 11, wherein the pharmaceutically acceptable excipient is a carrier or diluent.

13. A method for ameliorating HIV infection in a subject in need thereof comprising administering to the subject a therapeutically effective amount of a compound according to claim 1.

14. A method for ameliorating HIV infection in a subject in need thereof comprising administering to the subject the pharmaceutical composition according to claim 11 comprising a therapeutically effective amount of the compound.

* * * * *